US012661433B2

(12) United States Patent
Shah et al.

(10) Patent No.:     US 12,661,433 B2
(45) Date of Patent:          Jun. 23, 2026

(54) BIOENGINEERED SCAFFOLDS FOR MODULATION OF IMMUNE SYSTEM AND THE USES THEREOF

(71) Applicants:President and Fellows of Harvard College, Cambridge, MA (US); The General Hospital Corporation, Boston, MA (US)

(72) Inventors: Nisarg J. Shah, San Diego, CA (US); Angelo S. Mao, Cambridge, MA (US); Matthew D. Kerr, Carlsbad, CA (US); David J. Mooney, Sudbury, MA (US); David T. Scadden, Weston, MA (US)

(73) Assignees: President and Fellows of Harvard College, Cambridge, MA (US); The General Hospital Corporation, Boston, MA (US)

( * ) Notice:   Subject to any disclaimer, the term of this patent is extended or adjusted under 35 U.S.C. 154(b) by 778 days.

(21) Appl. No.: 17/414,037

(22) Filed:     Jun. 15, 2021

(65) Prior Publication Data

US 2022/0047778 A1     Feb. 17, 2022

Related U.S. Application Data

(63) Continuation     of     application     No. PCT/US2019/066086, filed on Dec. 12, 2019.

(60) Provisional application No. 62/798,100, filed on Jan. 29, 2019, provisional application No. 62/780,727, filed on Dec. 17, 2018.

(51) Int. Cl.
| | |
|---|---|
| *A61K 35/28* | (2015.01) |
| *A61K 35/32* | (2015.01) |
| *A61K 38/18* | (2006.01) |
| *A61K 38/19* | (2006.01) |
| *A61L 27/20* | (2006.01) |
| *A61L 27/26* | (2006.01) |
| *A61L 27/52* | (2006.01) |
| *A61L 27/54* | (2006.01) |
| *A61L 27/56* | (2006.01) |

(52) U.S. Cl.
CPC .............. *A61L 27/54* (2013.01); *A61K 35/28* (2013.01); *A61K 35/32* (2013.01); *A61K 38/1841* (2013.01); *A61K 38/19* (2013.01); *A61L 27/20* (2013.01); *A61L 27/26* (2013.01); *A61L 27/52* (2013.01); *A61L 27/56* (2013.01); *A61L 2300/414* (2013.01); *A61L 2300/426* (2013.01); *A61L 2400/06* (2013.01); *A61L 2400/12* (2013.01)

(58) Field of Classification Search
CPC .......... A61L 27/54; A61L 27/20; A61L 27/26; A61L 27/52; A61L 27/56; A61L 2300/414; A61L 2300/426; A61L 2400/06; A61L 2400/12; A61K 35/28; A61K 35/32; A61K 38/1841; A61K 38/19
See application file for complete search history.

(56) References Cited

U.S. PATENT DOCUMENTS

| | | |
|---|---|---|
| 3,773,919 A | 11/1973 | Boswell et al. |
| 4,465,827 A | 8/1984 | Kawasaki et al. |
| 4,522,811 A | 6/1985 | Eppstein et al. |
| 4,946,778 A | 8/1990 | Ladner et al. |
| 5,091,513 A | 2/1992 | Huston et al. |
| 5,132,405 A | 7/1992 | Huston et al. |
| 5,885,829 A | 3/1999 | Mooney et al. |
| 5,888,987 A | 3/1999 | Haynes et al. |
| 5,906,826 A | 5/1999 | Emery et al. |
| 5,951,976 A | 9/1999 | Segal |
| 6,129,716 A | 10/2000 | Steer |
| 6,160,084 A | 12/2000 | Langer et al. |
| 6,187,762 B1 | 2/2001 | Mandeville, III et al. |
| 6,193,970 B1 | 2/2001 | Pardoll et al. |
| 6,251,396 B1 | 6/2001 | Gaur et al. |
| 6,281,256 B1 | 8/2001 | Harris et al. |
| 6,334,968 B1 | 1/2002 | Shapiro et al. |
| 6,352,694 B1 | 3/2002 | June et al. |
| 6,403,374 B1 | 6/2002 | Tsien et al. |
| 6,429,199 B1 | 8/2002 | Krieg et al. |
| 6,511,511 B1 | 1/2003 | Slivka et al. |
| 6,511,650 B1 | 1/2003 | Eiselt et al. |
| 6,541,022 B1 | 4/2003 | Murphy et al. |
| 6,642,363 B1 | 11/2003 | Mooney et al. |
| 6,685,963 B1 | 2/2004 | Taupin et al. |
| 6,748,954 B2 | 6/2004 | Lee et al. |
| 6,767,928 B1 | 7/2004 | Murphy et al. |
| 6,783,712 B2 | 8/2004 | Slivka et al. |
| 6,790,840 B1 | 9/2004 | Lee et al. |
| 6,797,738 B2 | 9/2004 | Harris et al. |

(Continued)

FOREIGN PATENT DOCUMENTS

| AU | 2014200405 A1 | 2/2014 |
|---|---|---|
| AU | 2018201930 A1 | 4/2018 |

(Continued)

OTHER PUBLICATIONS

T. M. Schmitt and J. C. Zuniga-Pflucker. "Induction of T Cell Development from Hematopoietic Progenitor Cells by Delta-like-1 In Vitro," Immunity, vol. 17, 749-756, Dec. 2002. (Year: 2002).*
F. Gao, et al. "Mesenchymal stem cells and immunomodulation: current status and future prospects," Cell Death and Disease (2016) 7, e2062. (Year: 2016).*
Abrahams et al., Expression and secretion of antiviral factors by trophoblast cells following stimulation by the TLR-3 agonist, Poly(I : C). Hum Reprod. Sep. 2006;21(9):2432-9.
Agache et al., Mechanical properties and Young's modulus of human skin in vivo. Arch Dermatol Res. 1980;269(3):221-32.

(Continued)

*Primary Examiner* — Michael P Cohen
(74) *Attorney, Agent, or Firm* — McCarter & English, LLP; Maria Laccotripe Zacharakis; Maneesh Gulati, Esq.

(57) ABSTRACT

The present invention provides compositions and methods that modulate the immune system in a subject.

20 Claims, 56 Drawing Sheets

US 12,661,433 B2

Page 2

(56) References Cited

U.S. PATENT DOCUMENTS

| | | | |
|---|---|---|---|
| 6,800,733 | B2 | 10/2004 | Tsien et al. |
| 6,858,222 | B2 | 2/2005 | Nelson et al. |
| 6,974,698 | B1 | 12/2005 | Miller et al. |
| 7,015,205 | B1 | 3/2006 | Wallack et al. |
| 7,157,566 | B2 | 1/2007 | Tsien et al. |
| 7,186,413 | B2 | 3/2007 | Bouhadir et al. |
| 7,192,693 | B2 | 3/2007 | Bryant et al. |
| 7,244,714 | B1 | 7/2007 | Gonda et al. |
| 7,357,936 | B1 | 4/2008 | Garcon |
| 7,410,953 | B2 | 8/2008 | Kawasaki |
| 7,427,602 | B1 | 9/2008 | Shea et al. |
| 7,569,850 | B2 | 8/2009 | Noy et al. |
| 7,575,759 | B2 | 8/2009 | Murphy et al. |
| 7,687,241 | B2 | 3/2010 | Chen |
| 7,709,458 | B2 | 5/2010 | Karaolis et al. |
| 7,790,699 | B2 | 9/2010 | Melvik et al. |
| 8,067,237 | B2 | 11/2011 | Mooney et al. |
| 8,188,058 | B2 | 5/2012 | Hackam et al. |
| 8,273,373 | B2 | 9/2012 | Alsberg et al. |
| 8,354,119 | B2 | 1/2013 | Geistlich et al. |
| 8,367,628 | B2 | 2/2013 | Goodwin et al. |
| 8,535,719 | B2 | 9/2013 | Badylak et al. |
| 8,709,464 | B2 | 4/2014 | Ma et al. |
| 8,728,456 | B2 | 5/2014 | Sands et al. |
| 8,883,308 | B2 | 11/2014 | Polshettiwar et al. |
| 8,932,583 | B2 | 1/2015 | Mooney et al. |
| 9,012,399 | B2 | 4/2015 | Cao et al. |
| 9,132,210 | B2 | 9/2015 | Mooney et al. |
| 9,139,809 | B2 | 9/2015 | Porcelli et al. |
| 9,150,631 | B2 | 10/2015 | Super et al. |
| 9,370,558 | B2 | 6/2016 | Ali et al. |
| 9,381,235 | B2 | 7/2016 | Sands et al. |
| 9,446,107 | B2 | 9/2016 | Mooney et al. |
| 9,486,512 | B2 | 11/2016 | Kim et al. |
| 9,591,360 | B2 | 3/2017 | Jennings et al. |
| 9,610,328 | B2 | 4/2017 | Mooney et al. |
| 9,675,561 | B2 | 6/2017 | Bencherif et al. |
| 9,770,535 | B2 | 9/2017 | Mooney et al. |
| 9,821,045 | B2 | 11/2017 | Ali et al. |
| 9,937,249 | B2 | 4/2018 | Kim et al. |
| 10,045,947 | B2 | 8/2018 | Bencherif et al. |
| 10,080,789 | B2 | 9/2018 | Sands et al. |
| 10,137,184 | B2 | 11/2018 | Mooney et al. |
| 10,149,897 | B2 | 12/2018 | Mooney et al. |
| 10,258,677 | B2 | 4/2019 | Mooney et al. |
| 10,328,133 | B2 | 6/2019 | Mooney et al. |
| 10,406,216 | B2 | 9/2019 | Kim et al. |
| 10,568,949 | B2 | 2/2020 | Ali et al. |
| 10,682,400 | B2 | 6/2020 | Ali et al. |
| 10,813,988 | B2 | 10/2020 | Super et al. |
| 11,059,050 | B2 | 7/2021 | Kang et al. |
| 11,096,997 | B2 | 8/2021 | Mooney et al. |
| 11,150,242 | B2 | 10/2021 | Ali et al. |
| 11,202,759 | B2 | 12/2021 | Huebsch et al. |
| 11,278,604 | B2 | 3/2022 | Kim et al. |
| 11,555,177 | B2 | 1/2023 | Cheung et al. |
| 11,638,748 | B2 | 5/2023 | Super et al. |
| 11,684,638 | B2 | 6/2023 | Prabha et al. |
| 11,752,238 | B2 | 9/2023 | Shah et al. |
| 11,786,457 | B2 | 10/2023 | Sandeep et al. |
| 2002/0045672 | A1 | 4/2002 | Harris et al. |
| 2002/0131853 | A1 | 9/2002 | Nagasawa |
| 2002/0131953 | A1 | 9/2002 | Takashima et al. |
| 2002/0150604 | A1 | 10/2002 | Yi et al. |
| 2003/0075822 | A1 | 4/2003 | Slivka et al. |
| 2003/0082806 | A1 | 5/2003 | Berenson et al. |
| 2003/0095994 | A1 | 5/2003 | Geistlich et al. |
| 2003/0100527 | A1 | 5/2003 | Krieg et al. |
| 2003/0194397 | A1 | 10/2003 | Mishra |
| 2003/0232895 | A1 | 12/2003 | Omidian et al. |
| 2003/0235557 | A1 | 12/2003 | Gaiger et al. |
| 2004/0028745 | A1 | 2/2004 | Bouhadir et al. |
| 2004/0043034 | A1 | 3/2004 | Jensenius et al. |
| 2004/0058883 | A1 | 3/2004 | Phillips et al. |
| 2004/0063206 | A1 | 4/2004 | Rowley et al. |
| 2004/0136968 | A1 | 7/2004 | Zheng et al. |
| 2004/0151764 | A1 | 8/2004 | Zamora |
| 2004/0213795 | A1 | 10/2004 | Collins et al. |
| 2004/0220111 | A1 | 11/2004 | Kleinman et al. |
| 2004/0228858 | A1 | 11/2004 | Hanson et al. |
| 2004/0242469 | A1 | 12/2004 | Lee et al. |
| 2004/0242482 | A1 | 12/2004 | Gehring et al. |
| 2005/0002915 | A1 | 1/2005 | Atala et al. |
| 2005/0037330 | A1 | 2/2005 | Fischer et al. |
| 2005/0053667 | A1 | 3/2005 | Irvine et al. |
| 2005/0079159 | A1 | 4/2005 | Shastri et al. |
| 2005/0090008 | A1 | 4/2005 | Segura et al. |
| 2005/0106211 | A1 | 5/2005 | Nelson et al. |
| 2005/0154376 | A1 | 7/2005 | Riviere et al. |
| 2005/0177249 | A1 | 8/2005 | Kladakis et al. |
| 2005/0202394 | A1 | 9/2005 | Dobson |
| 2006/0083712 | A1 | 4/2006 | Anversa |
| 2006/0141018 | A1 | 6/2006 | Cochrum et al. |
| 2006/0264380 | A1 | 11/2006 | Hellstrom et al. |
| 2006/0292134 | A1 | 12/2006 | Stohs |
| 2007/0003595 | A1 | 1/2007 | Wang et al. |
| 2007/0020232 | A1 | 1/2007 | Rossignol et al. |
| 2007/0026518 | A1 | 2/2007 | Healy et al. |
| 2007/0081972 | A1 | 4/2007 | Sandler et al. |
| 2007/0116680 | A1 | 5/2007 | Stegemann et al. |
| 2007/0178159 | A1 | 8/2007 | Chen et al. |
| 2007/0190646 | A1 | 8/2007 | Engler et al. |
| 2008/0044900 | A1 | 2/2008 | Mooney et al. |
| 2008/0044990 | A1 | 2/2008 | Lee |
| 2008/0051490 | A1 | 2/2008 | Williams et al. |
| 2008/0113929 | A1 | 5/2008 | Lipford et al. |
| 2008/0138416 | A1 | 6/2008 | Rauh et al. |
| 2008/0152624 | A1 | 6/2008 | Paludan et al. |
| 2008/0159993 | A1 | 7/2008 | Stauss et al. |
| 2008/0206308 | A1 | 8/2008 | Jabbari et al. |
| 2008/0233181 | A1 | 9/2008 | Nagy et al. |
| 2008/0268019 | A1 | 10/2008 | Badylak et al. |
| 2008/0268052 | A1 | 10/2008 | Voytik-Harbin et al. |
| 2008/0279812 | A1 | 11/2008 | Boyd et al. |
| 2009/0017096 | A1 | 1/2009 | Lowman et al. |
| 2009/0029912 | A1* | 1/2009 | Gronthos ............... A61P 19/10 435/325 |
| 2009/0041825 | A1 | 2/2009 | Kotov et al. |
| 2009/0192079 | A1 | 7/2009 | Santos et al. |
| 2009/0238853 | A1 | 9/2009 | Liu et al. |
| 2009/0252752 | A1 | 10/2009 | Tahara et al. |
| 2009/0297551 | A1 | 12/2009 | Sattentau et al. |
| 2009/0297579 | A1 | 12/2009 | Semino et al. |
| 2009/0305983 | A1 | 12/2009 | Ying et al. |
| 2010/0015709 | A1 | 1/2010 | Rehfeldt et al. |
| 2010/0055102 | A1 | 3/2010 | Langermann |
| 2010/0055186 | A1 | 3/2010 | Dadsetan et al. |
| 2010/0080816 | A1 | 4/2010 | Hadeiba et al. |
| 2010/0129422 | A1 | 5/2010 | Han et al. |
| 2010/0159008 | A1 | 6/2010 | Barron et al. |
| 2010/0174346 | A1 | 7/2010 | Boyden et al. |
| 2010/0189760 | A1 | 7/2010 | Schaffer et al. |
| 2010/0190741 | A1 | 7/2010 | Cohen et al. |
| 2010/0272771 | A1 | 10/2010 | Harlow et al. |
| 2011/0008443 | A1 | 1/2011 | Alsberg et al. |
| 2011/0020216 | A1 | 1/2011 | Mooney et al. |
| 2011/0117170 | A1 | 5/2011 | Cao et al. |
| 2011/0159023 | A1 | 6/2011 | Langermann |
| 2011/0207166 | A1 | 8/2011 | Vaiselbuh |
| 2011/0223255 | A1 | 9/2011 | Thiesen et al. |
| 2011/0253643 | A1 | 10/2011 | Polshettiwar et al. |
| 2011/0256184 | A1 | 10/2011 | Lei et al. |
| 2011/0300186 | A1 | 12/2011 | Hellstrom et al. |
| 2012/0040011 | A9 | 2/2012 | Boons et al. |
| 2012/0121539 | A1 | 5/2012 | Sands et al. |
| 2012/0122218 | A1 | 5/2012 | Huebsch et al. |
| 2012/0134967 | A1 | 5/2012 | Mooney et al. |
| 2012/0207795 | A1 | 8/2012 | Zink et al. |
| 2012/0256336 | A1 | 10/2012 | Yano et al. |
| 2012/0264599 | A1 | 10/2012 | Komatsu et al. |
| 2012/0294888 | A1 | 11/2012 | Kishimoto et al. |
| 2012/0329791 | A1 | 12/2012 | Ashwell et al. |
| 2013/0029030 | A1 | 1/2013 | Larsen |
| 2013/0035283 | A1 | 2/2013 | Super et al. |

(56)  References Cited

U.S. PATENT DOCUMENTS

| | | | |
|---|---|---|---|
| 2013/0045246 A1 | 2/2013 | Edwards et al. | |
| 2013/0052117 A1 | 2/2013 | Imai et al. | |
| 2013/0072547 A1 | 3/2013 | Hackam et al. | |
| 2013/0145488 A1 | 6/2013 | Wang et al. | |
| 2013/0202707 A1 | 8/2013 | Ali et al. | |
| 2013/0225502 A1 | 8/2013 | Sugiyama et al. | |
| 2013/0251784 A1 | 9/2013 | Kim et al. | |
| 2013/0302396 A1 | 11/2013 | Mooney et al. | |
| 2013/0331343 A1 | 12/2013 | Cao et al. | |
| 2014/0072510 A1 | 3/2014 | Shea et al. | |
| 2014/0112990 A1* | 4/2014 | Bencherif | A61L 27/54 |
| | | | 424/277.1 |
| 2014/0178964 A1 | 6/2014 | Mooney et al. | |
| 2014/0227327 A1* | 8/2014 | Bencherif | A61L 27/50 |
| | | | 424/277.1 |
| 2014/0227723 A1 | 8/2014 | Ingber et al. | |
| 2014/0234423 A1 | 8/2014 | Sands et al. | |
| 2015/0024026 A1 | 1/2015 | Mooney et al. | |
| 2015/0030669 A1 | 1/2015 | Platscher et al. | |
| 2015/0072009 A1 | 3/2015 | Kim et al. | |
| 2015/0080321 A1 | 3/2015 | Li et al. | |
| 2015/0094518 A1 | 4/2015 | Wu et al. | |
| 2015/0202291 A1 | 7/2015 | Bosch et al. | |
| 2015/0352201 A1 | 12/2015 | Scheinberg et al. | |
| 2015/0359928 A1 | 12/2015 | Gu et al. | |
| 2015/0366956 A1 | 12/2015 | Mooney et al. | |
| 2016/0033511 A1 | 2/2016 | Pannell et al. | |
| 2016/0060360 A1 | 3/2016 | Moore et al. | |
| 2016/0120984 A1 | 5/2016 | Navale et al. | |
| 2016/0129053 A1 | 5/2016 | Brass et al. | |
| 2016/0220668 A1 | 8/2016 | Mooney et al. | |
| 2016/0228543 A1 | 8/2016 | Mooney et al. | |
| 2016/0271298 A1 | 9/2016 | Mooney et al. | |
| 2016/0279219 A1* | 9/2016 | Mooney | A61L 27/3826 |
| 2016/0279220 A1 | 9/2016 | Mooney et al. | |
| 2016/0296611 A1 | 10/2016 | Ali et al. | |
| 2017/0362307 A1 | 12/2017 | Ingber et al. | |
| 2017/0368169 A1 | 12/2017 | Loew et al. | |
| 2018/0117171 A1 | 5/2018 | Mooney et al. | |
| 2018/0243231 A1 | 8/2018 | Bencherif et al. | |
| 2018/0298047 A1 | 10/2018 | Cheng et al. | |
| 2018/0320157 A1 | 11/2018 | Super et al. | |
| 2018/0326073 A1 | 11/2018 | Mooney et al. | |
| 2018/0371058 A1 | 12/2018 | Watters et al. | |
| 2019/0076373 A1 | 3/2019 | Bencherif et al. | |
| 2019/0183992 A1 | 6/2019 | Sands et al. | |
| 2019/0216910 A1 | 7/2019 | Mooney et al. | |
| 2019/0290696 A1 | 9/2019 | De Miroschedji | |
| 2019/0367550 A1 | 12/2019 | Cheng et al. | |
| 2020/0024339 A1 | 1/2020 | Springer et al. | |
| 2020/0206333 A1 | 7/2020 | Shah et al. | |
| 2020/0276290 A1 | 9/2020 | Ali et al. | |
| 2020/0297854 A1 | 9/2020 | Ingber et al. | |
| 2021/0205233 A1 | 7/2021 | Bencherif et al. | |
| 2021/0284776 A1 | 9/2021 | Wang et al. | |
| 2022/0107308 A1 | 4/2022 | Ali et al. | |
| 2022/0192986 A1 | 6/2022 | Huebsch et al. | |
| 2022/0339274 A1 | 10/2022 | Najibi et al. | |
| 2023/0000961 A1 | 1/2023 | Kim et al. | |
| 2023/0085214 A1 | 3/2023 | Wang et al. | |
| 2023/0340404 A1 | 10/2023 | Cheung et al. | |
| 2023/0404936 A1 | 12/2023 | Bencherif et al. | |
| 2024/0108709 A1 | 4/2024 | Super et al. | |
| 2024/0165302 A1 | 5/2024 | Shah et al. | |
| 2024/0269252 A1 | 8/2024 | Shah et al. | |

FOREIGN PATENT DOCUMENTS

| | | | |
|---|---|---|---|
| CN | 1487839 A | 4/2004 | |
| CN | 1527697 A | 9/2004 | |
| CN | 1757662 A | 4/2006 | |
| CN | 101584612 A | 11/2009 | |
| CN | 101655611 A | 2/2010 | |
| CN | 101829361 A | 9/2010 | |
| CN | 101861165 A | 10/2010 | |
| CN | 102000689 A | 4/2011 | |
| CN | 102006891 A | 4/2011 | |
| CN | 102170903 A | 8/2011 | |
| CN | 102802686 A | 11/2012 | |
| CN | 102947341 A | 2/2013 | |
| CN | 103237885 A | 8/2013 | |
| CN | 104244929 A | 12/2014 | |
| CN | 104411331 A | 3/2015 | |
| EP | 0562862 A1 | 9/1993 | |
| EP | 1452191 A2 | 9/2004 | |
| EP | 1561481 A2 | 8/2005 | |
| EP | 1712238 A1 | 10/2006 | |
| EP | 1975230 A1 | 10/2008 | |
| EP | 2254602 A2 | 12/2010 | |
| JP | 2000-503884 A | 4/2000 | |
| JP | 2001-049018 A | 2/2001 | |
| JP | 2001-524136 A | 11/2001 | |
| JP | 2003-506401 A | 2/2003 | |
| JP | 2003-180815 A | 7/2003 | |
| JP | 2004-159849 A | 6/2004 | |
| JP | 2004-520043 A | 7/2004 | |
| JP | 2005-160669 A | 6/2005 | |
| JP | 2005-168760 A | 6/2005 | |
| JP | 2005-170816 A | 6/2005 | |
| JP | 2005-528401 A | 9/2005 | |
| JP | 2007-500673 A | 1/2007 | |
| JP | 2007-503881 A | 3/2007 | |
| JP | 2007-505827 A | 3/2007 | |
| JP | 2007-528848 A | 10/2007 | |
| JP | 2008-515503 A | 5/2008 | |
| JP | 2008-528114 A | 7/2008 | |
| JP | 2009-519042 A | 5/2009 | |
| JP | 2009-521406 A | 6/2009 | |
| JP | 2009-540921 A | 11/2009 | |
| JP | 2010-502824 A | 1/2010 | |
| JP | 2010-508976 A | 3/2010 | |
| JP | 2010-227012 A | 10/2010 | |
| JP | 2010-228961 A | 10/2010 | |
| JP | 2011-511684 A | 4/2011 | |
| JP | 2011-511834 A | 4/2011 | |
| JP | 2012-062236 A | 3/2012 | |
| JP | 2013-531043 A | 8/2013 | |
| JP | 2014-532071 A | 12/2014 | |
| JP | 2015-503626 A | 2/2015 | |
| JP | 2015-516398 A | 6/2015 | |
| JP | 2015-134766 A | 7/2015 | |
| JP | 2018-117680 A | 8/2018 | |
| JP | 2019-522486 A | 8/2019 | |
| WO | WO-1996/02555 A1 | 2/1996 | |
| WO | WO-1996/16086 A1 | 5/1996 | |
| WO | WO-1998/012228 A1 | 3/1998 | |
| WO | WO-1998/16266 A1 | 4/1998 | |
| WO | WO-1999/44583 A2 | 9/1999 | |
| WO | WO-1999/51259 A2 | 10/1999 | |
| WO | WO-1999/52356 A1 | 10/1999 | |
| WO | WO-2000/50006 A2 | 8/2000 | |
| WO | WO-2001/10421 A1 | 2/2001 | |
| WO | WO-2001/35932 A2 | 5/2001 | |
| WO | WO-2001/37810 A2 | 5/2001 | |
| WO | WO-2002/16557 A2 | 2/2002 | |
| WO | WO-2002/40071 A1 | 5/2002 | |
| WO | WO-2002/058723 A2 | 8/2002 | |
| WO | WO-2002/092054 A2 | 11/2002 | |
| WO | WO-2003/020161 A2 | 3/2003 | |
| WO | WO-2003/020884 A2 | 3/2003 | |
| WO | WO-2003/070291 A1 | 8/2003 | |
| WO | WO-2003/088905 A2 | 10/2003 | |
| WO | WO-2004/006990 A2 | 1/2004 | |
| WO | WO-2004/029230 A2 | 4/2004 | |
| WO | WO-2004/030706 A2 | 4/2004 | |
| WO | WO-2004/031371 A2 | 4/2004 | |
| WO | WO-2004/089413 A1 | 10/2004 | |
| WO | WO-2005/013896 A2 | 2/2005 | |
| WO | WO-2005/013933 A1 | 2/2005 | |
| WO | WO-2005/020849 A2 | 3/2005 | |
| WO | WO-2005/025614 A2 | 3/2005 | |
| WO | WO-2005/026318 A2 | 3/2005 | |
| WO | WO-2005/037190 A2 | 4/2005 | |

(56)                    References Cited

FOREIGN PATENT DOCUMENTS

| WO | WO-2005/037293 A1 | 4/2005 |
| WO | WO-2005/046748 A1 | 5/2005 |
| WO | WO-2005/072088 A2 | 8/2005 |
| WO | WO-2005/104755 A2 | 11/2005 |
| WO | WO-2006/039045 A2 | 4/2006 |
| WO | WO-2006/040128 A1 | 4/2006 |
| WO | WO-2006/078987 A2 | 7/2006 |
| WO | WO-2006/113407 A2 | 10/2006 |
| WO | WO-2006/119619 A1 | 11/2006 |
| WO | WO-2006/136905 A2 | 12/2006 |
| WO | WO-2007/001332 A2 | 1/2007 |
| WO | WO-2007/030901 A1 | 3/2007 |
| WO | WO-2007/039150 A2 | 4/2007 |
| WO | WO-2007/042554 A2 | 4/2007 |
| WO | WO-2007/051120 A2 | 5/2007 |
| WO | WO-2007/063075 A1 | 6/2007 |
| WO | WO-2007/064152 A1 | 6/2007 |
| WO | WO-2007/068489 A2 | 6/2007 |
| WO | WO-2007/070660 A2 | 6/2007 |
| WO | WO-2007/078196 A1 | 7/2007 |
| WO | WO-2007/087585 A1 | 8/2007 |
| WO | WO-2007/089870 A2 | 8/2007 |
| WO | WO-2007/107739 A1 | 9/2007 |
| WO | WO-2007/149161 A2 | 12/2007 |
| WO | WO-2007/150020 A1 | 12/2007 |
| WO | WO-2008/008266 A2 | 1/2008 |
| WO | WO-2008/018707 A1 | 2/2008 |
| WO | WO-2008/031525 A1 | 3/2008 |
| WO | WO-2008/043157 A1 | 4/2008 |
| WO | WO-2008/057600 A2 | 5/2008 |
| WO | WO-2008/109852 A2 | 9/2008 |
| WO | WO-2008/114149 A2 | 9/2008 |
| WO | WO-2008/148761 A1 | 12/2008 |
| WO | WO-2008/157394 A2 | 12/2008 |
| WO | WO-2009/002401 A2 | 12/2008 |
| WO | WO-2009/005769 A2 | 1/2009 |
| WO | WO-2009/018500 A1 | 2/2009 |
| WO | WO-2009/024775 A1 | 2/2009 |
| WO | WO-2009/072767 A2 | 6/2009 |
| WO | WO-2009/074341 A1 | 6/2009 |
| WO | WO-2009/100716 A2 | 8/2009 |
| WO | WO-2009/102465 A2 | 8/2009 |
| WO | WO-2009/146456 A1 | 12/2009 |
| WO | WO-2009/155583 A1 | 12/2009 |
| WO | WO-2010/078209 A2 | 7/2010 |
| WO | WO-2010/120749 A2 | 10/2010 |
| WO | WO-2011/014871 A1 | 2/2011 |
| WO | WO-2011/043834 A1 | 4/2011 |
| WO | WO-2011/043835 A1 | 4/2011 |
| WO | WO-2011/063336 A2 | 5/2011 |
| WO | WO-2011/109834 A2 | 9/2011 |
| WO | WO-2011/130753 A2 | 10/2011 |
| WO | WO-2011/150240 A1 | 12/2011 |
| WO | WO-2011/151431 A1 | 12/2011 |
| WO | WO-2011/163669 A2 | 12/2011 |
| WO | WO-2012/009611 A2 | 1/2012 |
| WO | WO-2012/019049 A1 | 2/2012 |
| WO | WO-2012/048165 A2 | 4/2012 |
| WO | WO-2012/064697 A2 | 5/2012 |
| WO | WO-2012/148684 A1 | 11/2012 |
| WO | WO-2012/149358 A1 | 11/2012 |
| WO | WO-2012/167230 A1 | 12/2012 |
| WO | WO-2013/012924 A2 | 1/2013 |
| WO | WO-2013/106852 A1 | 7/2013 |
| WO | WO-2013/158673 A1 | 10/2013 |
| WO | WO-2013/172967 A1 | 11/2013 |
| WO | WO-2013/190555 A1 | 12/2013 |
| WO | WO-2014/063128 A1 | 4/2014 |
| WO | WO-2014/189805 A1 | 11/2014 |
| WO | WO-2014/190229 A1 | 11/2014 |
| WO | WO-2015/066535 A1 | 5/2015 |
| WO | WO-2015/095811 A2 | 6/2015 |
| WO | 2015/164674 A1 | 10/2015 |
| WO | WO-2015/148775 A1 | 10/2015 |
| WO | WO-2015/154078 A1 | 10/2015 |
| WO | WO-2015/168379 A2 | 11/2015 |
| WO | WO-2016/004068 A1 | 1/2016 |
| WO | WO-2016/123573 A1 | 8/2016 |
| WO | WO-2016/161372 A1 | 10/2016 |
| WO | WO-2017075055 A1 * | 5/2017 | ............ A61K 47/36 |
| WO | WO-2017/136837 A1 | 8/2017 |
| WO | WO-2017/143024 A2 | 8/2017 |
| WO | WO-2018/013797 A1 | 1/2018 |
| WO | WO-2018/026884 A1 | 2/2018 |
| WO | WO-2018/144966 A1 | 8/2018 |
| WO | WO-2018/148650 A1 | 8/2018 |
| WO | WO-2018/170414 A1 | 9/2018 |
| WO | WO-2018/213631 A1 | 11/2018 |
| WO | WO-2018/227205 A1 | 12/2018 |
| WO | WO-2020/061129 A1 | 3/2020 |
| WO | WO-2021/155297 A1 | 8/2021 |

OTHER PUBLICATIONS

Agrawal et al., Cutting edge: different Toll-like receptor agonists instruct dendritic cells to induce distinct Th responses via differential modulation of extracellular signal-regulated kinase-mitogen-activated protein kinase and c-Fos. J Immunol. Nov. 15, 2003;171(10):4984-9.

Aguado et al., Improving viability of stem cells during syringe needle flow through the design of hydrogel cell carriers. Tissue Eng Part A. Apr. 2012;18(7-8):806-15.

Akira et al., Pathogen recognition and innate immunity. Cell. Feb. 24, 2006;124(4):783-801.

Akira et al., Toll-like receptors: critical proteins linking innate and acquired immunity. Nat Immunol. Aug. 2001;2(8):675-80.

Akpalo et al., Fibrin-polyethylene oxide interpenetrating polymer networks: new self-supported biomaterials combining the properties of both protein gel and synthetic polymer. Acta Biomater. Jun. 2011;7(6):2418-27.

Aldhous, Print Me a Heart and a Set of Arteries. New Scientist. 2006;2547:19.

Ali et al., Biomaterial-based vaccine induces regression of established intracranial glioma in rats. Pharm Res. May 2011;28(5):1074-80.

Ali et al., Controlled Local Delivery of GM-CSF From Polymer-Based Vaccines Enhances Anti-Tumor Immune Responses by Priming Host Dendritic Cells. 2007 AACR Annual Meeting. 2007;48:652, Abstract #2736.

Ali et al., Converging Cell Therapy with Biomaterials. Cell Transplantation from Laboratory to Clinic. 2006:591-609.

Ali et al., Identification of immune factors regulating antitumor immunity using polymeric vaccines with multiple adjuvants. Cancer Res. Mar. 15, 2014;74(6):1670-81.

Ali et al., In situ regulation of DC subsets and T cells mediates tumor regression in mice. Sci Transl Med. Nov. 25, 2009;1(8):8ra19, 1-10.

Ali et al., Infection-mimicking materials to program dendritic cells in situ. Nat Mater. Feb. 2009;8(2):151-8.

Ali et al., Inflammatory cytokines presented from polymer matrices differentially generate and activate DCs in situ . . . Adv Funct Mater. Aug. 1, 2013;23(36):4621-4628.

Ali et al., Relationship of vaccine efficacy to the kinetics of DC and T-cell responses induced by PLG-based cancer vaccines. Biomater. 2011;1(1):66-75.

Ali et al., Sustained GM-CSF and PEI condensed pDNA presentation increases the level and duration of gene expression in dendritic cells. J Control Release. Dec. 18, 2008;132(3):273-8.

Ali et al., The efficacy of intracranial PLG-based vaccines is dependent on direct implantation into brain tissue. J Control Release. Sep. 25, 2011;154(3):249-57.

Allen et al., Regulation of satellite cells during skeletal muscle growth and development. Proc Soc Exp Biol Med. Jun. 1990; 194(2):81-6.

Allen et al., Regulation of skeletal muscle satellite cell proliferation by bovine pituitary fibroblast growth factor. Exp Cell Res. May 1984; 152(1):154-60.

(56)                    References Cited

OTHER PUBLICATIONS

Almarza et al., Evaluation of three growth factors in combinations of two for temporomandibular joint disc tissue engineering. Arch Oral Biol. Mar. 2006;51(3):215-21.

Alsberg et al., Cell-interactive alginate hydrogels for bone tissue engineering. J Dent Res. Nov. 2001;80(11):2025-9.

Alsberg et al., Engineering growing tissues. Proc Natl Acad Sci U S A. Sep. 17, 2002;99(19):12025-30.

Alsberg et al., Regulating bone formation via controlled scaffold degradation. J Dent Res. Nov. 2003;82(11):903-8.

Ambrosini et al., Astrocytes produce dendritic cell-attracting chemokines in vitro and in multiple sclerosis lesions. J Neuropathol Exp Neurol. Aug. 2005;64(8):706-15.

Anderson et al., Biomaterial microarrays: rapid, microscale screening of polymer-cell interaction. Biomaterials. Aug. 2005;26(23):4892-7.

Anderson et al., Crosslinking CD3 with CD2 using sepharose-immobilized antibodies enhances T lymphocyte proliferation. Cell Immunol. Sep. 1988;115(2):246-56.

Anderson et al., Nanoliter-scale synthesis of arrayed biomaterials and application to human embryonic stem cells. Nat Biotechnol. Jul. 2004;22(7):863-6.

Anderson, A role for nitric oxide in muscle repair: nitric oxide-mediated activation of muscle satellite cells. Mol Biol Cell. May 2000;11(5):1859-74.

Andersson et al., HSP70 promoter-driven activation of gene expression for immunotherapy using gold nanorods and near infrared light. Vaccines (Basel). Mar. 25, 2014;2(2):216-27.

Annabi et al., Controlling the porosity and microarchitecture of hydrogels for tissue engineering. Tissue Eng Part B Rev. Aug. 2010;16(4):371-83.

Annual Review. pp. 122-131, (2008).

Arany et al., At the edge of translation—materials to program cells for directed differentiation. Oral Dis. Apr. 2011;17(3):241-51.

Aschner et al., Metabolic memory for vascular disease in diabetes. Diabetes Technol Ther. Jun. 2012;14 Suppl 1:S68-74.

Atala et al., Endoscopic treatment of vesicoureteral reflux with a chondrocyte-alginate suspension. J Urol. Aug. 1994;152(2 Pt 2):641-3.

Aubin et al., Directed 3D cell alignment and elongation in microengineeredBiomaterials. Sep. 2010;31(27):6941-6951.

Augst et al., Alginate hydrogels as biomaterials. Macromol Biosci. 2006.

Babensee et al., Host response to tissue engineered devices. Advanced Drug Delivery Reviews. Aug. 3, 1998;33(1-2):111-139.

Bachelder et al., Acid-degradable polyurethane particles for protein-based vaccines: biological evaluation and in vitro analysis of particle degradation products. Mol Pharm. Sep.-Oct. 2008;5(5):876-84.

Bachem et al., Superior antigen cross-presentation and XCR1 expression define human CD11c+CD141+ cells as homologues of mouse CD8+ dendritic cells. J Exp Med. Jun. 7, 2010;207(6):1273-81.

Badovinac et al., Regulation of CD8+ T cells undergoing primary and secondary responses to infection in the same host. J Immunol. May 15, 2003;170(10):4933-42.

Bakri et al., Pharmacokinetics of intravitreal bevacizumab (Avastin). Ophthalmology. May 2007;114(5):855-9.

Balakrishna et al., Structural correlates of antibacterial and membrane-permeabilizing activities in acylpolyamines. Antimicrob Agents Chemother. Mar. 2006;50(3):852-61.

Banchereau et al., Dendritic cells and the control of immunity. Nature. Mar. 19, 1998;392(6673):245-52.

Bar-Cohen et al., Electroactive Polymer Actuators and Sensors. MRS Bullet. 2008;33(3):173-181.

Bar-Or et al., Induction of antigen-specific tolerance in multiple sclerosis after immunization with DNA encoding myelin basic protein in a randomized, placebo-controlled phase 1/2 trial. Arch Neurol. Oct. 2007;64(10):1407-15.

Barbero et al., Growth factor supplemented matrigel improves ectopic skeletal muscle formation—a cell therapy approach. J Cell Physiol. Feb. 2001;186(2):183-92.

Barbucci et al., Hyaluronic acid hydrogel in the treatment of osteoarthritis. Biomaterials. Dec. 2002;23(23):4503-13.

Baroja et al., The anti-T cell monoclonal antibody 9.3 (anti-CD28) provides a helper signal and bypasses the need for accessory cells in T cell activation with immobilized anti-CD3 and mitogens. Cell Immunol. Apr. 15, 1989;120(1):205-17.

Barrio et al., A two-dimensional numerical study of spatial pattern formation in interacting Turing systems. Bull Math Biol. May 1999;61(3):483-505.

Baskin et al., Copper-free click chemistry for dynamic in vivo imaging. Proc Natl Acad Sci U S A. Oct. 23, 2007;104(43):16793-7.

Bates, Improved muscle regeneration by combining VEGF with IGF1. Regen Med. Nov. 2010;5(6):853-4.

Beaucage et al., The Functionalization of Oligonucleotides via Phosphoramidite Derivatives. Tetrahedron. Mar. 5, 1993;49(10)1925-1963.

Beauchamp et al., Dynamics of myoblast transplantation reveal a discrete minority of precursors with stem cell-like properties as the myogenic source. J Cell Biol. Mar. 22, 1999;144(6):1113-22.

Becker et al., Cytological demonstration of the clonal nature of spleen colonies derived from transplanted mouse marrow cells. Nature. Feb. 2, 1963;197:452-4.

Beduer et al., A compressible scaffold for minimally invasive delivery of large intact neuronal networks. Adv Healthc Mater. Jan. 28, 2015;4(2):301-12.

Beebe et al., Functional hydrogel structures for autonomous flow control inside microfluidic channels. Nature. Apr. 6, 2000;404(6778):588-90.

Bekiari et al., Study of poly(N,N-dimethylacrylamide)/CdS nanocomposite organic/inorganic gels. Langmuir. Sep. 14, 2004;20(19):7972-5.

Bell, Models for the specific adhesion of cells to cells. Science. May 12, 1978;200(4342):618-27.

Bencherif et al., End-group effects on the properties of PEG-co-PGA hydrogels. Acta Biomater. Jul. 2009;5(6):1872-83.

Bencherif et al., Influence of cross-linker chemistry on release kinetics of PEG-co-PGA hydrogels. J Biomed Mater Res A. Jul. 2009;90(1):142-53.

Bencherif et al., Influence of the degree of methacrylation on hyaluronic acid hydrogels properties. Biomaterials. Apr. 2008;29(12):1739-49.

Bencherif et al., Injectable preformed scaffolds with shape-memory properties. Proc Natl Acad Sci U S A. Nov. 27, 2012;109(48):19590-5.

Bencherif et al., Nanostructured hybrid hydrogels prepared by a combination of atom transfer radical polymerization and free radical polymerization. Biomaterials. Oct. 2009;30(29):5270-8.

Bencherif et al., Synthesis by AGET ATRP of degradable nanogel precursors for in situ formation of nanostructured hyaluronic acid hydrogel. Biomacromolecules. Sep. 14, 2009;10(9):2499-507.

Benton et al., Photocrosslinking of gelatin macromers to synthesize porous hydrogels that promote valvular interstitial cell function. Tissue Eng Part A. Nov. 2009;15(11):3221-30.

Berg et al., Il-10 is a central regulator of cyclooxygenase-2 expression and prostaglandin production. J Immunol. Feb. 15, 2001;166(4):2674-80.

Bergstraesser et al., Stimulation and inhibition of human mammary epithelial cell duct morphogenesis in vitro. Proc Assoc Am Physicians. Mar. 1996;108(2):140-54.

Bhardwaj et al., TLR Agonists: Are They Good Adjuvants? Cancer J. 2010;16(4):382-391.

Bianco et al., The meaning, the sense and the significance: translating the science of mesenchymal stem cells into medicine. Nat Med. Jan. 2013;19(1):35-42.

Bierer et al., T cell receptors: adhesion and signaling. Adv Cancer Res. 1991;56:49-76.

Bilodeau et al., Regular Pyramid Punch Problem. J Appl Mech. 1992;59(3):519-523.

Bischoff, Proliferation of muscle satellite cells on intact myofibers in culture. Dev Biol. May 1986; 115(1):129-39.

(56)     References Cited

OTHER PUBLICATIONS

Bjork et al., Tuning the shape of mesoporous silica particles by alterations in parameter space: from rods to platelets. Langmuir. Nov. 5, 2013;29(44):13551-61.

Blumenthal et al., Polyurethane scaffolds seeded with genetically engineered skeletal myoblasts: a promising tool to regenerate myocardial function. Artif Organs. Feb. 2010;34(2):E46-54.

Boateng et al., Wound healing dressings and drug delivery systems: a review. J Pharm Sci. Aug. 2008;97(8):2892-923.

Boerckel et al., Mechanical regulation of vascular growth and tissue regeneration in vivo. Proc Natl Acad Sci U S A. Sep. 13, 2011;108(37):E674-80.

Bohl et al., Role of synthetic extracellular matrix in development of engineered dental pulp. J Biomater Sci Polym Ed. 1998;9(7):749-64.

Bojarova et al., Sugared biomaterial binding lectins: achievements and perspectives. Biomater Sci. Jul. 19, 2016;4(8):1142-60.

Bonauer et al., MicroRNA-92a controls angiogenesis and functional recovery of ischemic tissues in mice. Science. Jun. 26, 2009;324(5935):1710-3.

Boontheekul et al., Controlling alginate gel degradation utilizing partial oxidation and bimodal molecular weight distribution. Biomaterials. May 2005;26(15):2455-65.

Boontheekul et al., Regulating myoblast phenotype through controlled gel stiffness and degradation. Tissue Eng. Jul. 2007;13(7):1431-42.

Borselli et al., Functional muscle regeneration with combined delivery of angiogenesis and myogenesis factors. Proc Natl Acad Sci U S A. Feb. 23, 2010;107(8):3287-92.

Bouhadir et al., Degradation of partially oxidized alginate and its potential application for tissue engineering. Biotechnol Prog. Sep.-Oct. 2001;17(5):945-50.

Bouhadir et al., Synthesis of Cross-Linked Poly(aldehyde guluronate) Hydrogels. Polymer. Jun. 1999;40(12):3575-3584.

Bowne et al., Injection of DNA encoding granulocyte-macrophage colony-stimulating factor recruits dendritic cells for immune adjuvant effects. Cytokines Cell Mol Ther. Dec. 1999;5(4):217-25.

Brignone et al., A phase I pharmacokinetic and biological correlative study of IMP321, a novel MHC class II agonist, in patients with advanced renal cell carcinoma. Clin Cancer Res. Oct. 1, 2009;15(19):6225-31.

Brinkman et al., Photo-cross-linking of type I collagen gels in the presence of smooth muscle cells: mechanical properties, cell viability, and function. Biomacromolecules. Jul.-Aug. 2003;4(4):890-5.

Brinkmann et al., Neutrophil extracellular traps kill bacteria. Science. Mar. 5, 2004;303(5663):1532-5.

Bristol-Myers Squibb, Investigational Anti-PD-1 Immunotherapy BMS-936558 Showed Clinical Activity in Phase 1 Trial of Patients with Previously-Treated non-Small-Cell Lung Cancer, Metastatic Melanoma adn Renal Cell Cancer. Financial Times. 3 pages, Jun. 2, 2012.

Brodie et al., In vivo migration and function of transferred HIV-1-specific cytotoxic T cells. Nat Med. Jan. 1999;5(1):34-41.

Brouwers et al., Can the growth factors PTHrP, Ihh and VEGF, together regulate the development of a long bone? J Biomech. 2006;39(15):2774-82.

Broxmeyer, Insights into the biology of cord blood stem/progenitor cells. Cell Prolif. Apr. 2011;44 Suppl 1:55-9.

Brunner et al., Enhanced dendritic cell maturation by TNF-alpha or cytidine-phosphate-guanosine DNA drives T cell activation in vitro and therapeutic anti-tumor immune responses in vivo. J Immunol. Dec. 1, 2000;5(11):6278-86.

Bryant et al., Photo-patterning of porous hydrogels for tissue engineering. Biomaterials. Jul. 2007;28(19):2978-86.

Buckwalter et al., Form of Antigen Dictates Immunity: Irradiated Cell vs. Whole Cell Lysate Vaccination. J Immunol. Apr. 1, 2007;178(1 Suppl):S77.

Bullard et al., Fetal wound healing: current biology. World J Surg. Jan. 2003;27(1):54-61.

Buonaguro et al., Translating tumor antigens into cancer vaccines. Clin Vaccine Immunol. Jan. 2011;18(1):23-34.

Burdick et al., Controlled degradation and mechanical behavior of photopolymerized hyaluronic acid networks. Biomacromolecules. Jan.-Feb. 2005;6(1):386-91.

Burdick et al., Photoencapsulation of osteoblasts in injectable RGD-modified PEG hydrogels for bone tissue engineering. Biomaterials. Nov. 2002;23(22):4315-23.

Burdick et al., Stimulation of neurite outgrowth by neurotrophins delivered from degradable hydrogels. Biomaterials. Jan. 2006;27(3):452-9.

Burger et al., Effect of VEGF and its receptor antagonist SU-5416, an inhibitor of angiogenesis, on processing of the beta-amyloid precursor protein in primary neuronal cells derived from brain tissue of Tg2576 mice. Int J Dev Neurosci. Nov. 2010;28(7):597-604.

Butler et al., Long-lived antitumor CD8+ lymphocytes for adoptive therapy generated using an artificial antigen-presenting cell. Clin Cancer Res. Mar. 15, 2007;13(6):1857-67.

Bégué et al., Vaccination against human papillomavirus. Implementation and efficacy against cervical cancer control. Bull Acad Natl Med. Dec. 2007;191(9):1805-16.

Callahan et al., At the bedside: CTLA-4- and PD-1-blocking antibodies in cancer immunotherapy. J Leukoc Biol. Jul. 2013;94(1):41-53.

Calvert, Electroactive Polymer Gels. Electroactive Polymer (EAP) Acutators as Artificial Muscle: Reality, Potential, and Challenges. Bar-Cohen, (Ed.), Spie Press, Bellingham, WA. 151-170. (2004).

Calvert, Gel Sensors and Actuators. MRS Bullet. 2008;33(3):207-212.

Cameron et al., The influence of substrate creep on mesenchymal stem cell behaviour and phenotype. Biomaterials. Sep. 2011;32(26):5979-93.

Cao et al., Promoting angiogenesis via manipulation of VEGF responsiveness with notch signaling. Biomaterials. Sep. 2009;30(25):4085-93.

Care.diabetesjournals.org, Standards of Medical Care in Diabetes. Diabetes Care. Jan. 2013;36(Suppl 1):S1-S2.

Carlson et al., Notch signaling pathway and tissue engineering. Front Biosci. Sep. 1, 2007;12:5143-56.

Carmeliet et al., Angiogenesis in cancer and other diseases. Nature. Sep. 14, 2000;407(6801):249-57.

Carmeliet, Mechanisms of angiogenesis and arteriogenesis. Nat Med. Apr. 2000;6(4):389-95.

Casanova et al., Human Mannose-binding Lectin in Immunity: Friend, Foe, or Both ?. J Exp Med. 2004;199(10):1295-1299.

Caulfield et al., Regulation of major histocompatibility complex class II antigens on human alveolar macrophages by granulocyte-macrophage colony-stimulating factor in the presence of glucocorticoids. Immunology. Sep. 1999;98(1):104-10.

Ceriello et al., Clinical review 2: The "metabolic memory": is more than just tight glucose control necessary to prevent diabetic complications? J Clin Endocrinol Metab. Feb. 2009;94(2):410-5.

Ceriello et al., The emerging challenge in diabetes: the "metabolic memory". Vascul Pharmacol. Nov.-Dec. 2012;57(5-6):133-8.

Champion et al., Shape induced inhibition of phagocytosis of polymer particles. Pharm Res. Jan. 2009;26(1):244-9.

Chan et al., Antifibrotic effects of suramin in injured skeletal muscle after laceration. J Appl Physiol. Sep. 2003;95(2):771-80.

Chan et al., Helix induction in antimicrobial peptides by alginate in biofilms. J Biol Chem. Sep. 10, 2004;279(37):38749-54.

Chan et al., Traction dynamics of filopodia on compliant substrates. Science. Dec. 12, 2008;322(5908):1687-91.

Chang, Mouse models for studies of retinal degeneration and diseases. Methods Mol Biol. 2013;935:27-39.

Chao et al., Morphological control on SBA-15 mesoporous silicas via a slow self-assembling rate. J Mater Sci. 2009;44:6453-62.

Chapman, Endosomal proteases in antigen presentation. Curr Opin Immunol. Feb. 2006;18(1):78-84.

Che et al., Synthesis and characterization of chiral mesoporous silica. Nature. May 20, 2004;429(6989):281-4.

Chen et al., Adipogenic differentiation of adipose tissue-derived human mesenchymal stem cells: effect of gastric bypass surgery. Surg Endosc. Dec. 2012;26(12):3449-56.

(56)        References Cited

OTHER PUBLICATIONS

Chen et al., Enhanced humoral and cell-mediated immune responses generated by cationic polymer-coated PLA microspheres with adsorbed HBsAg. Mol Pharm. Jun. 2, 2014;11(6):1772-84.

Chen et al., Functional Human Vascular Network Generated in Photocrosslinkable Gelatin Methacrylate Hydrogels. Adv Funct Mater. May 23, 2012;22(10):2027-2039.

Chen et al., Improved antigen cross-presentation by polyethyleneimine-based nanoparticles. Int J Nanomedicine. Jan. 6, 2011;6:77-84.

Chen et al., Integrated approach to designing growth factor delivery systems. FASEBJ. Dec. 2007;21(14):3896-903.

Chen et al., Morphological control of mesoporous silica SBA-15 synthesized at low temperature without additives. J Porous Mater. 2011;18:211-6.

Chen et al., Polymeric growth factor delivery strategies for tissue engineering. Pharm Res. Aug. 2003;20(8):1103-12.

Chen et al., Quantitative proteomic profiling of pancreatic cancer juice. Proteomics. Jul. 2006;6(13):3871-9.

Chen et al., Skeletal muscle stem cells. Reprod Biol Endocrinol. Nov. 13, 2003;1:101. 7 pages.

Chen et al., Spatio-temporal VEGF and PDGF delivery patterns blood vessel formation and maturation. Pharm Res. Feb. 2007;24(2):258-64.

Cheung et al., Engineered Materials for Cancer Immunotherapy. Nano Today. Aug. 1, 2015;10(4):511-531.

Cheung et al., Scaffolds that mimic antigen-presenting cells enable ex vivo expansion of primary T cells. Nat Biotechnol. Feb. 2018;36(2):160-169.

Chiang et al., Whole tumor antigen vaccines. Semin Immunol. Jun. 2010;22(3):132-43.

Choi et al., Facile synthesis of high quality mesoporous SBA-15 with enhanced control of the porous network connectivity and wall thickness. Chem Commun (Camb). Jun. 21, 2003;(12):1340-1.

Choi et al., In vitro mineralization by preosteoblasts in poly(DL-lactide-co-glycolide) inverse opal scaffolds reinforced with hydroxyapatite nanoparticles. Langmuir. Jul. 20, 2010;26(14):12126-31.

Choi et al., Three-dimensional scaffolds for tissue engineering: the importance of uniformity in pore size and structure. Langmuir. Dec. 21, 2010;26(24):19001-6.

Choi, Replacement Organs, Hot Off the Press. New Scientist. 2003;177(2379):16.

Chou et al., Characterization of Photocross Linked Alginate Hydrogels for Nucleus Pulposus Cell Encapsulation. J Biomed Mater Res A. 2009;91A(1):187-194.

Chromiak et al., Bioreactor perfusion system for the long-term maintenance of tissue-engineered skeletal muscle organoids. In Vitro Cell Dev Biol Anim. Oct. 1998;34(9):694-703.

Clark et al., Myosin II and mechanotransduction: a balancing act. Trends Cell Biol. Apr. 2007;17(4):178-86.

Clauss et al., Interstitial transport of rabbit and sheep antibodies in normal and neoplastic tissues. Cancer Res. Jun. 15, 1990;50(12):3487-92.

ClinicalTrials.gov, NCT00729664, Multiple Ascending Dose (MDX1105-01) (Anti-PDL1). 4 pages, Sep. 3, 2015.

ClinicalTrials.gov, NCT00730639, A Phase 1 Study of Nivolumab (BMS-936558) in Subjects with Advanced or Recurrent Malignancies (MDX1106-03). 5 pages, Mar. 24, 2016.

ClinicalTrials.gov, NCT01352884, Study to Assess the Safety, and Pharmacokinetics of AMP-224 in Patients with Advanced Cancer. 3 pages, Sep. 2, 2016.

ClinicalTrials.gov, NCT01391143, Safety Study of MGA271 in Refractory Cancer. 4 pages, Sep. 28, 2016.

Cohen et al., Controlled delivery systems for proteins based on poly(lactic/glycolic acid) microspheres. Pharm Res. Jun. 1991;8(6):713-20.

Comisar et al., Engineering RGD nanopatterned hydrogels to control preosteoblast behavior: a combined computational and experimental approach. Biomaterials. Oct. 2007;28(30):4409-17.

Conboy et al., The regulation of Notch signaling controls satellite cell activation and cell fate determination in postnatal myogenesis. Dev Cell. Sep. 2002;3(3):397-409.

Conconi et al., In vitro and in vivo evaluation of acellular diaphragmatic matrices seeded with muscle precursors cells and coated with VEGF silica gels to repair muscle defect of the diaphragm. J Biomed Mater Res A. May 2009;89(2):304-16.

Conn et al., Purification of a glycoprotein vascular endothelial cell mitogen from a rat glioma-derived cell line. Proc Natl Acad Sci U S A. Feb. 1990;87(4):1323-7.

Cook et al., A sialomucopeptide liberated by trypsin from the human erythrocyte. Nature. Dec. 17, 1960;188:1011-2.

Cooper et al., Extended amplification in vitro and replicative senescence: key factors implicated in the success of human myoblast transplantation. Hum Gene Ther. Aug. 10, 2003;14(12):1169-79.

Cooper, A Genetic Pathogen Capture Technology for Sepsis Diagnosis. Submitted to the Department of Chemical Engineering in Partial Fulfillment of the Requirements for the Degree of Doctor of Philosophy in Medical and Engineering Physics at the Massachusetts Institute of Technology. 130 pages, May 1, 2013.

Cooper, Metabolic memory: implications for diabetic vascular complications. Pediatr Diabetes. Aug. 2009;10(5):343-6.

Corcione et al., CCL19 and CXCL12 trigger in vitro chemotaxis of human mantle cell lymphoma B cells. Clin Cancer Res. Feb. 1, 2004;10(3):964-71.

Cornelison et al., Single-cell analysis of regulatory gene expression in quiescent and activated mouse skeletal muscle satellite cells. Dev Biol. Nov. 15, 1997;191(2):270-83.

Cornelison et al., Syndecan-3 and syndecan-4 specifically mark skeletal muscle satellite cells and are implicated in satellite cell maintenance and muscle regeneration. Dev Biol. Nov. 1, 2001;239(1):79-94.

Coulson et al., Flow of Fluids through Granular Beds and Packed Columns. Chemical Engineering, vol. 2. Third Edition. Pergamon Press. Chapter 4, pp. 125-171, (1978).

Crameri et al., Improved green fluorescent protein by molecular evolution using DNA shuffling. Nat Biotechnol. Mar. 1996;14(3):315-9.

Cuda et al., In vitro actin filament sliding velocities produced by mixtures of different types of myosin. Biophys J. Apr. 1997;72(4):1767-79.

Cukierman et al., Taking cell-matrix adhesions to the third dimension. Science. Nov. 23, 2001;294(5547):1708-12.

Cullen et al., Investigation of vascular endothelial growth factor effects on pulmonary endothelial monolayer permeability and neutrophil transmigration. Gen Pharmacol. Sep. 2000;35(3):149-57.

Curiel et al., Tumor immunotherapy: inching toward the finish line. J Clin Invest. Feb. 2002;109(3):311-2.

Curran et al., PD-1 and CTLA-4 combination blockade expands infiltrating T cells and reduces regulatory T and myeloid cells within B16 melanoma tumors. Proc Natl Acad Sci U S A. Mar. 2, 2010;107(9):4275-80.

D'Amico et al., The early progenitors of mouse dendritic cells and plasmacytoid predendritic cells are within the bone marrow hemopoietic precursors expressing Flt3. J Exp Med. Jul. 21, 2003;198(2):293-303.

Dainiak et al., Gelatin-fibrinogen cryogel dermal matrices for wound repair: preparation, optimisation and in vitro study. Biomaterials. Jan. 2010;31(1):67-76.

Damle et al., Stimulation via the CD3 and CD28 molecules induces responsiveness to IL-4 in CD4+CD29+CD45R-memory T lymphocytes. J Immunol. Sep. 15, 1989;143(6):1761-7.

Dar et al., Optimization of cardiac cell seeding and distribution in 3D porous alginate scaffolds. Biotechnol Bioeng. Nov. 5, 2002;80(3):305-12.

Daro et al., Polyethylene glycol-modified GM-CSF expands CD11b(high)CD11c(high) but not CD11b(low)CD11c(high) murine dendritic cells in vivo: a comparative analysis with Flt3 ligand. J Immunol. Jul. 1, 2000;165(1):49-58.

David et al., The in vitro Desensitization of Sensitive Cells by Trypsin. J Exp Med. Dec. 1, 1964;120:1189-200.

Davies et al., Antibody-antigen complexes. Annu Rev Biochem. 1990;59:439-73.

(56)          References Cited

OTHER PUBLICATIONS

De Jong et al., Regulation of Notch signaling genes during BMP2-induced differentiation of osteoblast precursor cells. Biochem Biophys Res Commun. Jul. 16, 2004;320(1):100-7.

De Temmerman et al., Particulate vaccines: on the quest for optimal delivery and immune response. Drug Discov Today. Jul. 2011;16(13-14):569-82.

Del Chiaro et al., Early detection and prevention of pancreatic cancer: is it really possible today? World J Gastroenterol. Sep. 14, 2014;20(34):12118-31.

Dembo et al., Stresses at the cell-to-substrate interface during locomotion of fibroblasts. Biophys J. Apr. 1999;76(4):2307-16.

Den Haan et al., CD8(+) but not CD8(-) dendritic cells cross-prime cytotoxic T cells in vivo. J Exp Med. Dec. 18, 2000; 192(12):1685-96.

Dengler et al., Mesoporous silica-supported lipid bilayers (protocells) for DNA cargo delivery to the spinal cord. J Control Release. Jun. 10, 2013;168(2):209-24.

Dennis et al., Excitability and contractility of skeletal muscle engineered from primary cultures and cell lines. Am J Physiol Cell Physiol. Feb. 2001;280(2):C288-95.

Dennis et al., Excitability and isometric contractile properties of mammalian skeletal muscle constructs engineered in vitro. In Vitro Cell Dev Biol Anim. May 2000;36(5):327-35.

Deshmane et al., Monocyte chemoattractant protein-1 (MCP-1): an overview. J Interferon Cytokine Res. Jun. 2009;29(6):313-26.

Dexter et al., Conditions controlling the proliferation of haemopoietic-Cell Physiol. Jun. 1977;91(3):335-44.

Diduch et al., Two cell lines from bone marrow that differ in terms of collagen synthesis, osteogenic characteristics, and matrix mineralization. J Bone Joint Surg Am. Jan. 1993;75(1):92-105.

Dieu et al., Selective recruitment of immature and mature dendritic cells by distinct chemokines expressed in different anatomic sites. J Exp Med. Jul. 20, 1998;188(2):373-86.

Diridollou et al., Skin ageing: changes of physical properties of humanCosmet Sci. Dec. 2001;23(6):353-62.

Discher et al., Tissue cells feel and respond to the stiffness of their substrate. Science. Nov. 18, 2005;310(5751):1139-43.

Disis et al., Granulocyte-macrophage colony-stimulating factor: an effective adjuvant for protein and peptide-based vaccines. Blood. Jul. 1, 1996;88(1):202-10.

Doan et al., Antigens and Receptors. Lippincott's Illustrated Reviews: Immunology. Wolters Kluwer/Lippincott Williams & Wilsons, Philadelphia. Chapter 12, pp. 11-23, (2008).

Doan et al., Subcellular localization of a sporulation membrane protein is achieved through a network of interactions along and across the septum. Mol Microbiol. Mar. 2005;55(6):1767-81.

Dolgin, Cancer vaccines: Material breach. Nature. Dec. 19, 2013;504(7480):S16-7.

Donati et al., New hypothesis on the role of alternating sequences inBiomacromolecules. Mar.-Apr. 2005;6(2):1031-40.

Dong et al., Antitumor effect of secreted Flt3-ligand can act at distant tumor sites in a murine model of head and neck cancer. Cancer Gene Ther. Feb. 2003;10(2):96-104.

Dor et al., Making vascular networks in the adult: branching morphogenesis without a roadmap. Trends Cell Biol. Mar. 2003;13(3):131-6.

Douay et al., Ex vivo production of human red blood cells from hematopoietic stem cells: what is the future in transfusion? Transfus Med Rev. Apr. 2007;21(2):91-100.

Drake et al., Koch Institute Symposium on Cancer Immunology and Immunotherapy. Cancer Immunology Researcy. 2013;1(4):217-22.

Dranoff et al., Vaccination with irradiated tumor cells engineered to secrete murine granulocyte-macrophage colony-stimulating factor stimulates potent, specific, and long-lasting anti-tumor immunity. Proc Natl Acad Sci U S A. Apr. 15, 1993;90(8):3539-43.

Dranoff, Cytokines in cancer pathogenesis and cancer therapy. Nat Rev Cancer. Jan. 2004;4(1):11-22.

Dranoff, GM-CSF-based cancer vaccines. Immunol Rev. Oct. 2002;188:147-54.

Drury et al., Hydrogels for tissue engineering: scaffold design variables and applications. Biomaterials. Nov. 2003;24(24):4337-51.

Dudley et al. Adoptive cell transfer therapy following non-myeloablative but lymphodepleting chemotherapy for the treatment of patients with refractory metastatic melanoma. J Clin Oncol. Apr. 1, 2005;23(10):2346-57.

Dudley et al., CD8+ enriched "young" tumor infiltrating lymphocytes can mediate regression of metastatic melanoma. Clin Cancer Res. Dec. 15, 2010;16(24):6122-31.

Dufort et al., Balancing forces: architectural control of mechanotransduction. Nat Rev Mol Cell Biol. May 2011;12(5):308-19.

Dupont et al., Role of YAP/TAZ in mechanotransduction. Nature. 20118;474(7350):179-83.

Duraiswamy et al., Dual blockade of PD-1 and CTLA-4 combined with tumor vaccine effectively restores T-cell rejection function in tumors—response. Cancer Res. Jan. 15, 2014;74(2):633-4.

Duraiswamy et al., Dual blockade of PD-1 and CTLA-4 combined with tumor vaccine effectively restores T-cell rejection function in tumors. Cancer Res. Jun. 15, 2013;73(12):3591-603.

Edwards et al., Evaluation of biomechanical properties of human skin. Clin Dermatol. Jul.-Aug. 1995;13(4):375-80.

Egea et al., Role of secreted glyceraldehyde-3-phosphate dehydrogenase in the infection mechanism of enterohemorrhagic and enteropathogenic *Escherichia coli*: interaction of the extracellular enzyme with human plasminogen and fibrinogen. Int J Biochem Cell Biol. 2007;39(6):1190-203.

Eggermont et al., Towards efficient cancer immunotherapy: advances in developing artificial antigen-presenting cells. Trends Biotechnol. Sep. 2014;32(9):456-65.

Egholm et al., Peptide Nucleic Acids (PNA). Oligonucleotide Analogues with an Achiral Peptide Backbone. J Am Chem Soc. 1992;114(5):1895-1897.

Egholm et al., PNA hybridizes to complementary oligonucleotides obeying the Watson-Crick hydrogen-bonding rules. Nature. Oct. 7, 1993;365(6446):566-8.

Ehrbar et al., Endothelial cell proliferation and progenitor maturation by fibrin-bound VEGF variants with differential susceptibilities to local cellular activity. J Control Release. Jan. 3, 2005;101(1-3):93-109.

Eiselt et al., Porous carriers for biomedical applications based on alginate hydrogels. Biomaterials. Oct. 2000;21(19):1921-7.

El-Backly et al., Regeneration of dentine/pulp-like tissue using a dental pulp stem cell/poly(lactic-co-glycolic) acid scaffold construct in New Zealand white rabbits. Aust Endod J. Aug. 2008;34(2):52-67.

El-Behi et al., The encephalitogenicity of T(H) 17 cells is dependent on IL-1- and IL-23-induced production of the cytokine GM-CSF. Nat Immunol. Jun. 2011;12(6):568-75.

Eldar et al., Elucidating mechanisms underlying robustness of morphogen gradients. Curr Opin Genet Dev. Aug. 2004; 14(4):435-9.

Eldar et al., Robustness of the BMP morphogen gradient in *Drosophila* embryonic patterning. Nature. Sep. 19, 2002;419(6904):304-8.

Eldar et al., Self-enhanced ligand degradation underlies robustness of morphogen gradients. Dev Cell. Oct. 2003;5(4):635-46.

Emens et al., The interplay of immunotherapy and chemotherapy: harnessing potential synergies. Cancer Immunol Res. May 2015;3(5):436-43.

Eming et al., Inflammation in wound repair: molecular and cellular mechanisms. J Invest Dermatol. Mar. 2007;127(3):514-25.

Engler et al., Matrix elasticity directs stem cell lineage specification. Cell. Aug. 25, 2006;126(4):677-89.

Engler et al., Microtissue elasticity: measurements by atomic force microscopy and its influence on cell differentiation. Methods Cell Biol. 2007;83:521-45.

Engler et al., Substrate compliance versus ligand density in cell on gel responses. Biophys J. Jan. 2004;86(1 Pt 1):617-28.

Ennett et al., Temporally regulated delivery of VEGF in vitro and in vivo. J Biomed Mater Res A. Oct. 2006;79(1):176-84.

Ennett, Temporal Delivery of Multiple Growth Factors from Polymer Scaffolds to Enhance Neovascularization. A dissertation sub-

(56)                References Cited

OTHER PUBLICATIONS mitted in partial fulfillment of the requirements for the degree of Doctor of Philosophy (Biomedical Engineering) in the University of Michigan. 186 pages, (2004).

Exposito et al., The fibrillar collagen family. Int J Mol Sci. Jan. 28, 2010;11(2):407-26.

Fadel et al., A carbon nanotube-polymer composite for T-cell therapy. Nat Nanotechnol. Aug. 2014;9(8):639-47.

Fadel et al., Enhanced cellular activation with single walled carbon nanotube bundles presenting antibody stimuli. Nano Lett. Jul. 2008;8(7):2070-6.

Faissner et al., Boundaries and inhibitory molecules in developing neural tissues. Glia. Apr. 1995; 13(4):233-54.

Falanga, Wound healing and its impairment in the diabetic foot. Lancet. Nov. 12, 2005;366(9498):1736-43.

Falsey et al., Peptide and small molecule microarray for high throughput cell adhesion and functional assays. Bioconjug Chem. May-Jun. 2001;12(3):346-53.

Farrar et al., T helper subset development: roles of instruction, selection, and transcription. J Clin Invest. Feb. 2002;109(4):431-5.

Fauquemberque et al., HLA-A*0201-restricted CEA-derived peptide CAP1 is not a suitable target for T-cell-based immunotherapy. J Immunother. May 2010;33(4):402-13.

Ferrara et al., Angiogenesis as a therapeutic target. Nature. Dec. 15, 2005;438(7070):967-74.

Ferrara et al., Discovery and development of bevacizumab, an anti-VEGF antibody for treating cancer. Nat Rev Drug Discov. May 2004;3(5):391-400.

Fesnak et al., Engineered T cells: the promise and challenges of cancer immunotherapy. Nat Rev Cancer. Aug. 23, 2016;16(9):566-81.

Fischbach et al., Polymeric Systems for Bioinspired Delivery of Angiogenic Molecules. Adv Polym Sci. 2006;203:191-221.

Fischer et al., A brilliant monomeric red fluorescent protein to visualize cytoskeleton dynamics in Dictyostelium. FEBS Lett. Nov. 5, 2004;577(1-2):227-32.

Fischer et al., Visualizing cytoskeleton dynamics in mammalian cells using a humanized variant of monomeric red fluorescent protein. FEBS Lett. May 1, 2006;580(10):2495-502.

Fisher et al., The study of protein mechanics with the atomic force microscope. Trends Biochem Sci. Oct. 1999;24(10):379-84.

Folkman, Angiogenesis. Annu Rev Med. 2006;57:1-18.

Fonseca et al., Capitalizing on the immunogenicity of dying tumor cells. Clin Cancer Res. Mar. 15, 2008;14(6):1603-8.

Fontaine et al., Surgical treatment of peripheral circulation disorders. Helv Chir Acta. Dec. 1954;21(5-6):499-533.

Fox, Management of worsening multiple sclerosis with mitoxantrone: a review. Clin Ther. Apr. 2006;28(4):461-74.

Fransen et al., Local immunomodulation for cancer therapy: Providing treatment where needed. Oncoimmunology. Nov. 1, 2013;2(11):e26493.

Friedenstein et al., Fibroblast precursors in normal and irradiated mouse hematopoietic organs. Exp Hematol. Sep. 1976;4(5):267-74.

Friedrich et al., Promoter traps in embryonic stem cells: a genetic screen to identify and mutate developmental genes in mice. Genes Dev. Sep. 1991;5(9):1513-23.

Fukushima et al., The use of an antifibrosis agent to improve muscle recovery after laceration. Am J Sports Med. Jul.-Aug. 2001;29(4):394-402.

Furdui et al., Immunomagnetic T cell capture from blood for PCR analysis using microfluidic systems. Lab Chip. Dec. 2004;4(6):614-8.

Furqan et al., STAT inhibitors for cancer therapy. J Hematol Oncol. Dec. 5, 2013;6:90. 11 pages.

Gamvrellis et al., Vaccines that facilitate antigen entry into dendritic cells. Immunol Cell Biol. Oct. 2004;82(5):506-16.

Gao et al., Immune cell recruitment and cell-based system for cancer therapy. Pharm Res. Apr. 2008;25(4):752-68.

Gardel et al., Traction stress in focal adhesions correlates biphasically with actin retrograde flow speed. J Cell Biol. Dec. 15, 2008;183(6):999-1005.

Garlie et al., T cells coactivated with immobilized anti-CD3 and anti-CD28 as potential immunotherapy for cancer. J Immunother. Jul. 1999;22(4):336-45.

Gasic et al., Removal and regeneration of the cell coating in tumour cells. Nature. Oct. 13, 1962;196:170.

Gauthier et al., Temporary increase in plasma membrane tension coordinates the activation of exocytosis and contraction during cell spreading. Proc Natl Acad Sci U S A. Aug. 30, 2011;108(35):14467-72.

Geerligs et al., Linear viscoelastic behavior of subcutaneous adipose tissue. Biorheology. 2008;45(6):677-88.

GenBank Accession No. 000082.2, May 10, 2014.

GenBank Accession No. 000091.4, May 10, 2014.

GenBank Accession No. 000230.2, Dec. 17, 2012.

GenBank Accession No. 000514.3, Aug. 19, 2012.

GenBank Accession No. 000572.2, May 18, 2014.

GenBank Accession No. 000601.4, Nov. 25, 2012.

GenBank Accession No. 000614.3, Sep. 9, 2012.

GenBank Accession No. 000629.3, May 4, 2014.

GenBank Accession No. 000638.3, May 4, 2014.

GenBank Accession No. 000660.4, Dec. 9, 2012.

GenBank Accession No. 000749.2, May 4, 2014.

GenBank Accession No. 000758.3, May 4, 2014.

GenBank Accession No. 000800.3, Mar. 4, 2012.

GenBank Accession No. 000876.3, Apr. 13, 2014.

GenBank Accession No. 000885.4, Apr. 13, 2014.

GenBank Accession No. 000954.1, Jun. 13, 2014.

GenBank Accession No. 000963.3, Jun. 13, 2014.

GenBank Accession No. 001001522.1, May 18, 2014.

GenBank Accession No. 001096124.1, Dec. 16, 2012.

GenBank Accession No. 001102654.1, Dec. 16, 2012.

GenBank Accession No. 001111283.1, Dec. 9, 2012.

GenBank Accession No. 001171630.1, Dec. 9, 2012.

GenBank Accession No. 001202.3, Nov. 18, 2012.

GenBank Accession No. 001836.2, May 3, 2014.

GenBank Accession No. 001845.4, May 3, 2014.

GenBank Accession No. 001892.1, May 18, 2014.

GenBank Accession No. 001901.2, May 18, 2014.

GenBank Accession No. 002010.2, Dec. 9, 2012.

GenBank Accession No. 002421.3. May 11, 2014.

GenBank Accession No. 002506.2, Dec. 9, 2012.

GenBank Accession No. 002632.4, May 4, 2011.

GenBank Accession No. 002973.1, May 3, 2014.

GenBank Accession No. 002982.3, May 3, 2014.

GenBank Accession No. 003236.2, Aug. 21, 2011.

GenBank Accession No. 003239.2, Feb. 18, 2014.

GenBank Accession No. 003254.2, Jan. 5, 2013.

GenBank Accession No. 003255.2, Jan. 6, 2013.

GenBank Accession No. 003259.2, Nov. 25, 2012.

GenBank Accession No. 003263.3, Jan. 5, 2013.

GenBank Accession No. 003264.3, Jan. 6, 2013.

GenBank Accession No. 003268.5, Nov. 25, 2012.

GenBank Accession No. 003368.1, May 5, 2014.

GenBank Accession No. 003377.4, May 5, 2014.

GenBank Accession No. 003383.2, May 5, 2014.

GenBank Accession No. 003392.4, May 5, 2014.

GenBank Accession No. 004460.1, May 25, 2014.

GenBank Accession No. 004469.4, May 25, 2014.

GenBank Accession No. 005420.1, May 11, 2014.

GenBank Accession No. 005429.3, Mar. 31, 2014.

GenBank Accession No. 006059.2, Oct. 28, 2012.

GenBank Accession No. 006068.4, Oct. 28, 2012.

GenBank Accession No. 015719.3, Feb. 26, 2014.

GenBank Accession No. 016562.3, Jan. 6, 2013.

GenBank Accession No. 030956.3, Oct. 28, 2012.

GenBank Accession No. 033023.4, Nov. 18, 2012.

GenBank Accession No. 056534.2, Feb. 26, 2014.

GenBank Accession No. 057646.1, Jan. 6, 2013.

GenBank Accession No. 112218.2, Oct. 28, 2012.

GenBank Accession No. 138554.4, Dec. 29, 2012.

(56) References Cited

OTHER PUBLICATIONS

GenBank Accession No. 138636.4, Dec. 23, 2012.
GenBank Accession No. 170731.4, Dec. 9, 2012.
GenBank Accession No. 205819.3, Dec. 6, 2012.
GenBank Accession No. 205820.1, Jan. 5, 2013.
GenBank Accession No. 205823.2, Jan. 6, 2013.
GenBank Accession No. 570912.2, Nov. 18, 2012.
GenBank Accession No. 612564.1, Dec. 29, 2012.
GenBank Accession No. 619542.1, Dec. 23, 2012.
GenBank Accession No. 991388.2, Dec. 6, 2012.
GenBank Accession No. 991389.1, Jan. 5, 2013.
GenBank Accession No. 991392.1, Jan. 6, 2013.
GenBank Accession No. A32848.1, Jul. 5, 2002.
GenBank Accession No. AAA35789.1, Apr. 27, 1993.
GenBank Accession No. AAA36738.1, Aug. 3, 1993.
GenBank Accession No. AAA56738.1, Dec. 7, 1994.
GenBank Accession No. AAA60022.1, Jan. 7, 1995.
GenBank Accession No. AAA60552.1, Nov. 24, 2003.
GenBank Accession No. AAA64239.1, Mar. 23, 1995.
GenBank Accession No. AAA64297.1, Mar. 24, 1995.
GenBank Accession No. AAB18786.3, Jul. 12, 1999.
GenBank Accession No. AAB21432.2, Jun. 5, 2000.
GenBank Accession No. AAB29057.2, Mar. 6, 2001.
GenBank Accession No. AAB31818.1, Jan. 25, 1995.
GenBank Accession No. AAC16450.1, May 15, 1998.
GenBank Accession No. AAH07789.1, Jun. 9, 2008.
GenBank Accession No. AAH32517.2, Jun. 9, 2008.
GenBank Accession No. AAH93731.1, Jul. 17, 2006.
GenBank Accession No. AAH94877.1, May 20, 2005.
GenBank Accession No. AAI44040, Mar. 18, 2009.
GenBank Accession No. ABC86910, Jan. 3, 2011.
GenBank Accession No. AEO22039.1, Sep. 17, 2011.
GenBank Accession No. AF344424.1, Apr. 8, 2002.
GenBank Accession No. AF414120.1, Sep. 26, 2001.
GenBank Accession No. AF450242.1, Feb. 11, 2002.
GenBank Accession No. AJ583695.1, Oct. 7, 2008.
GenBank Accession No. AY291313.1, Apr. 26, 2004.
GenBank Accession No. BC094887.1, Jul. 21, 2006.
GenBank Accession No. CAA01954.1, Jun. 15, 1995.
GenBank Accession No. CAA01955.1, Nov. 14, 2006.
GenBank Accession No. CAA40093.1, Oct. 7, 2008.
GenBank Accession No. CAA62632.1, Sep. 15, 1995.
GenBank Accession No. CAG29322.1, Oct. 16, 2008.
GenBank Accession No. CAG33149.1, Oct. 21, 2008.
GenBank Accession No. CAG46721.1, Jun. 29, 2004.
GenBank Accession No. CBI71013.1, Feb. 2, 2010.
GenBank Accession No. DQ103757.1, Jul. 25, 2005.
GenBank Accession No. EF064765.1, Nov. 13, 2006.
GenBank Accession No. EU826563.1, Jul. 23, 2008.
GenBank Accession No. JN602184.1, Sep. 17, 2011.
GenBank Accession No. M16006.1, Jan. 7, 1995.
GenBank Accession No. M24902.1, Jan. 7, 1995.
GenBank Accession No. M73239.1, Mar. 23, 1995.
GenBank Accession No. U76381.2, Jul. 12, 1999.
Genes et al., Effect of substrate mechanics on chondrocyte adhesion to modified alginate surfaces. Arch Biochem Biophys. Feb. 15, 2004;422(2):161-7.
Gerhardt et al., VEGF guides angiogenic sprouting utilizing endothelial tip cell filopodia. J Cell Biol. Jun. 23, 2003;161(6):1163-77.
Gilboa, DC-based cancer vaccines. J Clin Invest. May 2007;117(5):1195-203.
Gimmi et al., B-cell surface antigen B7 provides a costimulatory signal that induces T cells to proliferate and secrete interleukin 2. Proc Natl Acad Sci U S A. Aug. 1, 1991;88(15):6575-9.
Glasbey et al., Image Analysis and Three-Dimensional Modelling of Pores in Soil Aggregates. Eur J Soil Sci. Sep. 1991;42(3):479-486.
Gnjatic et al., Toll-like receptor agonists: are they good adjuvants? Cancer J. Jul.-Aug. 2010;16(4):382-91.

Godbey et al. Tracking the intracellular path of poly(ethylenimine)/DNA complexes for gene delivery. Proc Natl Acad Sci U S A. Apr. 27, 1999;96(9):5177-81.
Goddard et al., Polymer surface modification for the attachment of bioactive compounds. Progress in Polymer Science. Jul. 2007;32(7):698-725.
Gospodarowicz et al., Effect of fibroblast growth factor on the division and fusion of bovine myoblasts. J Cell Biol. Aug. 1976;70(2 pt 1):395-405.
Grabowska et al., Systemic in vivo delivery of siRNA to tumours using combination of polyethyleneimine and transferrin-polyethyleneimine conjugates. Biomater Sci. Nov. 2015;3(11):1439-48.
Graessley, Entangled Linear, Branched and Network Polymer Systems—Molecular Theories. Adv Poly Sci. 1982;47:67-117.
Griffith et al., Tissue engineering—current challenges and expanding opportunities. Science. Feb. 8, 2002;295(5557):1009-14.
Grimmer et al., Tracheal reconstruction using tissue-engineered cartilage. Arch Otolaryngol Head Neck Surg. Oct. 2004; 130(10):1191-6.
Gros et al., A common somitic origin for embryonic muscle progenitors and satellite cells. Nature. Jun. 16, 2005;435(7044):954-8.
Guillaume et al., Two abundant proteasome subtypes that uniquely process some antigens presented by HLA class I molecules. Proc Natl Acad Sci U S A. Oct. 26, 2010;107(43):18599-604.
Gullberg et al., Extracellular matrix and its receptors during development. Int J Dev Biol. Oct. 1995;39(5):845-54.
Guo et al., Droplet microfluidics for high-throughput biological assays. Lab Chip. Jun. 21, 2012;12(12):2146-55.
Gupta et al., Magnetically controlled targeted micro-carrier systems. Life Sci. 1989;44(3):175-86.
Gurkan et al., The mechanical environment of bone marrow: a review. Ann Biomed Eng. Dec. 2008;36(12):1978-91.
Gussoni et al., Dystrophin expression in the mdx mouse restored by stem cell transplantation. Nature. Sep. 23, 1999;401(6751):390-4.
Halim et al., Biologic and synthetic skin substitutes: An overview. Indian J Plast Surg. Sep. 2010;43(Suppl):S23-8.
Hamby et al., Small molecule inhibitors of tumor-promoted angiogenesis, including protein tyrosine kinase inhibitors. Pharmacol Ther. May-Jun. 1999;82(2-3): 169-93.
Hamdy et al., Targeting dendritic cells with nano-particulate PLGA cancer vaccine formulations. Adv Drug Deliv Rev. Sep. 10, 2011;63(10-11):943-55.
Hamilton et al., GM-CSF Biology. Growth Factors. Dec. 2004;22(4):225-31.
Hamilton, GM-CSF in inflammation and autoimmunity. Trends Immunol. Aug. 2002;23(8):403-8.
Han et al., Synthesis of rod-like mesoporous silica using mixed surfactants of cetyltrimethylammonium bromide and cetyltrimethylammonium chloride as templates. Materials Letters. 2003;57:4520-4.
Hanada, Efficacy of rehabilitative therapy in regional musculoskeletal conditions. Best Pract Res Clin Rheumatol. Feb. 2003; 17(1):151-66.
Hansen et al., Comparison of clinical grade type 1 polarized and standard matured dendritic cells for cancer immunotherapy. Vaccine. Jan. 11, 2013;31(4):639-46.
Hansen et al., Integrin binding and cell spreading on extracellular matrix act at different points in the cell cycle to promote hepatocyte growth. Mol Biol Cell. Sep. 1994;5(9):967-75.
Harding et al., CD28-mediated signalling co-stimulates murine T cells and prevents induction of anergy in T-cell clones. Nature. Apr. 16, 1992;356(6370):607-9.
Harris et al., Open pore biodegradable matrices formed with gas foaming. J Biomed Mater Res. Dec. 5, 1998;42(3):396-402.
Harrison, What is the status of reaction-diffusion theory thirty-four years after turing? J Theor Biol. Apr. 21, 1987;125(4):369-84.
Hartgerink et al., Peptide-amphiphile nanofibers: a versatile scaffold for the preparation of self-assembling materials. Proc Natl Acad Sci U S A. Apr. 16, 2002;99(8):5133-8.
Hartmann et al., CpG DNA: a potent signal for growth, activation, and Maturation of human dendritic cells. Proc Natl Acad Sci U S A. Aug. 3, 1999;96(16):9305-10.

(56) References Cited

OTHER PUBLICATIONS

Hasan et al., Artificial Antigen Presenting Cells: An Off the Shelf Approach for Generation of Desirable T-Cell Populations for Broad Application of Adoptive Immunotherapy. Advancements in Genetic Engineering. 2015;4(3):1-10.

Hashimoto et al., Development of alginate wound dressings linked with hybird peptides derived from laminin and elastin. Biomaterials. Mar.-Apr. 2004;25(7-8):1407-14.

Haso et al., Anti-CD22-chimeric antigen receptors targeting B-cell precursorlymphoblastic leukemia. Blood. Feb. 14, 2013;121(7):1165-74.

Hawke et al., Myogenic satellite cells: physiology to molecular biology. J Appl Physiol (1985). Aug. 2001;91(2):534-51.

Heath, Cells for tissue engineering. Trends Biotechnol. Jan. 2000; 18(1):17-9.

Helm et al., Synergy between interstitial flow and VEGF directs capillary morphogenesis in vitro through a gradient amplification mechanism. Proc Natl Acad Sci U S A. Nov. 1, 2005;102(44):15779-84.

Henry et al., VIVA Investigators. The VIVA trial: Vascular endothelial growth factor in Ischemia for Vascular Angiogenesis. Circulation. Mar. 18, 2003;107(10):1359-65.

Hermanson, Bioconjugate Techniques. Academic Press, New York. pp. 152-186, (1996).

Heslop et al., Transplanted primary neonatal myoblasts can give rise to functional satellite cells as identified using the Myf5nlacZI+ mouse. Gene Ther. May 2001;8(10):778-83.

Hildner et al., Batf3 deficiency reveals a critical role for CD8alpha+ dendritic cells in cytotoxic T cell immunity. Science. Nov. 14, 2008;322(5904):1097-100.

Hill et al., Designing scaffolds to enhance transplanted myoblast survival and migration. Tissue Eng. May 2006;12(5):1295-304.

Hill et al., Muscle satellite (stem) cell activation during local tissue injury and repair. J Anat. Jul. 2003;203(1):89-99.

Hill, Macroporous Scaffold Architecture, Peptide, HGF/FGF and Myoblast Incorporation Enhance Myogenesis. IADR/AADR/CADR 83rd General Session. Mar. 9-12, 2005. Poster #2829.

Hirano et al., Peptide and Protein Presenting Materials for Tissue Engineering. Adv Mat. Jan. 16, 2004;16(1):17-25.

Hodge-Dufour et al., Inhibition of interferon gamma induced interleukin 12 production: a potential mechanism for the anti-inflammatory activities of tumor necrosis factor. Proc Natl Acad Sci U S A. Nov. 10, 1998;95(23):13806-11.

Hodi et al., Immunologic and clinical effects of antibody blockade of cytotoxic T lymphocyte-associated antigen 4 in previously vaccinated cancer patients. Proc Natl Acad Sci U S A. Feb 26, 2008;105(8):3005-10.

Hodi et al., Improved survival with ipilimumab in patients with metastatic melanoma. N Engl J Med. Aug. 19, 2010;363(8):711-23.

Holland et al., Dual growth factor delivery from degradable oligo(poly(ethylene glycol) fumarate) hydrogel scaffolds for cartilage tissue engineering. Journal of Controlled Release. 2005;101:111-125.

Holland et al., Transforming growth factor-beta 1 release from oligo(poly(ethylene glycol) fumarate) hydrogels in conditions that model the cartilage wound healing environment. J Control Release. Jan. 8, 2004;94(1):101-14.

Hollyman et al., Manufacturing validation of biologically functional T cells targeted to CD19 antigen for autologous adoptive cell therapy. J Immunother. Feb.-Mar. 2009;32(2):169-80.

Horsley et al., IL-4 acts as a myoblast recruitment factor during mammalian muscle growth. Cell. May 16, 2003;113(4):483-94.

Hsiong et al., Differentiation stage alters matrix control of stem cells. J Biomed Mater Res A. Apr. 2008;85A(1):145-56.

Huang et al., Fabrication and in vitro Testing of Polymeric Delivery Systems for Condensed DNA. J Biomed Mater Res. 2003;67:1384-1392.

Huang et al., Long-Term In Vivo Gene Expression via Delivery of PEL-DNA Condensates From Porous Polymer Scaffolds. Hum Gene Ther. 2005;16(5):609-617.

Hubbell et al., Materials Engineering for Immunomodulation. Nature. 2009;462:449-460.

Hubbell, Biomaterials in tissue engineering. Biotechnology (N Y). Jun. 1995;13(6):565-76.

Huebsch et al., Harnessing traction-mediated manipulation of the cell/matrix interface to control stem-cell fate. Nat Mater. Jun. 2010;9(6):518-26.

Humphries et al., Integrin ligands at a glance. J Cell Sci. Oct. 1, 2006;119(Pt 19):3901-3.

Huppa et al., T-cell-antigen recognition and the immunological synapse. Nat Rev Immunol. Dec. 2003;3(12):973-83.

Huston et al., Protein engineering of antibody binding sites: recovery of specific activity in an anti-digoxin single-chain Fv analogue produced in *Escherichia coli*. Proc Natl Acad Sci U S A. Aug. 1988;85(16):5879-83.

Hutson et al., Synthesis and characterization of tunable poly(ethylene glycol): gelatin methacrylate composite hydrogels. Tissue Eng Part A. Jul. 2011;17(13-14):1713-23.

Hwang et al., Fabrication of three-dimensional porous cell-laden hydrogel for tissue engineering. Biofabrication. Sep. 2010;2(3):035003. 12 pages.

Ichida et al., A small-molecule inhibitor of tgf-Beta signaling replaces sox2 in reprogramming by inducing nanog. Cell Stem Cell. Nov. 6, 2009;5(5):491-503.

Iellem et al., Unique chemotactic response profile and specific expression of chemokine receptors CCR4 and CCR8 by CD4(+)CD25(+) regulatory T cells. J Exp Med. Sep. 17, 2001;194(6):847-53.

Ihnat et al., Hypothesis: the 'metabolic memory', the new challenge of diabetes. Diabet Med. Jun. 2007;24(6):582-6.

Il et al., A novel cyclohexene derivative, ethyl (6R)-6-[N-(2-Chloro-4-fluorophenyl)sulfamoyl]cyclohex-1-ene-1-carboxylate (TAK-242), selectively inhibits toll-like receptor 4-mediated cytokine production through suppression of intracellular signaling. Mol Pharmacol. Apr. 2006;69(4):1288-95.

Irintchev et al., Formation of Skeletal Muscle After Subcutaneous Implantation of Cultured Myoblasts. Bio/Technology. p. 366, Abstract 153.06, Jun. 1995.

Irvine et al., Engineering synthetic vaccines using cues from natural immunity. Nat Mater. Nov. 2013;12(11):978-90.

Isern et al., Self-renewing human bone marrow mesenspheres promote hematopoietic stem cell expansion. Cell Rep. May 30, 2013;3(5):1714-24.

Ishihara et al., Roles of bradykinin in vascular permeability and angiogenesis in solid tumor. Int Immunopharmacol. Mar. 2002;2(4):499-509.

Iwamoto et al., Preparation of an Ionic Polymer Gel Microactuator and Measurement of its Periodic Motions. Nippon Kagaku Kaishi. 1997;9:609-614.

Jain et al., Macroporous interpenetrating cryogel network of poly(acrylonitrile) and gelatin for biomedical applications. J Mater Sci Mater Med. Dec. 2009;20 Suppl 1:S173-9.

Jain, Molecular Regeneration of Vessel Maturation. Nat Med. Jun. 1, 2003;9:685-693.

Jain, The manufacturing techniques of various drug loaded biodegradable poly(lactide-co-glycolide) (PLGA) devices. Biomaterials. Dec. 2000;21(23):2475-90.

Jankovic et al., In the absence of IL-12, CD4(+) T cell responses to intracellular pathogens fail to default to a Th2 pattern and are host protective in an IL-10(-/-) setting. Immunity. Mar. 2002;16(3):429-39.

Janmey et al., From tissue mechanics to transcription factors. Differentiation. Oct. 2013;86(3):112-20.

Jego et al., Plasmacytoid dendritic cells induce plasma cell differentiation through type I interferon and interleukin 6. Immunity. Aug. 2003;19(2):225-34.

Jiang et al. Two-piconewton slip bond between fibronectin and the cytoskeleton depends on talin. Nature. Jul. 17, 2003;424(6946):334-7.

Jiang et al., Click hydrogels, microgels and nanogels: emerging platforms for drug delivery and tissue engineering. Biomaterials. Jun. 2014;35(18):4969-85.

(56) References Cited

OTHER PUBLICATIONS

Jiang et al., Self-organization of periodic patterns by dissociated feather mesenchymal cells and the regulation of size, number and spacing of primordia. Development. Nov. 1999;126(22):4997-5009.

Jiang, Application of polymers in nucleic acid delivery. Thesis in partial fulfillment of the requirements for the Doctor of Philosophy degree in Pharmacy in the Graduate College of The University of Iowa. 138 pages, Dec. 2011.

Jinushi et al., Enhancing the clinical activity of granulocyte-macrophage colony-stimulating factor-secreting tumor cell vaccines. Immunol Rev. Apr. 2008;222:287-98.

Jinushi et al., MFG-E8-mediated uptake of apoptotic cells by APCs links the pro- and antiinflammatory activities of GM-CSF. J Clin Invest. Jul. 2007;117(7):1902-13.

Johansson, Controlling the Pore Size and Morphology of Mesoporous Silica. Linkoping Studies in Science and Technology Licentiate Thesis No. 1451, 53 pages, (2010).

John et al., Passive and active mechanisms trap activated CD8+ T cells in the liver. J Immunol. May 1, 2004;172(9):5222-9.

Johnson et al., Activation of skeletal muscle satellite cells and the role of fibroblast growth factor receptors. Exp Cell Res. Aug. 1995;219(2):449-53.

Jokinen et al., Integrin-mediated cell adhesion to type I collagen fibrils. J Biol Chem. Jul. 23, 2004;279(30):31956-63.

Jugdutt et al., Aging and defective healing, adverse remodeling, and blunted post-conditioning in the reperfused wounded heart. J Am Coll Cardiol. Apr. 8, 2008;51(14):1399-403.

June et al., Adoptive cellular therapy: a race to the finish line. Sci Transl Med. Mar. 25, 2015;7(280):280ps7.

June et al., The B7 and CD28 receptor families. Immunol Today. Jul. 1994; 15(7):321-31.

Juntanon et al., Electrically controlled release of sulfosalicylic acid from crosslinked poly(vinyl alcohol) hydrogel. Int J Pharm. May 22, 2008;356(1-2):1-11.

Kang et al., Effect of Porous Structure on the Degradation of Freeze-Dried Gelatin Hydrogels. J Bioact Compat Poly. Jul. 1, 1999;14(4):331-343.

Kanzler et al., Therapeutic targeting of innate immunity with Toll-like receptor agonists and antagonists. Nat Med. May 2007;13(5):552-9.

Kared et al., Treatment with granulocyte colony-stimulating factor prevents diabetes in NOD mice by recruiting plasmacytoid dendritic cells and functional CD4(+)CD25(+) regulatory T-cells. Diabetes. Jan. 2005; 54(1):78-84.

Katayama et al., Integrated analysis of the genome and the transcriptome by Fantom. Brief Bioinform. Sep. 2004;5(3):249-58.

Kathuria et al., Synthesis and characterization of elastic and macroporous chitosan-gelatin cryogels for tissue engineering. Acta Biomater. Jan. 2009;5(1):406-18.

Kawai et al., Innate immune recognition of viral infection. Nat Immunol. Feb. 2006;7(2):131-7.

Kawashima et al., Pulmonary delivery of insulin with nebulized DL-lactide/glycolide copolymer (PLGA) nanospheres to prolong hypoglycemic effect. J Control Release. Nov. 1, 1999;62(1-2):279-87.

Kearney et al., Macroscale delivery systems for molecular and cellular payloads. Nat Mater. Nov. 2013;12(11):1004-17.

Kennedy et al., Rapid and extensive collapse from electrically responsive macroporous hydrogels. Adv Healthc Mater. Apr. 2014;3(4):500-7.

Khetan et al., Degradation-mediated cellular traction directs stem cell fate in covalently crosslinked three-dimensional hydrogels. Nat Mater. May 2013;12(5):458-65.

Khownium et al., Novel endotoxin-sequestering compounds with terephthalaldehyde-bis-guanylhydrazone scaffolds. Bioorg Med Chem Lett. Mar. 1, 2006;16(5):1305-8.

Kim et al., An overview of cartilage tissue engineering. Yonsei Med J. Dec. 2000;41(6):766-73.

Kim et al., Galectin-3 binding protein promotes cell motility in colon cancer by stimulating the shedding of protein tyrosine phosphatase kappa by proprotein convertase 5. Biochem Biophys Res Commun. Jan. 7, 2011;404(1):96-102.

Kim et al., Injectable, spontaneously assembling, inorganic scaffolds modulate immune cells in vivo and increase vaccine efficacy. Nat Biotechnol. Jan. 2015;33(1):64-72.

Kim et al., Multifunctional capsule-in-capsules for immunoprotection and trimodal imaging. Angew Chem Int Ed Engl. Mar. 1, 2011;50(10):2317-21.

Kim et al., The effect of VEGF on the myogenic differentiation of adipose tissue derived stem cells within thermosensitive hydrogel matrices. Biomaterials. Feb. 2010;31(6):1213-8.

Kinoshita et al., Successive injections in mdx mice of myoblasts grown with bFGF. Neuromuscul Disord. May 1996;6(3):187-93.

Kisak et al. The vesosome—a multicompartment drug delivery vehicle. Curr Med Chem. Jan. 2004;11(2):199-219.

Klebanoff et al., CD8+ T-cell memory in tumor immunology and immunotherapy. Immunol Rev. Jun. 2006;211:214-24.

Klein et al., Cell-Cycle Control by Physiological Matrix Elasticity and In Viivo Tissue Stiffening. Curr Biol. Sep. 29, 2009;19:1511-1518.

Klinman. Immunotherapeutic uses of CpG oligodeoxynucleotides. Nat Rev Immunol. Apr. 2004;4(4):249-58.

Kohane, Microparticles and nanoparticles for drug delivery. Biotechnol Bioeng. Feb. 1, 2007;96(2):203-9.

Kohrt et al., Donor immunization with WT1 peptide augments antileukemic activity after MHC-matched bone marrow transplantation. Blood. Nov. 10, 2011;118(19):5319-29.

Kondo et al., A reaction-diffusion wave on the skin of the marine angelfish Pomacanthus. Nature. Aug. 31, 1995;376(6543):765-8.

Kong et al., Controlling Degradation of Hydrogels via the Size of Cross-Linked Junctions. Adv Mater. Nov. 30, 2004;16(21): 1917-1921.

Kong et al., Controlling rigidity and degradation of alginate hydrogels via molecular weight districution. Biomacromolecules. 2004;5:1720-7.

Kong et al., Decoupling the Dependence of Rheological/Mechanical Properties of Hydrogels from Solids Concentration. Polymer. 2002;43(23):6239-6246.

Kong et al., Design of biodegradable hydrogel for the local and sustained delivery of angiogenic plasmid DNA. Pharm Res. May 2008;25(5):1230-8.

Kong et al., Designing alginate hydrogels to maintain viability of immobilized cells. Biomaterials. Oct. 2003;24(22):4023-9.

Kong et al., FRET measurements of cell-traction forces and nanoscale clustering of adhesion ligands varied by substrate stiffness. Proc Natl Acad Sci U S A. Mar. 22, 2005;102(12):4300-5.

Kong et al., Non-viral gene delivery regulated by stiffness of cell adhesion substrates. Nat Mater. Jun. 2005;4(6):460-4.

Koo et al., Bioorthogonal copper-free click chemistry in vivo for tumor-targeted delivery of nanoparticles. Angew Chem Int Ed Engl. Nov. 19, 2012;51(47):11836-40.

Kosuge et al., Morphological Control of Rod- and Fiberlike SBA-15 Type Mesoporous Silica Using Water-Soluble Sodium Silicate. Chem Mater. 2004;16:899-905.

Kratky et al., Direct activation of antigen-presenting cells is required for CD8+ T-cell priming and tumor vaccination. Proc Natl Acad Sci U S A. Oct. 18, 2011;108(42):17414-9.

Kratz, Albumin as a drug carrier: design of prodrugs, drug conjugates and nanoparticles. J Control Release. Dec. 18, 2008;132(3):171-83.

Krieg, Development of TLR9 agonists for cancer therapy. J Clin Invest. May 2007;117(5):1184-94.

Krishnamachari et al., PLGA Microparticles that Co-deliver Antigen and Toll Like Receptor Ligand Adjuvants for Applications in Cancer Immunotherapy. AAPS Annual Meeting and Exposition. Nov. 9, 2009. 1 page.

Kumamoto et al., Induction of tumor-specific protective immunity by in situ Langerhans cell vaccine. Nat Biotechnol. Jan. 2002;20(1):64-9.

Kumar et al., Toll-like receptors and innate immunity. Biochem Biophys Res Commun. Oct. 30, 2009;388(4):621-5.

(56) References Cited

OTHER PUBLICATIONS

Kupferschmidt et al., Mesoporous silica particles potentiate antigen-specific T-cell responses. Nanomedicine (Lond). 2014;9(12):1835-46.

Kuwahara et al., Cell delivery using an injectable and adhesive transglutaminase-gelatin gel. Tissue Eng Part C Methods. Aug. 2010;16(4):609-18.

Kwon et al., Electrically erodible polymer gel for controlled release of drugs. Nature. Nov. 28, 1991;354(6351):291-3.

Kwon et al., In vivo targeting of dendritic cells for activation of cellular immunity using vaccine carriers based on pH-responsive microparticles. Proc Natl Acad Sci U S A. Dec. 20, 2005;102(51):18264-8.

Kyi et al., Checkpoint blocking antibodies in cancer immunotherapy. FEBS Lett. Jan. 21, 2014;588(2):368-76.

Lacy et al., Cytokine release from innate immune cells: association with diverse membrane trafficking pathways. Blood. 2011;118(1):9-18.

Langenkamp et al., Kinetics of dendritic cell activation: impact on priming of TH1, TH2 and nonpolarized T cells. Nat Immunol. Oct. 2000;1(4):311-6.

Langer et al., Tissue engineering. Science. May 14, 1993;260(5110):920-6.

Lanzavecchia et al., Regulation of T cell immunity by dendritic cells. Cell. Aug. 10, 2001;106(3):263-6.

Lao et al., Magnetic and hydrogel composite materials for hyperthermia applications. J Mater Sci Mater Med. Oct. 2004;15(10):1061-4.

Latorre et al., Applications of magnetic nanoparticles in medicine: magnetic fluid hyperthermia. P R Health Sci J. Sep. 2009;28(3):227-38.

Latz et al., TLR9 signals after translocating from the ER to CpG DNA in the lysosome. Nat Immunol. Feb. 2004;5(2):190-8.

Lauterbach et al., Mouse CD8alpha+ DCs and human BDCA3+ DCs are major producers of IFN-lambda in response to poly IC. J Exp Med. Nov. 22, 2010;207(12):2703-17.

Lauw et al., Proinflammatory effects of IL-10 during human endotoxemia. J Immunol. Sep. 1, 2000;165(5):2783-9.

Leach et al., Coating of VEGF-releasing scaffolds with bioactive glass for angiogenesis and bone regeneration. Biomaterials. Jun. 2006;27(17):3249-55.

Lee et al., Chemical tumor-targeting of nanoparticles based on metabolic glycoengineering and click chemistry. ACS Nano. Mar. 25, 2014;8(3):2048-63.

Lee et al., Controlling Mechanical and Swelling Properties of Alginate Hydrogels Independently by Cross-Linker Type and Cross-Linking Density. Macromolecules. Apr. 2000;33(11):4291-4294.

Lee et al., Effect of dual treatment with SDF-1 and BMP-2 on ectopic and orthotopic bone formation. PLoS One. Mar. 17, 2015;10(3):e0120051, 15 pages.

Lee et al., Engineering liver tissue spheroids with inverted colloidal crystal scaffolds. Biomaterials. Sep. 2009;30(27):4687-94.

Lee et al., Hydrogel Formation via Vell Crosslinking. Advanced Materials. Nov. 2003;15(21):1828-1832.

Lee et al., Hydrogels for tissue engineering. Chem Rev. Jul. 2001;101(7):1869-79.

Lee et al., Intravenous hMSCs improve myocardial infarction in mice because cells embolized in lung are activated to secrete the anti-inflammatory protein TSG-6. Cell Stem Cell. Jul. 2, 2009;5(1):54-63.

Lee et al., The immunological synapse balances T cell receptor signaling and degradation. Science. Nov. 14, 2003;302(5648):1218-22.

Lefaucheur et al., The cellular events of injured muscle regeneration depend on the nature of the injury. Neuromuscul Disord. Nov. 1995;5(6):501-9.

Lele et al., Investigating complexity of protein-protein interactions in focal adhesions. Biochem Biophys Res Commun. May 9, 2008;369(3):929-34.

Lensch et al., Scientific and clinical opportunities for modeling blood disorders with embryonic stem cells. Blood. Apr. 1, 2006;107(7):2605-12.

Leor et al., Cells, scaffolds, and molecules for myocardial tissue engineering. Pharmacol Ther. Feb. 2005;105(2):151-63.

Leshem et al., Hepatocyte growth factor (HGF) inhibits skeletal muscle cell differentiation: a role for the bHLH protein twist and the cdk inhibitor p27. J Cell Physiol. Jul. 2000;184(1):101-9.

Letsinger et al., Phosphoramidate analogs of oligonucleotides. J Org Chem. Nov. 1970;35(11):3800-3.

Levental et al., Soft biological materials and their impact on cell function. Soft Matter. 2007;3:299-306.

Levine et al., Effects of CD28 costimulation on long-term proliferation of CD4+ T cells in the absence of exogenous feeder cells. J Immunol. Dec. 15, 1997;159(12):5921-30.

Li et al., Effect of growth factors and extracellular matrix materials on the proliferation and differentiation of microencapsulated myoblasts. J Biomater Sci Polym Ed. 2003;14(6):533-49.

Li et al., Effects of Three-Dimensional Scaffolds on Cell Organization and Tissue Development. Biotechnology and Bioprocess Engineering. Oct. 2001;6(5):311-325.

Li et al., Mesoporous silica nanoparticles in biomedical applications. Chem Soc Rev. Apr. 7, 2012;41(7):2590-605.

Li et al., pH sensitive Laponite/alginate hybrid hydrogels: swelling behaviour and release mechanism. Soft Matter. 2011;7:6231-6238.

Li et al., Purified hybrid cells from dendritic cell and tumor cell fusions are superior activators of antitumor immunity. Cancer Immunol Immunother. Nov. 2001;50(9):456-62.

Li et al., Recent advances of biomaterials in biotherapy. Regen Biomater. Jun. 2016;3(2):99-105.

Li et al., The effect of surface modification of mesoporous silica micro-rod scaffold on immune.

Li, TNF-alpha is a mitogen in skeletal muscle. Am J Physiol Cell Physiol. Aug. 2003;285(2):C370-6.

Liao et al., Synthesis of mesoporous silica nanoparticle-encapsulated alginate microparticles for sustained release and targeting therapy. J Biomed Mater Res B Appl Biomater. Feb. 2014;102(2):293-302.

Liederer et al., Enzymes involved in the bioconversion of ester-based prodrugs. J Pharm Sci. Jun. 2006;95(6):1177-95.

Lin et al., Transdermal regulation of vascular network bioengineering using a photopolymerizable methacrylated gelatin hydrogel. Biomaterials. Sep. 2013;34(28):6785-96.

Lindstein et al., Regulation of lymphokine messenger RNA stability by a surface-mediated T cell activation pathway. Science. Apr. 21, 1989;244(4902):339-43.

Linsley et al., The role of the CD28 receptor during T cell responses to antigen. Annu Rev Immunol. 1993;11:191-212.

Lipson et al., Ipilimumab: an anti-CTLA-4 antibody for metastatic melanoma. Clin Cancer Res. Nov. 15, 2011;17(22):6958-62.

Lipton et al., Developmental fate of skeletal muscle satellite cells. Science. Sep. 21, 1979;205(4412):1292-4.

Liu et al., Heterobifunctional poly(ethylene glycol)-tethered bone morphogenetic protein-2-stimulated bone marrow mesenchymal stromal cell differentiation and osteogenesis. Tissue Eng. May 2007;13(5):1113-24.

Liu et al., Immunostimulatory CpG oligodeoxynucleotides enhance the immune response to vaccine strategies involving granulocyte-macrophage colony-stimulating factor. Blood. Nov. 15, 1998;92(10):3730-6.

Liu et al., Nanostructured materials designed for cell binding and transduction. Biomacromolecules. 2001 Summer;2(2):362-8.

Liu et al., On the viscoelastic character of liver tissue: experiments and modelling of the linear behaviour. Biorheology. 2000;37(3):191-201.

Liu et al., Porous nanoparticle supported lipid bilayers (protocells) as delivery vehicles. J Am Chem Soc. Feb. 4, 2009;131(4):1354-5.

Liu et al., Preparation of uniform calcium alginate gel beads by membrane emulsification coupled with internal gelation. Journal of Applied Polymer Science. Nov. 22, 2002;87(5):848-852.

Liu, Dendritic cell subsets and lineages, and their functions in innate and adaptive immunity. Cell. Aug. 10, 2001;106(3):259-62.

(56) References Cited

OTHER PUBLICATIONS

Lo et al., Cell movement is guided by the rigidity of the substrate. Biophys J. Jul. 2000;79(1):144-52.

Lodish et al., Collagen: The Fibrous Proteins of the Matrix. Molecular Cell Biology. W.H. Freeman, New York. 2000;Section 22.3:979-985.

Lopez et al., Magnetic Applications of Polymer Gels. Macromol Symp. 2001; 166(1):173-178.

Lozinsky et al., Polymeric cryogels as promising materials of biotechnological interest. Trends Biotechnol. Oct. 2003;21(10):445-51.

Lu et al., Muscle-derived stem cells seeded into acellular scaffolds develop calcium- dependent contractile activity that is modulated by nicotinic receptors. Urology. Jun. 2003;61(6):1285-91.

Lubeck, The costs of musculoskeletal disease: health needs assessment and health economics. Best Pract Res Clin Rheumatol. Jun. 2003;17(3):529-39.

Ludewig et al., Immunotherapy with dendritic cells directed against tumor antigens shared with normal host cells results in severe autoimmune disease. J Exp Med. Mar. 6, 2000;191(5):795-804.

Lumelsky et al., Differentiation of embryonic stem cells to insulin-secreting structures similar to pancreatic islets. Science. May 18, 2001;292(5520):1389-94.

Lungu et al., Linear and Branched PEIs (Polyethylenimines) and Their Property Space. Int J Mol Sci. Apr. 13, 2016;17(4):555.

Lutolf et al., Repair of bone defects using synthetic mimetics of collagenous extracellular matrices. Nat Biotechnol. May 2003;21(5):513-8.

Lutterotti et al., Antigen-specific tolerance by autologous myelin peptide-coupled cells: a phase 1 trial in multiple sclerosis. Sci Transl Med. Jun. 5, 2013;5(188):188ra75.

Mach et al., Differences in dendritic cells stimulated in vivo by tumors engineered to secrete granulocyte-macrophage colony-stimulating factor or Flt3-ligand. Cancer Res. Jun. 15, 2000;60(12):3239-46.

Magram et al., IL-12-deficient mice are defective but not devoid of type 1 cytokine responses. Ann N Y Acad Sci. Oct. 31, 1996;795:60-70.

Mahony et al., Mesoporous silica nanoparticles act as a self-adjuvant for ovalbumin model antigen in mice. Small. Sep. 23, 2013;9(18):3138-46.

Mailander et al., Complete remission in a patient with recurrent acute myeloid leukemia induced by vaccination with WT1 peptide in the absence of hematological or renal toxicity. Leukemia. Jan. 2004;18(1):165-6.

Maini, Spatial and spatio-temporal patterns in a cell-haptotaxis model. J Math Biol. 1989;27(5):507-22.

Majeti et al., Identification of a hierarchy of multipotent hematopoietic progenitors in human cord blood. Cell Stem Cell. Dec. 13, 2007;1(6):635-45.

Maldonado et al., How tolerogenic dendritic cells induce regulatory T cells. Adv Immunol. 2010;108:111-65.

Maley et al., Extracellular matrix, growth factors,genetics: their influence on cell proliferation and myotube formation in primary cultures of adult mouse skeletal muscle. Exp Cell Res. Jul. 1995;219(1):169-79.

Malhotra et al., Use of an oncolytic virus secreting GM-CSF as combined oncolytic and immunotherapy for treatment of colorectal and hepatic adenocarcinomas. Surgery. Apr. 2007;141(4):520-9.

Malmqvist, Biospecific interaction analysis using biosensor technology. Nature. Jan. 14, 1993;361(6408):186-7.

Mammoto et al., Mechanical control of tissue and organ development. Development. May 2010;137(9):1407-20.

Manavski et al., Vascular niche controls organ regeneration. Circ Res. Mar. 28, 2014;114(7):1077-9.

Mandal et al., Polymer-based synthetic dendritic cells for tailoring robust and multifunctional T cell responses. ACS Chem Biol. Feb. 20, 2015;10(2):485-92.

Mangsbo et al., Enhanced tumor eradication by combining CTLA-4 or PD-1 blockade with CpG therapy. J Immunother. Apr. 2010;33(3):225-35.

Mansoor et al., Engineering T cells for cancer therapy. Br J Cancer. Nov. 14, 2005;93(10):1085-91.

Manzari-Tavakoli et al., The Cross-Talks Among Bone Morphogenetic Protein (BMP) Signaling and Other Prominent Pathways Involved in Neural Differentiation. Front Mol Neurosci. Mar. 15, 2022;15:827275, 15 pages.

Martinsen et al., Alginate as immobilization material: I. Correlation between chemical and physical properties of alginate gel beads. Biotechnol Bioeng. Jan. 5, 1989;33(1):79-89.

Marui et al., Simultaneous application of basic fibroblast growth factor and hepatocyte growth factor to enhance the blood vessels formation. J Vasc Surg. Jan. 2005;41(1):82-90.

Masedunskas et al., Role for the actomyosin complex in regulated exocytosis revealed by intravital microscopy. Proc Natl Acad Sci U S A. Aug. 16, 2011;108(33):13552-7.

Massia et al., An RGD spacing of 440 nm is sufficient for integrin alpha V beta 3-mediated fibroblast spreading and 140 nm for focal contact and stress fiber formation. J Cell Biol. Sep. 1991;114(5):1089-100.

Matthew et al., Subperiosteal behaviour of alginate and cellulose wound dressing materials. Biomaterials. Mar. 1995;16(4):275-8.

Maus et al., Ex vivo expansion of polyclonal and antigen-specific cytotoxic T lymphocytes by artificial APCs expressing ligands for the T-cell receptor, CD28 and 4-1BB. Nat Biotechnol. Feb. 2002;20(2):143-8.

McColl, Chemokines and dendritic cells: a crucial alliance. Immunol Cell Biol. Oct. 2002;80(5):489-96.

McConnell et al., Vaccination with outer membrane complexes elicits rapid protective immunity to multidrug-resistant Acinetobacter baumannii. Infect Immun. Jan. 2011;79(1):518-26.

McDonald et al., Early fracture callus displays smooth muscle-like viscoelastic properties ex vivo: implications for fracture healing. J Orthop Res. Nov. 2009;27(11):1508-13.

McKay et al., Click chemistry in complex mixtures: bioorthogonal bioconjugation. Chem Biol. Sep. 18, 2014;21(9):1075-101.

McKinney-Freeman et al., Muscle-derived hematopoietic stem cells are hematopoietic in origin. Proc Natl Acad Sci U S A. Feb. 5, 2002;99(3):1341-6.

McKinnon et al., Biophysically defined and cytocompatible covalently adaptable networks as viscoelastic 3D cell culture systems. Adv Mater. Feb. 12, 2014;26(6):865-72.

McPherron et al., Regulation of skeletal muscle mass in mice by a new TGF-beta superfamily member. Nature. May 1, 1997;387(6628):83-90.

McQualter et al., Granulocyte macrophage colony-stimulating factor: a new putative therapeutic target in multiple sclerosis. J Exp Med. Oct. 1, 2001;194(7):873-82.

McWhorter et al., Modulation of macrophage phenotype by cell shape. Proc Natl Acad Sci USA. Oct. 22, 2013;110(43):17253-8.

Mehta et al., Engineering New Approaches to Cancer Vaccines. Cancer Immunol Res. Aug. 2015;3(8):836-43.

Meier et al., Peptide Nucleic Acids(PNAs)—Unusual Properties of Noionic Oligonucleotide Analogues. Angewandte Chemie, Int'l Edition. Aug. 1992;31(8):1008-1010.

Melero-Martin et al., Engineering robust and functional vascular networks in vivo with human adult and cord blood-derived progenitor cells. Circ Res. Jul. 18, 2008;103(2):194-202. Includes supplementary materials.

Melief et al., Immunotherapy of established (pre)malignant disease by synthetic long peptide vaccines. Nat Rev Cancer. May 2008;8(5):351-60.

Melief et al., T-cell immunotherapy of tumors by adoptive transfer of cytotoxic T lymphocytes and by vaccination with minimal essential epitopes. Immunol Rev. Jun. 1995; 145:167-77.

Mellman et al., Dendritic cells: specialized and regulated antigen processing machines. Cell. Aug. 10, 2001;106(3):255-8.

Menetry et al., Suturing Versus Immobilization of a Muscle Laceration: A Morphological and Functional Study in a Mouse Model. Am J Sports Med. 1999;27(2):222-229.

(56) References Cited

OTHER PUBLICATIONS

Meng et al., Use of a lipid-coated mesoporous silica nanoparticle platform for synergistic gemcitabine and paclitaxel delivery to human pancreatic cancer in mice. ACS Nano. 2015;9(4):3540-57.

Meraz et al., Mesoporous Silicon Particles for the Presentation of Tumor Antigens and Adjuvant for Anti-Cancer Immunity. Cancer Res. 2011;71(S24):159s-160s, Abstract #P1-01-12.

Merck, Merck Announces Presentation of Interim Data from Phase 1B Study of MK-3475, Investigational anti-PD-1 Immunotherapy, in Previously-Treated Patients with Non-Small Cell Lung Cancer (NSCLC) at 15th World Conference on Lung Cancer. Merck Newsroom Home. 3 pages, Oct. 29, 2013.

Merkel et al., Using mechanobiological mimicry of red blood cells to extend circulation times of hydrogel microparticles. Proc Natl Acad Sci U S A. Jan. 11, 2011;108(2):586-91.

Merriam-Webster, Transient. Merriam-Webster Dictionary. Web. Jul. 18, 2014. www.merriam-webster.com/dictionary/transient. 3 pages.

MeSH, Nivolumab. Retrieved online at: https://www.ncbi.nlm.nih.gov/mesh/?term=nivolumab. 2 pages, (2010).

Metters et al., Fundamental studies of biodegradable hydrogels as cartilage replacement materials. Biomed Sci Instrum. 1999;35:33-8.

Meyer et al., Biodegradable nanoellipsoidal artificial antigen presenting cells for antigen specific T-cell activation. Small. Apr. 2015;11(13):1519-25.

Meyer et al., Clinical investigations of Toll-like receptor agonists. Expert Opin Investig Drugs. Jul. 2008;17(7):1051-65.

Meylan et al., Intracellular pattern recognition receptors in the host response. Nature. Jul. 6, 2006;442(7098):39-44.

MGI, Mouse Facts. Retrieved online at: http://www.informatics.jax.org/mgihome/other/mouse_facts1.shtml. 2 pages. Jul. 31, 2018.

Miljkovic et al., Chondrogenesis, bone morphogenetic protein-4 and mesenchymal stem cells. Osteoarthritis Cartilage. Oct. 2008;16(10):1121-30.

Millar et al., Prediction of local recurrence, distant metastases, and death after breast-conserving therapy in early-stage invasive breast cancer using a five-biomarker panel. J Clin Oncol. Oct. 1, 2009;27(28):4701-8.

Miller et al., Hepatocyte growth factor affects satellite cell activation and differentiation in regenerating skeletal muscle. Am J Physiol Cell Physiol. Jan. 2000;278(1):C174-81.

Miller et al., Lipopolysaccharide sequestrants: structural correlates of activity and toxicity in novel acylhomospermines. J Med Chem. Apr. 7, 2005;48(7):2589-99.

Miller et al., Melanoma. N Engl J Med. Jul. 6, 2006;355(1):51-65.

Milone et al., Powered and controlled T-cell production. Nat Biomed Eng. Mar. 2018;2(3):148-150.

Miralles et al., Actin dynamics control SRF activity by regulation of its coactivator MAL. Cell. May 2, 2003;113(3):329-42.

Mitchell et al., The exogenous administration of basic fibroblast growth factor to regenerating skeletal muscle in mice does not enhance the process of regeneration. Growth Factors. 1996;13(1-2):37-55.

Miyata et al., Biomolecule-sensitive hydrogels. Adv Drug Deliv Rev. Jan. 17, 2002;54(1):79-98.

Mohan et al., Novel Porous, Polysaccharide Scaffolds for Tissue Engineering Applications. Trends Biomater Artif Organs. 2005;18(2):219-224.

Moioli et al., Matrices and scaffolds for drug delivery in dental, oral and craniofacial tissue engineering. Adv Drug Deliv Rev. May 30, 2007;59(4-5):308-24.

Molinari et al., Modification of surface membrane antigens by trypsin. Proc Soc Exp Biol Med. Apr. 1975;148(4):991-4.

Molloy et al., Movement and force produced by a single myosin head. Nature. Nov. 9, 1995;378(6553):209-12.

Mooney et al., Cytoskeletal filament assembly and the control of cell spreading and function by extracellular matrix. J Cell Sci. Jun. 1995;108 (Pt 6):2311-20.

Mooney et al., Switching from differentiation to growth in hepatocytes: control by extracellular matrix. J Cell Physiol. Jun. 1992; 151(3):497-505.

Moser et al., Dendritic cell regulation of TH1-TH2 development. Nat Immunol. Sep. 2000;1(3):199-205.

Mu et al., Identification and characterization of a mannose-binding lectin from Nile tilapia (*Oreochromis niloticus*). Fish Shellfish Immunol. 2017;67:244-253.

Mulder et al., Wound Management: Past, Present, and Future. Clinicians' Pocket Guide to Chronic Wound Repair. Springhouse Corporation, Springhouse, Pennsylvania. 1998:85-90.

Muralidharan-Chari et al., ARF6-regulated shedding of tumor cell-derived plasma membrane microvesicles. Curr Biol. Dec. 1, 2009;19(22):1875-85.

Murdan, Electro-responsive drug delivery from hydrogels. J Control Release. Sep. 19, 2003;92(1-2):1-17.

Murray et al., Discussion: Turing's Theory of Morphogenesis—Its Influence on Modelling Biological Pattern and Form. Bull Math Biol. 1990;52(1-2):119-152.

Nagai et al., A variant of yellow fluorescent protein with fast and efficient maturation for cell-biological applications. Nat Biotechnol. Jan. 2002;20(1):87-90.

Naik et al., Development of plasmacytoid and conventional dendritic cell subtypes from single precursor cells derived in vitro and in vivo. Nat Immunol. Nov. 2007;8(11):1217-26.

NCBI Accession No. 000749.2, Apr. 1, 2012.

NCBI Accession No. 001020537, Jan. 30, 2011.

NCBI Accession No. 001020538, Jan. 30, 2011.

NCBI Accession No. 001020539, Jan. 30, 2011.

NCBI Accession No. 001020540, Jan. 30, 2011.

NCBI Accession No. 001028928, Jan. 30, 2011.

NCBI Accession No. 001193, May 3, 2014.

NCBI Accession No. 001552.2, Mar. 16, 2014.

NCBI Accession No. 001561.5, Mar. 16, 2014.

NCBI Accession No. 003237.2, May 25, 2014.

NCBI Accession No. 003265, Dec. 30, 2012.

NCBI Accession No. 003318.1, May 4, 2014.

NCBI Accession No. 003327.3, May 4, 2014.

NCBI Accession No. 003367, Jan. 30, 2011.

NCBI Accession No. 004119, Apr. 14, 2013.

NCBI Accession No. 004448.3, Apr. 23, 2014.

NCBI Accession No. 005009.2, Apr. 27, 2014.

NCBI Accession No. 005018.2, Apr. 27, 2014.

NCBI Accession No. 006274.2, Mar. 31, 2013.

NCBI Accession No. 017442, Apr. 14, 2012.

NCBI Accession No. 059138, Apr. 14, 2012.

NCBI Accession No. 181780.3, Jan. 27, 2014.

NCBI Accession No. 861445.3, Jan. 27, 2014.

NCBI, MeSH. Nivolumab. Retrieved online at: https://www.ncbi.nlm.nih/gov/mesh/?term=nivolumab. 3 pages, (2010).

Nehls et al., A novel, microcarrier-based in vitro assay for rapid and reliable quantification of three-dimensional cell migration and angiogenesis. Microvasc Res. Nov. 1995;50(3):311-22.

Nestle et al., Vaccination of melanoma patients with peptide- or tumorlysate-pulsed dendritic cells. Nature Medicine. Mar. 1, 1998;4(3):328-32.

Niamlang et al., Electrically controlled release of salicylic acid from poly(p-phenylene vinylene)/polyacrylamide hydrogels. Int J Pharm. Apr. 17, 2009;371(1-2):126-33.

Nichol et al., Cell-laden microengineered gelatin methacrylate hydrogels. Biomaterials. Jul. 2010;31(21):5536-44.

Nicodemus et al., Cell encapsulation in biodegradable hydrogels for tissue engineering applications. Tissue Eng Part B Rev. Jun. 2008;14(2):149-65.

Niessen et al., The alpha 6 beta 4 integrin is a receptor for both laminin and kalinin. Exp Cell Res. Apr. 1994;211(2):360-7.

NIH—National Cancer Institute, AMP-224, anti-PD-1 fusion protein AMP-224. Retrieved online at: https://www.cancer/gov/publications/dictionaries/cancer-drug/def/anti-pd-1-fusion-protein-amp-224. 1 page, (2019).

Noguera-Troise et al., Blockade of Dll4 inhibits tumour growth by promoting non-productive angiogenesis. Nature. Dec. 21, 2006;444(7122):1032-7.

(56)　　　　　References Cited

OTHER PUBLICATIONS

Nuttelman et al., Dexamethasone-functionalized gels induce osteogenic differentiation of encapsulated hMSCs. J Biomed Mater Res A. Jan. 2006;76(1):183-95.

Ní Annaidh et al., Characterization of the anisotropic mechanical properties of excised human skin. J Mech Behav Biomed Mater. Jan. 2012;5(1):139-48.

O'Garra et al., Are dendritic cells afraid of commitment? Nat Immunol. Dec. 2004;5(12):1206-8.

O'Shea et al., Type 1 IFNs and regulation of TH1 responses: enigmas both resolved and emerge. Nat Immunol. Jul. 2000;1(1):17-9.

Ohashi et al., Surgical excision combined with autologous whole tumor cell vaccination is an effective therapy for murine neuroblastoma. J Pediatr Surg. Aug. 2006;41(8):1361-8.

Ohlstein et al., The stem cell niche: theme and variations. Curr Opin Cell Biol. Dec. 2004;16(6):693-9.

Oldenburg et al., TLR13 recognizes bacterial 23S rRNA devoid of erythromycin resistance-forming modification. Science. Aug. 31, 2012;337(6098):1111-5.

Oldenhove et al., Decrease of Foxp3+ Treg cell number and acquisition of effector cell phenotype during lethal infection. Immunity. Nov. 20, 2009;31(5):772-86.

Oneto et al., Implantable biomaterial based on click chemistry for targeting small molecules. Acta Biomaterialia. 2014;10:5099-5105.

Orner et al., Arrays for the combinatorial exploration of cell adhesion. J Am Chem Soc. Sep. 8, 2004;126(35):10808-9.

Osunkoya et al., Synthesis and fate of immunological surface receptors on cultured Burkitt lymphoma cells. Int J Cancer. Mar. 15, 1969;4(2):159-65.

Ota et al., Percutaneous subxiphoid access to the epicardium using a miniature crawling robotic device. Innovations (Phila). 2006 Fall;1(5):227-31.

Overwijk et al., Tumor regression and autoimmunity after reversal of a functionally tolerant state of self-reactive CD8+ T cells. J Exp Med. Aug. 18, 2003;198(4):569-80.

Ozawa et al., Microenvironmental VEGF concentration, not total dose, determines a threshold between normal and aberrant angiogenesis. J Clin Invest. Feb. 2004;113(4):516-27.

Padilla et al., Insufficient TLR activation contributes to the slow development of CD8+ T cell responses in Trypanosoma cruzi infection. J Immunol. Jul. 15, 2009;183(2):1245-52.

Page-McCaw et al., Matrix metalloproteinases and the regulation of tissue remodelling. Nat Rev Mol Cell Biol. Mar. 2007;8(3):221-33.

Pailler-Mattei et al., In vivo measurements of the elastic mechanical properties of human skin by indentation tests. Med Eng Phys. Jun. 2008;30(5):599-606.

Pajonk et al., From sol-gel to aerogels and cryogels. J Non Cryst Solids. May 1990;121(1-3):66-67.

Palacio et al., Interleukin 10 and tumor necrosis factor alpha gene expression in respiratory and peripheral muscles. Relation to sarcolemmal damage. Arch Bronconeumol. Jul. 2002;38(7):311-6.

Paradee et al., Effects of crosslinking ratio, model drugs, and electric field strength on electrically controlled release for alginate-based hydrogel. J Mater Sci Mater Med. Apr. 2012;23(4):999-1010.

Pardoll, The blockade of immune checkpoints in cancer immunotherapy. Nat Rev Cancer. Mar. 22, 2012;12(4):252-64.

Parekh et al., Modulus-driven differentiation of marrow stromal cells in 3D scaffolds that is independent of myosin-based cytoskeletal tension. Biomaterials. Mar. 2011;32(9):2256-64.

Parekkadan et al., Mesenchymal stem cell-derived molecules reverse fulminant hepatic failure. PLoS One. Sep. 26, 2007;2(9):e941.

Park et al., Photopolymerized hyaluronic acid-based hydrogels and interpenetrating networks. Biomaterials. Mar. 2003;24(6):893-900.

Parker et al., Effect of mitoxantrone on outcome of children with first relapse of acute lymphoblastic leukaemia (All R3): an open-label randomised trial. Lancet. Dec. 11, 2010;376(9757):2009-17.

Partridge et al., Conversion of mdx myofibres from dystrophin-negative to -positive by injection of normal myoblasts. Nature. Jan. 12, 1989;337(6203):176-9.

Patterson et al., Differential binding of chemokines to macrophages and neutrophils in the human inflamed synovium. Arthritis Res. 2002;4(3):209-14.

Pawlaczyk et al., Age-dependent biomechanical properties of the skin. Postepy Dermatol Alergol. Oct. 2013;30(5):302-6.

Pedersen et al., Induction of regulatory dendritic cells by dexamethasone and 1alpha, 25-Dihydroxyvitamin D(3). Immunol Lett. Jan. 30, 2004;91(1):63-9.

Pek et al., The effect of matrix stiffness on mesenchymal stem cell differentiation in a 3D thixotropic gel. Biomaterials. Jan. 2010;31(3):385-91.

Pelinkovic et al., Tissue engineering and gene therapy of the musculoskeletal system with muscle cells. Z Orthop Ihre Grenzgeb. Sep.-Oct. 2000;138(5):402-6.

Pena et al., Effects of TGF-beta and TGF-beta neutralizing antibodies on fibroblast-induced collagen gel contraction: implications for proliferative vitreoretinopathy. Invest Ophthalmol Vis Sci. May 1994;35(6):2804-8.

Perica et al., Enrichment and Expansion with Nanoscale Artificial Antigen Presenting Cells for Adoptive Immunotherapy. ACS Nano. Jul. 28, 2015;9(7):6861-71.

Peters et al., Engineering vascular networks in porous polymer matrices. J Biomed Mater Res. Jun. 15, 2002;60(4):668-78.

Peyton et al., The use of poly(ethylene glycol) hydrogels to investigate the impact of ECM chemistry and mechanics on smooth muscle cells. Biomaterials. Oct. 2006;27(28):4881-93.

Phillippi, Patterning of Multiple Cell Lineages from a Single Stem Cell Population. Annual Meeting of the American Society for Cell Biology. Dec. 10, 2006.

Pinho et al., PDGFRa and CD51 mark human nestin+ sphere-forming mesenchymal stem cells capable of hematopoietic progenitor cell expansion. J Exp Med. Jul. 1, 2013;210(7):1351-67.

Platten et al., Cancer Immunotherapy by Targeting IDO1/TDO and Their Downstream Effectors. Front Immunol. Jan. 12, 2015;5:673. 7 pages.

Pluen et al., Role of tumor-host interactions in interstitial diffusion of macromolecules: cranial vs. subcutaneous tumors. Proc Natl Acad Sci U S A. Apr. 10, 2001;98(8):4628-33.

Pooyan et al., Conjugates bearing multiple formyl-methionyl peptides display enhanced binding to but not activation of phagocytic cells. Bioconjug Chem. Mar.-Apr. 2002;13(2):216-23.

Pope et al., Organ-specific regulation of the CD8 T cell response to Listeria monocytogenes infection. J Immunol. Mar. 1, 2001;166(5):3402-9.

Porter et al., Separation of Natural Populations of Coliform Bacteria from Freshwater and Sewage by Magnetic-Bead Cell Sorting. J Microbiol Meth. 1998;33(3):221-226.

Pouzet et al., Factors affecting functional outcome after autologous skeletal myoblast transplantation. Ann Thorac Surg. Mar. 2001;71(3):844-50; discussion 850-1.

PRNewswire, GlaxoSmithKline and Amplimmune Form Global Strategic Collaboration. Alliance to Focus on AMP-224 for Cancer and Other Diseases. 3 pages, Aug. 4, 2010.

Pulendran et al., Flt3-ligand and granulocyte colony-stimulating factor mobilize distinct human dendritic cell subsets in vivo. J Immunol. Jul. 1, 2000;165(1):566-72.

Qi et al., Patterned differentiation of individual embryoid bodies in spatially organized 3D hybrid microgels. Adv Mater. Dec. 7, 2010;22(46):5276-81.

Qiao et al., Synthesis and Bio-adsorptive Properties of Large-Pore Periodic Mesoporous Organosilica Rods. Chem Mater. 2005;17:6172-6.

Qin et al., CD22-Targeted Chimeric Antigen Receptor (CAR) T Cells Containing The 4-1BB Costimulatory Domain Demonstrate Enhanced Persistence and Superior Efficacy Against B-Cell Precursor Acute Lymphoblastic Leukemia (ALL) Compared to Those Containing CD28. Blood. 2013;122:1431.

Qin et al., Soft lithography for micro- and nanoscale patterning. Nat Protoc. Mar. 2010;5(3):491-502.

Qiu et al., Environment-sensitive hydrogels for drug delivery. Adv Drug Deliv Rev. Dec. 31, 2001;53(3):321-39.

Qu et al., Development of approaches to improve cell survival in myoblast transfer therapy. J Cell Biol. Sep. 7, 1998;142(5):1257-67.

(56) References Cited

OTHER PUBLICATIONS

Qu-Petersen et al., Identification of a novel population of muscle stem cells in mice: potential for muscle regeneration. J Cell Biol. May 27, 2002;157(5):851-64.

Quezada et al., CTLA4 blockade and GM-CSF combination immunotherapy alters the intratumor balance of effector and regulatory T cells. J Clin Invest. Jul. 2006;116(7):1935-45.

Quintana et al., Autoantibody patterns in diabetes-prone NOD mice and in standard C57BL/6 mice. J Autoimmun. Nov. 2001;17(3):191-7.

Raeber et al., Molecularly engineered PEG hydrogels: a novel model system for proteolytically mediated cell migration. Biophys J. Aug. 2005;89(2):1374-88.

Rajagopalan et al., Regional angiogenesis with vascular endothelial growth factor in peripheral arterial disease: a phase II randomized, double-blind, controlled study of adenoviral delivery of vascular endothelial growth factor 121 in patients with disabling intermittent claudication. Circulation. Oct. 21, 2003;108(16):1933-8.

Ramón-Azcón et al., Gelatin methacrylate as a promising hydrogel for 3D microscale organization and proliferation of dielectrophoretically patterned cells. Lab on a Chip. Aug. 21, 2012;12(16):2959-69.

Randolph et al., Migration of dendritic cell subsets and their precursors. Annu Rev Immunol. 2008;26:293-316.

Ranganath et al., Harnessing the mesenchymal stem cell secretome for the treatment of cardiovascular disease. Cell Stem Cell. Mar. 2, 2012;10(3):244-58.

Raposo et al., Extracellular vesicles: exosomes, microvesicles, and friends. J Cell Biol. Feb. 18, 2013;200(4):373-83.

Rappolee et al., Macrophage-derived growth factors. Curr Top Microbiol Immunol. 1992;181:87-140.

Rapraeger, Syndecan-regulated receptor signaling. J Cell Biol. May 29, 2000;149(5):995-8.

Reddy et al., Exploiting lymphatic transport and complement activation in nanoparticle vaccines. Nat Biotechnol. Oct. 2007;25(10):1159-64.

Reimann et al., Satellite Cells in Normal and Regenerated Soleus Muscles of mdx and Control Mice. Eur J Neurosci. 1998;10:366, Abstract No. 153.07.

Reis E Sousa., Activation of dendritic cells: translating innate into adaptive immunity. Curr Opin Immunol. Feb. 2004;16(1):21-5.

Research Results of National Institute of Advanced Industrial Science and Technology, retrieved online at: http://www.aist.go.jp/aist_j/press_release/pr2006/pr20060719.html. 4 pages, (2006).

Rhoads et al., Satellite cell-mediated angiogenesis in vitro coincides with a functional hypoxia-inducible factor pathway. Am J Physiol Cell Physiol. Jun. 2009;296(6):C1321-8.

Ribas et al., Phase III randomized clinical trial comparing tremelimumab with standard-of-care chemotherapy in patients with advanced melanoma. J Clin Oncol. Feb. 10, 2013;31(5):616-22.

Richards Grayson et al., Multi-pulse drug delivery from a resorbable polymeric microchip device. Nat Mater. Nov. 2003;2(11):767-72.

Richardson et al., Polymeric system for dual growth factor delivery. Nat Biotechnol. Nov. 2001;19(11):1029-34.

Riddell et al., Phase I Study of Cellular Adoptive Immunotherapy Using Genetically Modified CD8+ HIV-Specific T Cells for HIV Seropositive Patients Undergoing Allogeneic Bone Marrow Transplant. Fred Hutchinson Cancer Research Center and the University of Washington. Human Gene Therapy. Jun. 1992;3(3):319-338.

Riddell et al., Principles for adoptive T cell therapy of human viral diseases. Annu Rev Immunol. 1995;13:545-86.

Riddell et al., Restoration of viral immunity in immunodeficient humans by the adoptive transfer of T cell clones. Science. Jul. 10, 1992;257(5067):238-41.

Riddell et al., The use of anti-CD3 and anti-CD28 monoclonal antibodies to clone and expand human antigen-specific T cells. J Immunol Methods. Apr. 17, 1990;128(2):189-201.

Riddle et al., Role of poly(lactide-co-glycolide) particle size on gas-foamed scaffolds. J Biomater Sci Polym Ed. 2004;15(12):1561-70.

Ridgway et al., Inhibition of Dll4 signalling inhibits tumour growth by deregulating angiogenesis. Nature. Dec. 21, 2006;444(7122):1083-7.

Rinderknecht et al., The amino acid sequence of human insulin-like growth factor I and its structural homology with proinsulin. J Biol Chem. Apr. 25, 1978;253(8):2769-76.

Rizzo et al., An improved cyan fluorescent protein variant useful for FRET. Nat Biotechnol. Apr. 2004;22(4):445-9.

Roccaro et al., BM mesenchymal stromal cell-derived exosomes facilitate multiple myeloma progression. J Clin Invest. Apr. 2013; 123(4):1542-55.

Rodriguez et al., Minimal "Self" peptides that inhibit phagocytic clearance and enhance delivery of nanoparticles. Science. Feb. 22, 2013;339(6122):971-5.

Rosenberg et al., Adoptive cell transfer as personalized immunotherapy for human cancer. Science. Apr. 3, 2015;348(6230):62-8.

Rosenberg et al., Cancer immunotherapy: moving beyond current vaccines. Nat Med. Sep. 2004;10(9):909-15.

Rosenberg et al., Durable complete responses in heavily pretreated patients with metastatic melanoma using T-cell transfer immunotherapy. Clin Cancer Res. Jul. 1, 2011;17(13):4550-7.

Roth et al., SC68896, a novel small molecule proteasome inhibitor, exertsin vitro and in vivo. Clin Cancer Res. Nov. 1, 2009;15(21):6609-18.

Rowlands et al., Directing osteogenic and myogenic differentiation of MSCs: interplay of stiffness and adhesive ligand presentation. Am J Physiol Cell Physiol. Oct. 2008;295(4):C1037-44.

Rowley et al., Alginate hydrogels as synthetic extracellular matrix materials. Biomaterials. Jan. 1999;20(1):45-53.

Rowley et al., Alginate type and RGD density control myoblast phenotype. J Biomed Mater Res. May 2002;60(2):217-23.

Rowley et al., Biomaterials to Spatially Regulate Cell Fate. Adv Mater. Jun. 2002;14(12):886-889.

Rubbi et al., Evidence of surface antigen detachment during incubation of cells with immunomagnetic beads. J Immunol Methods. Dec. 3, 1993;166(2):233-41.

Rubin et al., Dissociation of heparan sulfate and receptor binding domains of hepatocyte growth factor reveals that heparan sulfate-c-met interaction facilitates signaling. J Biol Chem. Aug. 31, 2001;276(35):32977-83.

Ryten et al., ATP regulates the differentiation of mammalian skeletal muscle by activation of a P2X5 receptor on satellite cells. J Cell Biol. Jul. 22, 2002;158(2):345-55.

Ryu et al., The construction of three-dimensional micro-fluidic scaffolds of biodegradable polymers by solvent vapor based bonding of micro-molded layers. Biomaterials. Feb. 2007;28(6):1174-84.

Sacchetti et al., Self-renewing osteoprogenitors in bone marrow sinusoids can organize a hematopoietic microenvironment. Cell. Oct. 19, 2007;131(2):324-36.

Sahdev et al., Biomaterials for nanoparticle vaccine delivery systems. Pharm Res. Oct. 2014;31(10):2563-82.

Sakai et al., An injectable, in situ enzymatically gellable, gelatin derivative for drug delivery and tissue engineering. Biomaterials. Jul. 2009;30(20):3371-7.

Salem et al., Defining the antigen-specific T-cell response to vaccination and poly(I:C)/TLR3 signaling: evidence of enhanced primary and memory CD8 T-cell responses and antitumor immunity. J Immunother. May-Jun. 2005;28(3):220-8.

Salvador et al., Combination of immune stimulating adjuvants with poly(lactide-co-glycolide) microspheres enhances the immune response of vaccines. Vaccine. Jan. 11, 2012;30(3):589-96.

Salvay et al., Inductive tissue engineering with protein and DNA-releasing scaffolds. Mol Biosyst. Jan. 2006;2(1):36-48.

Sano et al., Swift development of protective effector functions in naive CD8(+) T cells against malaria liver stages. J Exp Med. Jul. 16, 2001;194(2):173-9.

Sansonetti, The innate signaling of dangers and the dangers of innate signaling. Nat Immunol. Dec. 2006;7(12):1237-42.

Sarkar et al., Condensation of oligonucleotides assembled into nicked and gapped duplexes: potential structures for oligonucleotide delivery. Nucleic Acids Res. Jan. 7, 2005;33(1):143-51.

Sato, Human dendritic cells. Biotherapy. Nov. 2004;18(6):467-77.

(56)          References Cited

OTHER PUBLICATIONS

Saxena et al., Skeletal muscle tissue engineering using isolated myoblasts on synthetic biodegradable polymers: preliminary studies. Tissue Eng. Dec. 1999;5(6):525-32.
Schaefer et al., Innate immunity in the human female reproductive tract: antiviral response of uterine epithelial cells to the TLR3 agonist poly(I:C). J Immunol. Jan. 15, 2005;174(2):992-1002.
Scheel et al., Toll-like receptor-dependent activation of several human blood cell types by protamine-condensed mRNA. Eur J Immunol. May 2005;35(5):1557-66.
Schijns et al., Mice lacking IL-12 develop polarized Th1 cells during viral infection. J Immunol. Apr. 15, 1998;160(8):3958-64.
Schnorrer et al., The dominant role of CD8+ dendritic cells in cross-presentation is not dictated by antigen capture. Proc Natl Acad Sci U S A. Jul. 11, 2006;103(28):10729-34.
Schofield, The relationship between the spleen colony-forming cell and the haemopoietic stem cell. Blood Cells. 1978;4(1-2):7-25.
Schuler et al., The use of dendritic cells in cancer immunotherapy. Curr Opin Immunol. Apr. 2003;15(2):138-47.
Schwartz, A cell culture model for T lymphocyte clonal anergy. Science. Jun. 15, 1990;248(4961):1349-56.
Schwartz, Integrins and extracellular matrix in mechanotransduction. Cold Spring Harb Perspect Biol. Dec. 2010;2(12):a005066.
Seale et al., Pax7 is required for the specification of myogenic satellite15;102(6):777-86.
Sensi et al., Unique tumor antigens: evidence for immune control of genome integrity and immunogenic targets for T cell-mediated patient-specific immunotherapy. Clin Cancer Res. Sep. 1, 2006;12(17):5023-32.
Shah et al., An injectable bone marrow-like scaffold enhances T cell immunity after hematopoietic stem cell transplantation. Nat Biotechnol. Mar. 2019;37(3):293-302, with correction Nat Biotechnol. Nov. 2021;39:1466.
Shakweh et al., Design and characterisation of poly(lactide-co-glycolide) small particulate systems for the delivery of immunostimulant CpG oligonucleotide. J Nanosci Nanotechnol. Sep.-Oct. 2006;6(9-10):2811-20.
Shaner et al., Improved monomeric red, orange and yellow fluorescent proteins derived from *Discosoma* sp. red fluorescent protein. Nat Biotechnol. Dec. 2004;22(12):1567-72.
Shansky et al., A simplified method for tissue engineering skeletal muscle organoids in vitro. In Vitro Cell Dev Biol Anim. Oct. 1997;33(9):659-61.
Shapiro et al., Sizing it up: cellular MRI using micron-sized iron oxideMed. Feb. 2005;53(2):329-38.
Sheehan et al., Skeletal muscle satellite cell proliferation in response to members of the fibroblast growth factor family and hepatocyte growth factor. J Cell Physiol. Dec. 1999;181(3):499-506.
Sheppard et al., Polyethyleneimine is a potent systemic adjuvant for glycoprotein antigens. Int Immunol. Oct. 2014;26(10):531-8.
Sheridan et al., Bioabsorbable polymer scaffolds for tissue engineering capable of sustained growth factor delivery. J Control Release. Feb. 14, 2000;64(1-3):91-102.
Shi et al., A novel Toll-like receptor that recognizes vesicular stomatitis virus. J Biol Chem. Feb. 11, 2011;286(6):4517-24.
Shi et al., Granulocyte-macrophage colony-stimulating factor (GM-CSF) and T-cell responses: what we do and don't know. Cell Res. Feb. 2006;16(2):126-33.
Shibuya et al., Anti-CD3/anti-CD28 bead stimulation overcomes CD3 unresponsiveness in patients with head and neck squamous cell carcinoma. Arch Otolaryngol Head Neck Surg. Apr. 2000;126(4):473-9.
Shin et al., Contractile forces sustain and polarize hematopoiesis from stem and progenitor cells. Cell Stem Cell. Jan. 2, 2014;14(1):81-93.
Shin et al., Lamins regulate cell trafficking and lineage maturation of adult human hematopoietic cells. Proc Natl Acad Sci U S A. Nov. 19, 2013;110(47):18892-7.

Shin et al., Myosin-II inhibition and soft 2D matrix maximize multinucleation and cellular projections typical of platelet-producing megakaryocytes. Proc Natl Acad Sci U S A. Jul. 12, 2011;108(28):11458-63.
Shoichet et al., Stability of hydrogels used in cell encapsulation: An in vitro comparison of alginate and agarose. Biotechnol Bioeng. May 20, 1996;50(4):374-81.
Shortman et al., Steady-state and inflammatory dendritic-cell development. Nat Rev Immunol. Jan. 2007;7(1):19-30.
Shukla, Controlled Generation of Progenitor T-cells from Hematopoietic Stem Cells and Pluripotent Stem Cells. A thesis submitted in conformity with the requirements for the degree of Doctorate of Philosophy, Institute of Biomaterials and Biomedical Engineering, University of Toronto. 214 pages, (2017).
Sick et al., WNT and DKK determine hair follicle spacing through a reaction-diffusion mechanism. Science. Dec. 1, 2006;314(5804):1447-50.
Siegwart et al., Synthesis, characterization, and in vitro cell culture viability of degradable poly(N-isopropylacrylamide-co-5,6-benzo-2-methylene-1,3-dioxepane)-based polymers and crosslinked gels. J Biomed Mater Res A. Nov. 2008;87(2):345-58.
Silva et al., Effects of VEGF temporal and spatial presentation on angiogenesis. Biomaterials. Feb. 2010;31(6):1235-41.
Silva et al., Material-based deployment enhances efficacy of endothelial progenitor cells. Proc Natl Acad Sci U S A. Sep. 23, 2008;105(38):14347-52.
Silva et al., Spatiotemporal control of vascular endothelial growth factor delivery from injectable hydrogels enhances angiogenesis. J Thromb Haemost. Mar. 2007;5(3):590-8.
Simmons et al., GM-CSF as a systemic adjuvant in a phase II prostate cancer vaccine trial. Prostate. Jun. 1, 1999;39(4):291-7.
Simpson et al., Fc-dependent depletion of tumor-infiltrating regulatory T cells co-defines the efficacy of anti-CTLA-4 therapy against melanoma. J Exp Med. Aug. 26, 2013;210(9):1695-710.
Singer et al., Cutaneous wound healing. N Engl J Med. Sep. 2, 1999;341(10):738-46.
Singh et al., Hydrogels and scaffolds for immunomodulation. Adv Mater. Oct. 2014;26(38):6530-41.
Skokos et al., CD8- DCs induce IL-12-independent Th1 differentiation through Delta 4 Notch-like ligand in response to bacterial LPS. J Exp Med. Jul. 9, 2007;204(7):1525-31.
Skuk et al., Efficacy of myoblast transplantation in nonhuman primates following simple intramuscular cell injections: toward defining strategies applicable to humans. Exp Neurol. May 2002;175(1):112-26.
Skuk et al., Myoblast transplantation: the current status of a potential therapeutic tool for myopathies. J Muscle Res Cell Motil. 2003;24(4-6):285-300.
Sletten et al., A hydrophilic azacyclooctyne for Cu-free click chemistry. Org Lett. Jul. 17, 2008;10(14):3097-9.
Smidsrød et al., Alginate as immobilization matrix for cells. Trends Biotechnol. Mar. 1990;8(3):71-8.
Sobral et al., Antigen-free cancer vaccine to treat poorly immunogenic tumors. Cancer Immunol Res. 2019;7(2 Suppl):Abstract B045.
Sohier et al., Critical factors in the design of growth factor releasing scaffolds for cartilage tissue engineering. Expert Opin Drug Deliv. May 2008;5(5):543-66.
Solon et al., Fibroblast adaptation and stiffness matching to soft elastic substrates. Biophys J. Dec. 15, 2007;93(12):4453-61.
Sonawane et al., Chloride accumulation and swelling in endosomes enhances DNA transfer by polyamine-DNA polyplexes. J Biol Chem. Nov. 7, 2003;278(45):44826-31.
Springer et al., The lymphocyte function-associated LFA-1, CD2, and LFA-3 molecules: cell adhesion receptors of the immune system. Annu Rev Immunol. 1987;5:223-52.
Stachowiak et al., Inverse opal hydrogel-collagen composite scaffolds as a supportive microenvironment for immune cell migration. J Biomed Mater Res A. Jun. 1, 2008;85(3):815-28.
Stanley et al., Transjugular intrahepatic portosystemic shunt as a treatment for protein-losing enteropathy caused by portal hypertension. Gastroenterology. Dec. 1996;111(6):1679-82.

(56) References Cited

OTHER PUBLICATIONS

Steenblock et al., A comprehensive platform for ex vivo T-cell expansion based on biodegradable polymeric artificial antigen-presenting cells. Mol Ther. Apr. 2008; 16(4):765-72.

Steenblock et al., An artificial antigen-presenting cell with paracrine delivery of IL-2 impacts the magnitude and direction of the T cell response. J Biol Chem. Oct. 7, 2011;286(40):34883-92.

Steinman et al., Taking dendritic cells into medicine. Nature. Sep. 27, 2007;449(7161):419-26.

Stephen et al., Biopolymer implants enhance the efficacy of adoptive T-cell therapy. Nat Biotechnol. Jan. 2015;33(1):97-101.

Stockmann et al., Exploring isonitrile-based click chemistry for ligation with biomolecules. Organic & Biomolecular Chemistry. 2011;9:7300-7302.

Storrie et al., Sustained delivery of plasmid DNA from polymeric scaffolds for tissue engineering. Adv Drug Deliv Rev. Jul. 7, 2006;58(4):500-14.

Straub et al., Animal models for muscular dystrophy show different patterns of sarcolemmal disruption. J Cell Biol. Oct. 20, 1997;139(2):375-85.

Sun et al., Biomimetic interpenetrating polymer network hydrogels based on methacrylated alginate and collagen for 3D pre-osteoblast spreading and osteogenic differentiation. Soft Matter. Jan. 12, 2012;8:2398-2404.

Sun et al., Highly stretchable and tough hydrogels. Nature. Sep. 6, 2012;489(7414):133-6.

Sun et al., Sustained vascular endothelial growth factor delivery enhances angiogenesis and perfusion in ischemic hind limb. Pharm Res. Jul. 2005;22(7):1110-6.

Sunshine et al., Nanoengineering approaches to the design of artificial antigen-presenting cells. Nanomedicine. 2013;8(7):1173-89.

Sunshine et al., Particle shape dependence of CD8+ T cell activation by artificial antigen presenting cells. Biomaterials. Jan. 2014;35(1):269-277.

Super et al., Biomaterial vaccines capturing pathogen-associated molecular patterns protect against bacterial infections and septic shock. Nat Biomed Eng. Jan. 2022;6(1):8-18.

Suri et al., Photopatterned collagen-hyaluronic acid interpenetrating polymer network hydrogels. Acta Biomater. Sep. 2009;5(7):2385-97.

Suzuki et al., A novel small-molecule inhibitor of transforming growth factor beta type I receptor kinase (SM16) inhibits murine mesothelioma tumor growth in vivo and prevents tumor recurrence after surgical resection. Cancer Res. Mar. 1, 2007;67(5):2351-9.

Swift et al., Nuclear lamin-A scales with tissue stiffness and enhances matrix-directed differentiation. Science. Aug. 30, 2013;341(6149):1240104. 17 pages.

Syed et al., Stem cell therapy market. Nat Rev Drug Discov. Mar. 2013;12(3):185-6.

Tabata et al., Enhanced Vascularization and Tissue Granulation by Basic Fibroblast Growth Factor Impregnated in Gelatin Hydrogels. Journal of Controlled Release. Sep. 1994;31(2):189-199.

Takahashi et al., Induction of pluripotent stem cells from adult human fibroblasts by defined factors. Cell. Nov. 30, 2007;131(5):861-72.

Takamura et al., Regulatory role of lymphoid chemokine CCL19 and CCL21 in the control of allergic rhinitis. J Immunol. 2007;179(9):5897-5906.

Takeshita et al., Therapeutic angiogenesis. A single intraarterial bolus of vascular endothelial growth factor augments revascularization in a rabbit ischemic hind limb model. J Clin Invest. Feb. 1994;93(2):662-70.

Tamura et al., Immunotherapy of tumors with autologous tumor-derived heat shock protein preparations. Science. Oct. 3, 1997;278(5335):117-20.

Tanaka et al., Collapse of gels in an electric field. Science. Oct. 29, 1982;218(4571):467-9.

Tang et al., Combining radiation and immunotherapy: a new systemictumors? Cancer Immunol Res. Sep. 2014;2(9):831-8.

Tannous, Gaussia luciferase reporter assay for monitoring biological processes in culture and in vivo. Nat Protoc. 2009;4(4):582-91.

Tatsumi et al., HGF/SF is present in normal adult skeletal muscle and is capable of activating satellite cells. Dev Biol. Feb. 1, 1998;194(1):114-28.

Ten Dijke et al., Growth Factors for Wound Healing. Nat Biotechnol. 1989;7:792-798.

Thelin et al., In Vivo Enrichment of Diabetogenic T Cells. Diabetes. Aug. 2017;66(8):2220-2229.

Thielemann et al., Pore structure and surface area of silica SBA-15: influence of washing and scale-up. Beilstein J Nanotechnol. 2011;2:110-8.

Thomas et al., Intravenous infusion of bone marrow in patients receiving radiation and chemotherapy. N Engl J Med. Sep. 12, 1957;257(11):491-6.

Thornton et al., Shape retaining injectable hydrogels for minimally invasive bulking. J Urol. Aug. 2004;172(2):763-8.

Thurner et al., Vaccination with mage-3A1 peptide-pulsed mature, monocyte-derived dendritic cells expands specific cytotoxic T cells and induces regression of some metastases in advanced stage IV melanoma. J Exp Med. Dec. 6, 1999;190(11):1669-78.

Thurston et al., The Delta paradox: DLL4 blockade leads to more tumour vessels but less tumour growth. Nat Rev Cancer. May 2007;7(5):327-31.

Tidball, Inflammatory cell response to acute muscle injury. Med Sci Sports Exerc. Jul. 1995;27(7):1022-32.

Titan et al., Growth Factor Delivery to a Bovine Defect Using Leukocyte-Rich Platelet-Rich Concentrates on a Hyaluronic Acid Scaffold. Arthroscopy: The Journal of Arthroscopic and Related Surgery. Pre-publication edition, 33 pages, Dec. 2019.

Tomer et al., Electrically Controlled Release of Macromolecules from Cross-Linked Hyaluronic Acid Hydrogels. Journal of Controlled Release. Mar. 1995;33(3):405-413.

Tong et al., Engineering interpenetrating network hydrogels as biomimetic cell niche with independently tunable biochemical and mechanical properties. Biomaterials. Feb. 2014;35(6):1807-15.

Tourniaire et al., Polymer microarrays for cellular adhesion. Chem Commun (Camb). May 28, 2006;(20):2118-20.

Trappmann et al., Extracellular-matrix tethering regulates stem-cell fate. Nat Mater. May 27, 2012;11(7):642-9.

Trappmann et al., How cells sense extracellular matrix stiffness: a material's perspective. Curr Opin Biotechnol. Oct. 2013;24(5):948-53.

Tripathi et al., Elastic and macroporous agarose-gelatin cryogels with isotropic and anisotropic porosity for tissue engineering. J Biomed Mater Res A. Sep. 1, 2009;90(3):680-94.

Tsien, The green fluorescent protein. Annu Rev Biochem. 1998;67:509-44.

Turing, The Chemical Basis of Morphogenesis. Philosophical Transactions of the Royal Society of London. Series B. 1952;237(641):37-72.

Turtle et al., Anti-CD19 Chimeric Antigen Receptor-Modified T Cell Therapy for B Cell Non-Hodgkin Lymphoma and Chronic Lymphocytic Leukemia: Fludarabine and Cyclophosphamide Lymphodepletion Improves In Vivo Expansion and Persistence of CAR-T Cells and Clinical Outcomes. Blood. 2015;126:184.

Turtle et al., CD19 CAR-T cells of defined CD4+:CD8+ composition inpatients. J Clin Invest. Jun. 1, 2016;126(6):2123-38.

Uchida et al., Immunization by particle bombardment of antigen-loaded poly-(DL-lactide-co-glycolide) microspheres in mice. Vaccine. Mar. 15, 2006;24(12):2120-30.

Udono, Cancer immunotherapy with blocking of immune checkpoint. Journal of Okayama Medical Association. Apr. 2013; 125:13-18.

Ugarte et al., Notch signaling enhances osteogenic differentiation while inhibiting adipogenesis in primary human bone marrow stromal cells. Exp Hematol. Jul. 2009;37(7):867-875.e1.

Uhlenbruck, Action of proteolytic enzymes on the human erythrocyte surface. Nature. Apr. 8, 1961;190:181.

Ulrich et al., Probing cellular mechanobiology in three-dimensional culture with collagen-agarose matrices. Biomaterials. Mar. 2010;31(7):1875-84.

UniProtKB/Swiss-Prot Accession No. P02751.4, Apr. 16, 2014.

(56) References Cited

OTHER PUBLICATIONS

UniProtKB/Swiss-Prot Accession No. P02778.2, Jun. 11, 2014.
UniProtKB/Swiss-Prot Accession No. P04626.1, Apr. 16, 2014.
UniProtKB/Swiss-Prot Accession No. P05121.1, Apr. 16, 2014.
UniProtKB/Swiss-Prot Accession No. P05231.1, Jun. 11, 2014.
UniProtKB/Swiss-Prot Accession No. P09038.3, Jun. 11, 2014.
UniProtKB/Swiss-Prot Accession No. P10145.1, Jun. 11, 2014.
UniProtKB/Swiss-Prot Accession No. P13500.1, Jun. 11, 2014.
UniProtKB/Swiss-Prot Accession No. P14210.2, Jun. 11, 2014.
UniProtKB/Swiss-Prot Accession No. P14780.3, Jun. 11, 2014.
UniProtKB/Swiss-Prot Accession No. P14902.1, May 14, 2014.
UniProtKB/Swiss-Prot Accession No. P15692.2, Jun. 11, 2014.
UniProtKB/Swiss-Prot Accession No. P16035.2, Jun. 11, 2014.
UniProtKB/Swiss-Prot Accession No. P16410.3, Apr. 16, 2014.
UniProtKB/Swiss-Prot Accession No. P48061.1, Jun. 18, 2014.
UniProtKB/Swiss-Prot Accession No. P80162.4, Jun. 11, 2014.
UniProtKB/Swiss-Prot Accession No. P98066.2, Feb. 19, 2014.
UniProtKB/Swiss-Prot Accession No. Q8TDQ0.3, Mar. 19, 2014.
UniProtKB/Swiss-Prot Accession No. Q96HF1.2, May 14, 2014.
UniProtKB/Swiss-Prot Accession No. Q9BQ51.2, Mar. 19, 2014.
UniProtKB/Swiss-Prot Accession No. Q9HCB6.2, Jun. 11, 2014.
UniProtKB/Swiss-Prot Accession No. Q9NZQ7.1, Apr. 16, 2014.
Urbanek et al., Stem cell niches in the adult mouse heart. Proc Natl Acad Sci U S A. Jun. 13, 2006;103(24):9226-31.
Van Berkel et al., Metal-free triazole formation as a tool for bioconjugation. Chembiochem. Sep. 3, 2007;8(13):1504-8.
Van De Walle et al., Jagged2 acts as a Delta-like Notch ligand during early hematopoietic cell fate decisions. Blood. Apr. 28, 2011;117(17):4449-59.
Van Der Bruggen et al., Peptide Database: T cell-defined tumor antigens. Cancer Immunity. Retrieved online at: http://www.cancerimmunity.org/peptide/ 59 pages. (2013).
Van Duin et al., Triggering TLR signaling in vaccination. Trends Immunol. Jan. 2006;27(1):49-55.
Van Elsas et al., Combination immunotherapy of B16 melanoma using anti-cytotoxic T lymphocyte-associated antigen 4 (CTLA-4) and granulocyte/macrophage colony-stimulating factor (GM-CSF)-producing vaccines induces rejection of subcutaneous and metastatic tumors accompanied by autoimmune depigmentation. J Exp Med. Aug. 2, 1999;190(3):355-66.
Van Elsas et al., Elucidating the autoimmune and antitumor effector mechanisms of a treatment based on cytotoxic T lymphocyte antigen-4 blockade in combination with a B16 melanoma vaccine: comparison of prophylaxis and therapy. J Exp Med. Aug. 20, 2001;194(4):481-9.
Van Tendeloo et al., Induction of complete and molecular remissions in acute myeloid leukemia by Wilms' tumor 1 antigen-targeted dendritic cell vaccination. Proc Natl Acad Sci U S A. Aug. 3, 2010;107(31):13824-9.
Vandenburgh et al., Tissue-engineered skeletal muscle organoids for reversible gene therapy. Hum Gene Ther. Nov. 10, 1996;7(17):2195-200.
Veldhoen et al., TGFbeta1, a "Jack of all trades": the link with pro-inflammatory IL-17-producing T cells. Trends Immunol. Aug. 2006;27(8):358-61.
Venturoni et al., Investigations into the polymorphism of rat tail tendon fibrils using atomic force microscopy. Biochem Biophys Res Commun. Apr. 4, 2003;303(2):508-13.
Vieira et al., Polysaccharide-based hydrogels: preparation, characterization, and drug interaction behaviour. Biomacromolecules. Apr. 2008;9(4):1195-9.
Vieira et al., The bulk of endogenously produced IgG2a is eliminated from the serum of adult C57BL/6 mice with a half-life of 6-8 days. Eur J Immunol. Jul. 1986;16(7):871-4.
Vieira et al., The half-lives of serum immunoglobulins in adult mice. Eur J Immunol. Feb. 1988;18(2):313-6.
Villadangos et al., Intrinsic and cooperative antigen-presenting functions of dendritic-cell subsets in vivo. Nat Rev Immunol. Jul. 2007;7(7):543-55.

Villadangos, Presentation of antigens by MHC class II molecules: getting the most out of them. Mol Immunol. Sep. 2001;38(5):329-46.
Vincent et al., Stem cell differentiation: Post-degradation forces kick in. Nat Mater. May 2013;12(5):384-6.
Vogel et al., Local force and geometry sensing regulate cell functions. Nat Rev Mol Cell Biol. Apr. 2006;7(4):265-75.
Von Dassow et al., The segment polarity network is a robust developmental module. Nature. Jul. 13, 2000;406(6792):188-92.
W.H.O., World Health Organization, Global Burden of Musculoskeletal Disease Revealed in new WHO Report. Bull World Health Organ. 2003;81(11):853-854.
W.H.O., World Health Organization, The World Health Report 2004: Changing History. The World Health Report. 2004:1-169.
Wakim et al., Dendritic cell-induced memory T cell activation in nonlymphoid tissues. Science. Jan. 11, 2008;319(5860):198-202.
Wan et al., Peritoneal macrophage uptake, pharmacokinetics and biodistribution of macrophage-targeted PEG-fMLF (N-formyl-methionyl-leucyl-phenylalanine) nanocarriers for improving HIV drug delivery. Pharm Res. Nov. 2007;24(11):2110-9.
Wang et al., Biological activity of bevacizumab, a humanized anti-VEGF antibody in vitro. Angiogenesis. 2004;7(4):335-45.
Wang et al., Biomaterial-based scaffold for in situ chemo-immunotherapy to treat poorly immunogenic tumors. Nat Commun. Nov. 10, 2020;11(1):5696, 41 pages with supplementary materials.
Wang et al., Bone Morphogenetic Protein (BMP) signaling in development and human diseases. Genes Dis. Sep. 2014;1(1):87-105.
Wang et al., Evolution of new nonantibody proteins via iterative somatic hypermutation. Proc Natl Acad Sci U S A. Nov. 30, 2004;101(48):16745-9.
Wang et al., Mechanotransduction at a distance: mechanically coupling the extracellular matrix with the nucleus. Nat Rev Mol Cell Biol. Jan. 2009;10(1):75-82.
Wang et al., Mouse CD229 Ligation Co-stimulates T Cell Activation. The Journal of Immunology. May 2012;188(suppl 1):176.7.
Wang et al., Photothermal effects of supramolecularly assembled gold nanoparticles for the targeted treatment of cancer cells. Angew Chem Int Ed Engl. May 17, 2010;49(22):3777-81.
Wang-Gillam et al., A phase I study of IMP321 and gemcitabine as the front-line therapy in patients with advanced pancreatic adenocarcinoma. Invest New Drugs. Jun. 2013;31(3):707-13.
Warner et al., Cyclooxygenases: new forms, new inhibitors, and lessons from the clinic. FASEB J. May 2004;18(7):790-804.
Weeks et al., The effects of chemokine, adhesion and extracellular matrix molecules on binding of mesenchymal stromal cells to poly(I-lactic acid). Cytotherapy. Oct. 2012; 14(9):1080-8.
Wegman et al., Combination of bone morphogenetic protein-2 plasmid DNA with chemokine CXCL12 creates an additive effect on bone formation onset and vol. Eur Cell Mater. Jul. 27, 2015;30:1-11.
Wegmann et al., Polyethyleneimine is a potent mucosal adjuvant for viral glycoprotein antigens. Nat Biotechnol. Sep. 2012;30(9):883-8.
Wei et al., Global mapping of H3K4me3 and H3K27me3 reveals specificity and plasticity in lineage fate determination of differentiating CD4+ T cells. Immunity. Jan. 16, 2009;30(1):155-67.
Weiner et al., Immunostimulatory oligodeoxynucleotides containing the CpG motif are effective as immune adjuvants in tumor antigen immunization. Proc Natl Acad Sci U S A. Sep. 30, 1997;94(20):10833-7.
Weiner, Induction and mechanism of action of transforming growth factor-beta-secreting Th3 regulatory cells. Immunol Rev. Aug. 2001;182:207-14.
Weisenberger et al., Comprehensive DNA Methylation Analysis on the Illumina® Infinium® Assay Platform. Illumina, Inc., 4 pages, Mar. 25, 2008.
Weiss et al., The demonstration of rupture of cell surfaces by an immunological technique. Exp Cell Res. Apr. 1963;30:331-8.
Wen et al., Mechanically Robust Gelatin-Alginate IPN Hydrogels by a Combination of Enzymatic and Ionic Crosslinking Approaches. Macromol Mater Eng. Apr. 2014;299(4):504-513.

(56)  References Cited

OTHER PUBLICATIONS

Wernig et al., Function of skeletal muscle tissue formed after myoblast transplantation into irradiated mouse muscles. J Physiol. Jan. 15, 2000;522 Pt 2:333-45.

White et al., Leukemia inhibitory factor enhances regeneration in skeletal muscles after myoblast transplantation. Muscle Nerve. May 2001;24(5):695-7.

Wieland et al., Engineering molecular circuits using synthetic biology in mammalian cells. Annu Rev Chem Biomol Eng. 2012;3:209-34.

Wikipedia, Matrigel. Retrieved online at: https://en.wikipedia.org/wiki/Matrigel. 4 pages, Oct. 10, 2018.

Wipff et al., Myofibroblast contraction activates latent TGF-beta1 from the extracellular matrix. J Cell Biol. Dec. 17, 2007;179(6):1311-23.

Wolchok et al., Nivolumab plus ipilimumab in advanced melanoma. N Engl J Med. Jul. 11, 2013;369(2):122-33.

Wong et al., Focal adhesion kinase links mechanical force to skin fibrosis via inflammatory signaling. Nat Med. Dec. 11, 2011;18(1):148-52.

Wong et al., Mechanical force prolongs acute inflammation via T-cell-dependent pathways during scar formation. FASEB J. Dec. 2011;25(12):4498-510.

Wong et al., Pushing back: wound mechanotransduction in repair and regeneration. J Invest Dermatol. Nov. 2011;131(11):2186-96.

Wozniak et al., Mechanotransduction in development: a growing role for contractility. Nat Rev Mol Cell Biol. Jan. 2009; 10(1):34-43.

Wright et al., Muscle-based gene therapy and tissue engineering for the musculoskeletal system. Drug Discov Today. Jul. 1, 2001;6(14):728-733.

Wu et al., Intraperitoneal administration of poly(I:C) with polyethylenimine leads to significant antitumor immunity against murine ovarian tumors. Cancer Immunol Immunother. Aug. 2011;60(8):1085-96.

Xia et al., Polyethyleneimine coating enhances the cellular uptake of mesoporous silica nanoparticles and allows safe delivery of siRNA and DNA constructs. ACS Nano. Oct. 27, 2009;3(10):3273-86.

Xie et al., Preparation and Application of Surface-Coated Superparamagnetic Nanobeads in the Isolation of Genomic DNA. J Magn Magnetic Mater. Jun. 2004;277(1-2):16-23.

Xiong et al., Transcription Factor STAT3 as a Novel Molecular Target for Cancer Prevention. Cancers (Basel). Apr. 16, 2014;6(2):926-57.

Xue et al., Efficient cancer cell capturing SiNWAs prepared via surface-initiated SET-LRP and click chemistry. Polymer Chemistry. 2015;6:3708-15. Pre-publication edition.

Yamazaki et al., CD8+ CD205+ splenic dendritic cells are specialized to induce Foxp3+ regulatory T cells. J Immunol. Nov. 15, 2008;181(10):6923-33.

Yancopoulos et al., Vascular-specific growth factors and blood vessel formation. Nature. Sep. 14, 2000;407(6801):242-8.

Yang et al., The effect of incorporating RGD adhesive peptide in polyethylene glycol diacrylate hydrogel on osteogenesis of bone marrow stromal cells. Biomaterials. Oct. 2005;26(30):5991-8.

Yee et al., Melanocyte destruction after antigen-specific immunotherapy of melanoma: direct evidence of t cell-mediated vitiligo. J Exp Med. Dec. 4, 2000;192(11):1637-44.

Yeung et al., Effects of substrate stiffness on cell morphology, cytoskeletal structure, and adhesion. Cell Motil Cytoskeleton. Jan. 2005;60(1):24-34.

Yoo et al., Bio-inspired, bioengineered and biomimetic drug delivery carriers. Nat Rev Drug Discov. Jul. 1, 2011;10(7):521-35.

Yoon, Hidden Markov Models and their Applications in Biological Sequence Analysis. Curr Genomics. Sep. 2009;10(6):402-15.

Young et al., Gelatin as a delivery vehicle for the controlled release of bioactive molecules. J Control Release. Dec. 5, 2005;109(1-3):256-74.

Yu et al., Induced pluripotent stem cell lines derived from human somatic cells. Science. Dec. 21, 2007;318(5858):1917-20.

Yu et al., Specific bone cells produce DLL4 to generate thymus-seeding progenitors from bone marrow. J Exp Med. May 4, 2015;212(5):759-74.

Yu, Designed synthesis of mono-dispersed silica-based nanostructures and their applications in drug/gene delivery. A thesis submitted for the degree of Doctor of Philosophy at The University of Queensland in 2014, 196 pages.

Yuen et al., Mimicking nature by codelivery of stimulant and inhibitor to create temporally stable and spatially restricted angiogenic zones. Proc Natl Acad Sci U S A. Oct. 19, 2010;107(42):17933-8.

Yuk et al., Electric current-sensitive drug delivery systems using sodium alginate/polyacrylic acid composites. Pharm Res. Jul. 1992;9(7):955-7.

Zammit et al., Kinetics of myoblast proliferation show that resident satellite cells are competent to fully regenerate skeletal muscle fibers. Exp Cell Res. Nov. 15, 2002;281(1):39-49.

Zammit et al., Muscle satellite cells adopt divergent fates: a mechanism for self-renewal? J Cell Biol. Aug. 2, 2004;166(3):347-57.

Zappasodi et al., The effect of artificial antigen-presenting cells with preclustered anti-CD28/-CD3/-LFA-1 monoclonal antibodies on the induction of ex vivo expansion of functional human antitumor T cells. Haematologica. Oct. 2008;93(10):1523-34.

Zeltinger et al., Effect of pore size and void fraction on cellular adhesion, proliferation, and matrix deposition. Tissue Eng. Oct. 2001;7(5):557-72.

Zemel et al., Optimal matrix rigidity for stress fiber polarization in stem cells. Nat Phys. Jun. 1, 2010;6(6):468-473.

Zhang et al., A comparative study of the antigen-specific immune response induced by co-delivery of CpG ODN and antigen using fusion molecules or biodegradable microparticles. J Pharm Sci. Dec. 2007;96(12):3283-92.

Zhang et al., A tension-induced mechanotransduction pathway promotes epithelial morphogenesis. Nature. Mar. 3, 2011;471(7336):99-103.

Zhang et al., Generation of a syngeneic mouse model to study the effects of vascular endothelial growth factor in ovarian carcinoma. Am J Pathol. Dec. 2002;161(6):2295-309.

Zhang et al., Talin depletion reveals independence of initial cell spreading from integrin activation and traction. Nat Cell Biol. Sep. 2008;10(9):1062-8.

Zhao et al., A cell-permeable Stat3 SH2 domain mimetic inhibits Stat3 activation and induces antitumor cell effects in vitro. J Biol Chem. Nov. 12, 2010;285(46):35855-65.

Zhao et al., Active scaffolds for on-demand drug and cell delivery. Proc Natl Acad Sci U S A. Jan. 4, 2011;108(1):67-72.

Zhao et al., Directed cell migration via chemoattractants released from degradable microspheres. Biomaterials. Aug. 2005;26(24):5048-63.

Zhao et al., Stress-relaxation behavior in gels with ionic and covalent crosslinks. J Appl Phys. Mar. 15, 2010;107(6):63509.

Zhou et al., Instability of the transcription factor Foxp3 leads to the generation of pathogenic memory T cells in vivo. Nat Immunol. Sep. 2009;10(9):1000-7.

Zhou et al., Microstructure and Mechanical Properties of Poly(L-lactide) Scaffolds Fabricated by Gelatin Particle Leaching Method. J Appl Polymer Sci. Nov. 5, 2005;98(3):1373-1379.

Zizzari et al., The Macrophage Galactose-Type C-Type Lectin (MGL) Modulates Regulatory T Cell Functions. PLoS One. Jul. 6, 2015;10(7):e0132617. 12 pages.

Japanese Office Action for Application No. 2016-565339, dated Jan. 8, 2019. 9 pages.

U.S. Appl. No. 15/434,781, filed Feb. 16, 2017, U.S. Pat. No. 10,813,988, Issued.

U.S. Appl. No. 17/015,177, filed Sep. 9, 2020, U.S. Pat. No. 11,638,74, Issued.

U.S. Appl. No. 18/186,588, filed Mar. 20, 2023, Pending.

U.S. Appl. No. 13/386,950, filed Jan. 25, 2012, U.S. Pat. No. 8,728,456, Issued.

U.S. Appl. No. 14/185,494, filed Feb. 20, 2014, U.S. Pat. No. 9,381,235, Issued.

U.S. Appl. No. 15/147,442, filed May 5, 2016, U.S. Pat. No. 10,080,789, Issued.

(56) References Cited

OTHER PUBLICATIONS

U.S. Appl. No. 16/121,988, filed Sep. 5, 2018, 2019-0183992, Abandoned.
U.S. Appl. No. 15/564,905, filed Oct. 6, 2017, U.S. Pat. No. 11,150,242, Issued.
U.S. Appl. No. 17/501,821, filed Oct. 14, 2021, 2022-0107308, Published.
U.S. Appl. No. 16/316,778, filed Jan. 10, 2019, U.S. Pat. No. 11,555,177, Issued.
U.S. Appl. No. 18/072,449, filed Nov. 30, 2022, Pending.
U.S. Appl. No. 11/638,796, filed Dec. 13, 2006, U.S. Pat. No. 8,067,237, Issued.
U.S. Appl. No. 13/305,088, filed Nov. 28, 2011, U.S. Pat. No. 8,932,583, Issued.
U.S. Appl. No. 14/223,759, filed Mar. 24, 2014, U.S. Pat. No. 9,132,210, Issued.
U.S. Appl. No. 14/750,423, filed Jun. 25, 2015, U.S. Pat. No. 9,446,107, Issued.
U.S. Appl. No. 15/085,858, filed Mar. 30, 2016, 2016-0271298, Abandoned.
U.S. Appl. No. 15/135,207, filed Apr. 21, 2016, U.S. Pat. No. 10,149,897, Issued.
U.S. Appl. No. 15/135,213, filed Apr. 21, 2016, U.S. Pat. No. 10,137,184, Issued.
U.S. Appl. No. 16/170,313, filed Oct. 25, 2018, U.S. Pat. No. 11,096,997, Issued.
U.S. Appl. No. 17/381,031, filed Jul. 20, 2021, Abandoned.
U.S. Appl. No. 13/877,572, filed Nov. 19, 2013, U.S. Pat. No. 11,202,759, Issued.
U.S. Appl. No. 17/522,297, filed Nov. 9, 2021, 2022-0192986, Published.
U.S. Appl. No. 14/112,096, filed Dec. 27, 2014, U.S. Pat. No. 10,045,947, Issued.
U.S. Appl. No. 14/166,689, filed Jan. 28, 2014, U.S. Pat. No. 9,675,561, Issued.
U.S. Appl. No. 15/617,837, filed Jun. 8, 2017, 2018-0243231, Abandoned.
U.S. Appl. No. 16/033,025, filed Jul. 11, 2018, 2019-0076373, Abandoned.
U.S. Appl. No. 17/083,720, filed Oct. 29, 2020, 2021-0205233, Published.
U.S. Appl. No. 18/095,488, filed Jan. 10, 2023, Pending.
U.S. Appl. No. 14/394,552, filed Oct. 15, 2014, U.S. Pat. No. 9,937,249, Issued.
U.S. Appl. No. 15/935,392, filed Mar. 26, 2018, U.S. Pat. No. 11,278,604, Issued.
U.S. Appl. No. 17/693,017, filed Mar. 11, 2022, 2023-0000961, Published.
U.S. Appl. No. 15/303,985, filed Oct. 13, 2016, U.S. Pat. No. 10,682,400, Issued.
U.S. Appl. No. 16/877,274, filed May 18, 2020, 2020-0276290, Published.
U.S. Appl. No. 16/263,098, filed Jan. 31, 2019, 2019-0216910, Published.
U.S. Appl. No. 12/867,426, filed Jan. 13, 2012, U.S. Pat. No. 10,328,133, Issued.

U.S. Appl. No. 15/135,255, filed Apr. 21, 2016, U.S. Pat. No. 10,258,677, Issued.
U.S. Appl. No. 15/135,290, filed Apr. 21, 2016, 2016-0228543, Abandoned.
U.S. Appl. No. 15/135,294, filed Apr. 21, 2016, 2016-0220668, Abandoned.
U.S. Appl. No. 13/510,356, filed May 17, 2012, Abandoned.
U.S. Appl. No. 14/123,615, filed Mar. 17, 2014, U.S. Pat. No. 9,486,512, Issued.
U.S. Appl. No. 15/345,131, filed Nov. 7, 2016, U.S. Pat. No. 10,406,216, Issued.
U.S. Appl. No. 13/741,271, filed Jan. 14, 2013, U.S. Pat. No. 9,370,558, Issued.
U.S. Appl. No. 15/135,216, filed Apr. 21, 2016, U.S. Pat. No. 9,821,045, Issued.
U.S. Appl. No. 15/818,509, filed Nov. 20, 2017, U.S. Pat. No. 10,568,949, Issued.
U.S. Appl. No. 15/563,878, filed Oct. 2, 2017, 2018-0117171, Abandoned.
U.S. Appl. No. 15/546,852, filed Jul. 27, 2017, U.S. Pat. No. 11,786,457, Issued.
U.S. Appl. No. 17/206,050, filed Mar. 18, 2021, 2021-0284776, Published.
U.S. Appl. No. 16/075,937, filed Aug. 6, 2018, U.S. Pat. No. 11,752,238, Issued.
U.S. Appl. No. 18/224,444, filed Jul. 20, 2023, Pending.
U.S. Appl. No. 16/708,218, filed Dec. 9, 2019, 2020-0206333, Published.
U.S. Appl. No. 17/701,270, filed Mar. 22, 2022, 2022-0339274, Published.
U.S. Appl. No. 17/869,611, filed Jul. 20, 2022, 2023-0085214, Published.
Chen et al., Vascular Endothelial Cells in Pharmacology and Clinical. People's Military Medical Press. p.65, Dec. 31, 2012.
Chew et al., Biomaterial-Based Implantable Devices for Cancer Therapy. Adv Healthcare Mater. 2017;6:1600766, 22 pages.
Chong et al., Combining cancer vaccines with chemotherapy. Expert Opin Pharmacother. Dec. 2005;6(16):2813-20.
Melchionna et al., Induction of myogenic differentiation by SDF-1 via CXCR4 and CXCR7 receptors. Muscle Nerve. Jun. 2010;41(6):828-35.
Poldervaart et al., Sustained release of BMP-2 in bioprinted alginate for osteogenicity in mice and rats. PLoS One. Aug. 19, 2013;8(8):e72610, 10 pages.
Sakai et al., Clinical effect and immunological response in patients with advanced malignant glioma treated with WT1-pulsed dendritic cell-based immunotherapy: A report of two cases. Interdisciplinary Neurosurgery: Advanced Techniques and Care Management. 2017;9:24-29.
Shen et al., Sequential and sustained release of SDF-1 and BMP-2 from silk fibroin-nanohydroxyapatite scaffold for the enhancement of bone regeneration. Biomaterials. Nov. 2016; 106:205-16.
Thornton et al., Shape-defining scaffolds for minimally invasive tissue engineering. Transplantation. Jun. 27, 2004;77(12):1798-803.
Chinese Office Action for Application No. 202210961302.X, dated Jun. 4, 2025, 20 pages.

* cited by examiner

GFP Alginate

Transplant only    ■ Bolus    ▲ BMP-2 BMC    ▼ Dual BMC

Donor          Host

● NSG-BLT          ■ NSG-BLT + BMC

1

BIOENGINEERED SCAFFOLDS FOR MODULATION OF IMMUNE SYSTEM AND THE USES THEREOF

RELATED APPLICATIONS

This application is a continuation of International Patent Application No.: PCT/US2019/066086, filed Dec. 12, 2019, which claims the benefit of U.S. Provisional Application No. 62/780,727, filed Dec. 17, 2018 and U.S. Provisional Application No. 62/798,100, filed Jan. 29, 2019. The entire contents of each of the foregoing applications are hereby incorporated herein by reference.

GOVERNMENT SUPPORT

This invention was made with Government support under HL129903, EB015498, EB014703, and EB023287 awarded by the National Institutes of Health. The Government has certain rights in the invention.

BACKGROUND OF THE INVENTION

Long-term immunodeficiency in patients receiving a hematopoietic stem cell transplantation (HSCT) remains one of the most serious impediments in managing life threatening diseases of the blood or bone marrow, such as multiple myeloma and leukemia. Before transplantation, the recipient undergoes a conditioning cytotoxic radiation and chemotherapy regimen to destroy the diseased cells. A side effect of the conditioning process is severe lymphopenia as a result of T- and B-cell destruction of the adaptive immune system. The profound post-transplantation immunodeficiency, which is characterized by a dramatic reduction in the number of T- and B-cells and a reduction in their diversity, can persist for one to two years. Immunodeficiency related severe opportunistic infections (–30%), cancer relapse (>50% for acute myeloid leukemia) and graft-versus-host disease (GVHD) (–40%) are the most common complications and cause of morbidity and mortality in patients receiving a HSCT.

There is a need for novel compositions and methods that are useful for improving the reconstitution of the immune system post-HSCT. There is also a need for compositions and methods that are able to reduce the risk associated with HSCT and improve patient outcomes.

SUMMARY OF THE INVENTION

Disclosed herein are novel compositions and methods for modulating the immune system of a subject. The composition and methods disclosed herein provide a means to treat and/or prevent diseases associated with deficiency and/or dysregulation of T-cells.

Accordingly, in one aspect, the present invention provides a composition for modulating the immune system in a subject. The composition includes a porous scaffold, a growth factor present at between about 1 ng to about 1000 ng per scaffold, and in an amount effective for inducing formation of a tissue or an organ within the scaffold and recruiting a cell into the scaffold, and a differentiation factor that induces the differentiation of the recruited cell into a T cell progenitor cell. In one embodiment, the growth factor is present at about 0.03 $ng/mm^3$ to about 350 $ng/mm^3$ by volume of the scaffold.

In another aspect, the present invention provides a composition for modulating the immune system in a subject. The composition includes a porous scaffold, a growth factor present at between about 0.03 $ng/mm^3$ to about 350 $ng/mm^3$ by volume of scaffold, and in an amount effective for inducing formation of a tissue or an organ within the scaffold and recruiting a cell into the scaffold, and a differentiation factor that induces the differentiation of the recruited cell into a T cell progenitor cell.

In various embodiments of the above aspects or any other aspect of the invention delineated herein, the scaffold includes a hydrogel. In one embodiment, the scaffold includes a cryogel. In another embodiment, the scaffold includes a polymer or co-polymer selected from the group consisting of polylactic acid, polyglycolic acid, PLGA, alginate or an alginate derivative, gelatin, collagen, agarose, hyaluronic acid, poly(lysine), polyhydroxybutyrate, poly-epsilon-caprolactone, polyphosphazines, poly(vinyl alcohol), poly(alkylene oxide), poly(ethylene oxide), poly(allylamine), poly(acrylate), poly(4-aminomethylstyrene), pluronic polyol, polyoxamer, poly(uronic acid), poly(anhydride), poly(vinylpyrrolidone), and any combination thereof. In still another embodiment, the scaffold includes a polymer or co-polymer selected from the group consisting of alginate, alginate derivative, and the combination thereof. In yet another embodiment, the scaffold includes a polymer or co-polymer selected from the group consisting of hyaluronic acid, hyaluronic acid derivative, and the combination thereof.

In various embodiments of the above aspects or any other aspect of the invention delineated herein, the scaffold includes pores having a diameter between about 1 μm and 100 μm. In one embodiment, the scaffold includes a macropore. In another embodiment, the macropore has a diameter between about 50 μm and 80 μm. In still another embodiment, the scaffold includes macropores of different sizes.

In various embodiments of the above aspects or any other aspect of the invention delineated herein, the scaffold is injectable.

In various embodiments of the above aspects or any other aspect of the invention delineated herein, the scaffold includes methacrylated alginate (MA-alginate).

In various embodiments of the above aspects or any other aspect of the invention delineated herein, the scaffold comprises a hyaluronic acid or a hyaluronic acid-derivative.

In various embodiments of the above aspects or any other aspect of the invention delineated herein, the scaffold includes a click-hydrogel or click cryogel. In one embodiment, the scaffold includes a click-alginate, a click gelatin, or a click hyaluronic acid.

In various embodiments of the above aspects or any other aspect of the invention delineated herein, the scaffold includes porogen hydrogel microbeads and a bulk hydrogel, wherein the porogen hydrogel microbeads degrade at least 10% faster than the bulk hydrogel polymer scaffold following administration of the scaffold into a subject. In one embodiment, the porogen hydrogel microbeads include oxidized alginate.

In various embodiments of the above aspects or any other aspect of the invention delineated herein, the cell is a stem cell. In one embodiment, the stem cell is a hematopoietic stem cell.

In various embodiments of the above aspects or any other aspect of the invention delineated herein, the cell is a progenitor cell.

In various embodiments of the above aspects or any other aspect of the invention delineated herein, the tissue or the organ includes a bone tissue or a hematopoietic tissue. In one embodiment, the tissue or the organ is formed about 7-21 days after the composition is administered to the subject. In another embodiment, the tissue or the organ is formed about 14 days after the composition is administered to the subject.

In various embodiments of the above aspects or any other aspect of the invention delineated herein, the cell is a stromal cell.

In various embodiments of the above aspects or any other aspect of the invention delineated herein, the scaffold is between about 100 $\mu m^3$ to about 10 $cm^3$ in size. In one embodiment, the scaffold is between about 10 $mm^3$ to about 100 $mm^3$ in size. In another embodiment, the scaffold is about 30 $mm^3$ in size.

In various embodiments of the above aspects or any other aspect of the invention delineated herein, the growth factor includes a protein belonging to transforming growth factor protein beta (TGF-β) superfamily. In one embodiment, the growth factor includes a protein selected from the group consisting of a BMP-2, a BMP-4, a BMP-6, a BMP-7, a BMP-12, a BMP-14, a growth differentiation factor (GDF)-1, a GDG-2, a GDF-3, a GDF-5, a GDF-6, a GDF-8, a GDF-9, a GDF-10, a GDF-11, a GDF-15, an anti-Mullerian hormone (AMH), an activin, a Nodal, a TGF-β1, a TGF-β2, a TGF-β3, a TGF-β4, and any combination thereof. In another embodiment, the growth factor includes a BMP-2. In still another embodiment, the growth factor includes a TGF-β1.

In various embodiments of the above aspects or any other aspect of the invention delineated herein, the growth factor is present at between about 5 ng to about 500 ng. In one embodiment, the growth factor is present at between about 5 ng to about 250 ng. In another embodiment, the growth factor is present at between about 5 ng to about 200 ng. In still another embodiment, the growth factor is present at about 200 ng. In yet another embodiment, the growth factor is present at about 6 ng/mm³ to about 10 ng/mm³. In yet another embodiment, the growth factor is present at about 6.5 ng/mm³ to about 7.0 ng/mm³.

In various embodiments of the above aspects or any other aspect of the invention delineated herein, the growth factor retains its bioactivity for at least twelve days after the growth factor is incorporated into the scaffold.

In various embodiments of the above aspects or any other aspect of the invention delineated herein, the T cell progenitor cell is capable of differentiating to a T cell. In one embodiment, the T cell includes a cell selected from the group consisting of a CD4⁺ T cell, a CD8⁺ T cell, a regulatory T cell ($T_{reg}$), and any combination thereof. In another embodiment, the T cell includes a $T_{reg}$.

In various embodiments of the above aspects or any other aspect of the invention delineated herein, the differentiation factor binds to a Notch receptor. In one embodiment, the Notch receptor is selected from the group consisting of a Notch-1 receptor, a Notch-2 receptor, a Notch-3 receptor, a Notch-4 receptor, and any combination thereof. In another embodiment, the differentiation factor is selected from the group consisting of a Delta-like 1 (DLL-1), a Delta-like 2 (DLL-2), a Delta-like 3 (DLL-3), a Delta-like 3 (DLL-3), a Delta-like 4 (DLL-4), a Jagged 1, a Jagged 2, and any combination thereof.

In various embodiments of the above aspects or any other aspect of the invention delineated herein, the differentiation factor is covalently linked to the scaffold. In one embodiment, the differentiation factor is covalently linked to the scaffold utilizing click chemistry. In another embodiment, the differentiation factor is covalently linked to the scaffold utilizing N-hydroxysuccinimide (NHS) and 1-ethyl-3-(3- dimethylaminopropyl)carbodiimide hydrochloride (EDC) chemistry, NHS and dicyclohexylcarbodiimide (DCC) chemistry, avidin-biotin reaction, azide and dibenzocyclooctyne chemistry, tetrazine and transcyclooctene chemistry, tetrazine and norbornene chemistry, or di-sulfide chemistry.

In various embodiments of the above aspects or any other aspect of the invention delineated herein, the differentiation factor is present at an amount between about 1 ng to about 1000 μg per scaffold. In one embodiment, the differentiation factor is present at an amount between about 1 μg to about 100 μg per scaffold. In another embodiment, the differentiation factor is present at an amount between 1 μg to about 10 μg per scaffold. In still another embodiment, the differentiation factor is present about 6 μg per scaffold.

In various embodiments of the above aspects or any other aspect of the invention delineated herein, the differentiation factor retains its bioactivity for at least about three months after the differentiation factor is incorporated to the scaffold.

In various embodiments of the above aspects or any other aspect of the invention delineated herein, the recruited cell is a transplanted cell. In one embodiment, the recruited cell is autologous. In another embodiment, the recruited cell is allogeneic. In still another embodiment, the recruited cell is xenogeneic.

In various embodiments of the above aspects or any other aspect of the invention delineated herein, the recruited cell is not a transplanted cell.

In various embodiments of the above aspects or any other aspect of the invention delineated herein, the differentiated cell is capable of migrating out of the scaffold. In one embodiment, the differentiated cell is capable of homing to a tissue in a subject after the composition is administered to the subject.

In various embodiments of the above aspects or any other aspect of the invention delineated herein, the composition further includes a homing factor that is capable of promoting the recruitment of the cell to the scaffold. In one embodiment, the homing factor includes a stromal cell derived factor (SDF-1).

In one aspect, the present invention provides a method of modulating the immune system in a subject by administering the foregoing composition of the invention, thereby modulating the immune system in the subject.

In another aspect, the present invention provides a method of reducing immune over-reactivity in a subject by administering the foregoing composition of the invention, thereby reducing immune over-reactivity in the subject.

In still another aspect, the present invention provides a method of increasing donor chimerism in a subject receiving a transplantation by administering the foregoing composition of the invention, thereby increasing donor chimerism in the subject.

In yet another aspect, the present invention provides a method of promoting balanced reconstitution of T cells in a subject by administering the foregoing composition of the invention, thereby promoting balanced reconstitution of T cells in the subject.

In various embodiments of the above aspects or any other aspect of the invention delineated herein, the methods further include administering to the subject a hematopoietic stem cell or a hematopoietic progenitor cell. In one embodiment, wherein the composition is administered to the subject concurrently with, or after, the administration of the hematopoietic stem cell or the hematopoietic progenitor cell to the subject. In another embodiment, between about 1×10⁵ and about 50×10⁶ hematopoietic stem cells and/or hematopoietic progenitor cells per kilogram of the subject's weight are administered to the subject. In still another embodiment, between about $1\times10^5$ and about $1\times10^6$ hematopoietic stem cells or hematopoietic progenitor cells per kilogram of the subject's weight are administered to the subject.

In various embodiments of the above aspects or any other aspect of the invention delineated herein, the method enhances reconstitution of T cells in the subject. In one embodiment, the method enhances T cell neogenesis. In another embodiment, the enhanced T cell neogenesis is characterized by the enhanced T cell receptor excision circles (TRECs).

In various embodiments of the above aspects or any other aspect of the invention delineated herein, the method enhances T cell diversity in the subject. In one embodiment, the T cell diversity is characterized by an enhanced T cell receptor (TCR) repertoire.

In various embodiments of the above aspects or any other aspect of the invention delineated herein, the method increases the level of regulatory T ($T_{reg}$) cells.

In various embodiments of the above aspects or any other aspect of the invention delineated herein, the subject is a human who has a compromised immune system. In one embodiment, the subject has a compromised immune system due to immunosenescence. In another embodiment, the subject is over 30 years, 40 years, 50 years, 60 years, 70 years, or 80 years old. In one embodiment, the subject has a compromised immune system due to a congenital immunodeficiency. In still another embodiment, the subject has an acquired immunodeficiency.

In another aspect, the present invention provides a method of reducing immune over-reactivity in a subject, including administering to the subject a composition. The composition includes a porous scaffold, a growth factor present in an amount effective for inducing formation of a tissue or an organ within the scaffold and recruiting a cell into the scaffold, and a differentiation factor that induces the differentiation of the recruited cell into a T cell progenitor cell, thereby reducing immune over-reactivity in the subject.

In yet another aspect, the present invention provides a method of increasing donor chimerism in a subject receiving a transplantation, including administering to the subject a composition. The composition includes a porous scaffold, a growth factor present in an amount effective for inducing formation of a tissue or an organ within the scaffold and recruiting a cell into the scaffold, and a differentiation factor that induces the differentiation of the recruited cell into a T cell progenitor cell, thereby increasing donor chimerism in the subject.

In still another aspect, the present invention provides a method for promoting balanced reconstitution of T cells in a subject, including administering to the subject a composition. The composition includes a porous scaffold, a growth factor present in an amount effective for inducing formation of a tissue or an organ within the scaffold and recruiting a cell into the scaffold, and a differentiation factor that induces the differentiation of the recruited cell into a T cell progenitor cell, thereby leading to a balanced reconstitution of T cells in the subject.

In yet another aspect, the present invention provides a method of modulating the immune system of a human having a compromised immune system, including administering to the human a composition. The composition includes a porous scaffold, a growth factor present in an amount effective for inducing formation of a tissue or an organ within the scaffold and recruiting a cell into the scaffold, and a differentiation factor that induces the differentiation of the recruited cell into a T cell progenitor cell, thereby modulating the immune system of the human, wherein the human has a compromised immune system due to immunosenescence, congenital immunodeficiency, or acquired immunodeficiency.

In various embodiments of the above aspects, the scaffold includes a hydrogel. In one embodiment, the scaffold comprises a cryogel. In another embodiment, the scaffold includes a polymer or co-polymer selected from the group consisting of polylactic acid, polyglycolic acid, PLGA, alginate or an alginate derivative, gelatin, collagen, agarose, hyaluronic acid, poly(lysine), polyhydroxybutyrate, poly-epsilon-caprolactone, polyphosphazines, poly(vinyl alcohol), poly(alkylene oxide), poly(ethylene oxide), poly(allylamine), poly(acrylate), poly(4-aminomethylstyrene), pluronic polyol, polyoxamer, poly(uronic acid), poly(anhydride), poly(vinylpyrrolidone), and any combination thereof. In still another embodiment, the scaffold includes a polymer or co-polymer selected from the group consisting of an alginate, an alginate derivative, and the combination thereof. In still another embodiment, the scaffold comprises a polymer or co-polymer selected from the group consisting of hyaluronic acid, a hyaluronic acid derivative, and the combination thereof.

In various embodiments of the above aspects, the scaffold comprises a pore. In one embodiment, the pore has a diameter between about 1 μm and about 100 μm. In another embodiment, the pore has a diameter between about 50 μm and 80 μm. In still another embodiment, the scaffold includes pores of different size.

In various embodiments of the above aspects, the scaffold is injectable. In one embodiment, the scaffold includes methacrylated alginate (MA-alginate). In another embodiment, the scaffold comprises a hyaluronic acid or a hyaluronic acid derivative.

In various embodiments of the above aspects, the scaffold includes a click-hydrogel or click cryogel. In one embodiment, the scaffold includes a click-alginate, a click gelation or a click hyaluronic acid.

In various embodiments of the above aspects, the scaffold comprises porogen hydrogel microbeads and a bulk hydrogel, wherein the porogen hydrogel microbeads degrade at least 10% faster than the bulk hydrogel following administration into a subject. In one embodiment, the porogen hydrogel microbeads comprise oxidized alginate.

In various embodiments of the above aspects, the cell is a stem cell or a progenitor cell. In one embodiment, the cell is selected from a group consisting of a hematopoietic stem cell, a hematopoietic progenitor cell, a recombinant hematopoietic stem cell, a recombinant hematopoietic progenitor cell, and any combination thereof. In another embodiment, the cell is selected from the group consisting of a hematopoietic bone marrow cell, a mobilized peripheral blood cell, a recombinant hematopoietic bone marrow cell, a recombinant mobilized peripheral blood cell, and any combination thereof.

In various embodiments of the above aspects, the tissue or the organ includes a bone tissue or a hematopoietic tissue. In one embodiment, the tissue or the organ is formed about 7-21 days after the composition is administered to the subject. In another embodiment, the tissue or the organ is formed about 14 days after the composition is administered to the subject. In still another embodiment, at least two compositions are administered to the subject. In yet another embodiment, the compositions are of similar size.

In various embodiments of the above aspects, the cell is a stromal cell.

In various embodiments of the above aspects, the scaffold is between about 100 μm³ to about 10 cm³ in size. In one embodiment, the scaffold is between about 10 mm³ to about 100 mm³ in size. In another embodiment, the scaffold is about 30 mm³ in size.

In various embodiments of the above aspects, the growth factor includes a protein belonging to transforming growth factor protein beta (TGF-β) superfamily. In one embodiment, the growth factor includes a protein selected from the group consisting of a BMP-2, a BMP-4, a BMP-6, a BMP-7, a BMP-12, a BMP-14, a growth differentiation factor (GDF)-1, a GDG-2, a GDF-3, a GDF-5, a GDF-6, a GDF-8, a GDF-9, a GDF-10, a GDF-11, a GDF-15, an anti-Mullerian hormone (AMH), an activin, a Nodal, a TGF-β1, a TGF-β2, a TGF-β3, a TGF-β4, and any combination thereof. In another embodiment, the growth factor includes a BMP-2. In still another embodiment, the growth factor includes a TGF-β1.

In various embodiments of the above aspects, the growth factor retains its bioactivity for at least twelve days after the growth factor is incorporated into the scaffold.

In various embodiments of the above aspects, the T cell progenitor cell is capable of differentiating to a T cell. In one embodiment, the T cell includes a cell selected from the group consisting of a CD4⁺ T cell, a CD8⁺ T cell, a regulatory T cell (T$_{reg}$), and any combination thereof. In another embodiment, the T cell includes a T$_{reg}$.

In various embodiments of the above aspects, the differentiation factor binds to a Notch receptor. In one embodiment, the Notch receptor is selected from the group consisting of a Notch-1 receptor, a Notch-2 receptor, a Notch-3 receptor, a Notch-4 receptor, and any combination thereof. In another embodiment, the differentiation factor is selected from the group consisting of a Delta-like 1 (DLL-1), a Delta-like 2 (DLL-2), a Delta-like 3 (DLL-3), a Delta-like 3 (DLL-3), a Delta-like 4 (DLL-4), a Jagged 1, a Jagged 2, and any combination thereof.

In various embodiments of the above aspects, the differentiation factor is covalently linked to the scaffold. In one embodiment, the differentiation factor is covalently linked to the scaffold utilizing click chemistry. In another embodiment, the differentiation factor is covalently linked to the scaffold utilizing N-hydroxysuccinimide (NHS) and 1-ethyl-3-(3-dimethylaminopropyl)carbodiimide hydrochloride (EDC) chemistry, avidin-biotin reaction, azide and dibenzocyclooctyne chemistry, tetrazine and transcyclooctene chemistry, tetrazine and norbornene chemistry, or di-sulfide chemistry.

In various embodiments of the above aspects, the differentiation factor retains its bioactivity for at least about three months after the differentiation factor is incorporated to the scaffold.

In various embodiments of the above aspects, the recruited cell is a transplanted cell. In one embodiment, the recruited cell is autologous. In another embodiment, the recruited cell is allogeneic. In still another embodiment, the recruited cell is xenogeneic.

In various embodiments of the above aspects, the recruited cell is not a transplanted cell.

In various embodiments of the above aspects, the differentiated cell is capable of migrating out of the scaffold. In one embodiment, the differentiated cell is capable of homing to a tissue in a subject after the composition is administered to the subject.

In various embodiments of the above aspects, the composition further includes a homing factor that is capable of promoting the recruitment of the cell to the scaffold. In one embodiment, the homing factor comprises a stromal cell derived factor (SDF-1).

In various embodiments of the these aspects, the growth factor is present at between about 1 ng to about 1000 μg. In one embodiment, the growth factor is present at between about 1 ng to about 1000 ng. In another embodiment, the growth factor is present at between about 5 ng to about 500 ng. In still another embodiment, the growth factor is present at between about 5 ng to about 250 ng. In yet another embodiment, the growth factor is present at between about 5 ng to about 200 ng. In yet another embodiment, the growth factor is present at about 200 ng.

In various embodiments of the above aspects, the growth factor is present at about 0.03 ng/mm³ to about 350 ng/mm³ by volume of scaffold. In one embodiment, the growth factor is present at about 6 ng/mm³ to about 10 ng/mm³. In another embodiment, the growth factor is present at about 6.5 ng/mm³ to about 7.0 ng/mm³.

In various embodiments of the above aspects, between about 5×10⁵ and about 50×10⁶ hematopoietic stem cells and/or hematopoietic progenitor cells per kilogram of the subject's weight are administered to the subject. In one embodiment, about 5×10⁵ hematopoietic stem cells and/or hematopoietic progenitor cells per kilogram of the subject's weight are administered to the subject. In another embodiment, the hematopoietic cells are selected from the group consisting of hematopoietic stem cells, hematopoietic progenitor cells, recombinant hematopoietic stem cells, recombinant hematopoietic progenitor cells, and any combination thereof. In another embodiment, the hematopoietic cells are selected from the group consisting of hematopoietic bone marrow cells, mobilized peripheral blood cells, recombinant hematopoietic bone marrow cells, recombinant mobilized peripheral blood cells, and any combination thereof.

In various embodiments of the above aspects, the method reduces self-immunity in the subject.

In various embodiments of the above aspects, the method prevents or treats an autoimmune disease. In one embodiment, the autoimmune disease is a disease selected from the group consisting of type 1 diabetes, rheumatoid arthritis, psoriasis, arthritis, multiple sclerosis, systemic lupus erythematosus, inflammatory bowel disease, Addison's disease, Graves' disease, Sjogren's syndrome, Hashimoto's thyroiditis, Myasthenia gravis, Vasculitis, Pernicious anemia, Celiac disease, and allergy.

In various embodiments of the above aspects, the method mitigates graft versus host disease (GVHD). In one embodiment, the GVHD is associated with hematopoietic stem cell transplantation (HSCT) to the subject. In another embodiment, the composition is administered concurrently with or after hematopoietic stem cell transplantation (HSCT). In still another embodiment, the GVHD is associated with solid organ transplantation. In yet another embodiment, the composition is administered to a subject before the transplantation. In yet another embodiment, the GVHD is acute GVHD. In one embodiment, the GVHD is chronic GVHD. In another embodiment, the method mitigates GVHD associated morbidity, GVHD associated mortality, or GVHD associated deduction in long-term survival.

In various embodiments of the above aspects, the transplantation is a hematopoietic stem cell transplantation (HSCT).

In various embodiments of the above aspects, the increased donor chimerism includes a T cell chimerism. In one embodiment, the T cell includes a CD4⁺ T cell, a CD8⁺ T cell, or a T$_{reg}$ cell.

In various embodiments of the above aspects, the balanced reconstitution of T cells is characterized by homeostatic CD4+: CD8+ T cell ratio of between about 0.9 and about 2.5 in periphery blood.

In various embodiments of the above aspects, the human has a compromised immune system due to immunosenescence. In one embodiment, the human is over 30, 40, 50, 60, 70, or 80 years old.

In various embodiments of the above aspects, the human has a compromised immune system due to a congenital immunodeficiency.

In various embodiments of the above aspects, the human has a compromised immune system due to an acquired immunodeficiency.

In various embodiments of the above aspects, the method increases the level of regulatory T ($T_{reg}$) cells.

In various embodiments of the above aspects, the composition is administered by injection. In one embodiment, the injection is subcutaneous injection.

In yet a further aspect of the invention, the present invention provides a syringe. The syringe includes a needle, a reservoir that includes the composition of various embodiments of the above aspects or any other aspect of the invention delineated herein, and a plunger.

In yet a further aspect of the invention, the present invention provides a kit. The kit includes the composition of various embodiments of the above aspects or any other aspect of the invention delineated herein, and instructions to administer the composition.

In various embodiments of the above aspects, the method further includes administering to the subject a stem cell mobilization agent or a progenitor cell mobilization agent in an amount effective for inducing the movement of a stem cell or progenitor cell from the bone marrow into the blood. In one embodiment, the stem cell mobilization agent or the progenitor cell mobilization agent is selected from the group consisting of IL-1, IL-2, IL-3, IL-6, GM-CSF, G-CSF, plerixafor, PDGF, TGF-beta, NGF, IGFs, growth hormone, erythropoietin, thrombopoietin, or a combination thereof. In another embodiment, the stem cell mobilization agent or the progenitor cell mobilization agent is administered prior to, concurrently with, or following the administration of the composition. In still another embodiment, the method further includes administering to the subject a therapeutically-effective amount of electromagnetic radiation.

Other features and advantages of the invention will be apparent from the following detailed description and drawings.

BRIEF DESCRIPTION OF THE DRAWINGS

FIG. 1A is a schematic for the fabrication of covalently crosslinked BMC.

FIG. 1B is a representative cross sectional scanning electron micrograph (SEM) image of a BMC. Scale bar, 1 mm.

FIG. 1C is a representative SEM of the pore shape and structure within the cross section of the BMC. Scale bar=200 μm.

FIG. 1D shows release kinetics of the encapsulated BMP-2 and covalently tethered DLL4 (n=5 per group).

FIG. 1E shows surface plasmon resonance measuring the binding kinetics of the DLL4 before and after modification with the methacrylate linker.

FIG. 1F shows bioactivity of the pooled released BMP-2 measured using alkaline phosphatase enzyme activity in MC3T3-E1 pre-osteoblast cells, as compared to BMP-2 never incorporated into BMC (Native BMP-2) and medium with no added BMP-2 (Growth medium)

FIG. 1G shows bioactivity of BMP-2 quantified at discrete time intervals after release using alkaline phosphatase enzyme activity in MC3T3-E1 pre-osteoblast cells.

FIG. 1H shows in vitro bioactivity of Notch ligand DLL-4 measured using a colorimetric assay.

FIG. 1I shows representative fluorescence microscopy images of citrine expression in a CHO-K1+2×HS4-UAS-H2B-Citrine-2×HS4 cH1+hNECD-Gal4esn c9 Notch-reporter cell line at different time intervals on dual BMCs (top row) and blank BMCs (bottom row).

FIG. 1J shows in vitro differentiation of isolated mouse and human hematopoietic stem and progenitor cells into CLPs as a function of the degree of functionalization of methacrylate groups on the polymer backbone (n=5).

FIGS. 1K and 1L show fold expansion and viability of mouse (FIG. 1K) and human (FIG. 1L) hematopoietic cells after 7 days of in vitro culture.

Data in FIGS. 1F-1I, 1K and 1L are mean±s.d. of n=5 and are representative from 3 independent experiments. (*P<0.05,  P<0.01, *P<0.001, analysis of variance (ANOVA) with a Tukey post hoc test).

Figure 1A:
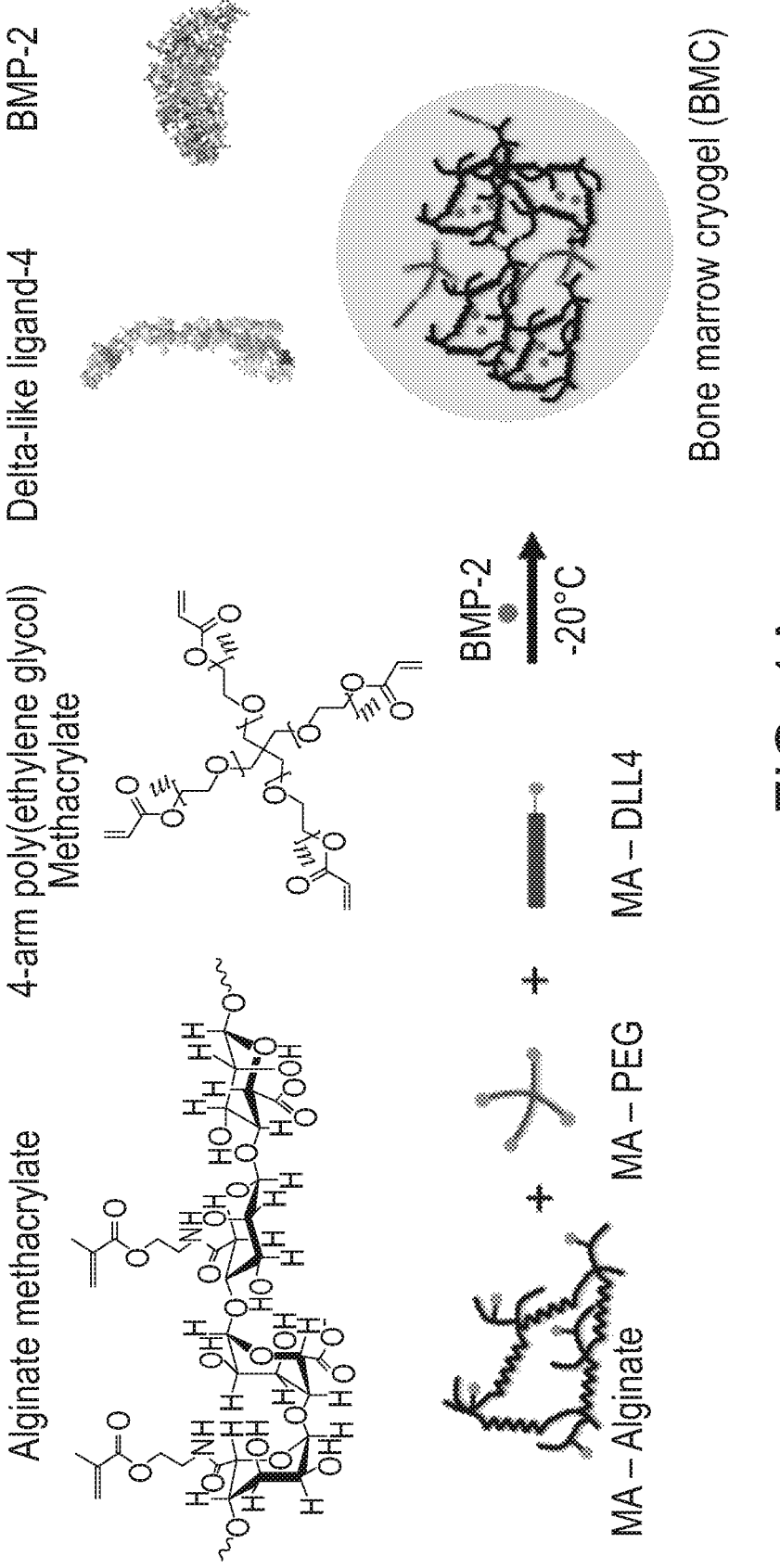
FIGS. 1A-1E, 1J, and 1M show that alginate-PEG-DLL4 based bone marrow cryogel (BMC) presents DLL4 and BMP-2, and preferentially expands common lymphoid progenitors (CLPs).
Figure 1B:
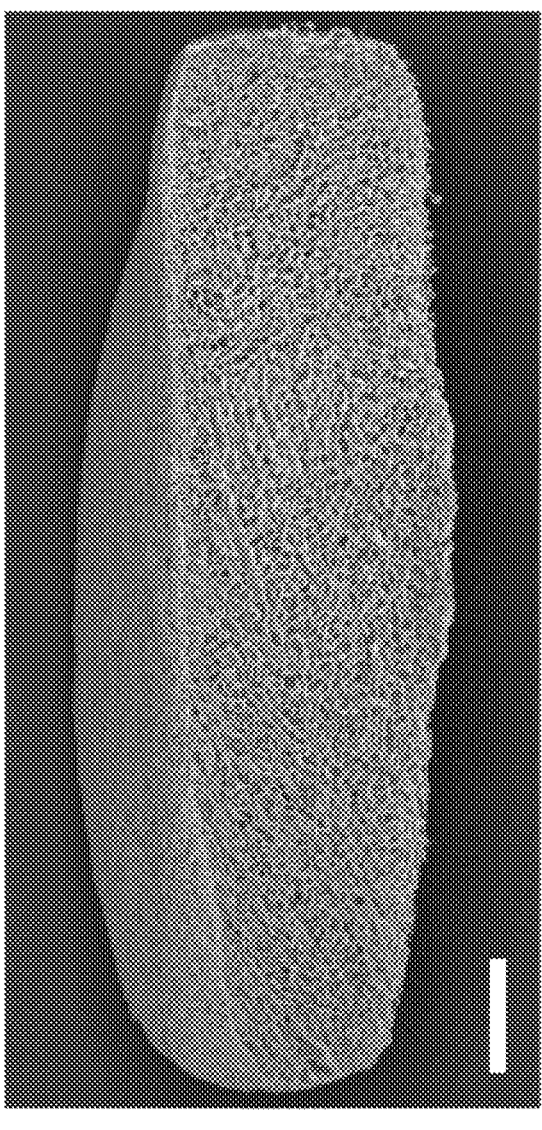
Figure 1C:
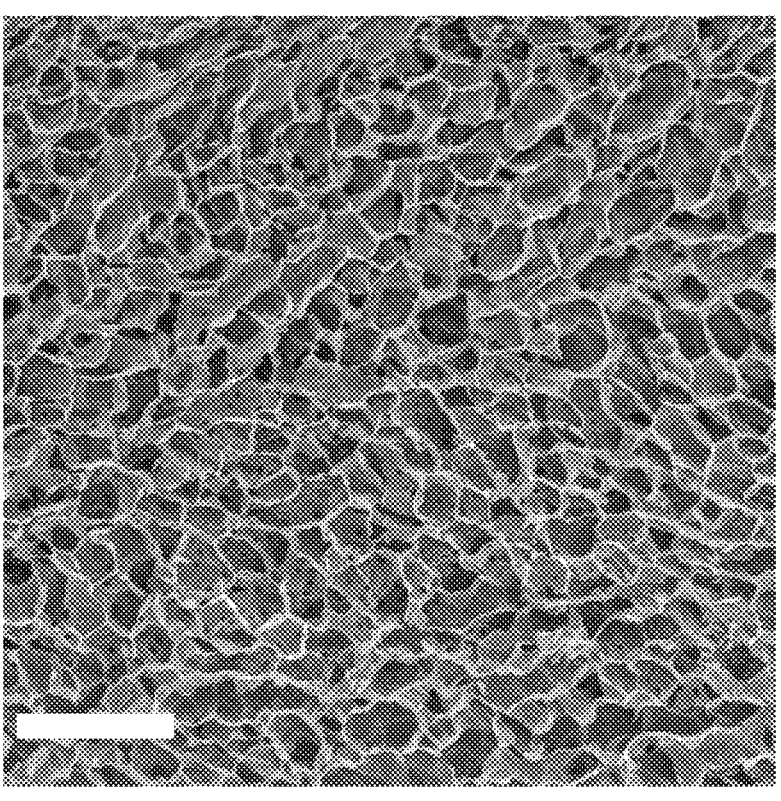
Figure 1D:
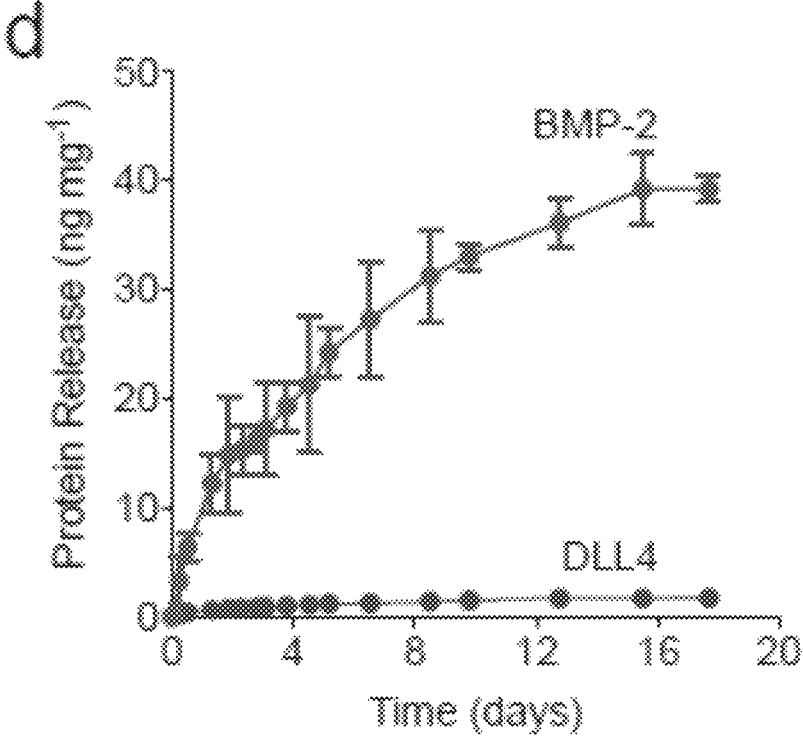
Figure 1E:
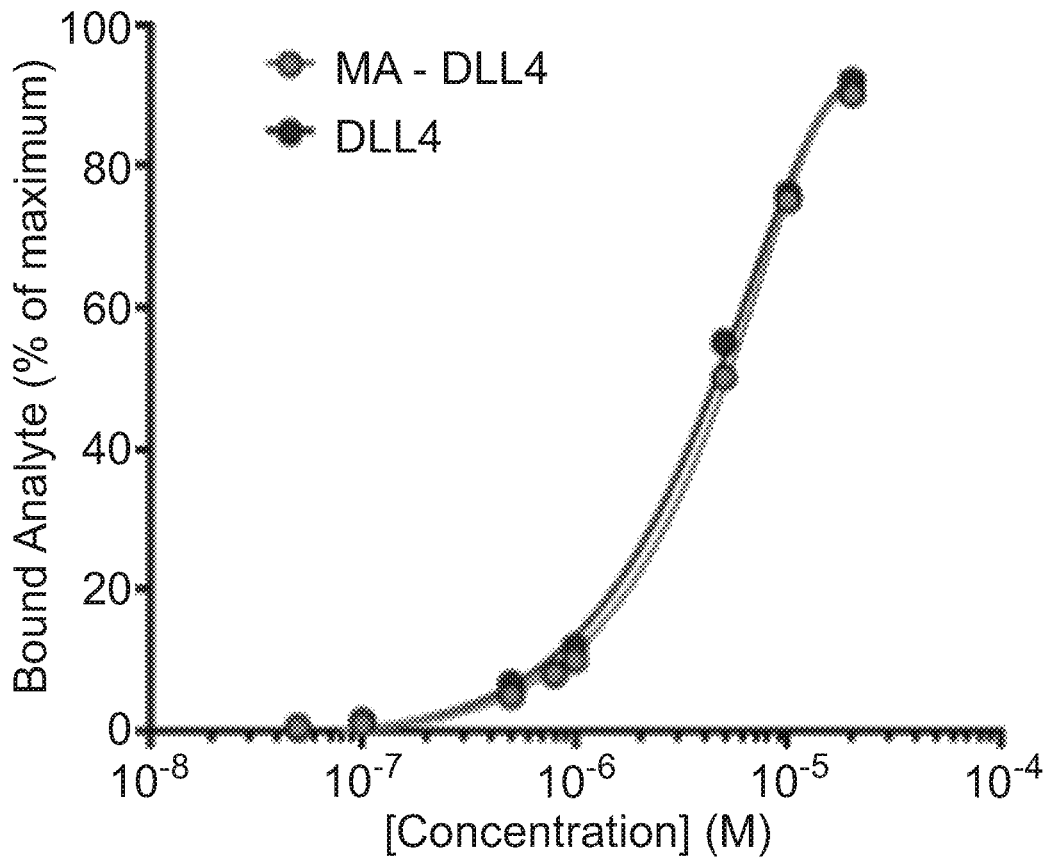
Figure 1F:
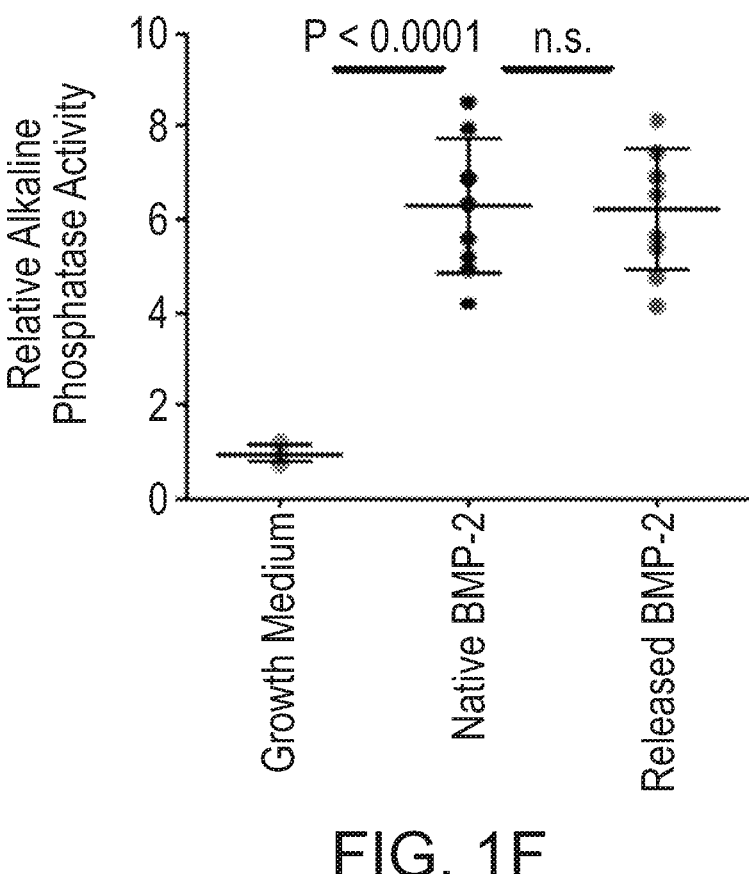
FIGS. 1F-1I, 1K and 1L show extended characterization of BMC bioactivity.
Figure 1G:
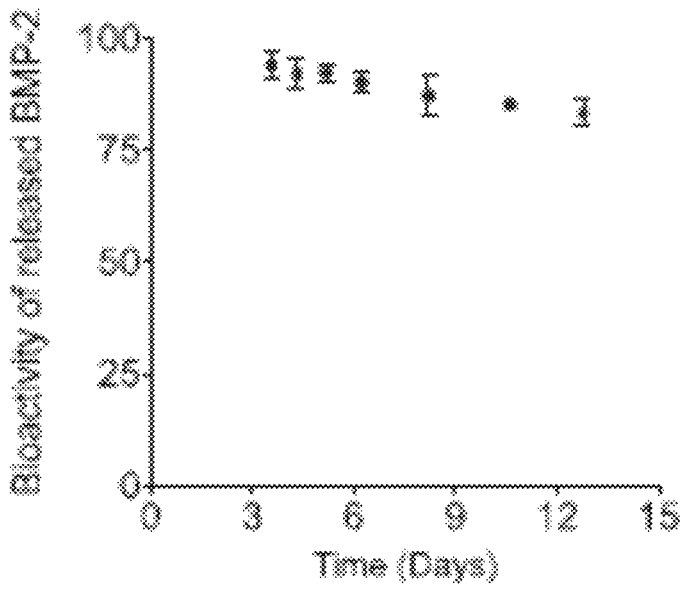
Figures 1H, 1I:
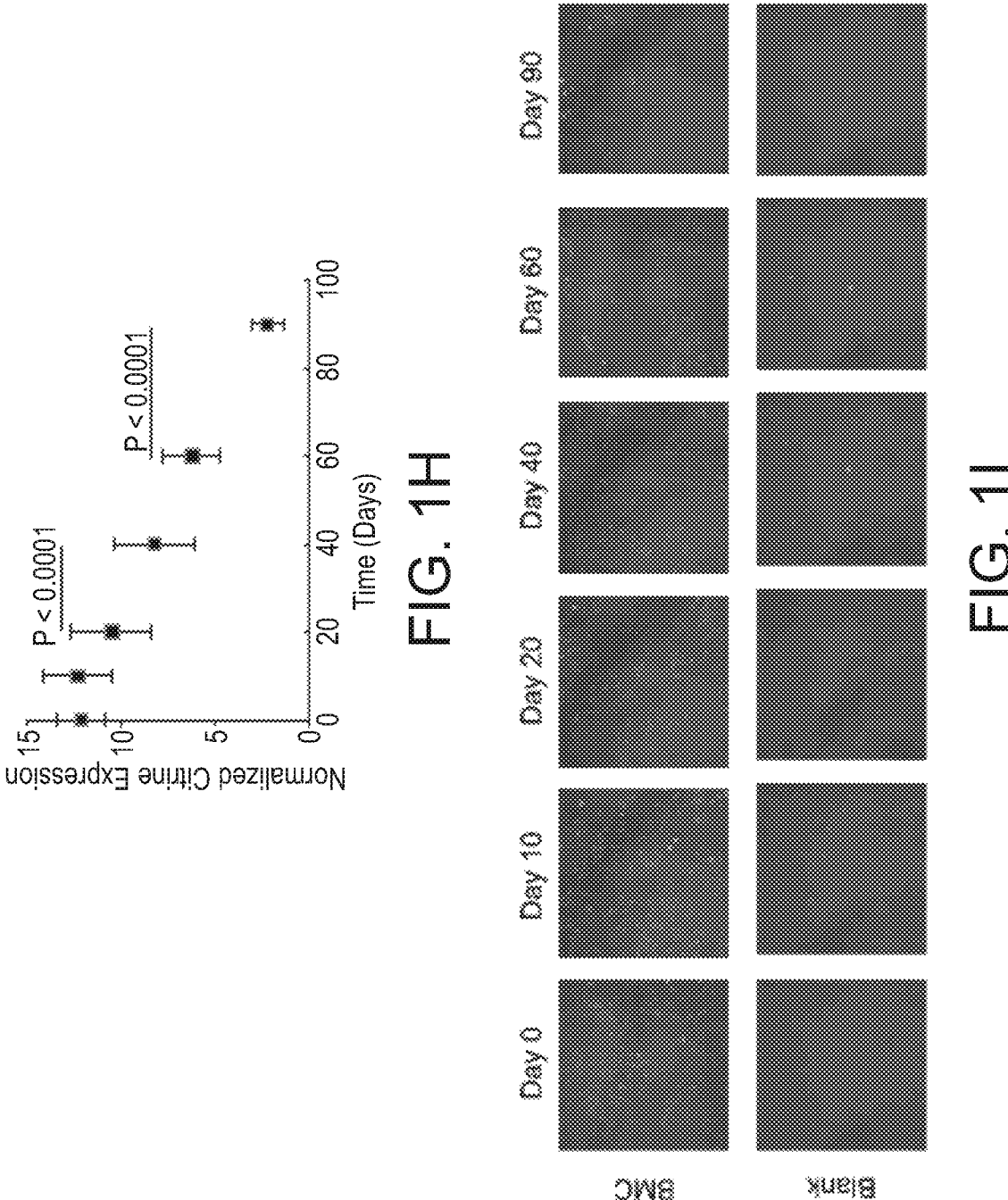
Figures 1J, 1K:
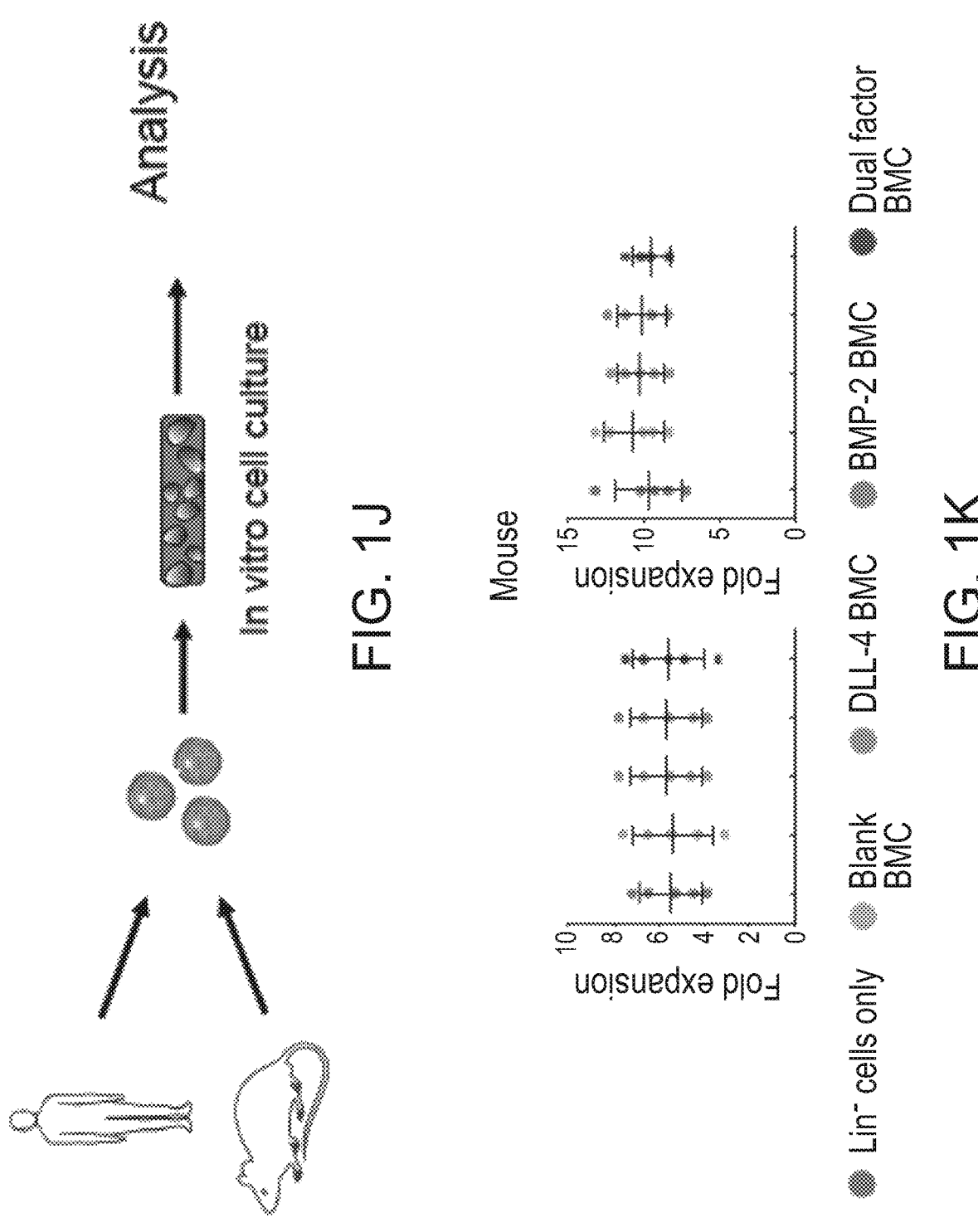
Figure 1L:
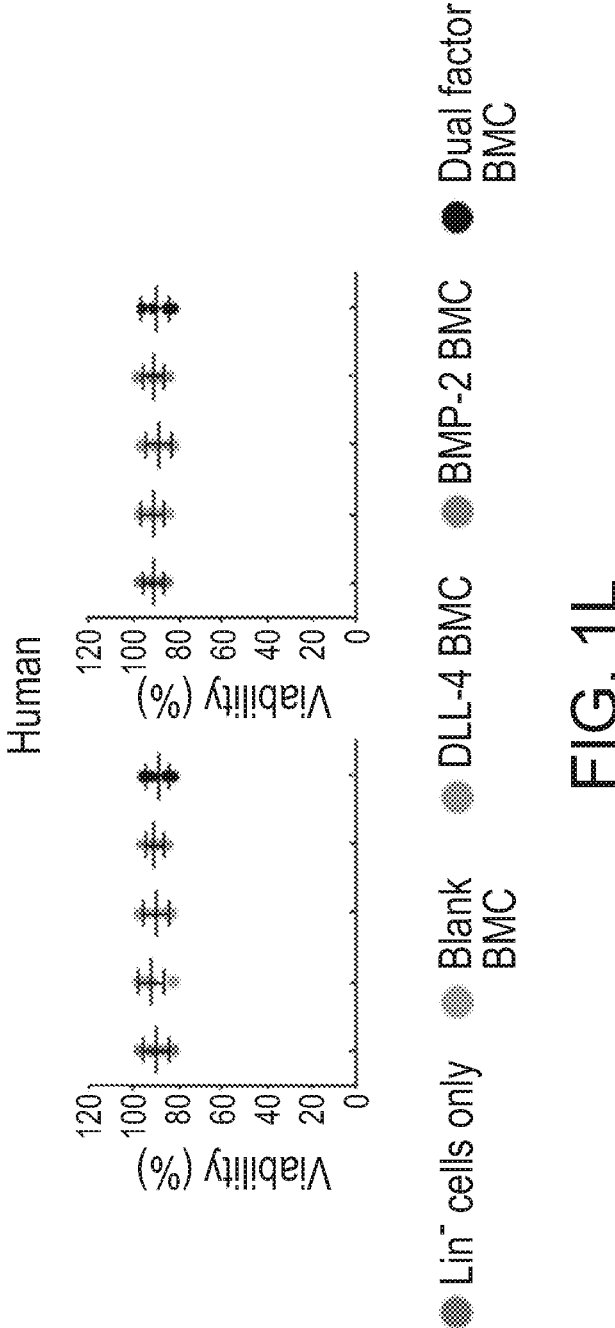
Figure 1M:
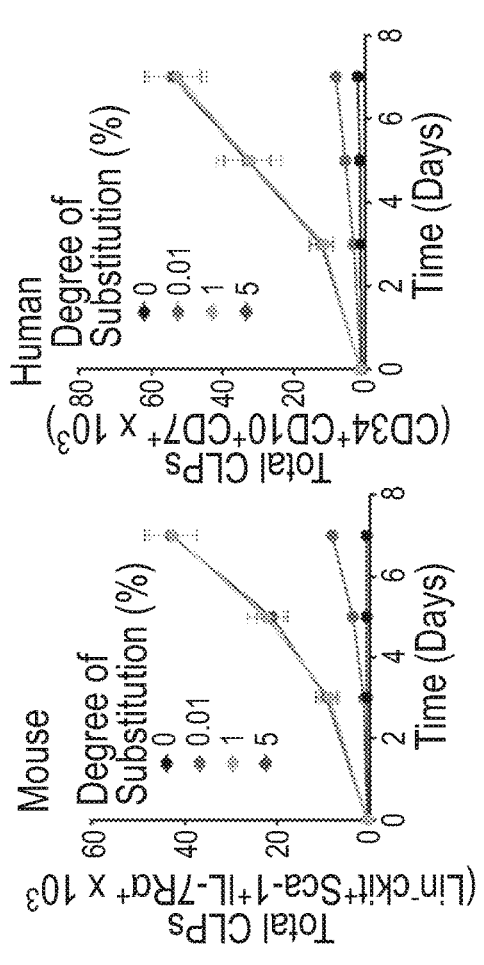
Figure 1M:
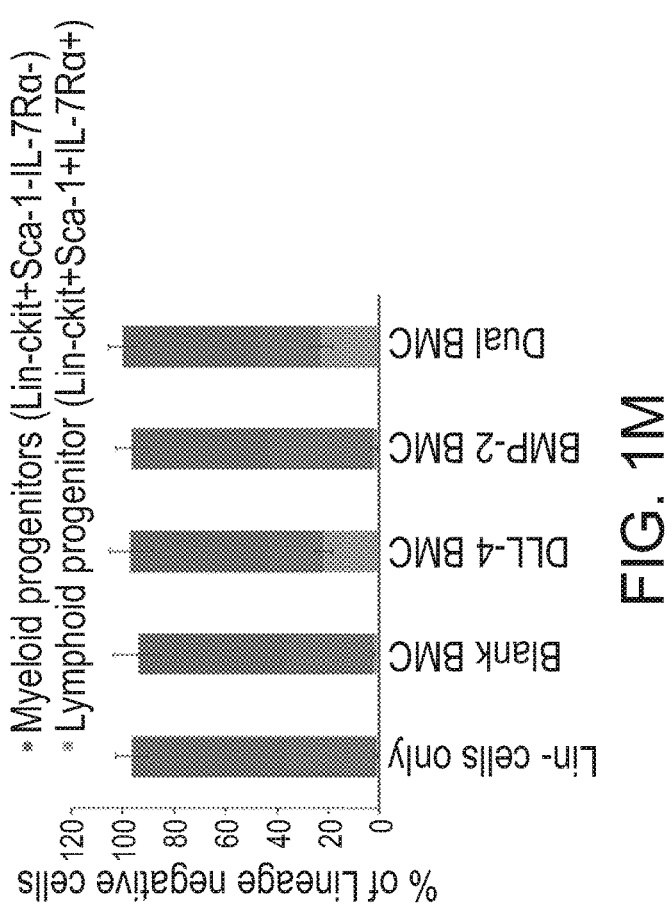

FIG. 1M shows proportion of Lin⁻ common lymphoid and myeloid mouse progenitor cells quantified in growth medium, blank, single factor and dual factor BMCs.

Images and pore size quantification in FIGS. 1B and 1C are representative of ten independent replicates. Data in FIGS. 1D, 1J and 1M represent the mean±s.d. of five 337 experimental replicates and are representative of three independent experiments. Distinct samples were assayed individually.

FIGS. 2B-2K show in vivo deployment and host integration of BMCs. FIGS. 2A, 2L, and 3B-3F show extended in vivo characterization of BMC.

Figures 2A, 2B:
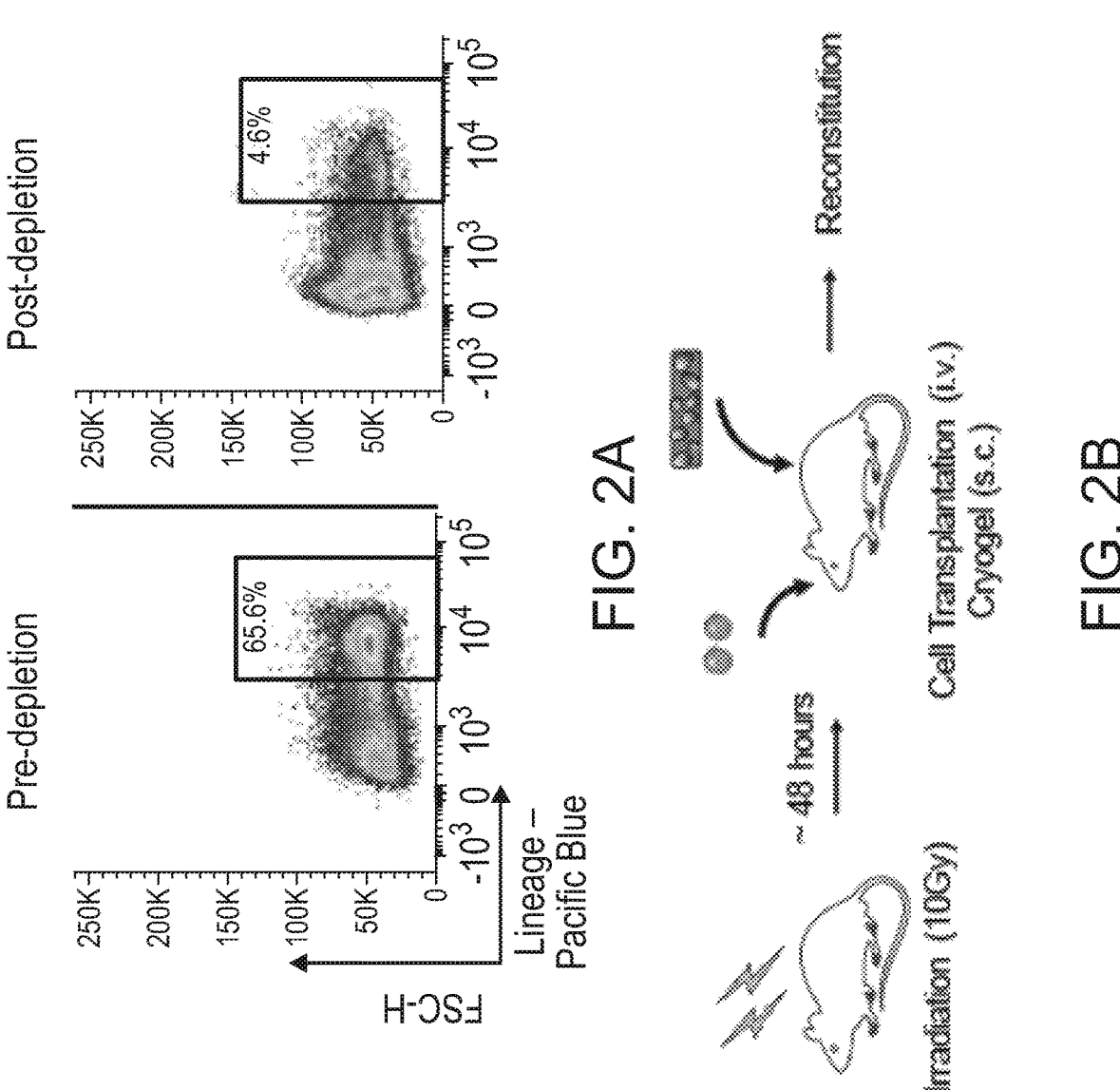

FIG. 2A shows representative flow cytometric profiles of pre- and post-lineage depleted bone marrow cells used for transplantation (5 independent experiments).

FIG. 2B shows the schedule of administration of L-TBI, HSCT and simultaneous injection of the BMCs. B6 mice irradiated with 1000 cGy (1 dose) and subsequently transplanted with $5\times10^5$ lineage depleted syngeneic GFP BM cells within 48 hours after L-TBI.

Figure 2C:
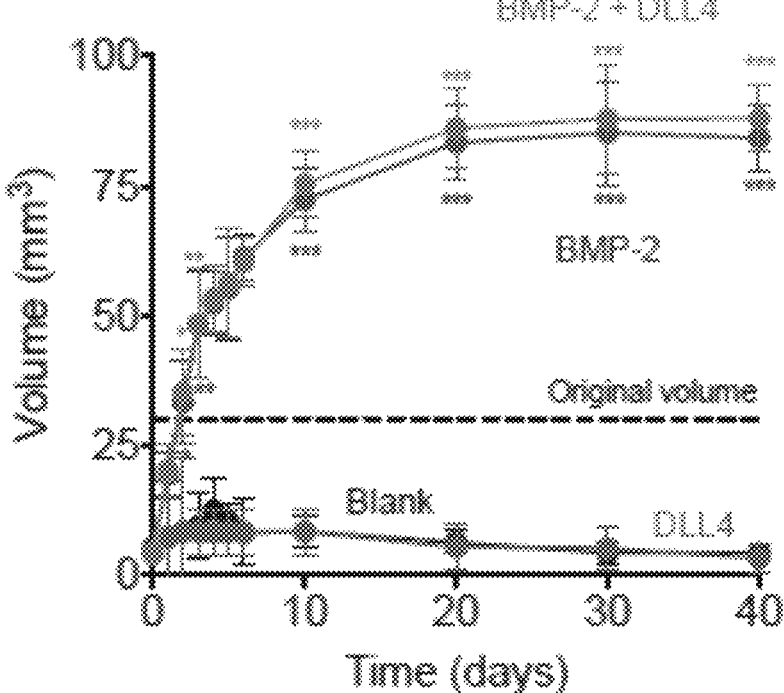

FIG. 2C shows the volume of the BMC nodule in vivo as a function of time post-delivery with various combinations of the BMP-2 and DLL-4 included in the BMC.

Figure 2D:
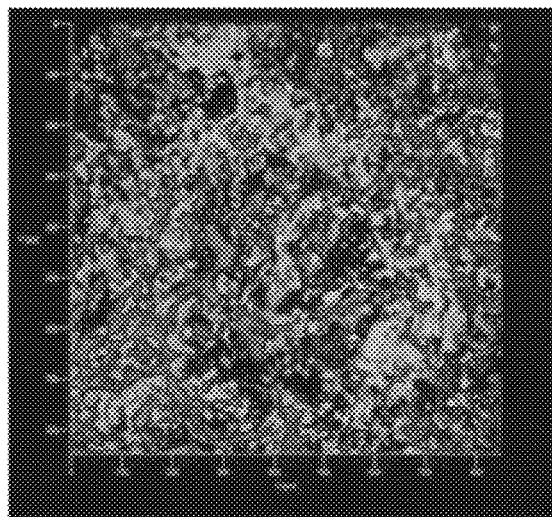

FIG. 2D shows confocal microscopy image of donor GFP+ cells (green) identified within the BMC (red)

Figure 2E:
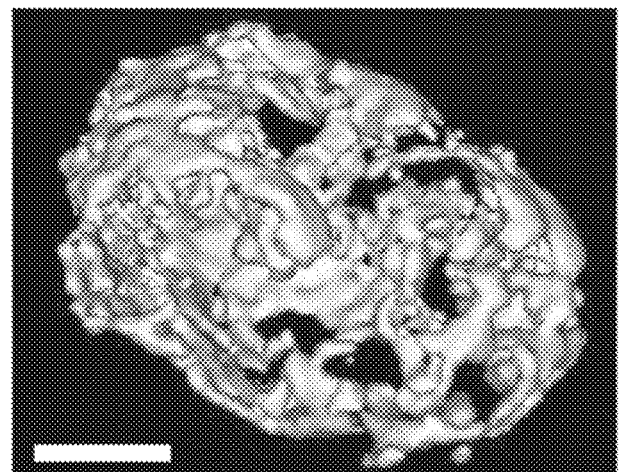
Figure 2F:
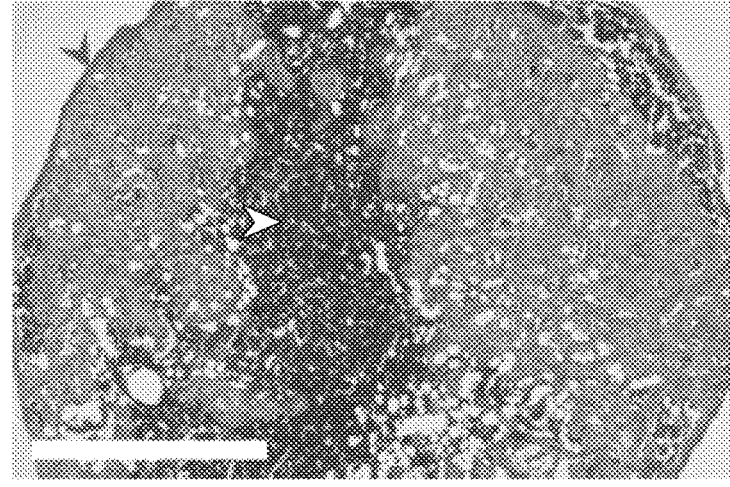

FIGS. 2E and 2F show representative microcomputed tomography (microCT, scale bar=1 mm) imaging (FIG. 2E) and histology (scale bar=1 mm) (FIG. 2F) of the dual functionalized BMC at 3 weeks post injection with the bone shell (green arrow) and the hematopoietic tissue (yellow arrow).

Figures 2G, 2H, 2I, 2J:
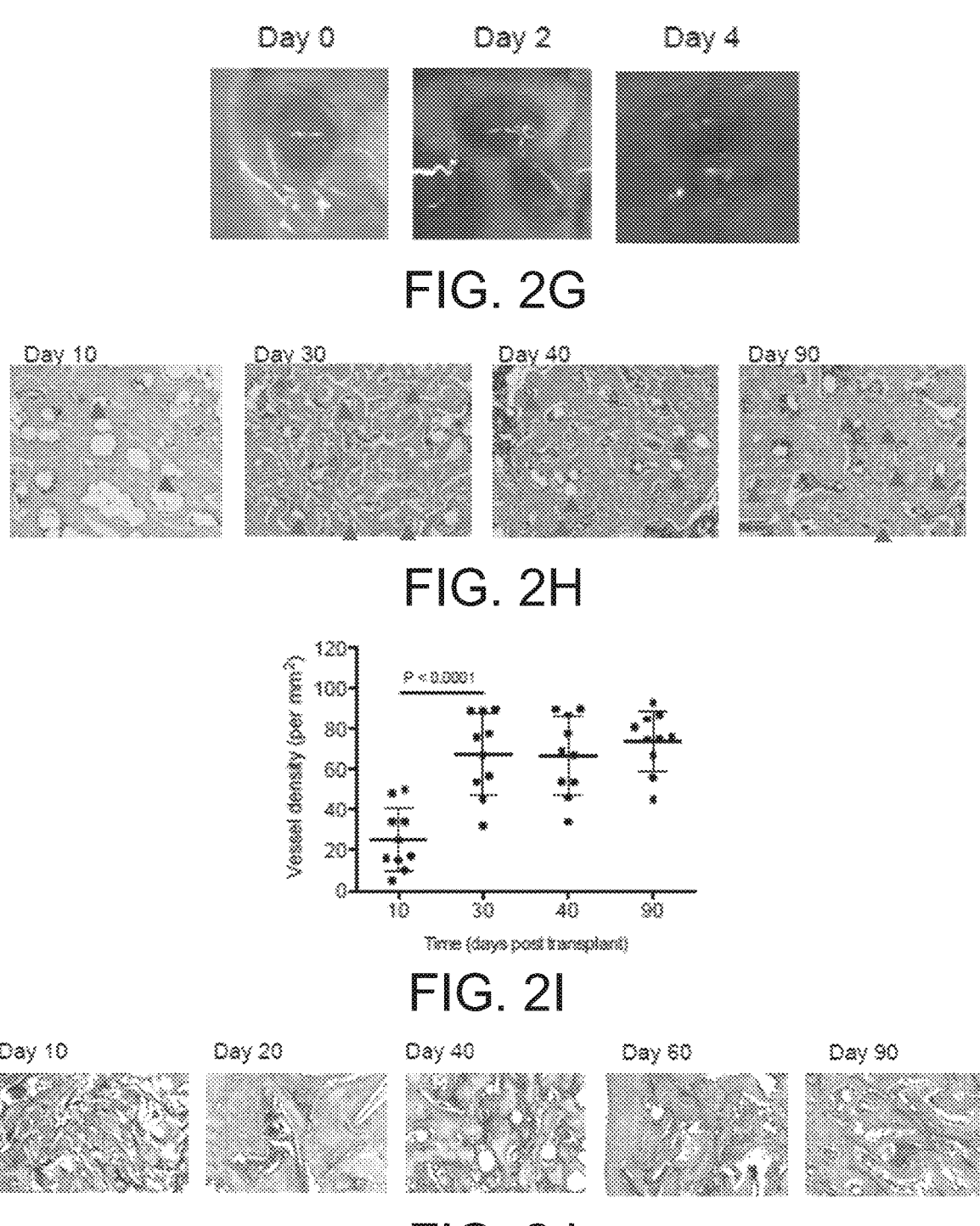

FIG. 2G shows images of the BMC (blue) in the subcutaneous tissue at various timepoints post-injection.

FIGS. 2H and 2I show histological Verhoeff-Van Gieson stained sections of the BMC with blood vessels identified (blue arrows) at Day 10, 30, 40 and 90 post-transplant (FIG. 2H) and quantification of the blood vessel density within these sections (FIG. 2I).

Figure 2K:
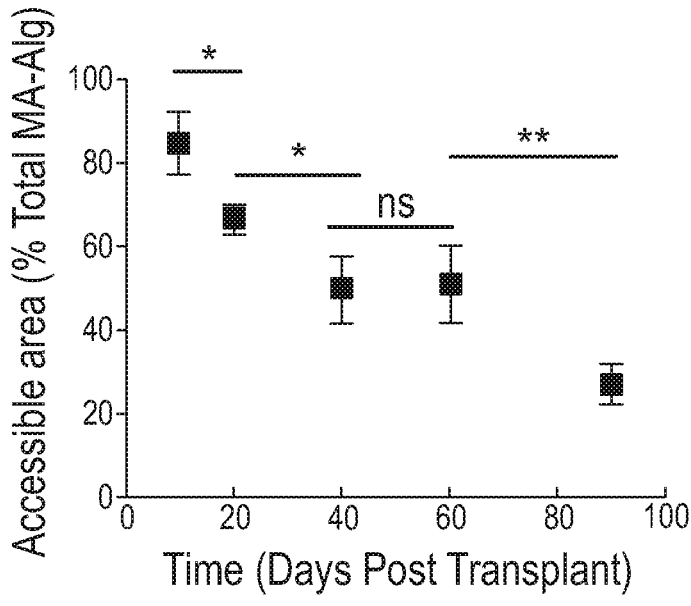

FIGS. 2J and 2K show histological Safranin-O stained sections of the BMC with alginate identified (red thread-like staining) at Day 10, 20, 40, 60 and 90 post-transplant (FIG. 2J) and quantification of the accessible area of alginate within these sections (FIG. 2K).

Figure 2L:
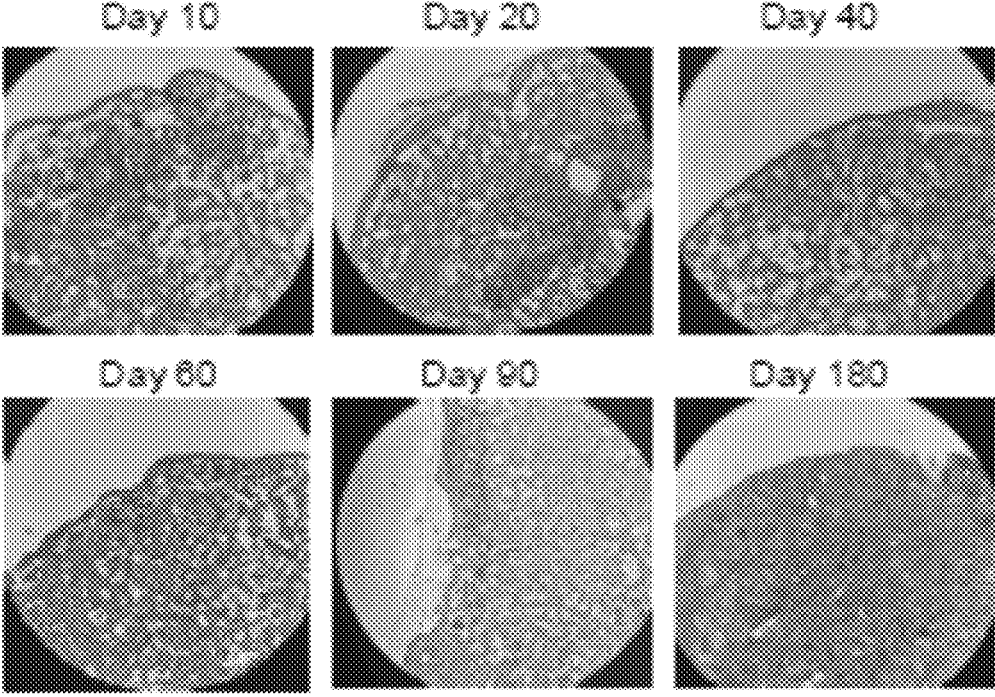

FIG. 2L shows images of the edge of BMCs extracted from the subcutaneous tissue at pre-determined time-intervals post-transplant identifying the margins of the BMCs with collagen (blue-green) and cells (black) and in some sections alginate (red) is observed using Safranin-O staining (10× objective magnification).

Data in FIG. 2C represent the mean±s.d. of five experimental replicates and are representative of two independent experiments. (*$P<0.05$,  $P<0.01$, *$P<0.001$, analysis of variance (ANOVA) with a Tukey post hoc test). Images in FIGS. 2D-2G, and 2J are representative of four independent samples. Data in FIGS. 2I and 2K represent the mean±s.d. from eight samples and are representative of two independent experiments (*$P<0.05$, $P<0.01$, ns, not significant, ANOVA with a Tukey post hoc test). Distinct samples were assayed individually. Data in FIG. 2L** are mean±s.d. of n=5 and are representative from 2 independent experiments.

FIGS. 3A, and 3G-3P show in vivo recruitment of donor cells to BMC and enhanced seeding of thymic progenitors.

Figure 3A:
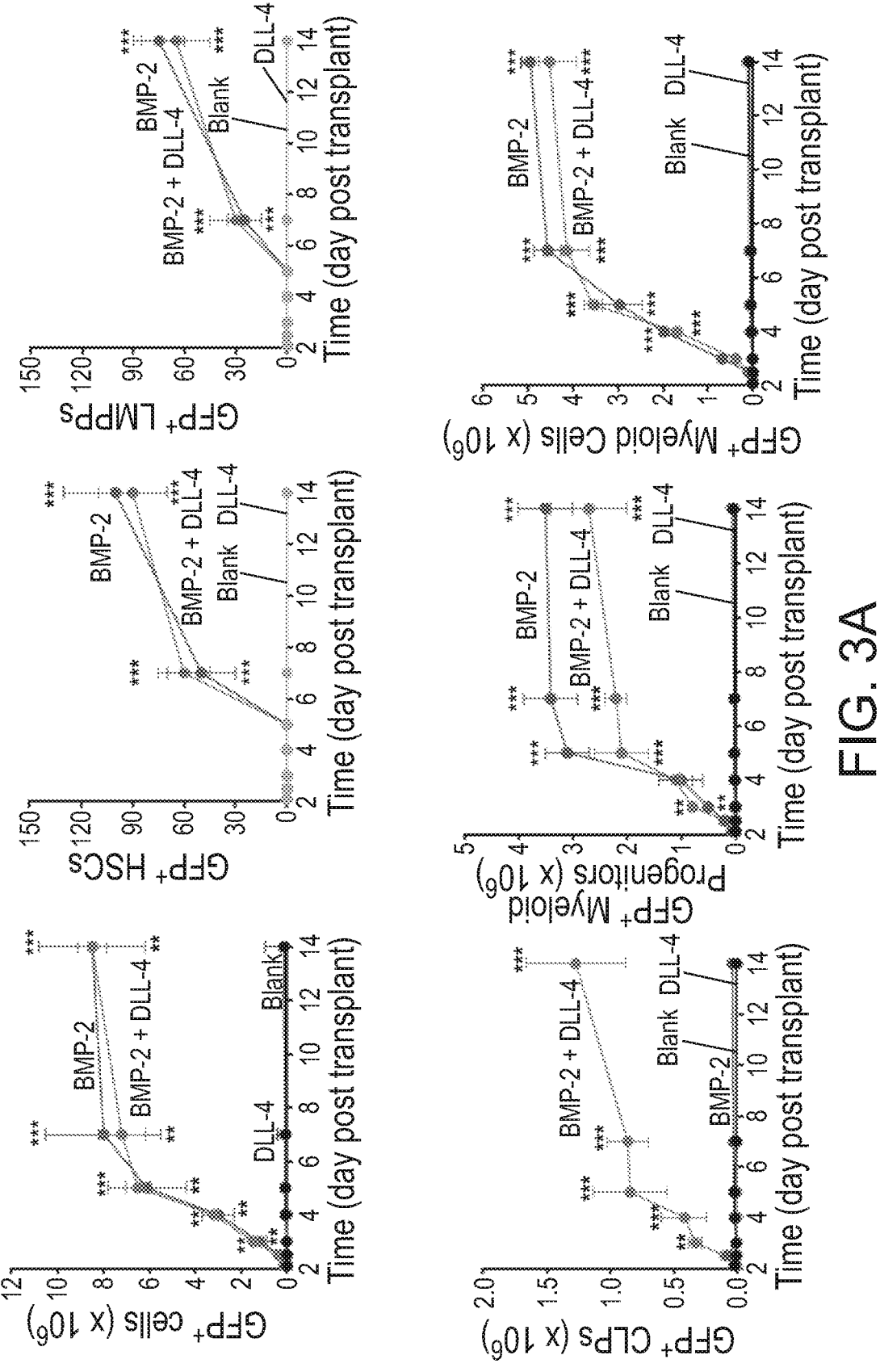

FIG. 3A shows total number and type of donor derived, GFP+ cells in the BMC containing combinations of BMP-2 and DLL-4 and blank BMCs.

Figure 3B:
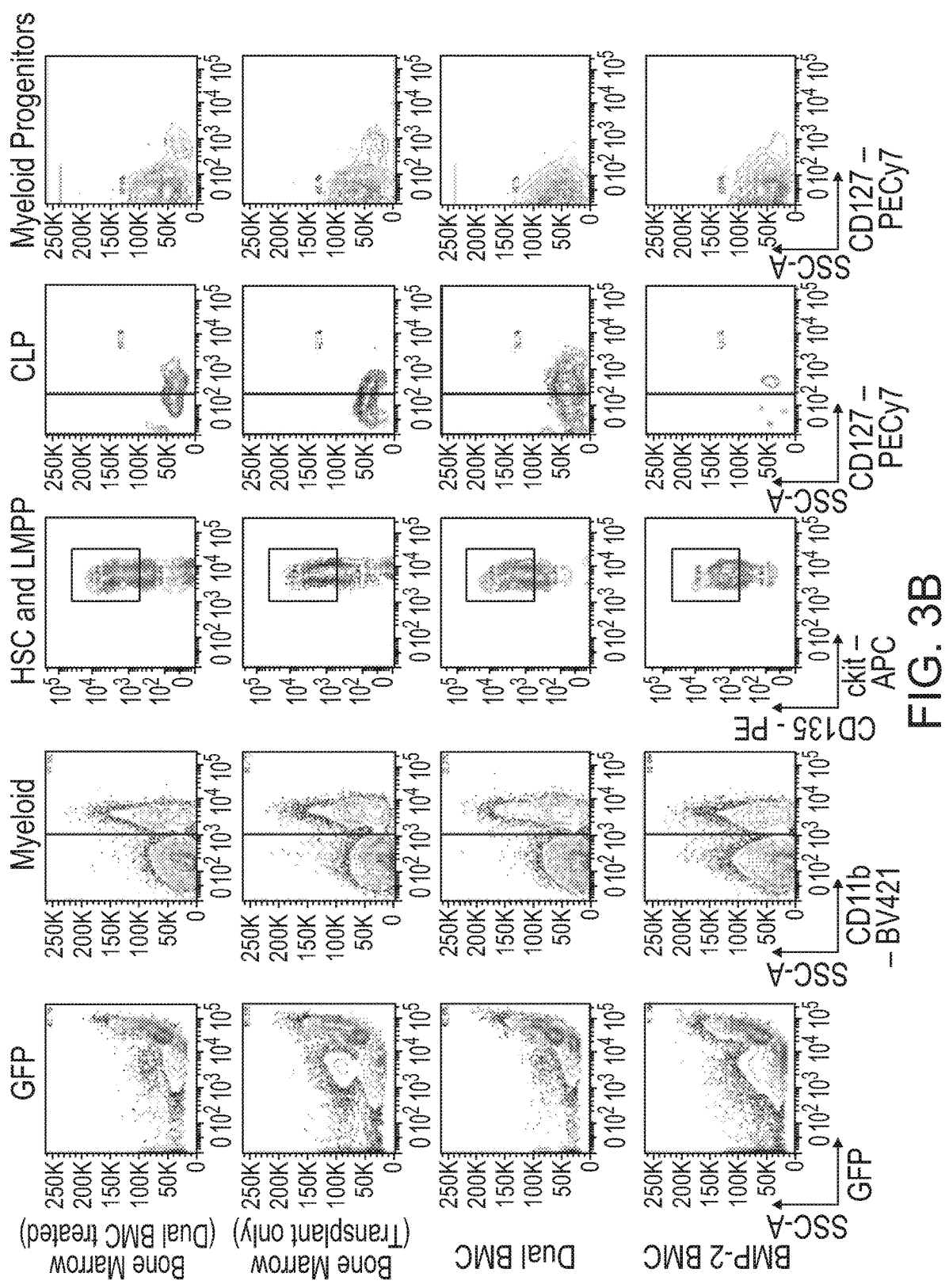

FIG. 3B shows representative flow cytometric profiles of the bone marrow and BMC (Dual and BMP-2 only) at Day 28 post-transplant. Donor GFP, myeloid, HSC, lymphoid-primed multipotential progenitors (LMPP), CLP and myeloid progenitors are identified.

Figure 3C:
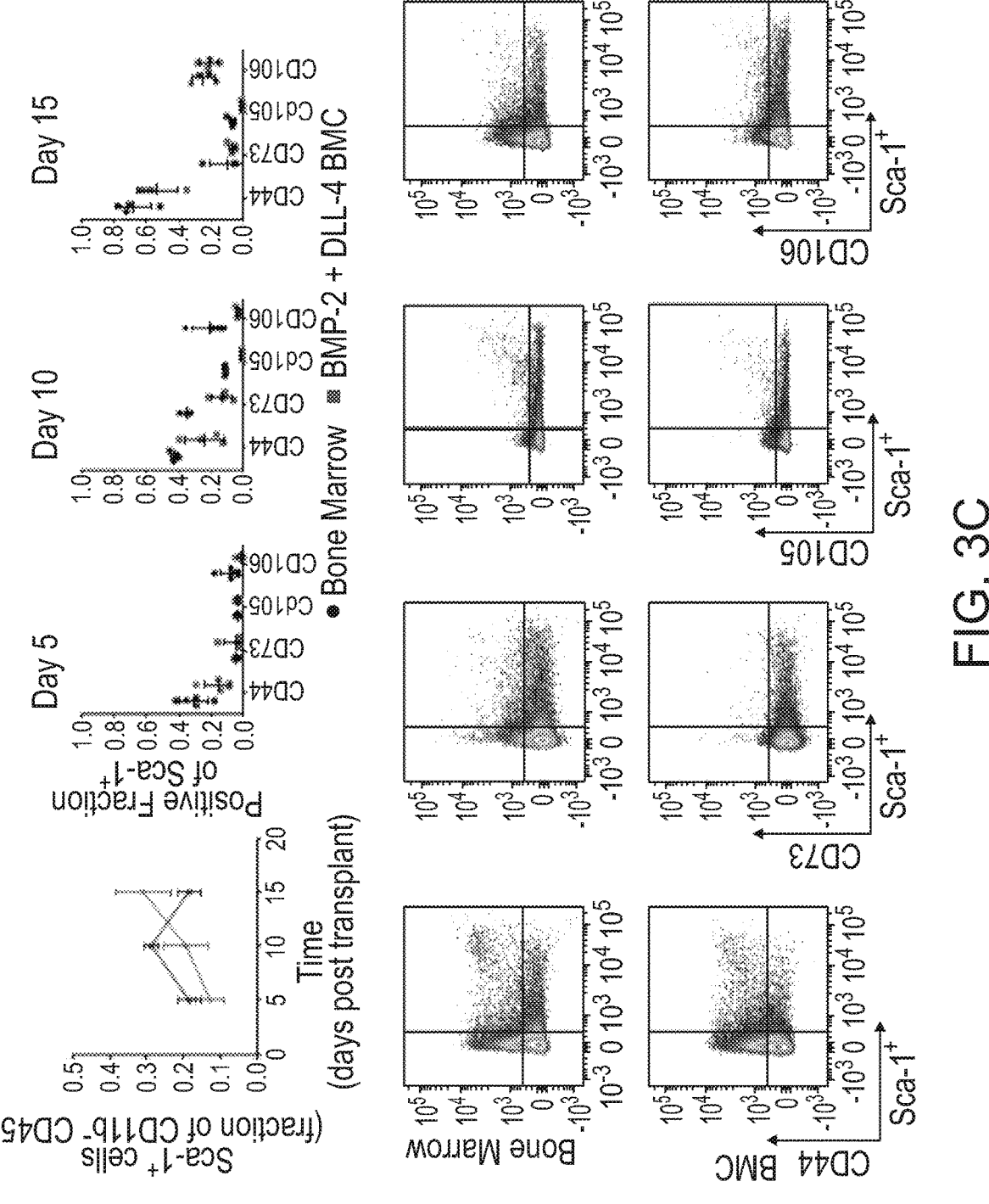

FIG. 3C shows host mesenchymal stromal cells in the BMC and endogenous bone marrow and representative flow cytometry plots. Sca-1$^+$ progenitors are represented as a fraction of CD45$^-$ cells. CD44, CD73, CD29, CD105 and CD106 expressing cells are represented as a fraction of Sca-1$^+$ progenitors.

Figure 3D:
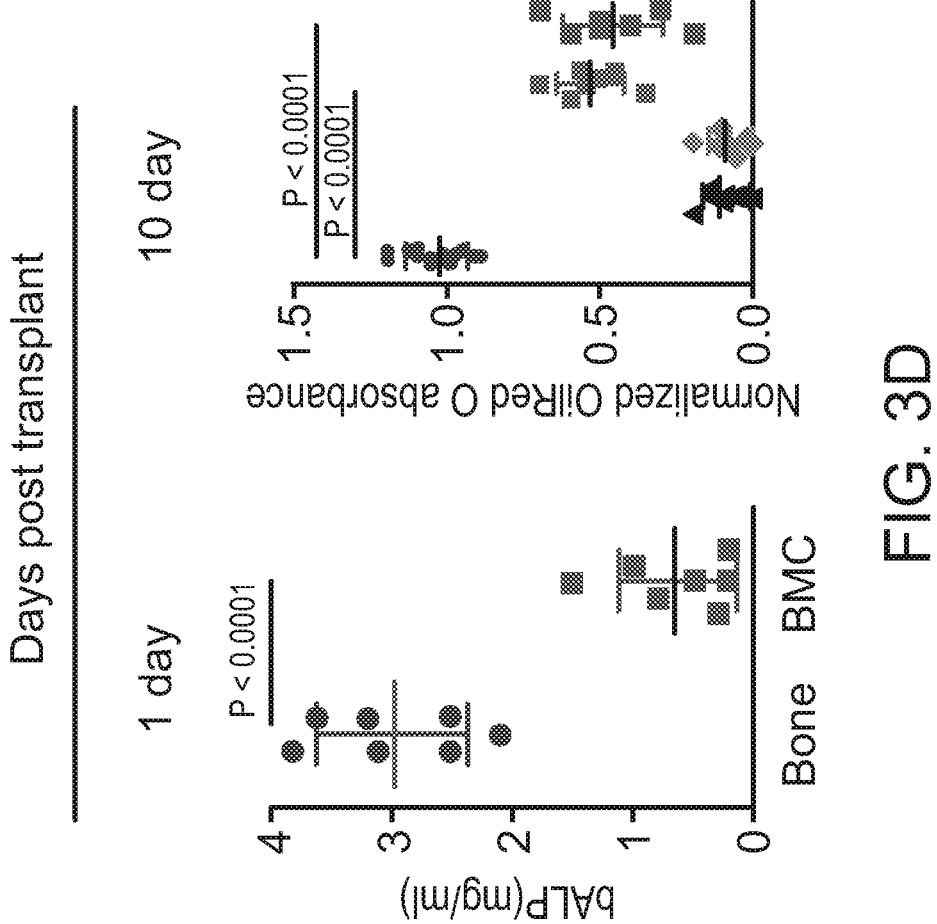

FIG. 3D shows quantification of bone alkaline phosphatase (bALP) and Oil-red-O (ORO) in bone and BMC at Day 20 after subcutaneous injection (n=6-7).

Figures 3E, 3F:
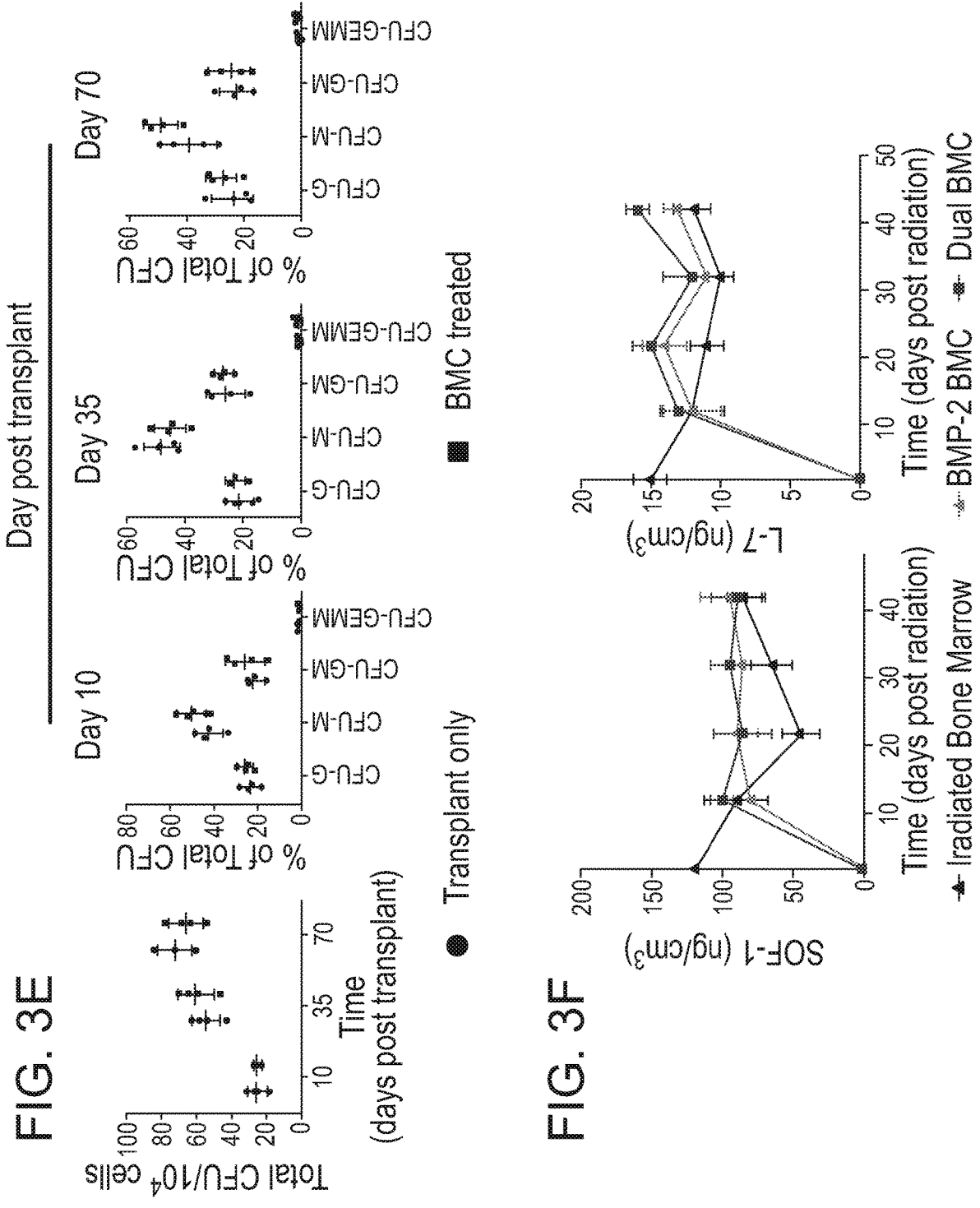

FIG. 3E shows colony-forming unit assays using bone marrow cells from transplant only and dual BMC treated mice at Days 10, 35 and 70 post-transplant.

FIG. 3F shows the concentrations of homing factor SDF-1α and lymphoid progenitor supporting cytokine IL-7 in harvested BMCs. Post-HSCT mice treated with a BMP-2 BMC, and post-HSCT mice treated with a Dual BMC were analyzed and compared to cytokine concentrations in the bone marrow of the same group.

Data in FIGS. 3C-3F are mean±s.d. of n=4, n=7, n=4 and n=4 respectively and are representative from 2 independent experiments. Data in FIG. 3B are from n=10 and are representative from 2 independent experiments (*$P<0.05$,  $P<0.01$, *$P<0.001$, analysis of variance (ANOVA) with a Tukey post hoc test).

Figures 3G, 3H:
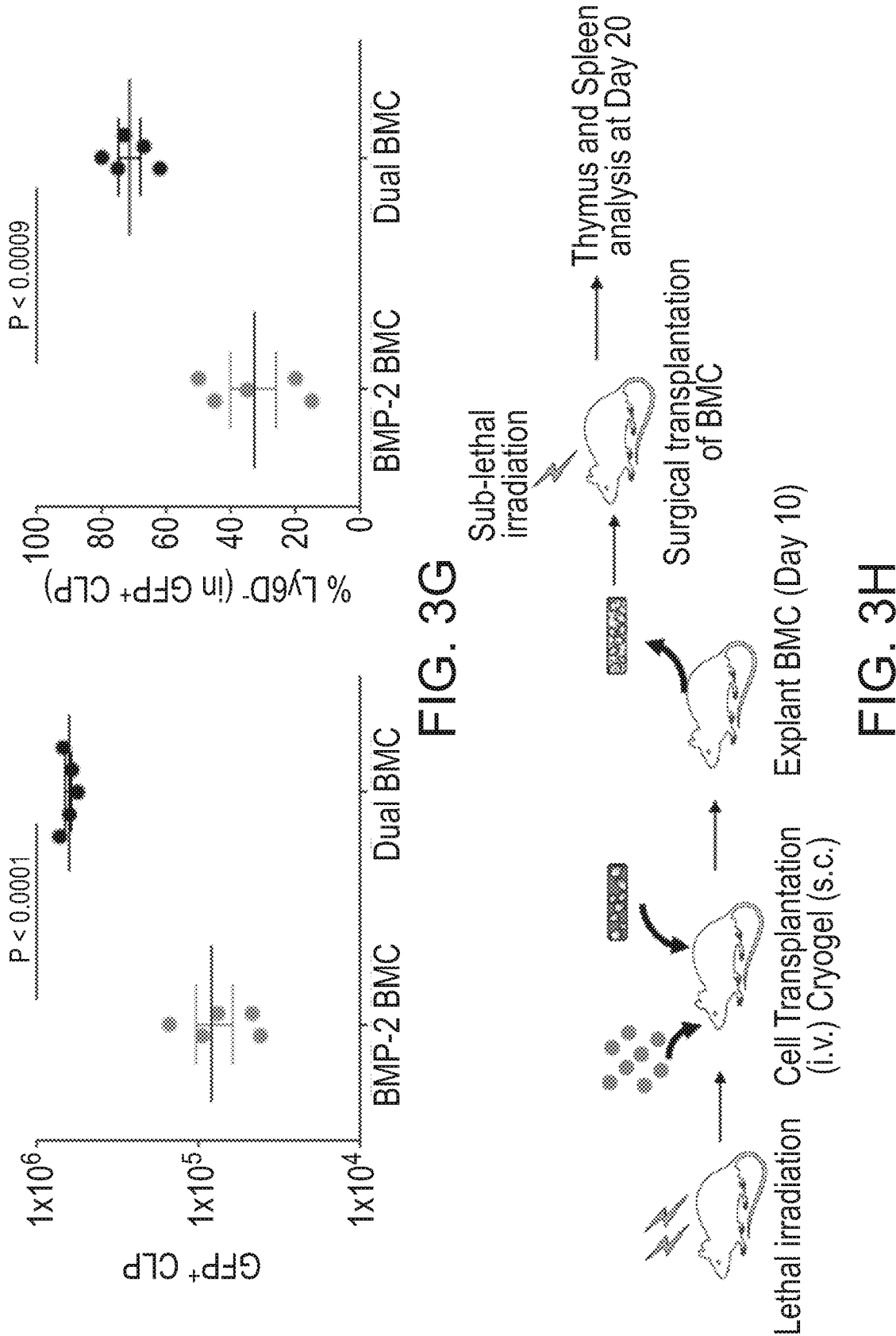

FIG. 3G shows absolute number of donor GFP+CLPs and the percentage of Ly6D-CLPs in BMP-2- and dual factor-BMCs.

FIG. 3H shows schematic of experimental setup for surgical transplantation of harvested BMCs from post-HSCT mice into sub-lethally irradiated mice.

Figure 3I:
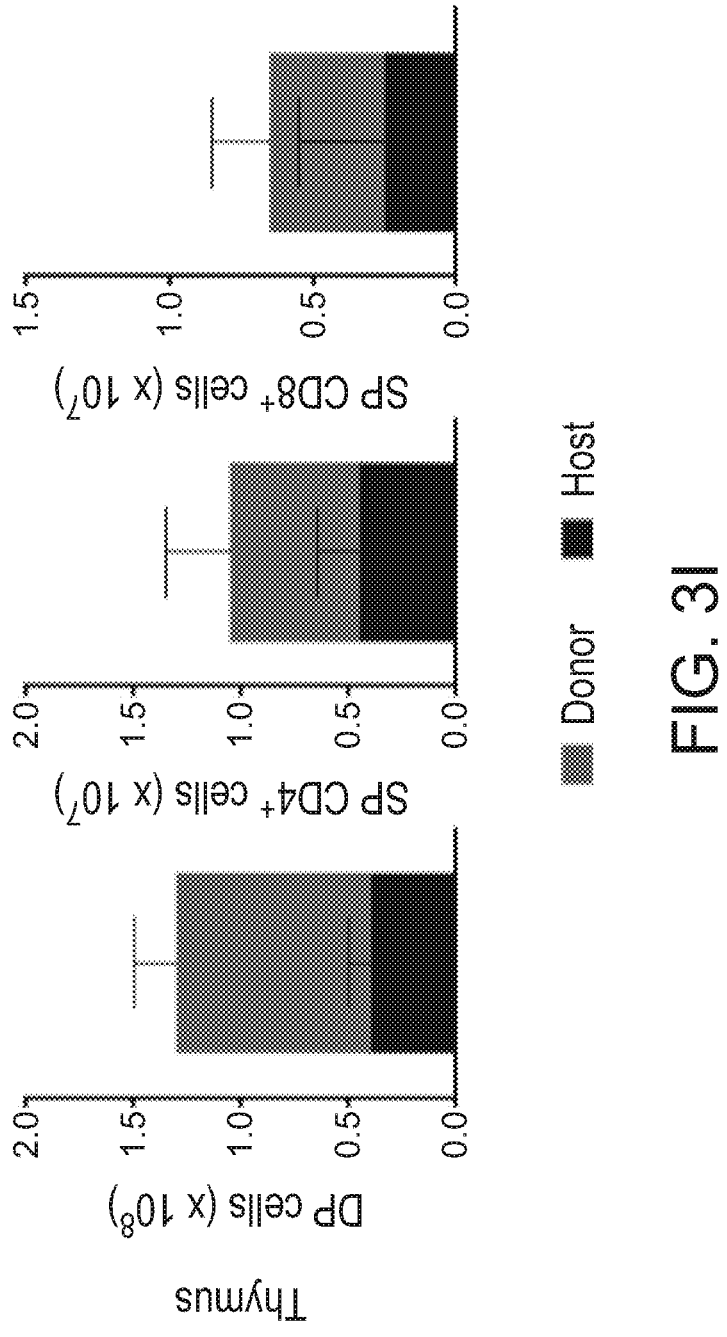

FIG. 3I shows double positive (DP), single positive (SP) CD4+ and SP CD8+ cells quantified in the thymus 20-days post surgical transplantation of BMC.

Figure 3J:
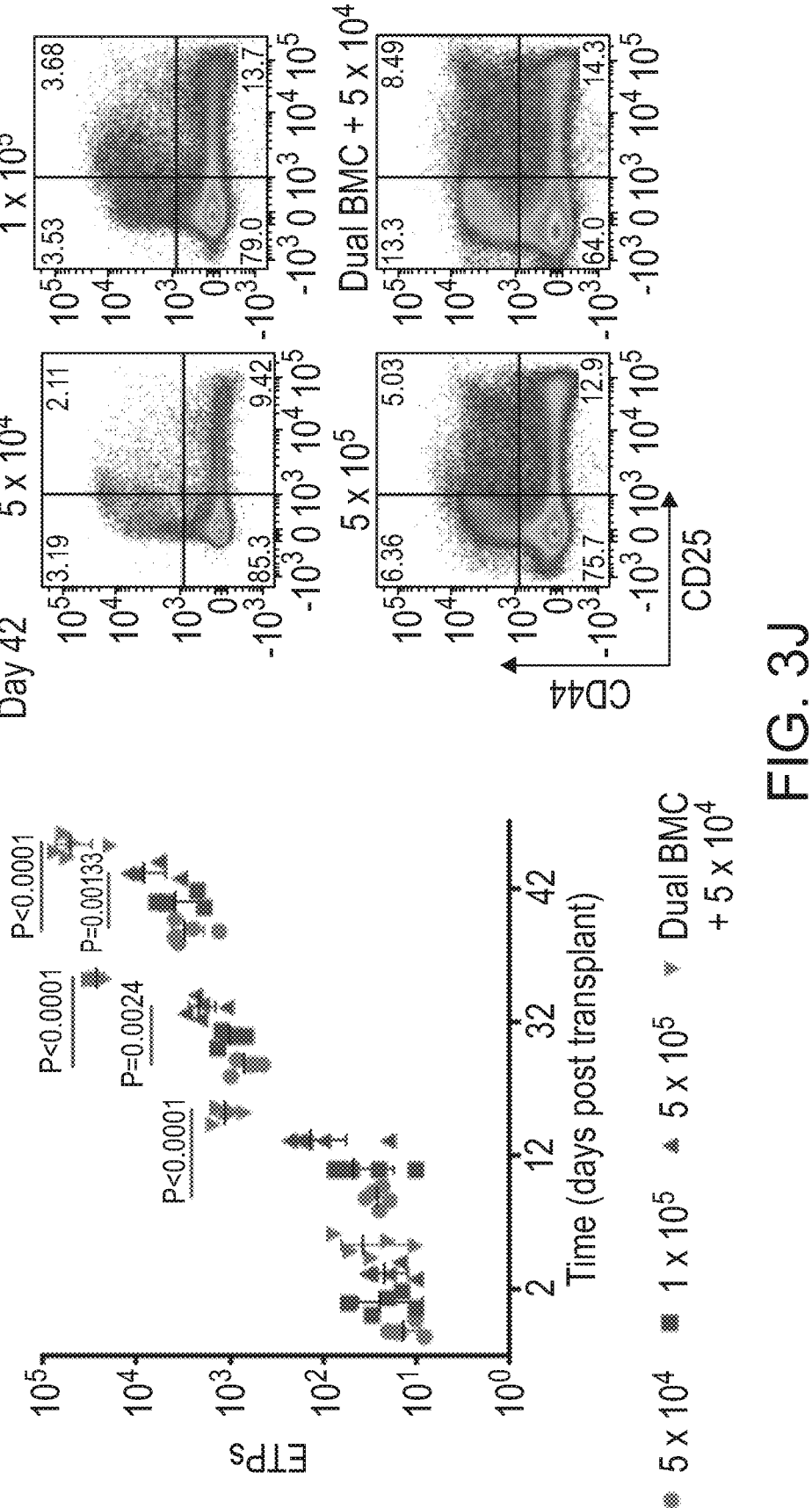
Figure 3K:
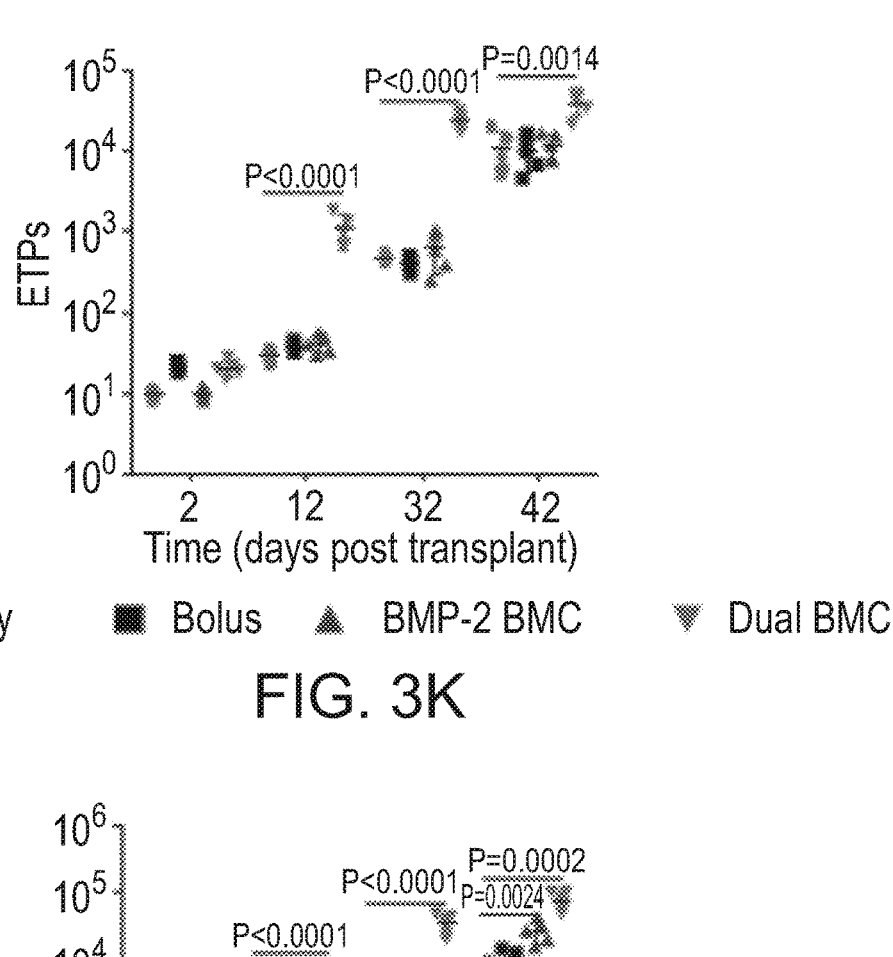
Figure 3L:
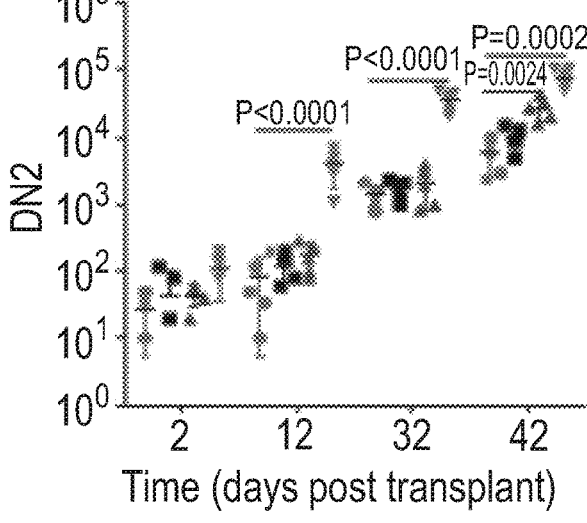
Figure 3M:
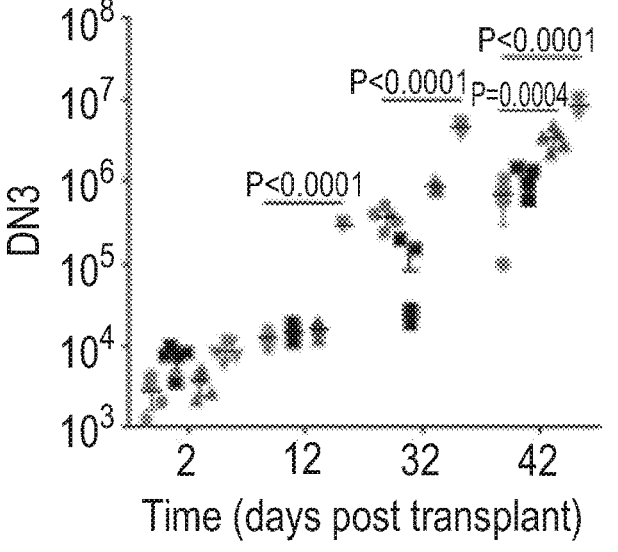
Figure 3N:
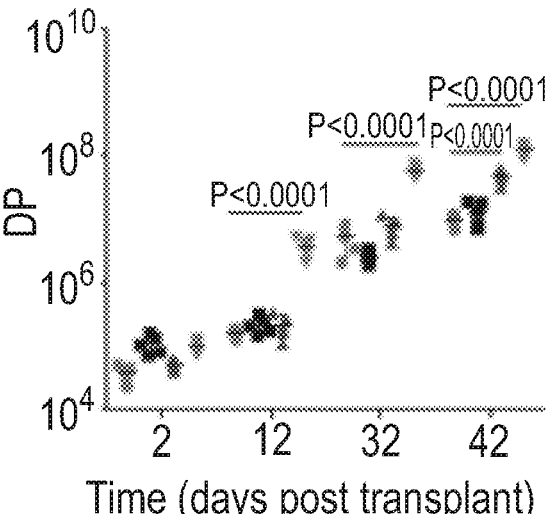
Figure 3O:
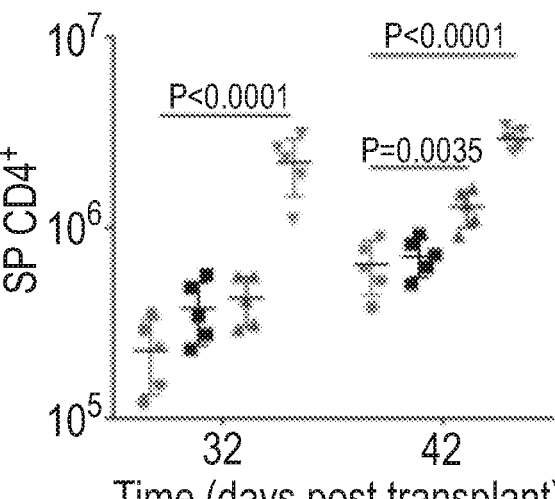
Figure 3P:
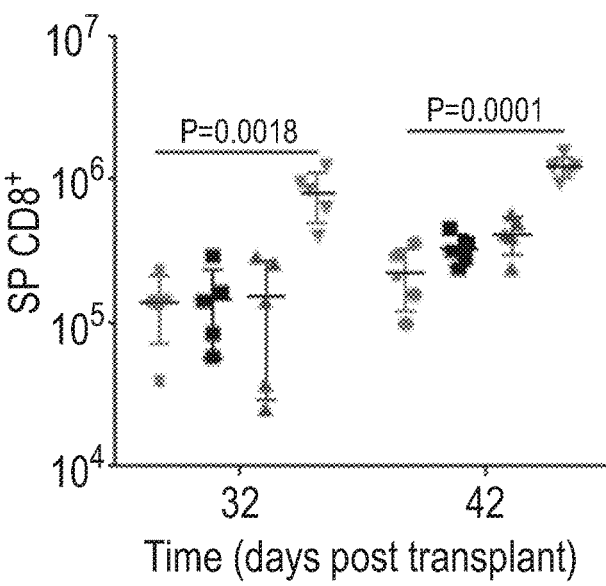
Figure 3P:

FIG. 3J shows total number of early T-lineage progenitors (ETP; CD44+CD25-c-kit+) quantified as a function of lineage-depleted transplanted cell dose compared with BMC treatment with the lowest cell dose at multiple time points post transplant with representative FACS plots (five experimental replicates at each time point, 2 independent experiments).

FIGS. 3K-3P show total number of early T-lineage progenitors (ETP; CD44+CD25-c-kit+), DN2 (CD44+CD25-), DN3 (CD44+CD25-), DP, SP4, SP8 thymocyte subsets compared across different treatment conditions at multiple time points post transplant.

For FIGS. 3A, 3G, and 3K-3P, the mice were transplanted with $5\times10^5$ lineage depleted syngeneic GFP BM cells within 48 hours after L-TBI 375 ($1\times1000$ cGy). In FIGS. 3H and 3I, an initial set of mice were transplanted with $5\times10^5$ lineage depleted syngeneic GFP BM cells within 48 hours after L-TBI. A subsequent set of mice received SL TBI ($1\times500$ cGy) without a subsequent cell transplant. In FIG. 3J, the mice were transplanted with $5\times10^4$ to $5\times10^5$ lineage depleted GFP cells. In FIG. 3A, all groups are compared with transplant only control (*$P<0.05$,  $P<0.01$, *$P<0.001$, analysis of variance (ANOVA) with a Tukey post hoc test). Data in FIG. 3A represents the mean±s.d. of ten mice per group and are representative of two independent experiments. Data in FIGS. 3G, and 3I-3P represent the mean±s.d. from five mice per group, and at each time point in FIGS. 3I-3P and are representative of two independent experiments. Comparisons are with the lowest cell dose group in FIG. 3J and the transplant only group in FIGS. 3I-3P. (*$P<0.05$,  $P<385\ 0.01$, *$P<0.001$, analysis of variance (ANOVA) with a Tukey post hoc test). Distinct samples were assayed individually.

FIGS. 3Q-3T show extended characterization of thymus cellularity and weight post transplant. B6 mice were irradiated with $1\times1000$ cGy L-TBI dose and were subsequently transplanted with $5\times10^5$ lineage depleted syngeneic GFP BM cells within 48 hours after L-TBI and treated as described in the figure.

Figure 3Q:
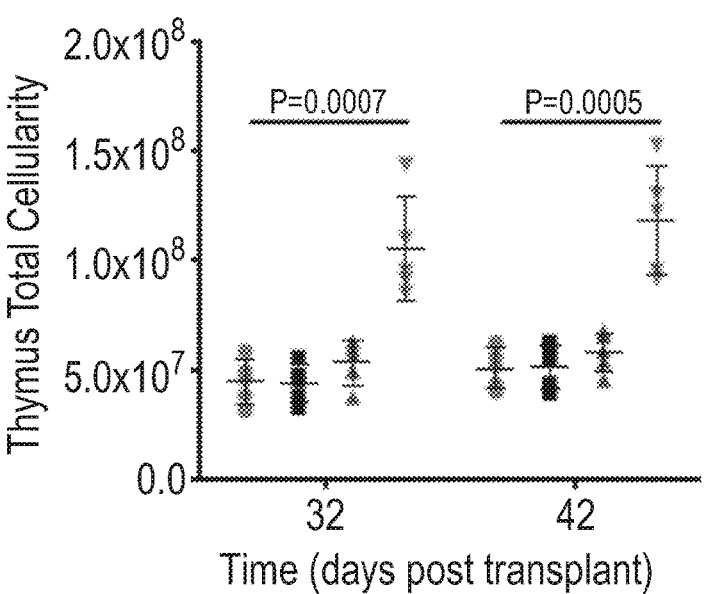

FIG. 3Q shows total thymocytes quantified at 32- and 42-days post-transplant.

Figure 3R:
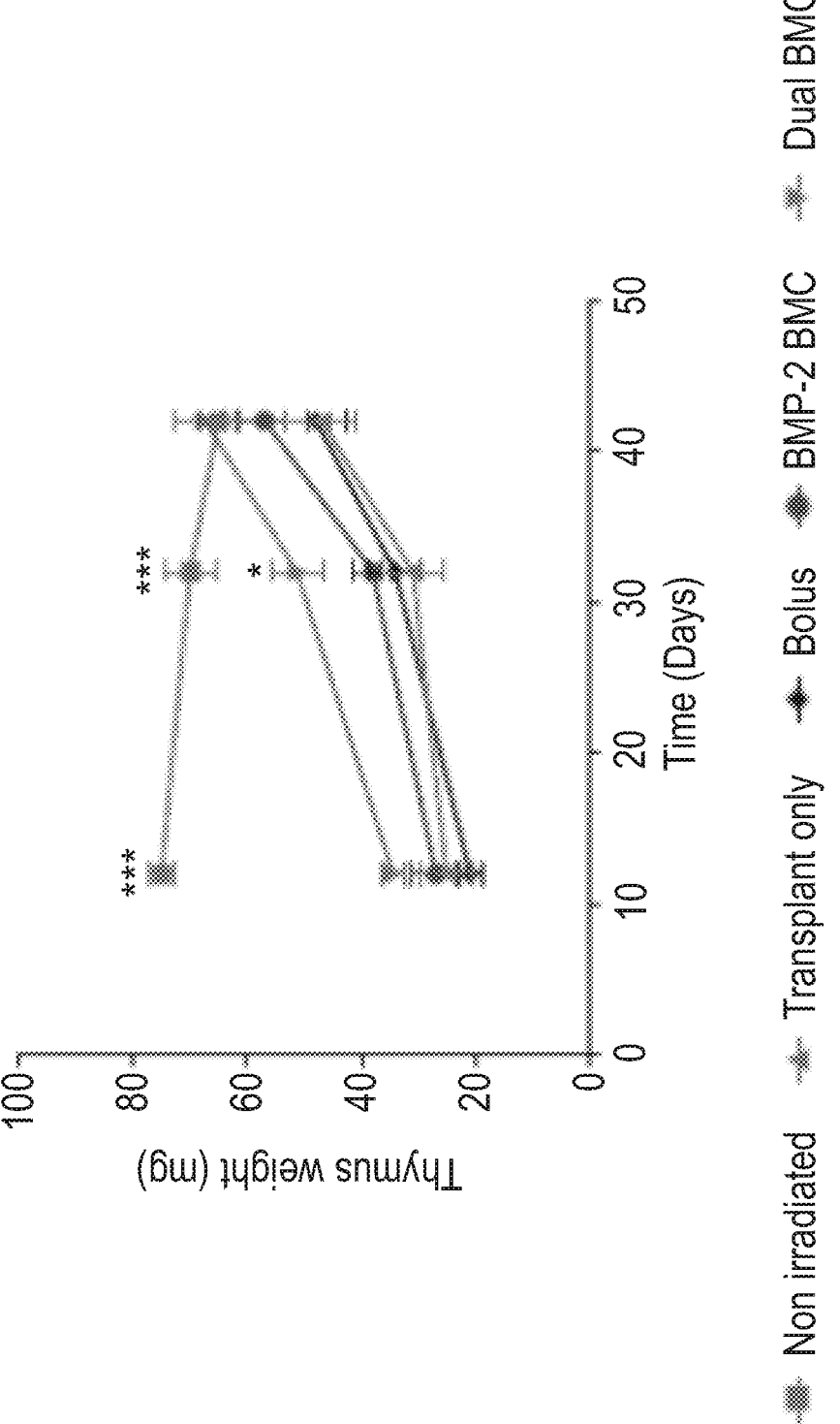

FIG. 3R shows thymus weight quantified between 12- and 42-days post-HSCT.

Figure 3S:
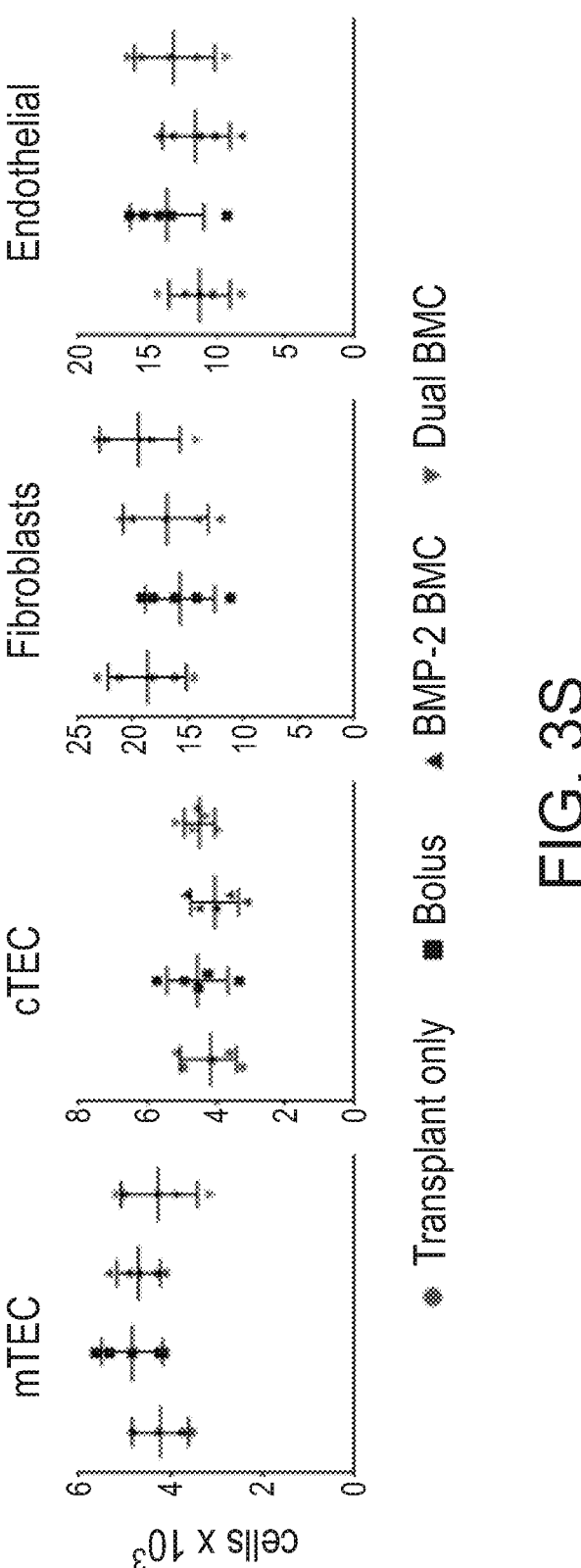

FIG. 3S shows that mTEC, cTEC, fibroblasts and endothelial cells were quantified 22-days post-HSCT.

Figure 3T:
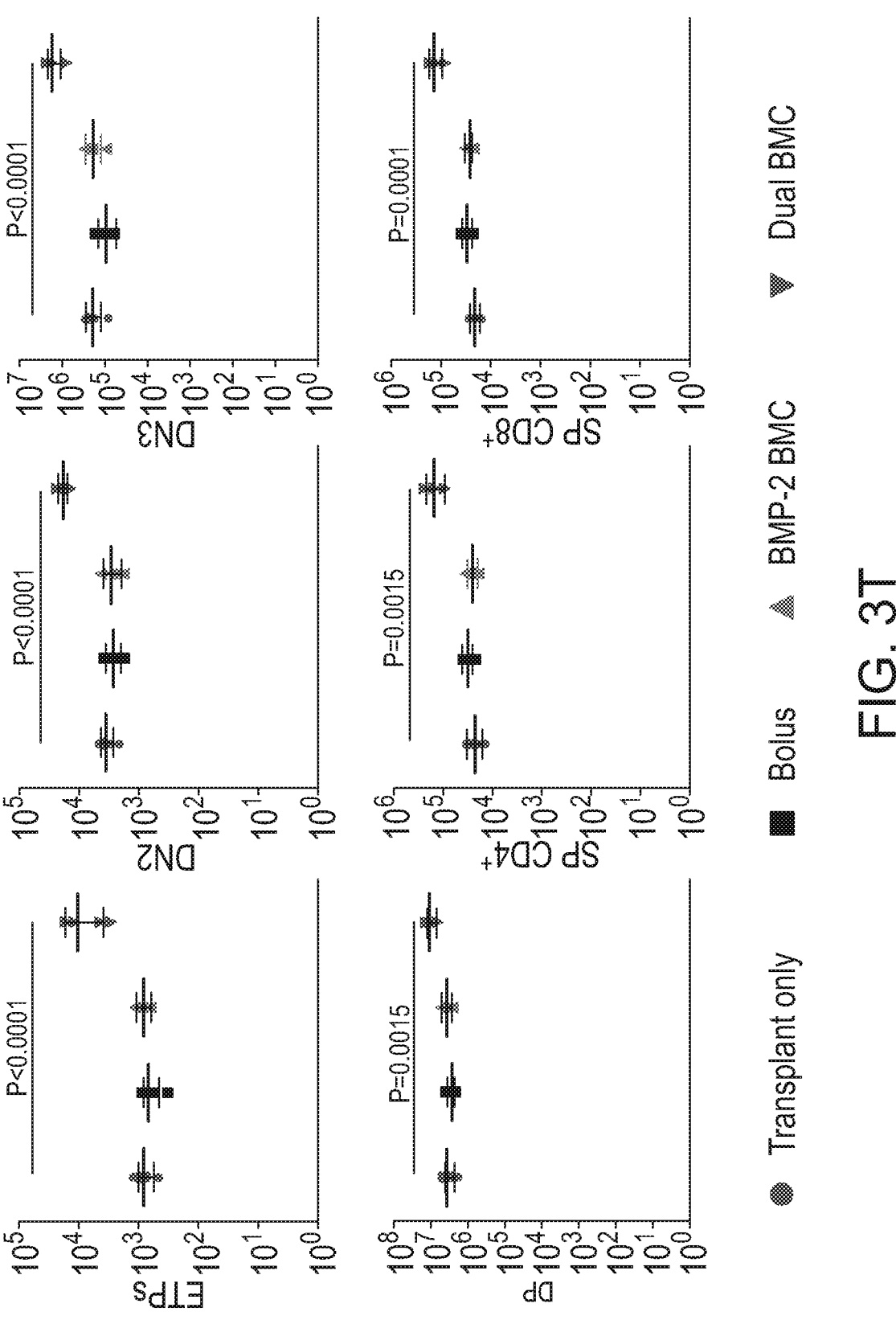

FIG. 3T shows the total number of early T-lineage progenitors (ETP; CD44$^+$CD25$^-$c-kit$^+$), DN2 (CD44$^+$CD25$^-$), DN3 (CD44$^+$CD25$^-$), DP, SP4, SP8 thymocyte subsets compared across different treatment conditions at 22-days post HSCT.

The thymus in post-HSCT mice with no BMC (Transplant only), post-HSCT mice treated with a BMP-2 BMC, and post-HSCT mice treated with a Dual BMC were harvested and weighed and were compared with that of non-radiated mice. All groups in FIGS. 3Q, 3S, and 3T are compared with transplant only control. 10-days post-HSCT, BMCs were explanted and surgically placed in the subcutaneous pocket of a second set of B6 mice that were irradiated with 500 cGy SL-TBI. Values are represented as absolute numbers. Data in FIGS. 3Q-3T represent the mean±s.d. from 5 mice per group at each time point and are representative of at least two independent experiments. (*$P<0.05$,  $P<0.01$, *$P<0.001$, analysis of variance (ANOVA) with a Tukey post hoc test).

FIGS. 4A, and 4D-4L show enhancement of T-cell reconstitution mediated by the BMC. FIGS. 4B, 4C, 4M, and 4N show extended characterization of blood cell analysis post-HSCT.

Figure 4A:
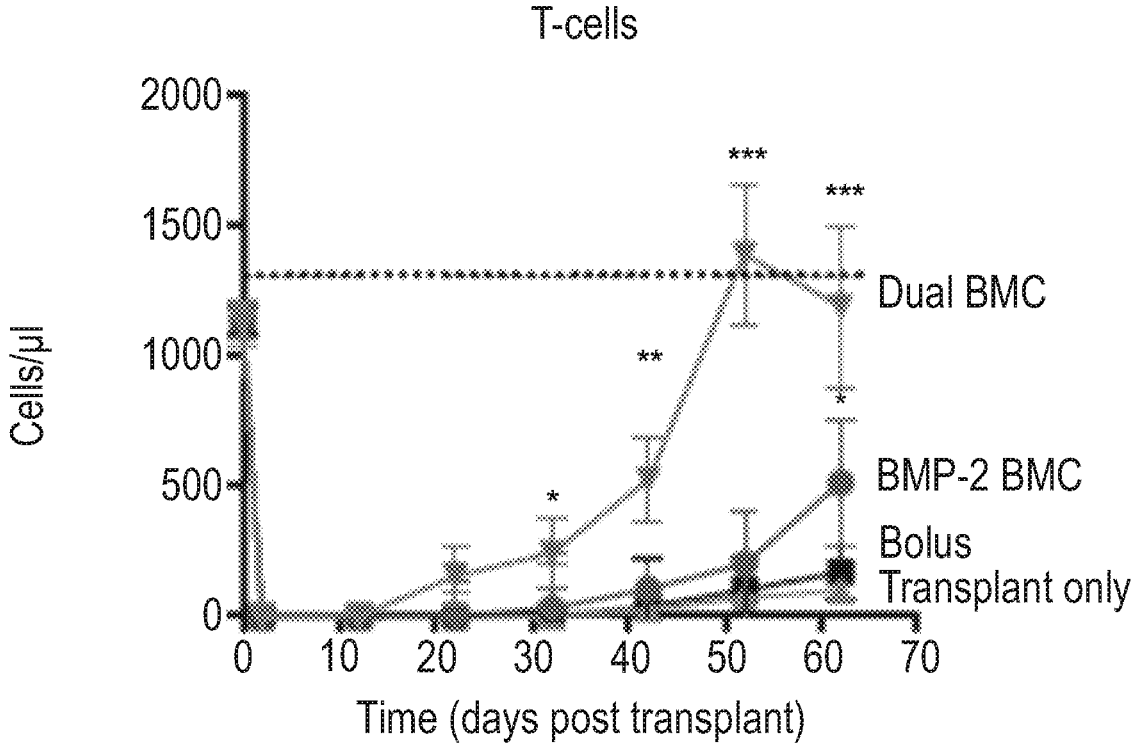

FIG. 4A shows the sum of CD3+CD4+ and CD3+CD8+ in the peripheral blood of mice post-HSCT. B6 mice were irradiated with 1×1000 cGy L-TBI dose. Mice were subsequently transplanted with $5×10^5$ lineage depleted syngeneic GFP BM cells within 48 hours after L-TBI and treated as indicated in the figure.

Figure 4B:
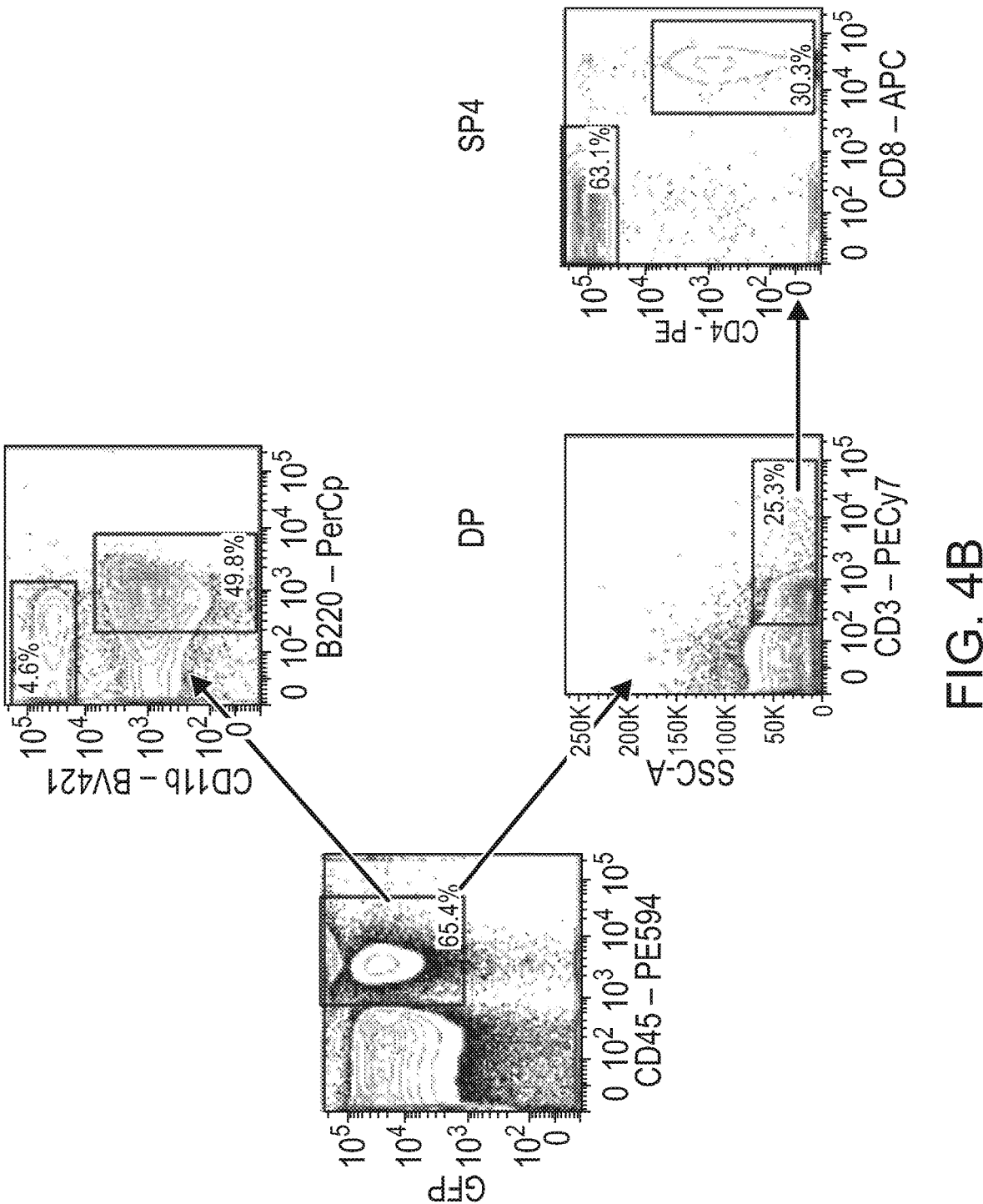

FIG. 4B shows representative FACS gating strategy for measuring post-HSCT immune cell reconstitution in C57BL/6J mice transplanted with GFP+ donor hematopoietic stem and progenitor cells from 5 independent experiments.

Figures 4C, 4D:
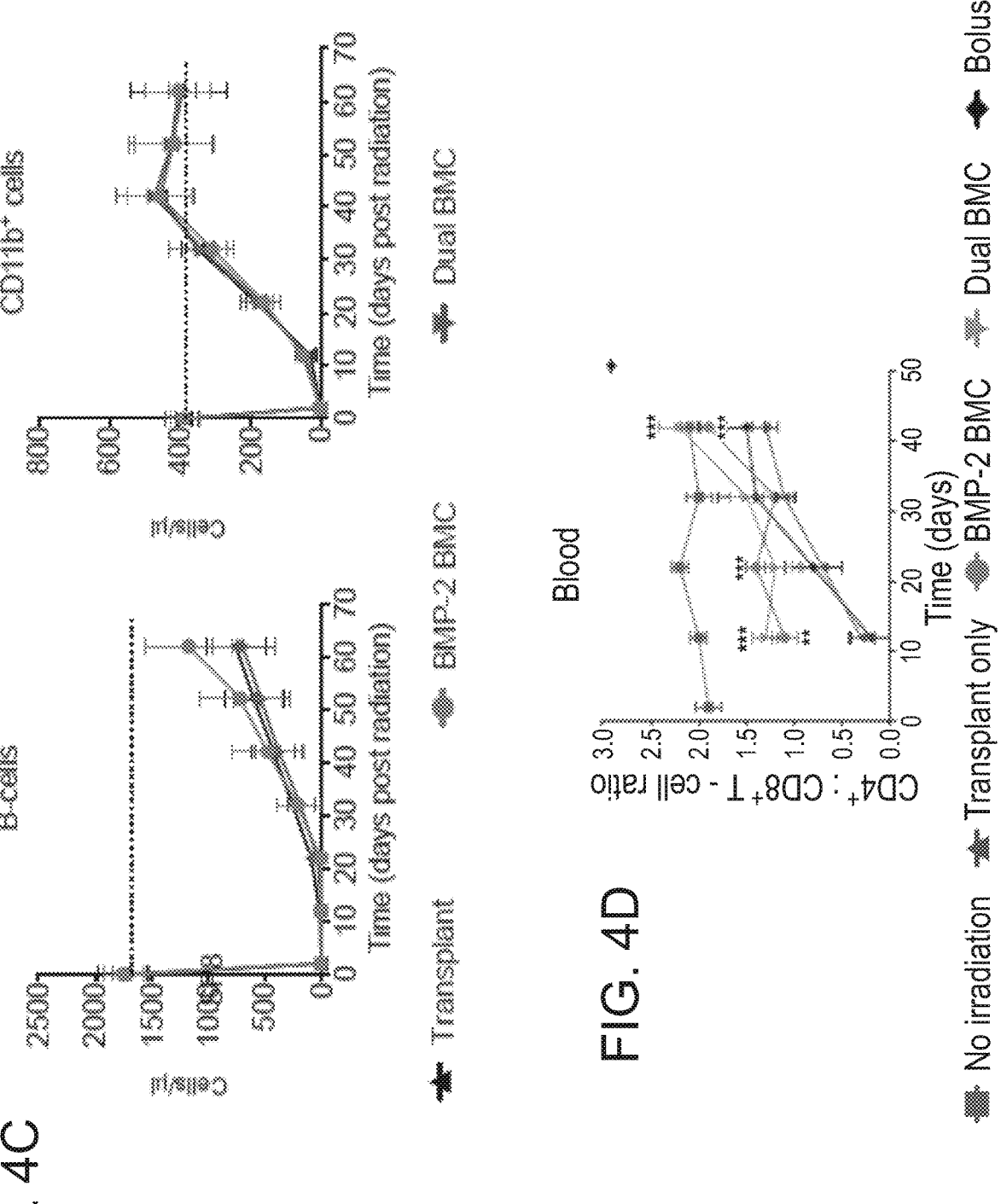

FIG. 4C shows reconstitution of B-cells and Myeloid cells in vivo. B6 mice were irradiated with 1×1000 cGy L-TBI dose and were subsequently transplanted with $5×10^5$ lineage depleted syngeneic GFP BM cells within 48 hours after L-TBI. The peripheral blood of post-HSCT mice with no BMC (Transplant only), post-HSCT mice treated with a BMP-2 BMC, and post-HSCT mice treated with a Dual BMC were analyzed and measured numbers were compared with pre-radiation immune cell concentrations.

Figures 4E, 4F:
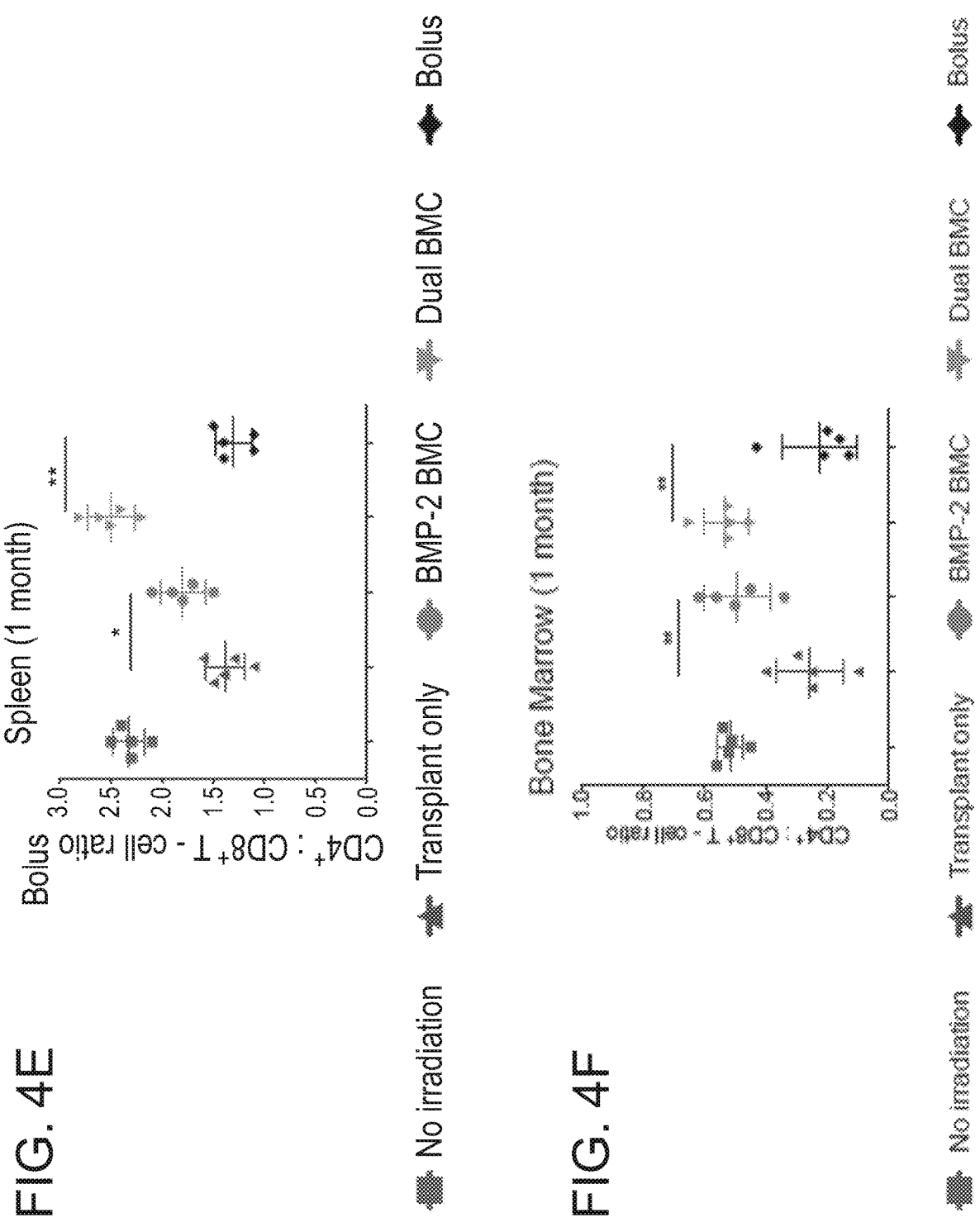

FIGS. 4D-4F show measurement of the recovery in CD4+ to CD8+ T-cell ratios in the blood (FIG. 4D), spleen (FIG. 4E) and bone marrow (FIG. 4F), as a function of time, with non-irradiated mice as for comparison for the same groups as in FIG. 4A. In FIGS. 4A and 4D-4F, post-HSCT mice treated with no BMC (Transplant only), with a bolus BMP-2 and DLL-4 injection, a BMC containing BMP-2 (BMP-2 BMC), or a BMC containing BMP-2 and DLL4 (Dual BMC) were analyzed.

In FIGS. 4G-4L, B6 mice were irradiated with 500 cGy SL-TBI and subsequently transplanted with 5×105 lineage-depleted bone marrow cells within 48 hours post-radiation. Total number of DP (FIG. 4G) SP4 (FIG. 4H) and SP8 (FIG. 4I) thymocytes and peripheral CD4+(FIG. 4J) and CD8+ T-cells (FIG. 4K) and B-cells (FIG. 4L) in the spleens of SL-TBI syn-HSCT mice that were treated with and without a dual BMC 28 days post-transplant. Data in FIGS. 4A, 4D-4F represent the mean±s.d. of n=8 mice per group for each time point and are representative of at least 3 independent experiments. Data in FIGS. 4G-4L represent the mean±s.d. of n=10 mice and are representative of 2 independent experiments. (*P<0.05,  P<0.01, *P<0.001, analysis of variance (ANOVA) with a Tukey post hoc test).

Figures 4G, 4H:
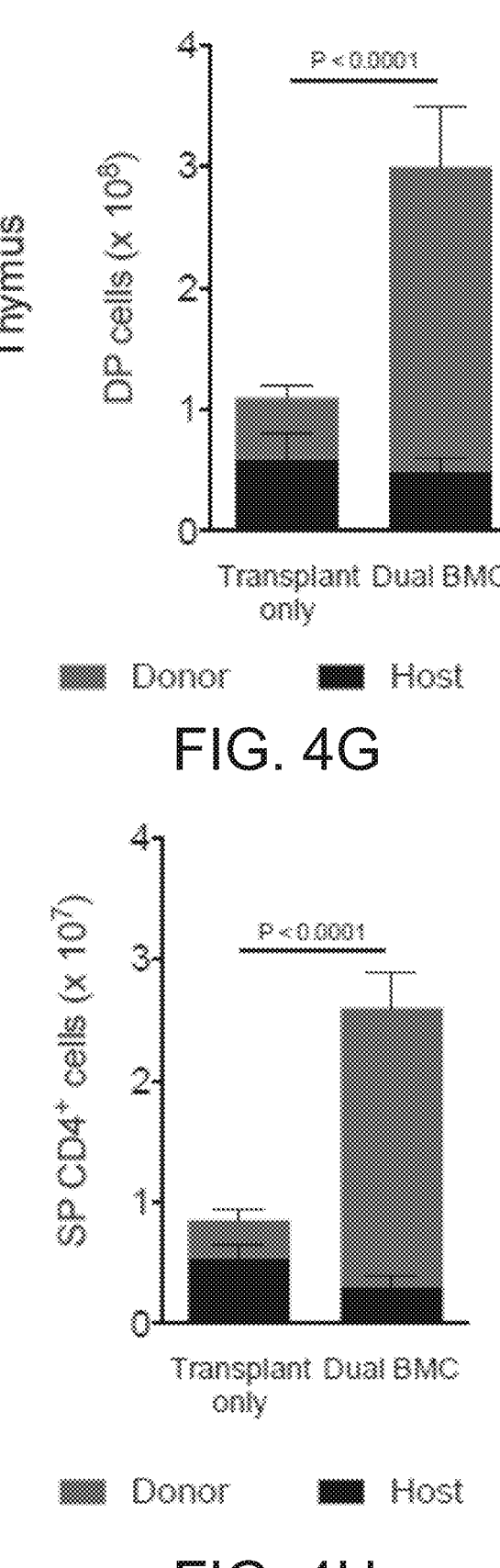
Figure 4I:
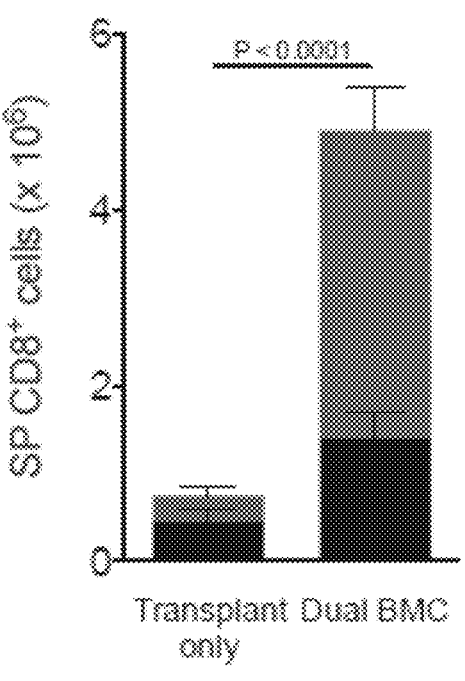
Figure 4J:
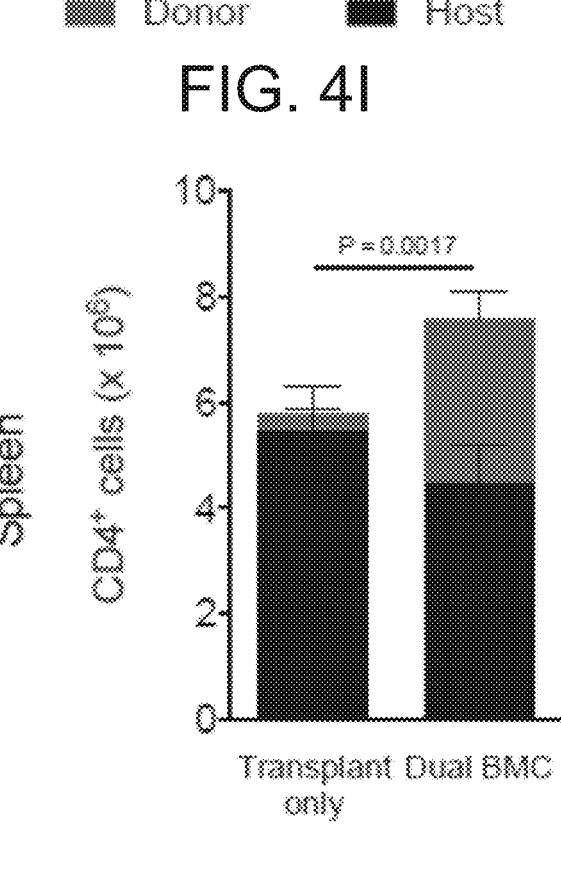
Figure 4K:
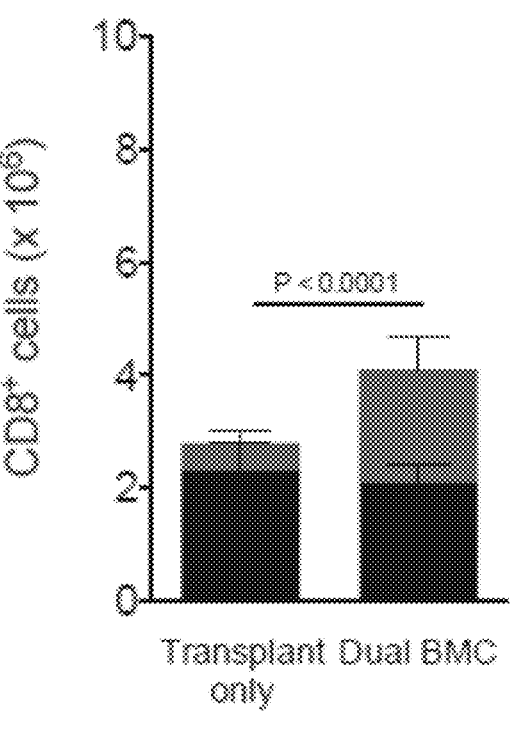
Figure 4K:
Figure 4L:
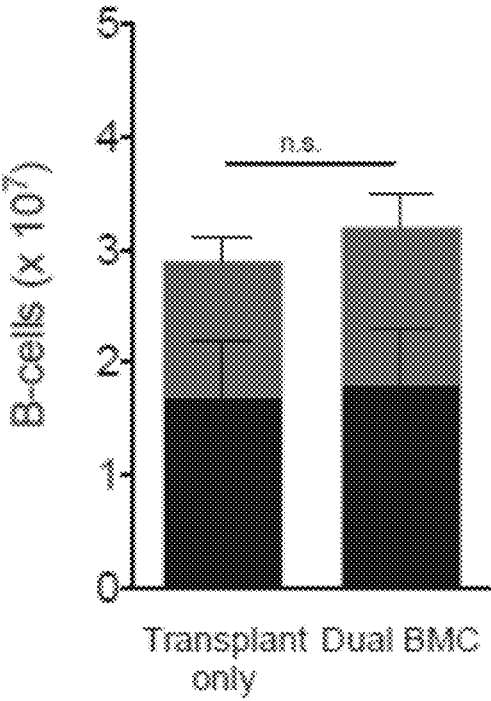
Figure 4M:
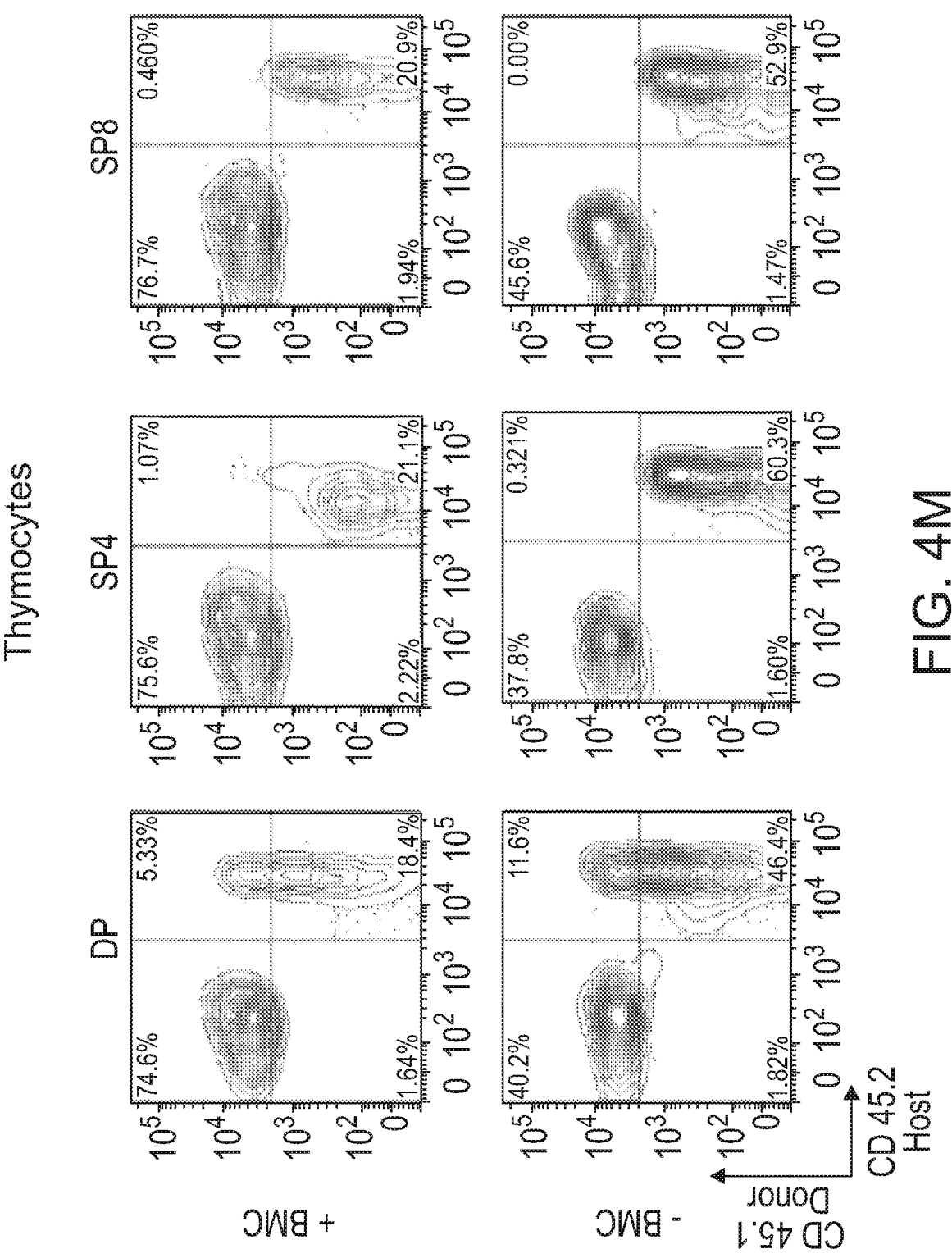

FIG. 4M shows representative FACS plots after post-HSCT of donor and host chimerism in thymocytes (DP, SP4, SP8) and in the splenocytes (CD4+, CD8+, B220+) at Day 28 post transplant in BM-treated and transplant only mice.

Figure 4N:
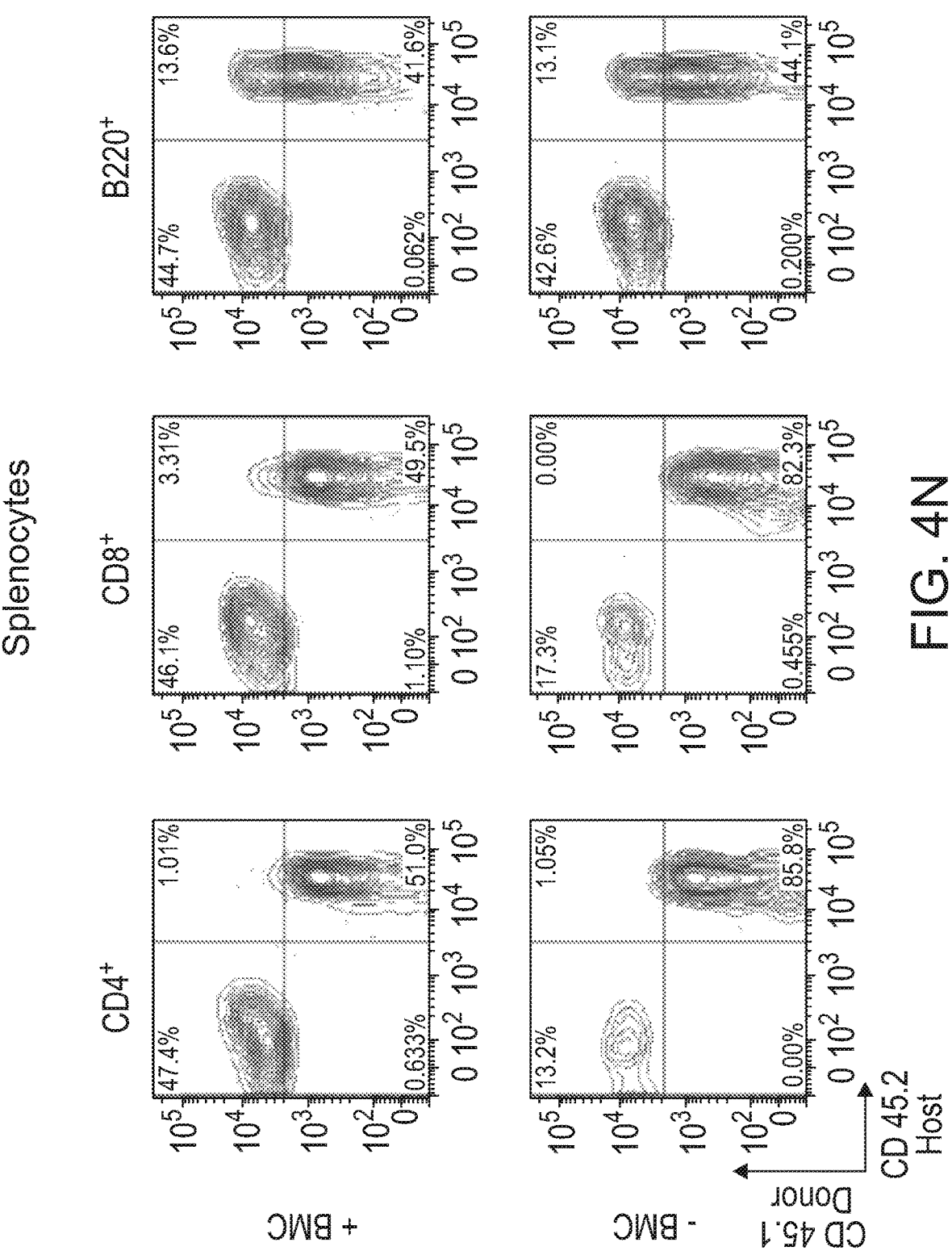

FIG. 4N shows representative flow cytometry plots of host (CD 45.2) and donor (CD 45.1) chimerism in sublethally irradiated mice 28 days post-transplant.

In FIGS. 4M and 4N, B6 mice were irradiated with 500 cGy SL-TBI and subsequently transplanted with $5×10^5$ lineage-depleted bone marrow cells within 48 hours post-radiation. One group was treated with the BMC. Data in FIG. 4C represent the mean±s.d. from 5 mice per group at each time point. Data in FIGS. 4C, 4M, and 4N are representative of two independent experiments. (*P<0.05,  P<0.01, *P<0.001, analysis of variance (ANOVA) with a Tukey post hoc test).

FIGS. 5A, 5B, 5D-5G, SI, 5J, and 5L-5P show enhanced reconstitution of T-cells and mitigation of GVHD in NSG-BLT mice and in mice after allogeneic HSCT. FIGS. 5H, 5K, and 5Q show extended flow cytometry characterization of BMC-generated T-cells and culture generated T-cell progenitors.

Figures 5A, 5B:
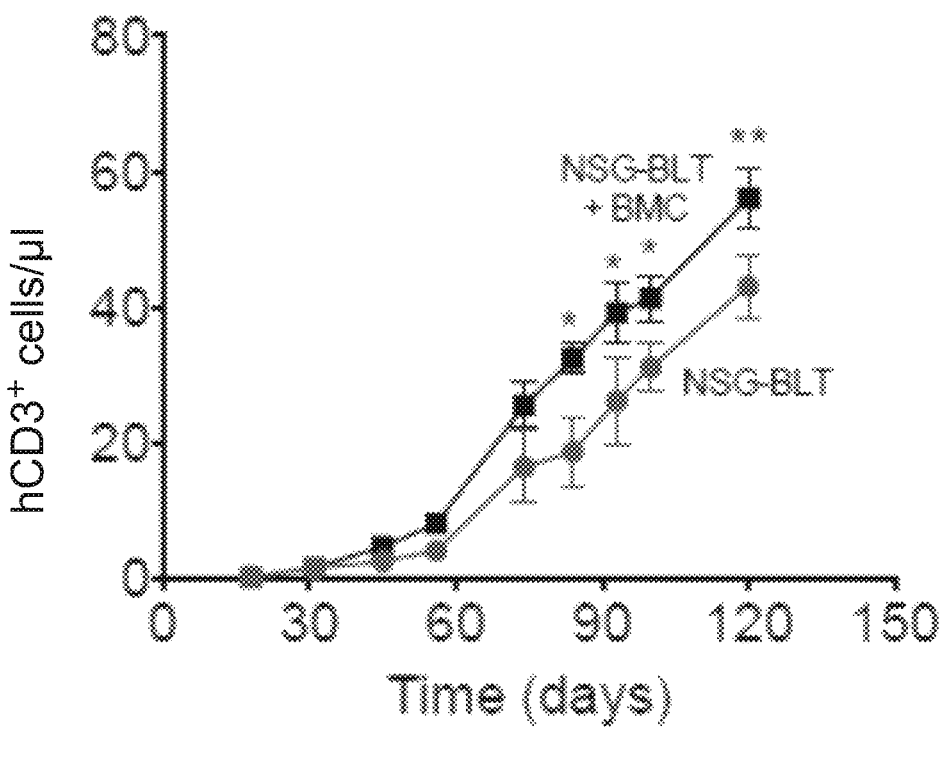
Figure 5C:
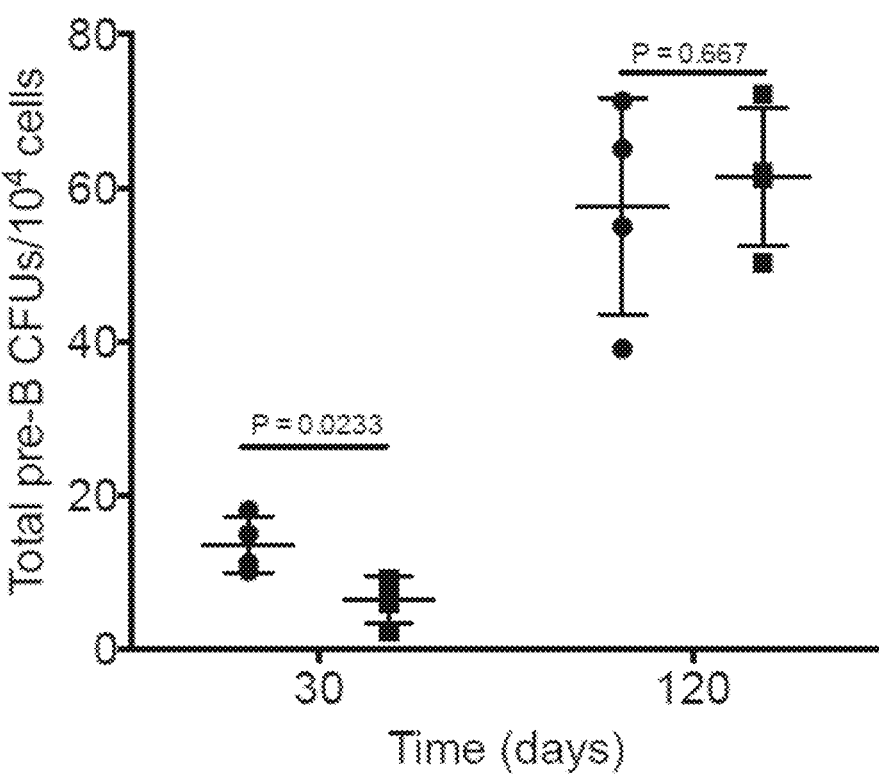
Figure 5D:
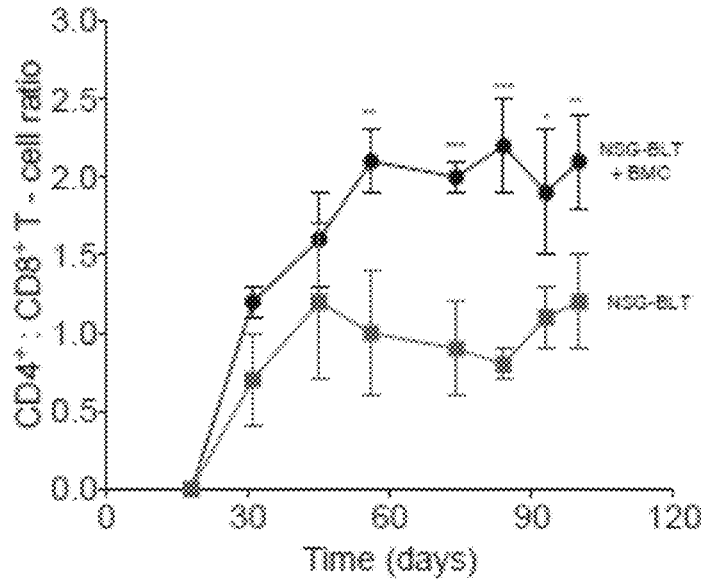

FIGS. 5A, 5B, and 5D show reconstitution of CD3+ T-cells (FIG. 5A) and CD19+ B-cells (FIG. 5B) with CD4+:

CD8+ ratio (FIG. 5D) in humanized NSG-BLT mice with exemplary flow cytometry plots at day 75.

FIG. 5C shows extended characterization of blood cell analysis in NSG-BLT mice. FIG. 5C shows pre-B CFUs quantified from the bone marrow of NSG-BLT mice with and without BMC treatment at two time points post-transplant. Data are mean±s.d. of n=4 and are from a single donor in one experiment. (*P<0.05,  P<0.01, *P<0.001, analysis of variance (ANOVA) with a Tukey post hoc test).

Figure 5E:
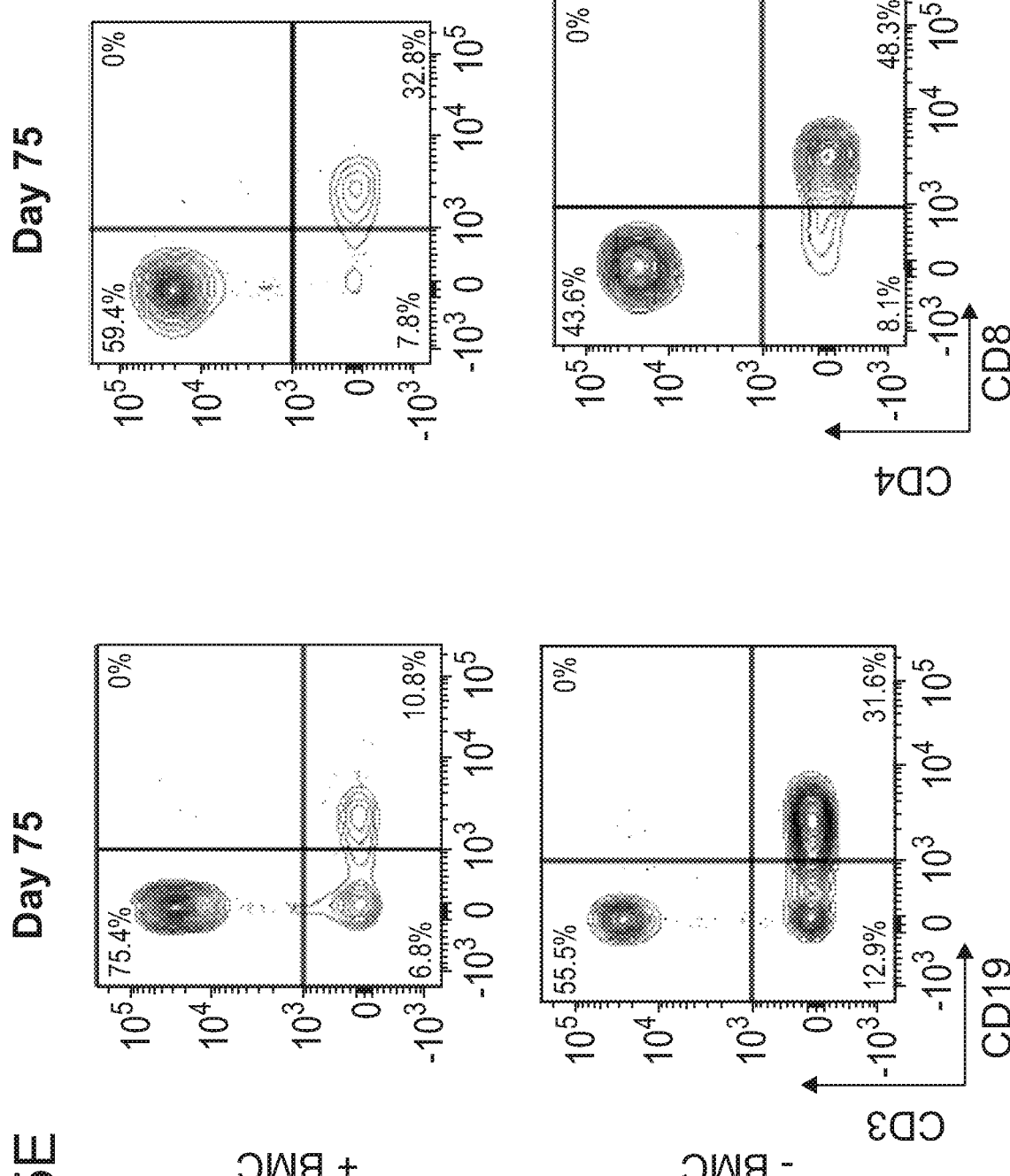

FIG. 5E shows exemplary flow cytometry plots at day 75.

Figure 5F:
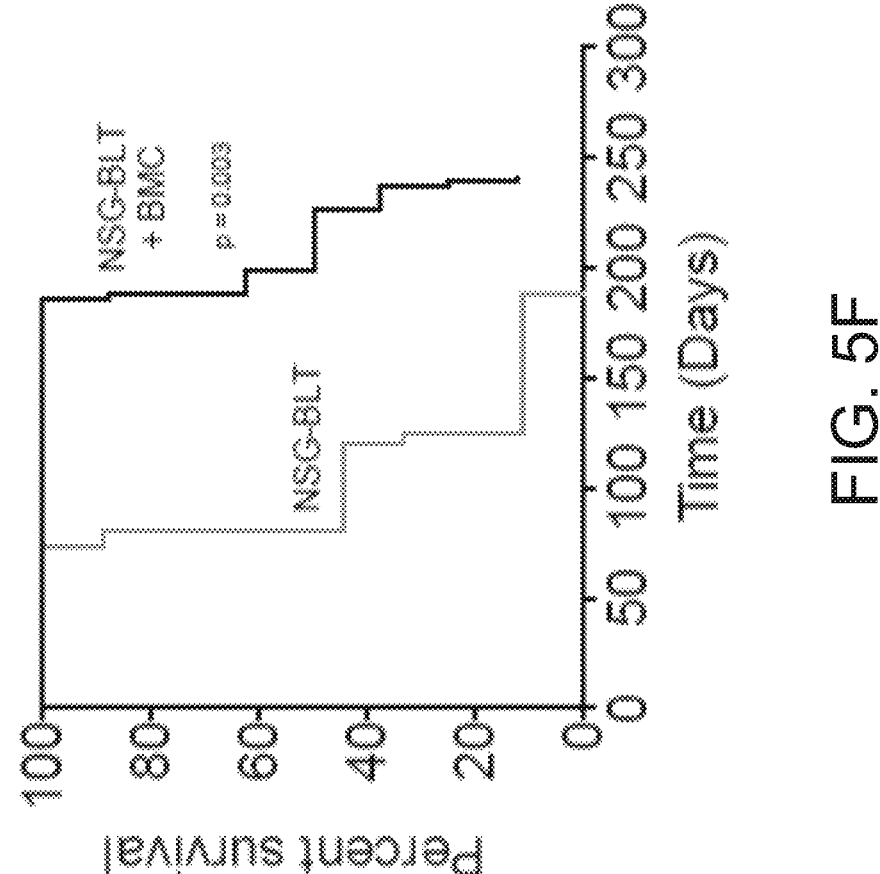
Figure 5G:
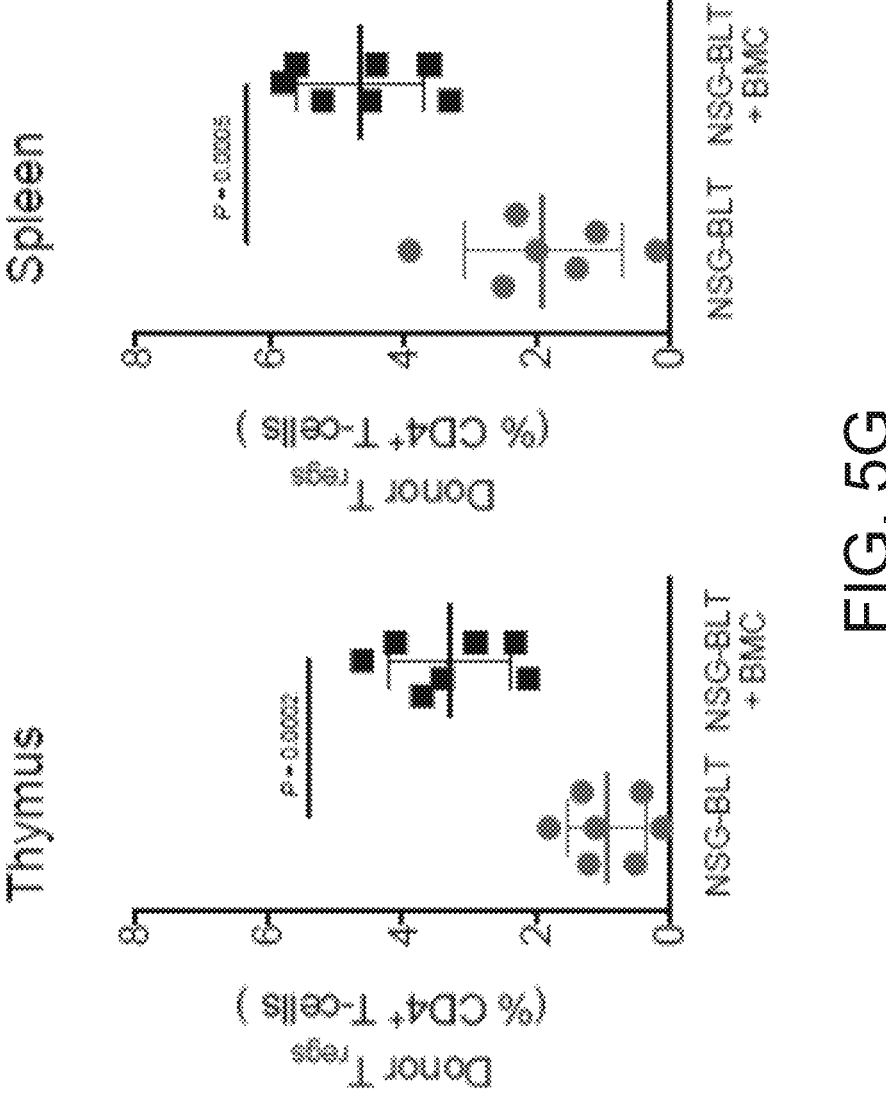
Figure 5H:
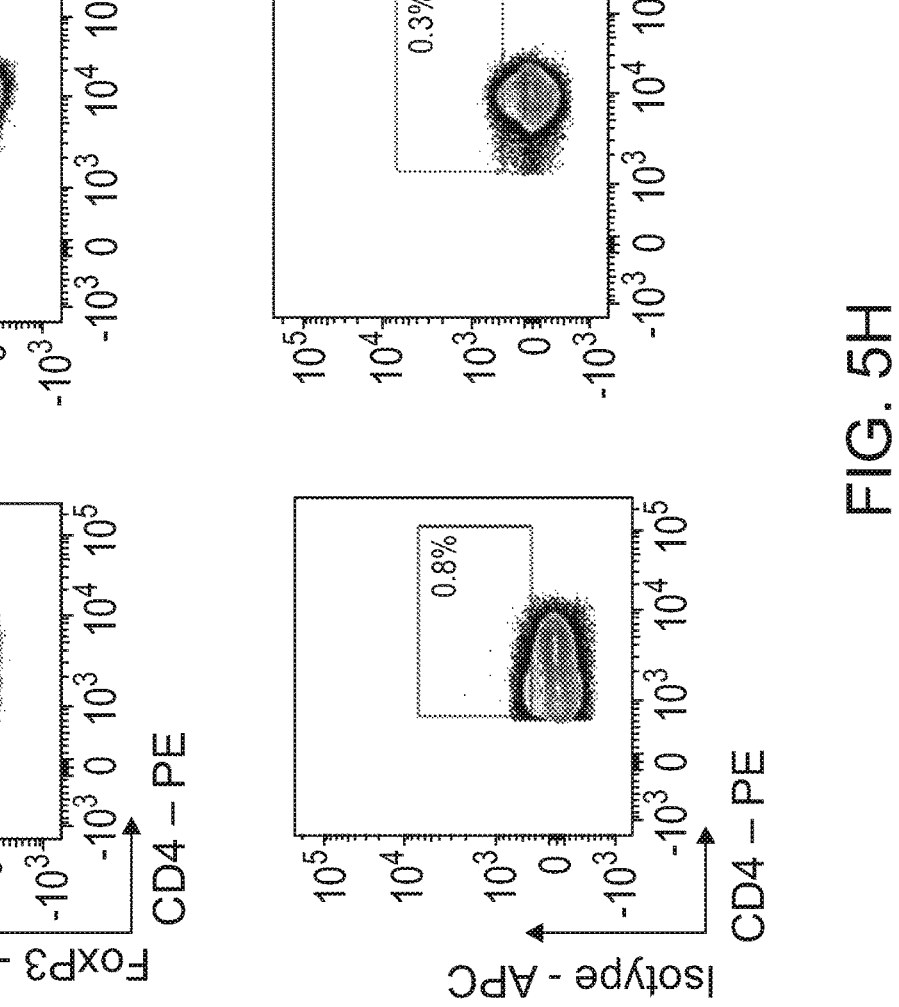

FIGS. 5F and 5G show survival rate in NSG-BLT mice (n=10 per group) (FIG. 5F) and reconstitution of human regulatory T-cells in the thymus and spleen of NSG-BLT mice (FIG. 5G).

In FIGS. 5A, 5B, and 5D-5G, xenogeneic humanized BLT (bone marrow-liver-thymus) mice were generated and used as described previously (Brainard, D. M. et al., Induction of robust cellular and humoral virus-specific adaptive immune responses in human immunodeficiency virus-infected humanized BLT mice. *Journal of virology* 83, 7305-7321 (2009)). Mice with no BMC (NSG-BLT) and mice with the Dual BMC (NSG-BLT+Dual BMC) with human donor tissue from the same source were analyzed.

FIG. 5H shows representative flow cytometric profiles of FoxP3+ cells among CD4+ cells and isotype used to identify $T_{reg}$ cells in the thymus and spleen (3 independent experiments).

Figure 5I:
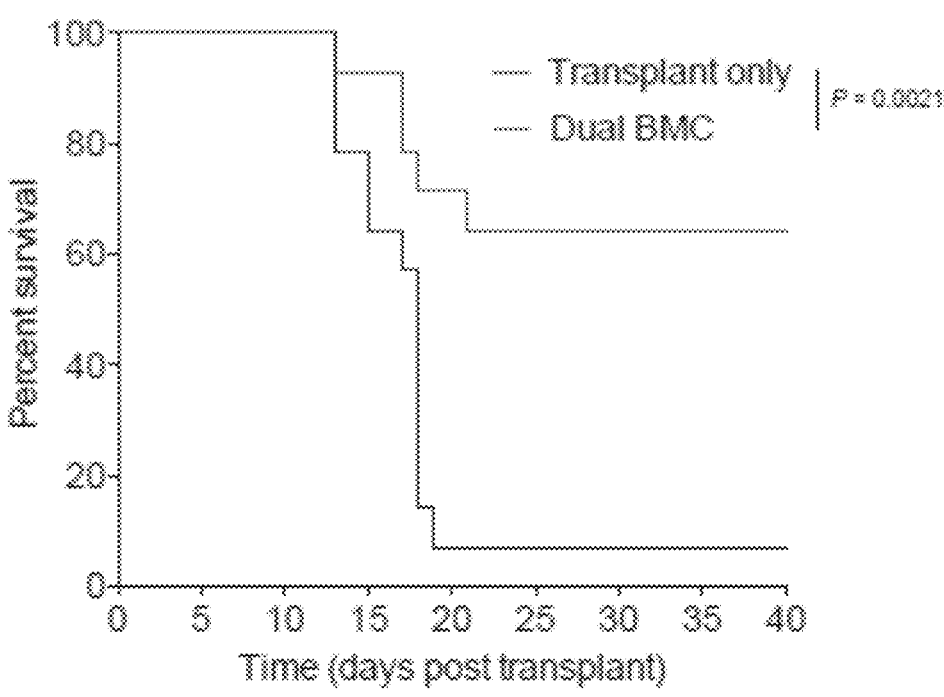
Figure 5J:
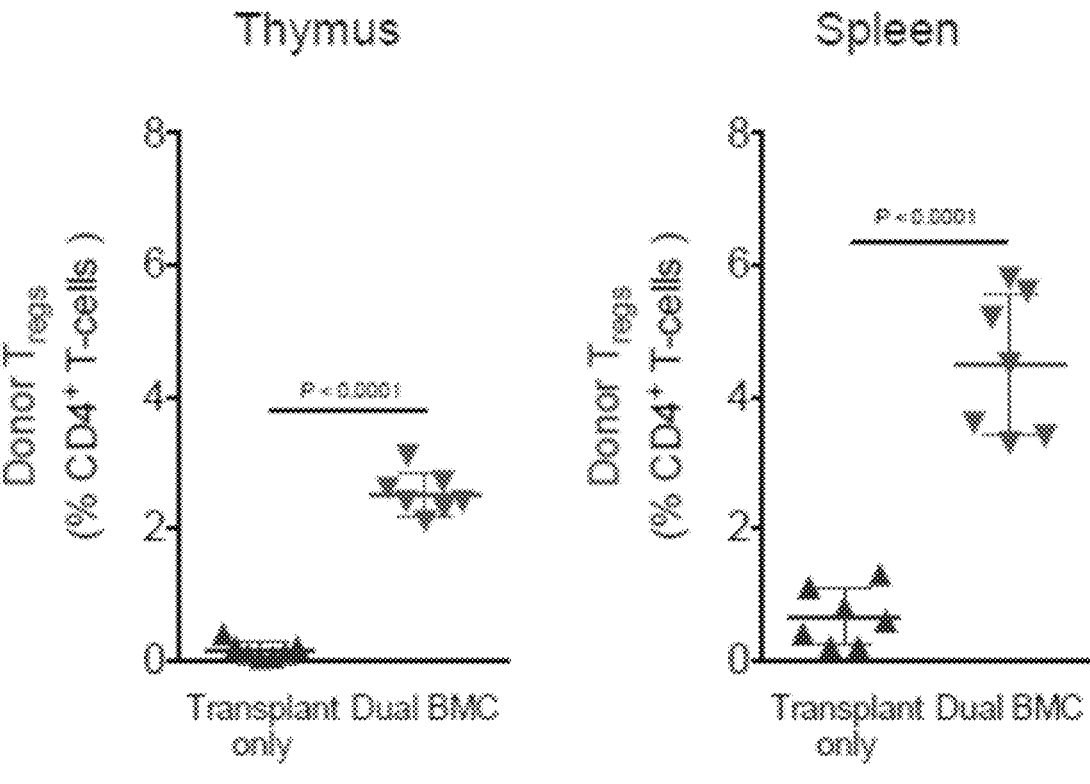
Figure 5K:
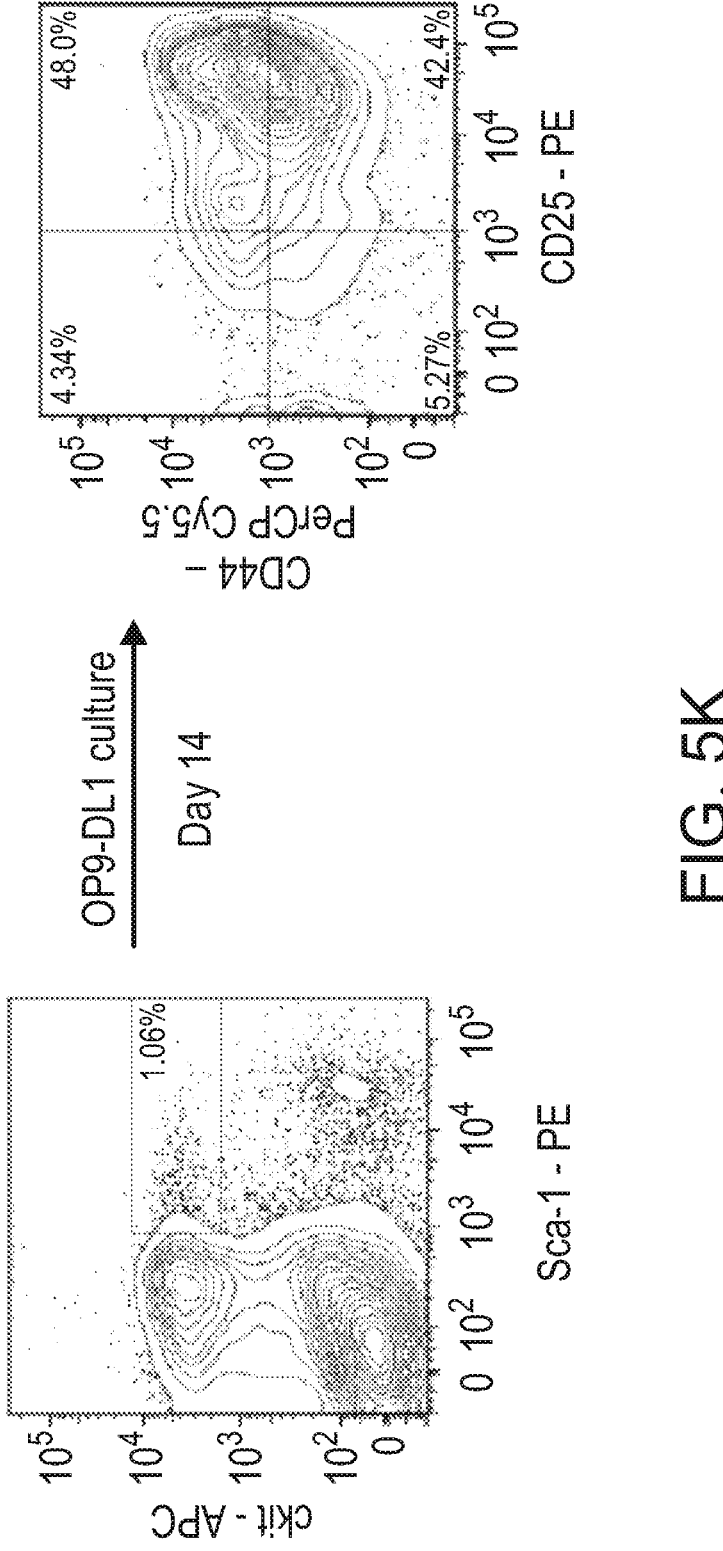

FIGS. 5I and 5J show survival rate (FIG. 5I) and reconstitution (FIG. 5J) of donor-derived regulatory Tcells in the thymus and spleen of allogeneically transplanted Balb/c mice. In FIGS. 5I and 5J, BALB/cJ recipient mice received 850 cGy of L-TBI. Within 48 hours post-radiation, mice were transplanted with allogeneic GFP $5×10^5$ lineage depleted GFP BM cells+$10^6$ GFP splenocytes. One group was simultaneously treated with the dual BMC.

FIG. 5K shows representative FACS profiles of sorted HSCs (Lin⁻ckit+Sca-1+) and CD44/CD25 expressing T-cell progenitors 14 Days after co-culture with OP9-DL1 cells (2 independent experiments).

FIGS. 5L-5P show comparison of T cell reconstitution in mice treated with BMC or OP9-DL1 derived pro-T-cells. Balb/cJ recipient mice received 850Gy L-TBI and were either provided OP9-DL1 culture derived $5×10^6$ allogeneic GFP T-cell progenitors+$10^3$ syngeneic HSCs or dual BMC+$5×10^5$ lineage depleted allogeneic GFP BM cells. Total number of DP (FIG. 5L) and SP4 (FIG. 5M) and SP8 thymocytes (FIG. 5N) in the thymus and peripheral CD4+ (FIG. 5O) and CD8+ T-cells (FIG. 5P) in the spleen of transplanted mice 424 28 days post-transplant. Data in a-d are the mean±s.d. of at n=10 mice at the start of the 425 study and are representative of 3 donors.

Data in FIGS. 5G and 5J are the mean±s.d. of n=7 mice. Data in FIG. 5I are the mean±s.d. of n=10 mice. Data in FIGS. 5G, 5I, and 5J are representative of 2 independent experiments. Data in FIGS. 5L-5P are mean±s.d. of n=10 mice, representative of 2 independent experiments. Distinct samples were assayed individually. (*P<0.05,  P<0.01, *P<0.001, analysis of variance (ANOVA) 429 with a Tukey post hoc test).

FIG. 5Q shows representative flow cytometric profiles of ckit and isotype used to identify ETPs in the thymus.

FIGS. 6A-6H show quantitative analysis of T-cell output, the immune repertoire and vaccination in mice with regenerated T-cells.

Figure 6A:
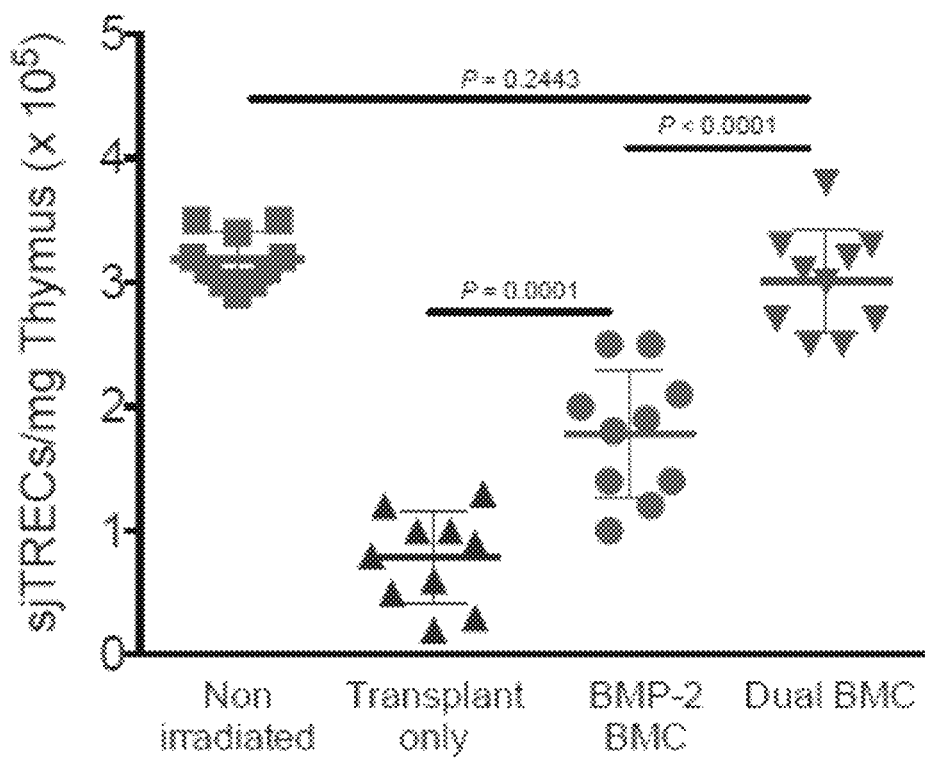
Figure 6B:
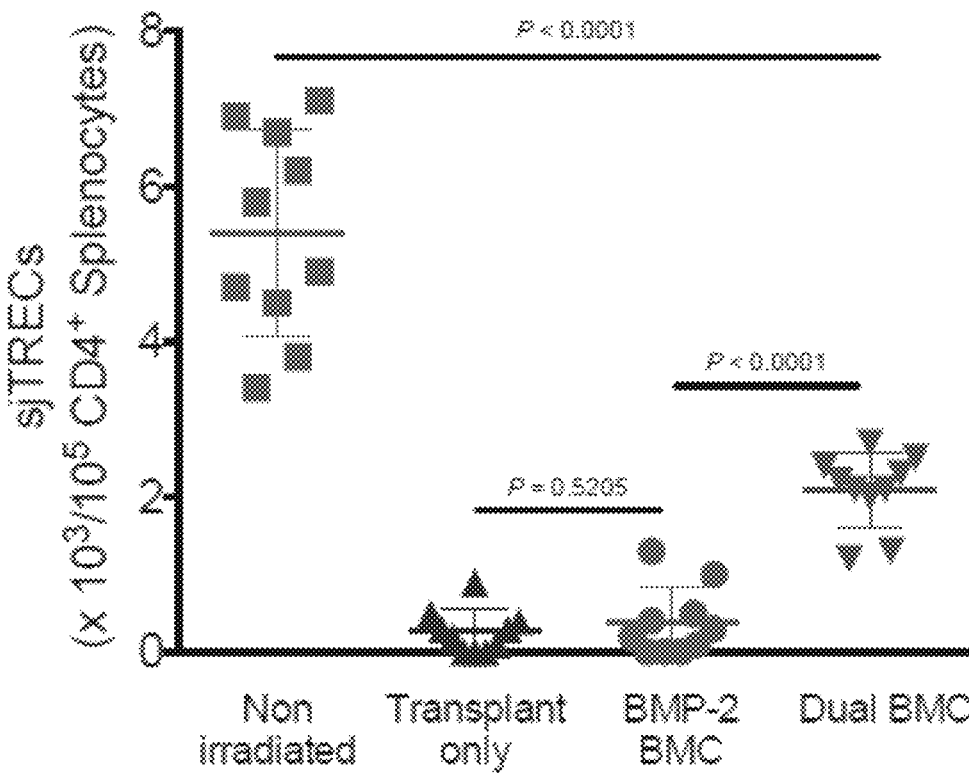

FIGS. 6A and 6B show signal joint T-cell receptor excision circle (sjTREC) analysis from the (a) isolated thymus (FIG. 6A) and spleen (FIG. 6B) in mice.

Figures 6C, 6D:
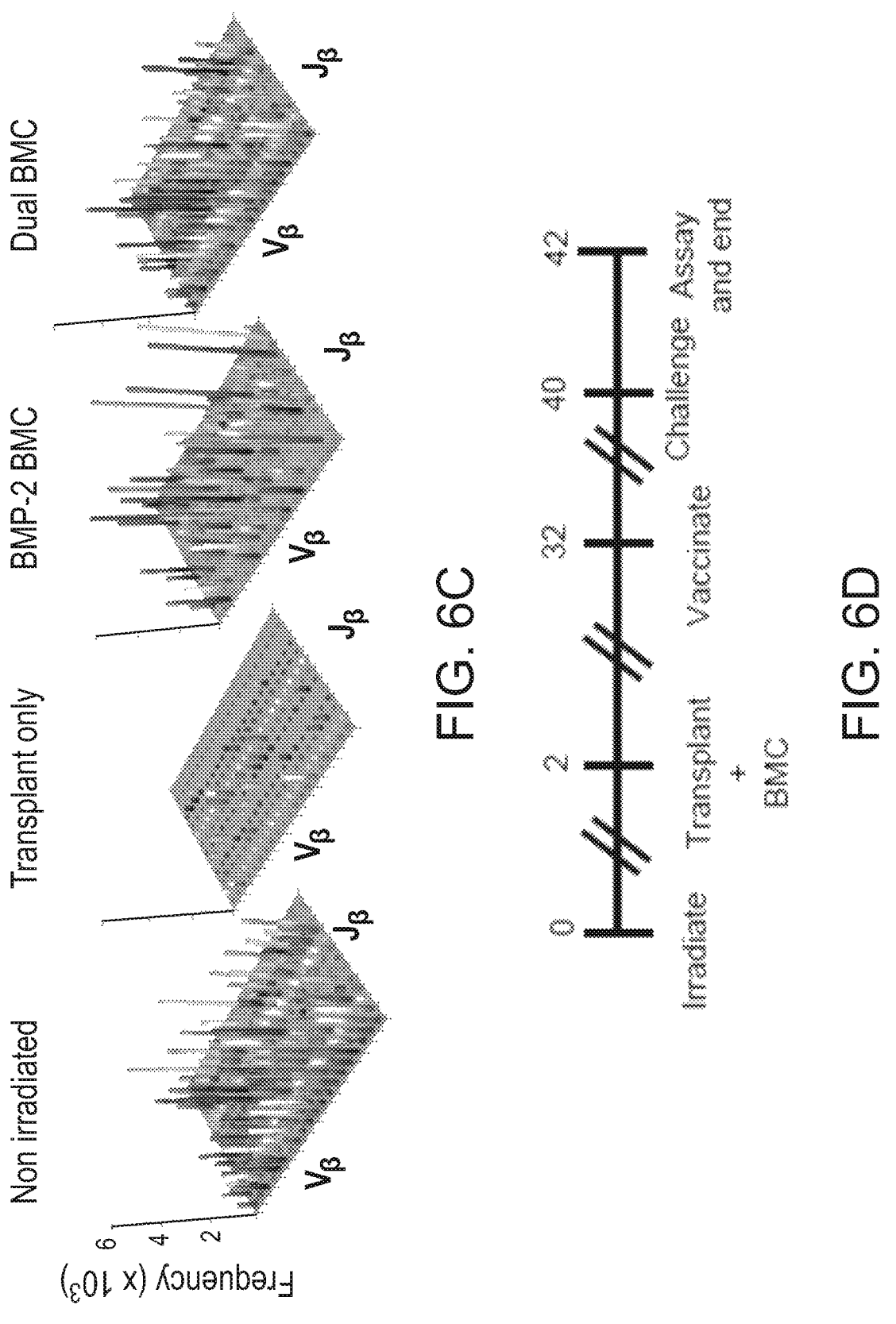

FIG. 6C shows the diversity in antigen receptors of T-cells as analyzed by the sequenced V and J segments of the CDR3 beta chain in the BMC and transplant mice. Each bar represents a single clone. The plot provides depth (length of bar) and diversity (number of bars) of T-cells in the mice. Samples were pooled from five mice for each group and the combined data are represented.

FIG. 6D shows the schedule of analyzing antigen-specific donor T-cell response through vaccination.

Figure 6E:
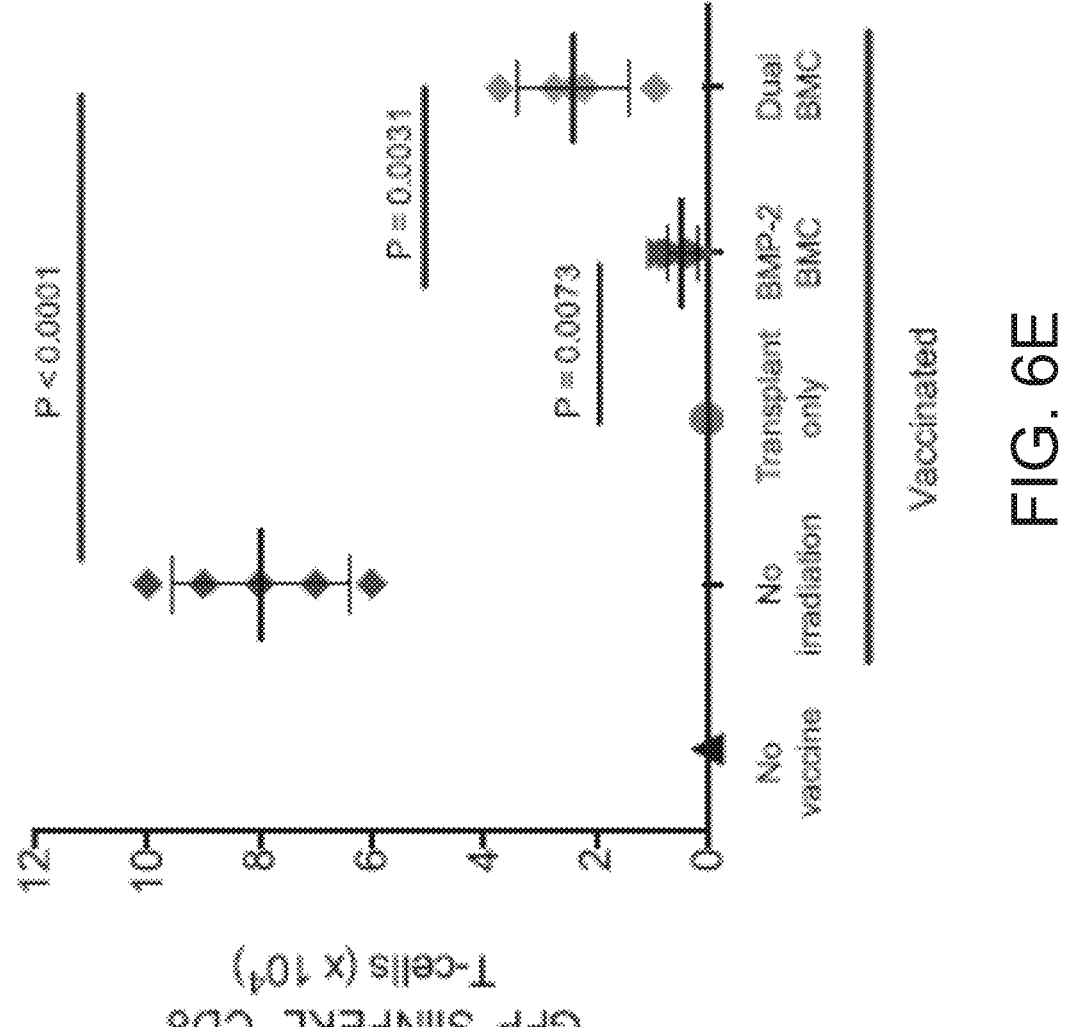
Figure 6F:
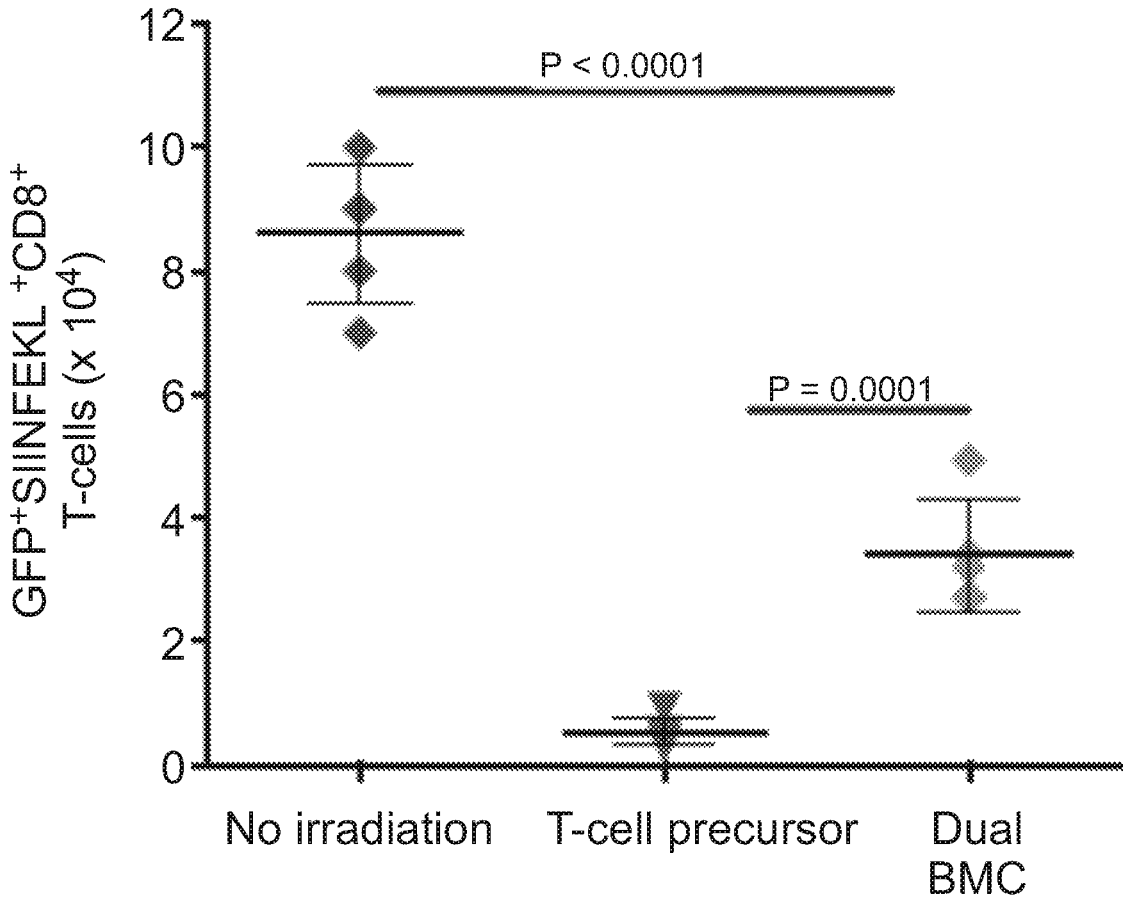

FIGS. 6E and 6F show SIINFEKL-tetramer⁺ donor CD8+ T-cells enumerated in vaccinated mice after syn-HSCT (FIG. 6E) and allo-HSCT (FIG. 6F).

Figure 6G:
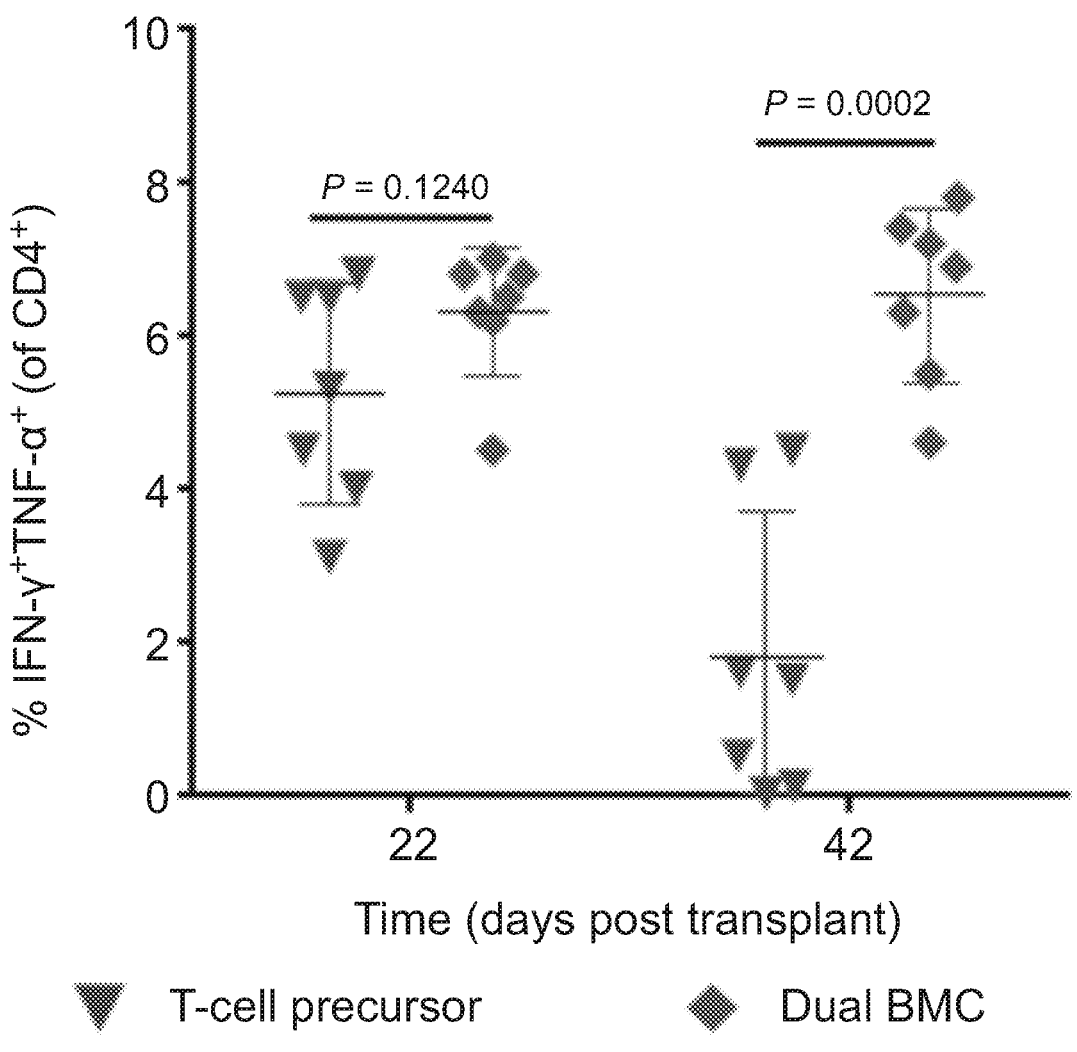
Figure 6H:
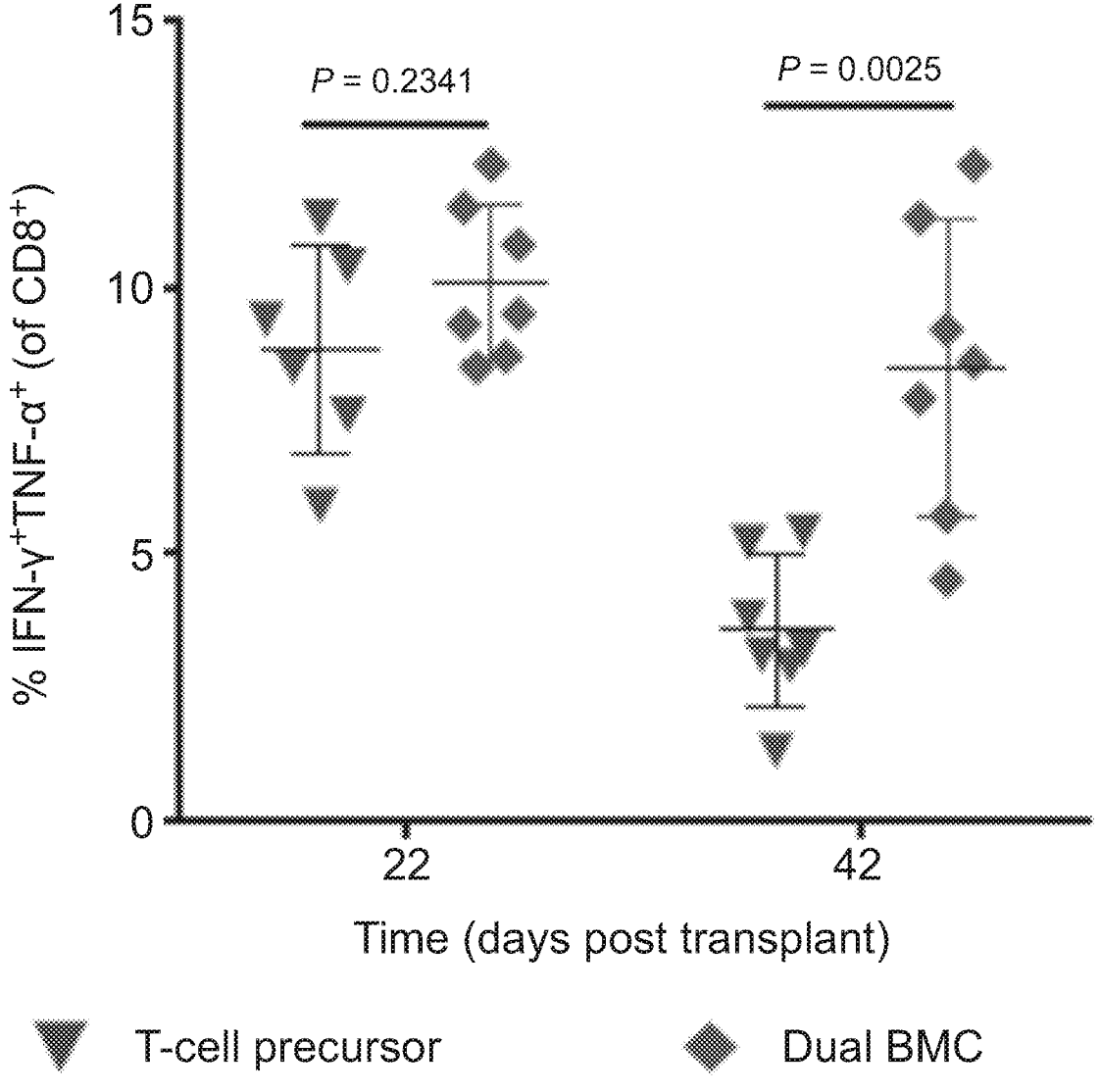

FIGS. 6G and 6H show that, at day 22 and 42 after HSCT, splenocytes of the 440 OP9-DL1 T-cell precursor group and the dual-BMC treated group were stimulated and stained for surface markers and intracellular cytokines using antibodies specific for CD45.1, CD4, IFN-γ and TNF-α. Cells were gated on CD4+ or CD8+ donor cells, and analyzed for IFN-γ- and TNF-α-positive cells. In FIGS. 6A-6C and 6E, B6 recipients received 1000 cGy L-TBI and $5×10^5$ lineage depleted syngeneic GFP BM cells. Post-HSCT mice with no BMC (Transplant only), post-HSCT mice treated with a BMP-2 BMC, and post-HSCT mice treated with a Dual BMC were analyzed and compared with non-irradiated mice that had not received a transplant or vaccine. In FIG. 6B, sjTRECs are normalized to $10^5$ CD4⁺ spelnocytes. In FIGS. 6F-6H, Balb/cJ recipient mice received 850Gy L-TBI and were either provided OP9-DL1 culture derived $5×10^6$ allo-geneic GFP T-cell progenitors+$10^3$ syngeneic HSCs or dual BMC+$5×10^5$ lineage depleted allogeneic GFP BM cells. Data in FIGS. 6A and 6B are mean±s.d. of n=10 mice, data in FIGS. 6E and 6F are mean±s.d. of n=5 mice, data in FIGS. 6G and 6H are mean±s.d. of n=7 mice. All experiments are representative of two independent experiments. (*P<0.05,  P<0.01, *P<0.001, analysis of variance (ANOVA) with a Tukey post hoc test).

DETAILED DESCRIPTION OF THE INVENTION

I. Definitions

In order that the present invention may be more readily understood, certain terms are first defined.

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition.

The use of the terms "a" and "an" and "the" and similar referents in the context of describing the invention (especially in the context of the following claims) are to be construed to cover both the singular and the plural (i.e., one or more), unless otherwise indicated herein or clearly contradicted by context. The terms "comprising, "having," "including," and "containing" are to be construed as open-ended terms (i.e., meaning "including, but not limited to") unless otherwise noted. Recitation of ranges of values herein are merely intended to serve as a shorthand method of referring individually to each separate value recited or falling within the range, unless otherwise indicated herein, and each separate value is incorporated into the specification as if it were individually recited.

The term "about" or "approximately" usually means within 5%, or more preferably within 1%, of a given value or range.

Generally, the term "treatment" or "treating" is defined as the application or administration of a therapeutic agent to a patient, or application or administration of a therapeutic agent to an isolated tissue or cell line from a patient, said patient having a disease, a symptom of disease or a predisposition toward a disease, with the purpose to cure, heal, alleviate, relieve, alter, remedy, ameliorate, improve or affect the disease, the symptoms of disease or the predisposition toward disease. Thus, treating can include suppressing, inhibiting, preventing, treating, or a combination thereof. Treating refers, inter alia, to increasing time to sustained progression, expediting remission, inducing remission, augmenting remission, speeding recovery, increasing efficacy of or decreasing resistance to alternative therapeutics, or a combination thereof "Suppressing" or "inhibiting", refers, inter alia, to delaying the onset of symptoms, preventing relapse to a disease, decreasing the number or frequency of relapse episodes, increasing latency between symptomatic episodes, reducing the severity of symptoms, reducing the severity of an acute episode, reducing the number of symptoms, reducing the incidence of disease-related symptoms, reducing the latency of symptoms, ameliorating symptoms, reducing secondary symptoms, reducing secondary infections, prolonging patient survival, or a combination thereof. In one embodiment the symptoms are primary, while in another embodiment, symptoms are secondary. "Primary" refers to a symptom that is a direct result of a disorder, e.g., diabetes, while, secondary refers to a symptom that is derived from or consequent to a primary cause. Symptoms may be any manifestation of a disease or pathological condition.

Accordingly, as used herein, the term "treatment" or "treating" includes any administration of a composition described herein and includes: (i) preventing the disease from occurring in a subject which may be predisposed to the disease but does not yet experience or display the pathology or symptomatology of the disease; (ii) inhibiting the disease in a subject that is experiencing or displaying the pathology or symptomatology of the diseased (i.e., arresting further development of the pathology and/or symptomatology); or (iii) ameliorating the disease in a subject that is experiencing or displaying the pathology or symptomatology of the diseased (i.e., reversing the pathology and/or symptomatology).

By "treatment", "prevention" or "amelioration" of a disease or disorder is meant delaying or preventing the onset of such a disease or disorder, reversing, alleviating, ameliorating, inhibiting, slowing down or stopping the progression, aggravation or deterioration the progression or severity of a condition associated with such a disease or disorder. In one embodiment, the symptoms of a disease or disorder are alleviated by at least 5%, at least 10%, at least 20%, at least 30%, at least 40%, or at least 50%.

Efficacy of treatment is determined in association with any known method for diagnosing the disorder. Alleviation of one or more symptoms of the disorder indicates that the composition confers a clinical benefit. Any of the therapeutic methods described to above can be applied to any suitable subject including, for example, mammals such as dogs, cats, cows, horses, rabbits, monkeys, and most preferably, humans.

As used herein, the term "subject" includes any subject who may benefit from being administered a hydrogel or an implantable drug delivery device of the invention. The term "subject" includes animals, e.g., vertebrates, amphibians, fish, mammals, non-human animals, including humans and primates, such as chimpanzees, monkeys and the like. In one embodiment of the invention, the subject is a human.

The term "subject" also includes agriculturally productive livestock, for example, cattle, sheep, goats, horses, pigs, donkeys, camels, buffalo, rabbits, chickens, turkeys, ducks, geese and bees; and domestic pets, for example, dogs, cats, caged birds and aquarium fish, and also so-called test animals, for example, hamsters, guinea pigs, rats and mice.

II. Compositions for Modulating Immune System

The present invention features compositions and methods that modulate the immune system of a subject. The compositions of the present invention include a porous scaffold, a growth factor present in an amount effective for recruiting a cell into the scaffold and/or inducing formation of a tissue or an organ, and a differentiation factor that induces differentiation of the recruited cell into a T cell progenitor cell.

The compositions and methods of the present invention provide advantages over the prior art. For example, the compositions and methods of the present invention enhance T-cell progenitor seeding of the thymus, T-cell neogenesis and broadening of the T-cell receptor repertoire. Furthermore, the compositions and methods of the present invention promote donor CD4+ regulatory T-cell generation and improved survival after allogeneic HSCT. Compared with adoptive transfer of T-cell progenitors, the compositions and methods of the present invention increase donor chimerism, T cell generation and induce more robust antigen-specific T-cell responses to stimulation. The compositions of the present invention may represent a simple to administer, off-the-shelf approach to T-cell regeneration and GVHD mitigation in HSCT.

In certain embodiments, the compositions and methods of the present invention also reduce toxicity stemming from the use of significantly reduced levels of growth factors, for example, 1 ng to about 1000 μg of growth factor or 1 ng to about 1000 ng of growth factor, as compared to that taught in the art. In addition, the compositions and methods of the present invention exhibit surprisingly enhanced activity, thereby allowing for comparable efficacy upon transplantation of a reduced number of cells.

Scaffolds

The composition of the present invention comprise a scaffold, e.g., a polymer scaffold. The scaffold can comprise one or more biomaterials. Preferably, the biomaterial is a biocompatible material that is non-toxic and/or non-immunogenic. As used herein, the term "biocompatible material" refers to any material that does not induce a significant immune response or deleterious tissue reaction, e.g., toxic reaction or significant irritation, over time when implanted into or placed adjacent to the biological tissue of a subject.

The scaffold can comprise biomaterials that are non-biodegradable or biodegradable. In certain embodiments, the biomaterial can be a non-biodegradable material. Exemplary non-biodegradable materials include, but are not limited to, metal, plastic polymer, or silk polymer. In certain embodiments, the polymer scaffold comprises a biodegradable material. The biodegradable material may be degraded by physical or chemical action, e.g., level of hydration, heat, oxidation, or ion exchange or by cellular action, e.g., elaboration of enzyme, peptides, or other compounds by nearby or resident cells. In certain embodiments, the polymer scaffold comprises both non-degradable and degradable materials.

In some embodiments, the scaffold composition can degrade at a predetermined rate based on a physical parameter selected from the group consisting of temperature, pH, hydration status, and porosity, the cross-link density, type, and chemistry or the susceptibility of main chain linkages to degradation. Alternatively, the scaffold composition degrades at a predetermined rate based on a ratio of chemical polymers. For example, a high molecular weight polymer comprised of solely lactide degrades over a period of years, e.g., 1-2 years, while a low molecular weight polymer comprised of a 50:50 mixture of lactide and glycolide degrades in a matter of weeks, e.g., 1, 2, 3, 4, 6, or 10 weeks. A calcium cross-linked gels composed of high molecular weight, high guluronic acid alginate degrade over several months (1, 2, 4, 6, 8, 10, or 12 months) to years (1, 2, or 5 years) in vivo, while a gel comprised of low molecular weight alginate, and/or alginate that has been partially oxidized, will degrade in a matter of weeks.

In certain embodiments, one or more compounds or proteins (e.g., the growth factors, the differentiation factors, and the homing factors), disclosed herein, are covalently or non-covalently linked or attached to the scaffold composition. In various embodiments, one or more compounds or proteins disclosed herein is incorporated on, into, or present within the structure or pores of, the scaffold composition.

In some embodiments, the scaffolds comprise biomaterials that are modified, e.g., oxidized or reduced. The degree of modification, such as oxidation, can be varied from about 1% to about 100%. As used herein, the degree of modification means the molar percentage of the sites on the biomaterial that are modified with a functional group. For example, the degree of modification can be about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. It is intended that values and ranges intermediate to the recited values are part of this invention. Exemplary modified biomaterials, e.g., hydrogels, include, but not limited to, reduced-alginate, oxidized alginate, MA-alginate (methacrylated alginate) or MA-gelatin.

Exemplary biomaterials suitable for use as scaffolds in the present invention include glycosaminoglycan, silk, fibrin, MATRIGEL®, poly-ethyleneglycol (PEG), polyhydroxy ethyl methacrylate, polyacrylamide, poly (N-vinyl pyrolidone), (PGA), poly lactic-co-glycolic acid (PLGA), poly e-carpolactone (PCL), polyethylene oxide, poly propylene fumarate (PPF), poly acrylic acid (PAA), polyhydroxybutyric acid, hydrolysed polyacrylonitrile, polymethacrylic acid, polyethylene amine, esters of alginic acid; pectinic acid; and alginate, fully or partially oxidized alginate, hyaluronic acid, carboxy methyl cellulose, heparin, heparin sulfate, chitosan, carboxymethyl chitosan, chitin, pullulan, gellan, xanthan, collagen, gelatin, carboxymethyl starch, carboxymethyl dextran, chondroitin sulfate, cationic guar, cationic starch, and combinations thereof. In certain embodiments, the biomaterial is selected from the group consisting of alginate, fully or partially oxidized alginate, and combinations thereof.

The scaffolds of the present invention may comprise an external surface. Alternatively, or in addition, the scaffolds may comprise an internal surface. External or internal surfaces of the scaffolds of the present invention may be solid or porous. Pore size of the scaffolds can be less than about 10 nm, between about 100 nm-20 μm, or greater than about 20 μm, e.g., up to and including 1000 μm in diameter. For example, the pores may be nanoporous, microporous, or macroporous. For example, the diameter of nanopores is less than about 10 nm; the diameter of micropores is in the range of about 100 nm-20 μm; and, the diameter of macropores is greater than about 20 μm, e.g., greater than about 50 μm, e.g., greater than about 100 μm, e.g., greater than about 400 μm, e.g., greater than 600 μm or greater than 800 μm. In some embodiment the diameter of the pore is between about 50 μm and about 80 μm.

In some embodiments, the scaffolds of the present invention are organized in a variety of geometric shapes (e.g., discs, beads, pellets), niches, planar layers (e.g., thin sheets). For example, discs of about 0.1-200 millimeters in diameter, e.g., 5, 10, 20, 40, or 50 millimeters may be implanted subcutaneously. The disc may have a thickness of 0.1 to 10 millimeters, e.g., 1, 2, or 5 millimeters. The discs are readily compressed or lyophilized for administration to a patient. An exemplary disc for subcutaneous administration has the following dimensions: 8 millimeters in diameter and 1 millimeter in thickness.

In some embodiments, the scaffolds may comprise multiple components and/or compartments. In certain embodiments, a multiple compartment device is assembled in vivo by applying sequential layers of similarly or differentially doped gel or other scaffold material to the target site. For example, the device is formed by sequentially injecting the next, inner layer into the center of the previously injected material using a needle, thereby forming concentric spheroids. In certain embodiments, non-concentric compartments are formed by injecting material into different locations in a previously injected layer. A multi-headed injection device extrudes compartments in parallel and simultaneously. The layers are made of similar or different biomaterials differentially doped with pharmaceutical compositions. Alternatively, compartments self-organize based on their hydrophilic/phobic characteristics or on secondary interactions within each compartment. In certain embodiments, multi-component scaffolds are optionally constructed in concentric layers each of which is characterized by different physical qualities such as the percentage of polymer, the percentage of crosslinking of polymer, chemical composition of the hydrogel, pore size, porosity, and pore architecture, stiffness, toughness, ductility, viscoelasticity, the growth factors, the differentiation factors, and/or homing factors incorporated therein and/or any other compositions incorporated therein.

Hydrogel and Cryogel Scaffolds

In certain embodiments, the scaffolds of present invention comprise one or more hydrogels. A hydrogel is a polymer gel comprising a network of crosslinked polymer chains. A hydrogel is usually a composition comprising polymer chains that are hydrophilic. The network structure of hydrogels allows them to absorb significant amounts of water. Some hydrogels are highly stretchable and elastic; others are viscoelastic. Hydrogel are sometimes found as a colloidal gel in which water is the dispersion medium. In certain embodiments, hydrogels are highly absorbent (they can contain over 99% water (v/v)) natural or synthetic polymers that possess a degree of flexibility very similar to natural tissue, due to their significant water content. In certain embodiments, a hydrogel may have a property that, when an appropriate shear stress is applied, the deformable hydrogel is dramatically and reversibly compressed (up to 95% of its volume), resulting in injectable macroporous preformed scaffolds. Hydrogels have been used for therapeutic applications, e.g., as vehicles for in vivo delivery of therapeutic agents, such as small molecules, cells and biologics. Hydrogels are commonly produced from polysaccharides, such as alginates. The polysaccharides may be chemically manipulated to modulate their properties and properties of the resulting hydrogels.

The hydrogels of the present invention may be either porous or non-porous. Preferably the compositions of the invention are formed of porous hydrogels. For example, the hydrogels may be nanoporous wherein the diameter of the pores is less than about 10 nm; microporous wherein the diameter of the pores is preferably in the range of about 100 nm-20 μm; or macroporous wherein the diameter of the pores is greater than about 20 μm, more preferably greater than about 100 μm and even more preferably greater than about 400 μm. In certain embodiments, the hydrogel is macroporous with pores of about 50-80 μm in diameter. In certain embodiments, the hydrogel is macroporous with aligned pores of about 400-500 μm in diameter. Methods of preparing porous hydrogel products are known in the art. (See, e.g., U.S. Pat. No. 6,511,650, incorporated herein by reference).

The hydrogel may be constructed out of a number of different rigid, semi-rigid, flexible, gel, self-assembling, liquid crystalline, or fluid compositions such as peptide polymers, polysaccharides, synthetic polymers, hydrogel materials, ceramics (e.g., calcium phosphate or hydroxyapatite), proteins, glycoproteins, proteoglycans, metals and metal alloys. The compositions are assembled into hydrogels using methods known in the art, e.g., injection molding, lyophilization of preformed structures, printing, self-assembly, phase inversion, solvent casting, melt processing, gas foaming, fiber forming/processing, particulate leaching or a combination thereof. The assembled devices are then implanted or administered to the body of an individual to be treated.

The composition comprising a hydrogel may be assembled in vivo in several ways. The hydrogel is made from a gelling material, which is introduced into the body in its ungelled form where it gels in situ. Exemplary methods of delivering components of the composition to a site at which assembly occurs include injection through a needle or other extrusion tool, spraying, painting, or methods of deposit at a tissue site, e.g., delivery using an application device inserted through a cannula. In some embodiments, the ungelled or unformed hydrogel material is mixed with at least one pharmaceutical composition prior to introduction into the body or while it is introduced. The resultant in vivo/in situ assembled device, e.g., hydrogel, contains a mixture of the at least one pharmaceutical composition.

In situ assembly of the hydrogel may occur as a result of spontaneous association of polymers or from synergistically or chemically catalyzed polymerization. Synergistic or chemical catalysis is initiated by a number of endogenous factors or conditions at or near the assembly site, e.g., body temperature, ions or pH in the body, or by exogenous factors or conditions supplied by the operator to the assembly site, e.g., photons, heat, electrical, sound, or other radiation directed at the ungelled material after it has been introduced. The energy is directed at the hydrogel material by a radiation beam or through a heat or light conductor, such as a wire or fiber optic cable or an ultrasonic transducer. Alternatively, a shear-thinning material, such as an amphiphile, is used which re-cross links after the shear force exerted upon it, for example by its passage through a needle, has been relieved.

In some embodiments, the hydrogel may be assembled ex vivo. In some embodiments, the hydrogel is injectable. For example, the hydrogels are created outside of the body as macroporous scaffolds. Upon injection into the body, the pores collapse causing the gel to become very small and allowing it to fit through a needle. See, e.g., WO2012/149358; and Bencherif et al., 2012, *Proc. Natl. Acad. Sci. USA* 109.48:19590-5, the content of which are incorporated herein by reference).

Suitable hydrogels for both in vivo and ex vivo assembly of hydrogel devices are well known in the art and described, e.g., in Lee et al., 2001, *Chem. Rev.* 7:1869-1879. The peptide amphiphile approach to self-assembly assembly is described, e.g., in Hartgerink et al., 2002, *Proc. Natl. Acad. Sci. USA* 99:5133-5138. A method for reversible gellation following shear thinning is exemplified in Lee et al., 2003, *Adv. Mat.* 15:1828-1832.

In certain embodiments, exemplary hydrogels are comprised of materials that are compatible with encapsulation of materials including polymers, nanoparticles, polypeptides, and cells. Exemplary hydrogels are fabricated from alginate, polyethylene glycol (PEG), PEG-acrylate, agarose, hyaluronic acid, or synthetic protein (e.g., collagen or engineered proteins (i.e., self-assembly peptide-based hydrogels)). For example, a commercially available hydrogel includes BD™ PuraMatrix™. BD™ PuraMatrix™ Peptide Hydrogel is a synthetic matrix that is used to create defined three dimensional (3D) micro-environments for cell culture.

In some embodiments, the hydrogel is a biocompatible polymer matrix that is biodegradable in whole or in part. Examples of materials which can form hydrogels include alginates and alginate derivatives, polylactic acid, polyglycolic acid, poly(lactic-co-glycolic acid) (PLGA) polymers, gelatin, collagen, agarose, hyaluronic acid, hyaluronic acid derivative, natural and synthetic polysaccharides, polyamino acids such as polypeptides particularly poly(lysine), polyesters such as polyhydroxybutyrate and poly-epsilon.-caprolactone, polyanhydrides; polyphosphazines, poly(vinyl alcohols), poly(alkylene oxides) particularly poly(ethylene oxides), poly(allylamines)(PAM), poly(acrylates), modified styrene polymers such as poly(4-aminomethylstyrene), pluronic polyols, polyoxamers, poly(uronic acids), poly (vinylpyrrolidone), and copolymers of the above, including graft copolymers. Synthetic polymers and naturally-occurring polymers such as, but not limited to, collagen, fibrin, hyaluronic acid, agarose, and laminin-rich gels may also be used. The term "derivative," as used herein, refers to a compound that is derived from a similar compound by a chemical reaction. For example, oxidized alginate, which is derived from alginate through oxidization reaction, is a derivative of alginate, The implantable composition can have virtually any regular or irregular shape including, but not limited to, spheroid, cubic, polyhedron, prism, cylinder, rod, disc, or other geometric shape. Accordingly, in some embodiments, the implant is of cylindrical form from about 0.5 to about 10 mm in diameter and from about 0.5 to about 10 cm in length. Preferably, its diameter is from about 1 to about 5 mm and its length from about 1 to about 5 cm.

In some embodiments, the compositions of the invention are of spherical form. When the composition is in a spherical form, its diameter can range, in some embodiments, from about 0.5 to about 50 mm in diameter. In some embodiments, a spherical implant's diameter is from about 5 to about 30 mm. In an exemplary embodiment, the diameter is from about 10 to about 25 mm.

In certain embodiments, the scaffold comprises click-hydrogels and/or click-cryogels. A click hydrogel or cryogel is a gel in which cross-linking between hydrogel or cryogel polymers is facilitated by click reactions between the polymers. Each polymer may contain one of more functional groups useful in a click reaction. Given the high level of specificity of the functional group pairs in a click reaction, active compounds can be added to the preformed device prior to or contemporaneously with formation of the hydrogel device by click chemistry. Non-limiting examples of click reactions that may be used to form click-hydrogels include Copper I catalyzed azide-alkyne cycloaddition, strain-promoted assize-alkyne cycloaddition, thiol-ene photocoupling, Diels-Alder reactions, inverse electron demand Diels-Alder reactions, tetrazole-alkene photo-click reactions, oxime reactions, thiol-Michael addition, and aldehyde-hydrazide coupling. Non-limiting aspects of click hydrogels are described in Jiang et al., 2014, *Biomaterials,* 35:4969-4985, the entire content of which is incorporated herein by reference.

In various embodiments, a click alginate is utilized (see, e.g., PCT International Patent Application Publication No. WO 2015/154078 published Oct. 8, 2015, hereby incorporated by reference in its entirety).

In certain embodiments, a hydrogel (e.g., cryogel) system can deliver one or more agent (e.g., a growth factor such as BMP-2, and/or a differentiation factor, such as a DLL-4, while creating a space for cells (e.g., stem cells such as hematopoietic stem cells (HSC) infiltration and trafficking). In some embodiments, the hydrogel system according to the present invention delivers BMP-2, which acts as a hematopoietic stem cell (HSC) and/or hematopoietic progenitor cell enhancement/recruitment factor, and DLL-4 as a differentiation factor, which facilitates T cell lineage specification of hematopoietic stem cell and/or hematopoietic progenitor cells.

In some embodiments, a cryogel composition, e.g., formed of MA-alginate, can function as a delivering platform by creating a local niche, such as a specific niche for enhancing T-lineage specification. In some embodiments, the cryogel creates a local niche in which the encounter of cells, such as recruited stem cells or progenitor cells, and various exemplary agent of the invention, such as the growth factor and/or differentiation factor can be controlled. In certain embodiments, the cells and the exemplary agents of the present invention are localized into a small volume, and the contacting of the cells and the agents can be quantitatively controlled in space and time.

In certain embodiments, the hydrogel (e.g., cryogel) can be engineered to coordinate the delivery of both growth factor and differentiation factor in space and time, potentially enhancing overall immune modulation performance by adjusting the differentiation and/or specification of recruited cells, such as hematopoietic stem cells or progenitor cells. In certain embodiments, the cells and growth factor/differentiation factor are localized into a small volume, and the delivery of factors in space and time can be quantitatively controlled. As the growth/differentiation factors are released locally, few systemic effects are anticipated, in contrast to systemically delivered agents, such as growth factors.

Examples of polymer compositions from which the cryogel or hydrogel is fabricated are described throughout the present disclosure, and include alginate, hyaluronic acid, gelatin, heparin, dextran, carob gum, PEG, PEG derivatives including PEG-co-PGA and PEG-peptide conjugates. The techniques can be applied to any biocompatible polymers, e.g., collagen, chitosan, carboxymethylcellulose, pullulan, polyvinyl alcohol (PVA), Poly(2-hydroxyethyl methacrylate) (PHEMA), Poly(N-isopropylacrylamide) (PNIPAAm), or Poly(acrylic acid) (PAAc). For example, in a particular embodiment, the composition comprises an alginate-based hydrogel/cryogel. In another example, the scaffold comprises a gelatin-based hydrogel/cryogel.

Cryogels are a class of materials with a highly porous interconnected structure that are produced using a cryotropic gelation (or cryogelation) technique. Cryogels also have a highly porous structure. Typically, active compounds are added to the cryogel device after the freeze formation of the pore/wall structure of the cryogel. Cryogels are characterized by high porosity, e.g., at least about 50, 55, 60, 65, 70, 75, 80, 85, 90, or 95% pores with thin pore walls that are characterized by high density of polymer crosslinking. As used herein, the term "porosity" refers to the percentage of the volume of pores to the volume of the scaffold. It is intended that values and ranges intermediate to the recited values are part of this invention. The walls of cryogels are typically dense and highly cross-linked, enabling them to be compressed through a needle into a subject without permanent deformation or substantial structural damage.

In various embodiments, the pore walls comprise at least about 10, 15, 20, 25, 30, 35, or 40% (w/v) polymer. It is intended that values and ranges intermediate to the recited values are part of this invention. In other embodiments, the pore walls comprise about 10-40% polymer. In some embodiments, a polymer concentration of about 0.5-4% (w/v) (before the cryogelation) is used, and the concentration increases substantially upon completion of cryogelation. Non-limiting aspects of cryogel gelation and the increase of polymer concentration after cryogelation are discussed in Beduer et al., 2015 *Advanced Healthcare Materials* 4.2: 301-312, the entire content of which is incorporated herein by reference.

In certain embodiments, cryogelation comprises a technique in which polymerization-crosslinking reactions are conducted in quasi-frozen reaction solution. Non-limiting examples of cryogelation techniques are described in U.S. Patent Application Publication No. 20140227327, published Aug. 14, 2014, the entire content of which is incorporated herein by reference. An advantage of cryogels compared to conventional macroporous hydrogels obtained by phase separation is their high reversible deformability. Cryogels may be extremely soft but can be deformed and reform their shape. In certain embodiments, cryogels can be very tough, can withstand high levels of deformations, such as elongation and torsion and can also be squeezed under mechanical force to drain out their solvent content. The improved deformability properties of alginate cryogels originate from the high crosslinking density of the unfrozen liquid channels of the reaction system.

In the cryogelation process, during freezing of the macromonomer (e.g., methacrylated alginate) solution, the macromonomers and initiator system (e.g., APS/TEMED) are expelled from the ice concentrate within the channels between the ice crystals, so that the reactions only take place in these unfrozen liquid channels. After polymerization and, after melting of ice, a porous material is produced whose microstructure is a negative replica of the ice formed. Ice crystals act as porogens. Desired pore size is achieved, in part, by altering the temperature of the cryogelation process. For example, the cryogelation process is typically carried out by quickly freezing the solution at −20° C. Lowering the temperature to, e.g., −80° C., would result in more ice crystals and lead to smaller pores. In some embodiments, the cryogel is produced by cryo-polymerization of at least methacrylated (MA)-alginate and MA-PEG. In some embodiments, the cryogel is produced by cryo-polymerization of at least MA-alginate, the growth factor, the differentiation factor, and MA-PEG.

In some embodiments, the invention also features gelatin scaffolds, e.g., gelatin hydrogels such as gelatin cryogels, which are a cell-responsive platform for biomaterial-based therapy. Gelatin is a mixture of polypeptides that is derived from collagen by partial hydrolysis. These gelatin scaffolds have distinct advantages over other types of scaffolds and hydrogels/cryogels. For example, the gelatin scaffolds of the invention support attachment, proliferation, and survival of cells and are degraded by cells, e.g., by the action of enzymes such as matrix metalloproteinases (MMPs) (e.g., recombinant matrix metalloproteinase-2 and -9).

In certain embodiments, prefabricated gelatin cryogels rapidly reassume their approximately original shape ("shape memory") when injected subcutaneously into a subject (e.g., a mammal such as a human, dog, cat, pig, or horse) and elicit little or no harmful host immune response (e.g., immune rejection) following injection.

In some embodiments, the hydrogel (e.g., cryogel) comprises polymers that are modified, e.g., sites on the polymer molecule are modified with a methacrylic acid group (methacrylate (MA)) or an acrylic acid group (acrylate). Exemplary modified hydrogels/cryogels are MA-alginate (methacrylated alginate) or MA-gelatin. In the case of MA-alginate or MA-gelatin, 50% corresponds to the degree of methacrylation of alginate or gelatin. This means that every other repeat unit contains a methacrylated group. The degree of methacrylation can be varied from about 1% to about 100%. Preferably, the degree of methacrylation varies from about 1% to about 90%.

In certain embodiments, polymers can also be modified with acrylated groups instead of methacrylated groups. The product would then be referred to as an acrylated-polymer. The degree of methacrylation (or acrylation) can be varied for most polymers. However, some polymers (e.g., PEG) maintain their water-solubility properties even at 100% chemical modification. After crosslinking, polymers normally reach near complete methacrylate group conversion indicating approximately 100% of cross-linking efficiency. As used herein, the term "cross-linking efficiency" refers to the percentage of macromonomers that are covalently linked. For example, the polymers in the hydrogel are 50-100% crosslinked (covalent bonds). The extent of cross-linking correlates with the durability of the hydrogel. Thus, a high level of crosslinking (90-100%) of the modified polymers is desirable.

For example, the highly crosslinked hydrogel/cryogel polymer composition is characterized by at least about 50% polymer crosslinking (e.g., about 75%, 80%, 85%, 90%, 95%, 98%, 99%, or 100%; it is intended that values and ranges intermediate to the recited values are part of this invention.). The high level of crosslinking confers mechanical robustness to the structure. Preferably, the percentage of crosslinking is less than about 100%. The composition is formed using a free radical polymerization process and a cryogelation process. For example, the cryogel is formed by cryopolymerization of methacrylated gelatin, methacrylated alginate, or methacrylated hyaluronic acid. In some embodiments, the cryogel comprises a methacrylated gelatin macro monomer or a methacrylated alginate macromonomer at concentration of about 1.5% (w/v) or less (e.g., about 1.5%, 1.4%, 1.3%, 1.2%, 1.1%, 1%, 0.9%, 0.8%, 0.7%, 0.6%, 0.5%, 0.4%, 0.3%, 0.2% or less; it is intended that values and ranges intermediate to the recited values are part of this invention.). In some embodiments, the methacrylated gelatin or alginate macromonomer concentration is about 1% (w/v).

In certain embodiments, the cryogel comprises at least about 75% (v/v) pores, e.g., about 80%, 85%, 90%, 91%, 92%, 93%, 94%, 95%, 96%, 97%, 98%, or 99% (v/v) or more pores. It is intended that values and ranges intermediate to the recited values are part of this invention. In some embodiments, the pores are interconnected. Interconnectivity is important to the function of the hydrogel and/or cryogel, as without interconnectivity, water would become trapped within the gel. Interconnectivity of the pores permits passage of water (and other compositions such as cells and compounds) in and out of the structure. In certain embodiments, in a fully hydrated state, the hydrogel (e.g., cryogel) comprises at least about 90% water (volume of water/volume of the scaffold) (e.g., between about 90-99%, at least about 92%, 95%, 97%, 99%, or more). For example, at least about 90% (e.g., at least about 92%, 95%, 97%, 99%, or more) of the volume of the cryogel is made of liquid (e.g., water) contained in the pores. It is intended that values and ranges intermediate to the recited values are part of this invention. In certain embodiments, in a compressed or dehydrated hydrogel, up to about 50%, 60%, 70% of that water is absent, e.g., the cryogel comprises less than about 25% (e.g., about 20%, 15%, 10%, 5% or less) water.

In certain embodiments, the cryogels of the invention comprise pores large enough for a cell to travel through. For example, the cryogel contains pores of about 20-500 μm in diameter, e.g., about 20-30 μm, about 30-150 μm, about 50-500 μm, about 50-450 μm, about 100-400 μm, about 200-500 μm. In some embodiments, the hydrated pore size is about 1-500 μm (e.g., about 10-400 μm, about 20-300 μm, about 50-250 μm). In certain embodiments, the cryogel contains pores about 50-80 μm in diameter.

In some embodiments, injectable hydrogels or cryogels are further functionalized by addition of a functional group selected from the group consisting of: amino, vinyl, aldehyde, thiol, silane, carboxyl, azide, or alkyne. Alternatively or in addition, the cryogel is further functionalized by the addition of a further cross-linker agent (e.g., multiple arms polymers, salts, aldehydes, etc.). The solvent can be aqueous, and in particular, acidic or alkaline. The aqueous solvent can comprise a water-miscible solvent (e.g., methanol, ethanol, DMF, DMSO, acetone, dioxane, etc).

For cryogels, the cryo-crosslinking may take place in a mold and the cryogels (which may be injected) can be degradable. The pore size can be controlled by the selection of the main solvent used, the incorporation of a porogen, the freezing temperature and rate applied, the crosslinking conditions (e.g. polymer concentration), and also the type and molecule weight of the polymer used. The shape of the cryogel may be dictated by a mold and can thus take on any shape desired by the fabricator, e.g., various sizes and shapes (disc, cylinders, squares, strings, etc.) are prepared by cryogenic polymerization.

Injectable cryogels can be prepared in the micrometer-scale to centimeter-scale. Exemplary volumes vary from a few hundred μm$^3$ (e.g., about 100-500 μm$^3$) to about 10 cm$^3$. In certain embodiment, an exemplary scaffold composition is between about 100 μm$^3$ to 100 mm$^3$ in size. In various embodiments, the scaffold is between about 10 mm$^3$ to about 100 mm$^3$ in size. In certain embodiments, the scaffold is about 30 mm$^3$ in size.

In some embodiments, the cryogels are hydrated, loaded with compounds and loaded into a syringe or other delivery apparatus. For example, the syringes are prefilled and refrigerated until use. In another example, the cryogel is dehydrated, e.g., lyophilized, optionally with a compound (such as a growth factor or differentiation factor) loaded in the gel and stored dry or refrigerated. Prior to administration, a cryogel-loaded syringe or apparatus may be contacted with a solution containing compounds to be delivered. For example, the barrel of the cryogel pre-loaded syringe is filled with a physiologically-compatible solution, e.g., phosphate-buffered saline (PBS). Alternatively, the cryogel may be administered to a desired anatomical site followed by administration of the physiologically-compatible solution, optionally containing other ingredients, e.g., a growth factor and/or a differentiation factor or together with one or more compounds disclosed herein. The cryogel is then rehydrated and regains its shape integrity in situ. In certain embodiments, the volume of PBS or other physiologic solution administered following cryogel placement is generally about 10 times the volume of the cryogel itself.

The cryogel also has the advantage that, upon compression, the cryogel composition maintains structural integrity and shape memory properties. For example, the cryogel is injectable through a hollow needle. For example, the cryogel returns to its approximately original geometry after traveling through a needle (e.g., a 16 gauge (G) needle, e.g., having a 1.65 mm inner diameter). Other exemplary needle sizes are 16-gauge, an 18-gauge, a 20-gauge, a 22-gauge, a 24-gauge, a 26-gauge, a 28-gauge, a 30-gauge, a 32-gauge, or a 34-gauge needle. Injectable cryogels have been designed to pass through a hollow structure, e.g., very fine needles, such as 18-30 G needles. In certain embodiments, the cryogel returns to its approximately original geometry after traveling through a needle in a short period of time, such as less than about 10 seconds, less than about 5 seconds, less than about 2 seconds, or less than about 1 second.

The cryogels may be injected to a subject using any suitable injection device. For example, the cryogels may be injected using syringe through a needle. A syringe may include a plunger, a needle, and a reservoir that comprises compositions of the present invention. The injectable cryogels may also be injected to a subject using a catheter, a cannula, or a stent.

The injectable cryogels may be molded to a desired shape, in the form of rods, square, disc, spheres, cubes, fibers, foams. In some cases, the cryogel is in the shape of a disc, cylinder, square, rectangle, or string. For example, the cryogel composition is between about 100 μm$^3$ to 10 cm$^3$ in size, e.g., between 10 mm$^3$ to 100 mm$^3$ in size. For example, the cryogel composition is between about 1 mm in diameter to about 50 mm in diameter (e.g., about 5 mm) Optionally, the thickness of the cryogel is between about 0.2 mm to about 50 mm (e.g., about 2 mm).

Three exemplary cryogel materials systems are described below.

a) Methacrylated gelatin cryogel (CryoGelMA)—An exemplary cryogel utilized methacrylated gelatin and the results are described in detail in U.S. Patent Application Publication No. 2014-0227327, published Aug. 14, 2014, the entire contents of which are incorporated herein by reference.

b) Methacrylated alginate cryogel (CryoMAAlginate)—An exemplary cryogel utilized methacrylated alginate and the results are described in detail in U.S. Patent Application Publication No. 2014-0227327, published Aug. 14, 2014, the entire contents of which are incorporated herein by reference.

c) Click Alginate cryogel with Laponite nanoplatelets (CryoClick)—The base material is click alginate (PCT International Patent Application Publication No. WO 2015/154078 published Oct. 8, 2015, hereby incorporated by reference in its entirety). In some examples, the base material contains laponite (commercially available silicate clay used in many consumer products such as cosmetics). Laponite has a large surface area and highly negative charge density which allows it to adsorb positively charged moieties on a variety of proteins and other biologically active molecules by an electrostatic interaction, thereby allowing drug loading. When placed in an environment with a low concentration of drug, adsorbed drug releases from the laponite in a sustained manner. This system allows release of a more flexible array of various agents, e.g., growth factors, compared to the base material alone.

Various embodiments of the present subject matter include delivery vehicles comprising a pore-forming scaffold composition. For example, pores (such as macropores) are formed in situ within a hydrogel following hydrogel injection into a subject. Pores that are formed in situ via degradation of a sacrificial porogen hydrogel within the surrounding hydrogel (bulk hydrogel) facilitate recruitment and trafficking of cells, as well as the release of any composition or agent of the present invention, for example, a growth factor, such as BMP-2, a differentiation factor, or a homing factor, or any combination thereof. In some embodiments, the sacrificial porogen hydrogel, the bulk hydrogel, or both the sacrificial porogen hydrogel and the bulk hydrogel may comprise any composition or agent of the present invention, for example, a growth factor, a differentiation factor, and/or, a homing factor, or any combination thereof.

In various embodiments, the pore-forming composition becomes macroporous over time when resident in the body of a recipient animal such as a mammalian subject. For example, the pore-forming composition may comprise a sacrificial porogen hydrogel and a bulk hydrogel, wherein the sacrificial porogen hydrogel degrades at least about 10% faster (e.g., at least about 15%, at least about 20%, at least about 25%, at least about 30%, at least about 35%, at least about 40%, at least about 45%, or at least about 50% faster) than the bulk hydrogel. It is intended that values and ranges intermediate to the recited values are part of this invention. The sacrificial porogen hydrogel may degrade leaving macropores in its place. In certain embodiments, the macropores are open interconnected macropores. In some embodiments, the sacrificial porogen hydrogel may degrade more rapidly than the bulk hydrogel, because the sacrificial porogen hydrogel (i) is more soluble in water (comprises a lower solubility index), (ii) is cross-linked to protease-mediated degradation motifs as described in U.S. Patent Application Publication No. 2005-0119762, published Jun. 2, 2005 (incorporated herein by reference in its entirety), (iii) comprises a shorter polymer that degrades more quickly compared to that of a longer bulk hydrogel polymer, (iv) is modified to render it more hydrolytically degradable than the bulk hydrogel (e.g., by oxidation), and/or (v) is more enzymatically degradable compared to the bulk hydrogel.

In various embodiments, a scaffold is loaded (e.g., soaked with) with one or more active compounds after polymerization. In certain embodiments, device or scaffold polymer forming material is mixed with one or more active compounds before polymerization. In some embodiments, a device or scaffold polymer forming material is mixed with one or more active compounds before polymerization, and then is loaded with more of the same or one or more additional active compounds after polymerization.

In some embodiments, pore size or total pore volume of a composition or scaffold is selected to influence the release of compounds from the device or scaffold. Exemplary porosities (e.g., nanoporous, microporous, and macroporous scaffolds and devices) and total pore volumes (e.g., about 5, 10, 15, 20, 25, 30, 35, 40, 45, 50, 55, 60, 65, 70, 75, 80, 85, 90, 95% or more of the volume of the scaffold) are described herein. It is intended that values and ranges intermediate to the recited values are part of this invention. Increased pore size and total pore volume increases the amount of compounds that can be delivered into or near a tissue, such as bone marrow. In some embodiments, a pore size or total pore volume is selected to increase the speed at which active ingredients exit the composition or scaffold. In various embodiments, an active ingredient may be incorporated into the scaffold material of a hydrogel or cryogel, e.g., to achieve continuous release of the active ingredient from the scaffold or device over a longer period of time compared to active ingredient that may diffuse from a pore cavity.

Porosity influences recruitment of the cells into devices and scaffolds and the release of substances from devices and scaffolds. Pores may be, e.g., nanoporous, microporous, or macroporous. For example, the diameter of nanopores is less than about 10 nm. Micropores are in the range of about 100 nm to about 20 μm in diameter. Macropores are greater than about 20 μm (e.g., greater than about 100 μm or greater than about 400 μm) in diameter. Exemplary macropore sizes include about 50 μm, about 100 μm, about 150 μm, about 200 μm, about 250 μm, about 300 μm, about 350 μm, about 400 μm, about 450 μm, about 500 μm, about 550 μm, and about 600 μm in diameter. It is intended that values and ranges intermediate to the recited values are part of this invention. Macropores are those of a size that permit a eukaryotic cell to traverse into or out of the composition. In one example, a macroporous composition has pores of about 400 μm to about 500 μm in diameter. The preferred pore size depends on the application. In certain embodiments, the pores have a diameter of about 50 μm to about 80 μm.

In various embodiments, the composition is manufactured in one stage in which one layer or compartment is made and infused or coated with one or more compounds. Exemplary bioactive compositions comprise polypeptides or polynucleotides. In certain embodiments, the composition is manufactured in two or more (3, 4, 5, 6, . . . 10 or more) stages in which one layer or compartment is made and infused or coated with one or more compounds followed by the construction of second, third, fourth or more layers, which are in turn infused or coated with one or more compounds in sequence. In some embodiments, each layer or compartment is identical to the others or distinguished from one another by the number or mixture of bioactive compositions as well as distinct chemical, physical and biological properties. Polymers may be formulated for specific applications by controlling the molecular weight, rate of degradation, and method of scaffold formation. Coupling reactions can be used to covalently attach bioactive agent, such as the differentiation factor to the polymer backbone.

In some embodiments, one or more compounds is added to the scaffold compositions using a known method including surface absorption, physical immobilization, e.g., using a phase change to entrap the substance in the scaffold material. For example, a growth factor is mixed with the scaffold composition while it is in an aqueous or liquid phase, and after a change in environmental conditions (e.g., pH, temperature, ion concentration), the liquid gels or solidi-fies thereby entrapping the bioactive substance. In some embodiments, covalent coupling, e.g., using alkylating or acylating agents, is used to provide a stable, long term presentation of a compound on the scaffold in a defined conformation. Exemplary reagents for covalent coupling of such substances are provided in the table below.

TABLE 1

| Methods to Covalently Couple Peptides/Proteins to Polymers | | |
|---|---|---|
| Functional Group of Polymer | Coupling Reagents and Cross-Liner | Reacting Groups on Proteins/Peptides |
| —OH | Cyanogen bromide (CNBr) Cyanuric chloride 4-(4,6-Dimethoxy-1,3,5-triazin-2-yl)-4-methylmorpholinium chloride (DMT-MM) | —NH$_2$ |
| —NH$_2$ | Diisocyanate compounds Diisothoncyanate compounds Glutaraldehyde Succinic anhydride | —NH$_2$ —OH |
| —NH$_2$ | Nitrous Acid Hydrazine + nitrous acid | —NH$_2$ —SH —Ph—OH |
| —NH2 | Carbodiimide compounds (e.g., EDC, DCC)[a] DMT-MM | —COOH |
| —COOH | Thiony I chloride N-hydroxysuccinimide N-hydroxysulfosuccinimide + EDC | —NH$_2$ |
| —SH | Disulfide compound | —SH |

[a] EDC: 1-ethyl-3-(3-dimethylaminopropyl) carbodiimide hydrochloride; DCC: dicyclohexylcarbodiimide Alginate Scaffolds In certain embodiments, the composition of the invention comprises an alginate hydrogel. Alginates are versatile poly-saccharide based polymers that may be formulated for specific applications by controlling the molecular weight, rate of degradation and method of scaffold formation. Alg-inate polymers are comprised of two different monomeric units, (1-4)-linked β-D-mannuronic acid (M units) and a L-guluronic acid (G units) monomers, which can vary in proportion and sequential distribution along the polymer chain. Alginate polymers are polyelectrolyte systems which have a strong affinity for divalent cations (e.g., Ca$^{+2}$, Mg$^{+2}$, Ba$^{+2}$) and form stable hydrogels when exposed to these molecules. See Martinsen A., et al., 1989, *Biotech. & Bioeng.*, 33: 79-89). For example, calcium cross-linked alginate hydrogels are useful for dental applications, wound dressings chondrocyte transplantation and as a matrix for other cell types. Without wishing to be bound by theory, it is believed that G units are preferentially crosslinked using calcium crosslinking, whereas click reaction based cross-linking is more indiscriminate with respect to G units or M units (i.e., both G and M units can be crosslinked by click chemistry). Alginate scaffolds and the methods for making them are known in the art. See, e.g., International Patent Application Publication No. WO2017/075055 A1, published on May 4, 2017, the entire contents of which are incorpo-rated herein by reference.

The alginate polymers useful in the context of the present invention can have an average molecular weight from about 20 kDa to about 500 kDa, e.g., from about 20 kDa to about 40 kDa, from about 30 kDa to about 70 kDa, from about 50 kDa to about 150 kDa, from about 130 kDa to about 300 kDa, from about 230 kDa to about 400 kDa, from about 300 kDa to about 450 kDa, or from about 320 kDa to about 500 kDa. In one example, the alginate polymers useful in the present invention may have an average molecular weight of about 32 kDa. In another example, the alginate polymers useful in the present invention may have an average molecu-lar weight of about 265 kDa. In some embodiments, the alginate polymer has a molecular weight of less than about 1000 kDa, e.g., less than about 900 KDa, less than about 800 kDa, less than about 700 kDa, less than about 600 kDa, less than about 500 kDa, less than about 400 kDa, less than about 300 kDa, less than about 200 kDa, less than about 100 kDa, less than about 50 kDa, less than about 40 kDa, less than about 30 kDa or less than about 25 kDa. In some embodi-ments, the alginate polymer has a molecular weight of about 1000 kDa, e.g., about 900 kDa, about 800 kDa, about 700 kDa, about 600 kDa, about 500 kDa, about 400 kDa, about 300 kDa, about 200 kDa, about 100 kDa, about 50 kDa, about 40 kDa, about 30 kDa or about 25 kDa. In one embodiment, the molecular weight of the alginate polymers is about 20 kDa.

Coupling reactions can be used to covalently attach bioactive agent, such as an atom, a chemical group, a nucleoside, a nucleotide, a nucleobase, a sugar, a nucleic acid, an amino acid, a peptide, a polypeptide, a protein, or a protein complex, to the polymer backbone.

The term "alginate", used interchangeably with the term "alginate polymers", includes unmodified alginate or modi-fied alginate. Modified alginate includes, but not limited to, oxidized alginate (e.g., comprising one or more algoxalate monomer units) and/or reduced alginate (e.g., comprising one or more algoxinol monomer units). In some embodi-ments, oxidized alginate comprises alginate comprising one or more aldehyde groups, or alginate comprising one or more carboxylate groups. In other embodiments, oxidized alginate comprises highly oxidized alginate, e.g., compris-ing one or more algoxalate units. Oxidized alginate may also comprise a relatively small number of aldehyde groups (e.g., less than 15%, e.g., 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, or 0.1% aldehyde groups or oxidation on a molar basis). It is intended that values and ranges intermediate to the recited values are part of this invention. The term "alginate" or "alginate polymers" may also include alginate, e.g., unmodified alginate, oxidized alginate or reduced alginate, or methacrylated alginate or acrylated alginate. Alginate may also refer to any number of derivatives of alginic acid (e.g., calcium, sodium or potas-sium salts, or propylene glycol alginate). See, e.g., WO1998012228A1, hereby incorporated by reference.

Hyaluronic Acid

In certain embodiments, the composition of the present invention comprises a hyaluronic acid hydrogel. Hyaluronic acid (HA; conjugate base hyaluronate), is an anionic, non-sulfated glycosaminoglycan distributed widely throughout connective, epithelial, and neural tissues. One of the chief components of the extracellular matrix, hyaluronic acid contributes significantly to cell proliferation and migration. Natural hyaluronic acid is an important component of articu-lar cartilage, muscular connective tissues, and skin.

Hyaluronic acid is a polymer of disaccharides, composed of D-glucuronic acid and N-acetyl-D-glucosamine, linked via alternating β-(1→4) and β-(1→3) glycosidic bonds. Hyaluronic acid can be 25,000 disaccharide repeats in length. Polymers of hyaluronic acid can range in size from 5,000 to 20,000,000 Da. Hyaluronic acid can also contain silicon.

Hyaluronic acid is energetically stable, in part because of the stereochemistry of its component disaccharides. Bulky groups on each sugar molecule are in sterically favored positions, whereas the smaller hydrogens assume the less-favorable axial positions.

Hyaluronic acid can be degraded by a family of enzymes called hyaluronidases, which are present in many mammals, e.g., a human Hyaluronic acid can also be degraded via non-enzymatic reactions. These include acidic and alkaline hydrolysis, ultrasonic disintegration, thermal decomposition, and degradation by oxidants.

Due to its high biocompatibility and its common presence in the extracellular matrix of tissues, hyaluronic acid is used to form hydrogels, e.g., cryogels, as a biomaterial scaffold in tissue engineering research. Hyaluronic acid hydrogels are formed through crosslinking Hyaluronic acid can form a hydrogel, e.g., cryogel, into a desired shape to deliver therapeutic molecules into a host. Hyaluronic acids, for use in the present compositions, can be crosslinked by attaching thiols, methacrylates, hexadecylamides, and tyramines. Hyaluronic acids can also be crosslinked directly with formaldehyde or with divinylsulfone.

The term "hyaluronic acid," includes unmodified hyaluronic acid or modified hyaluronic acid. Modified hyaluronic acid includes, but is not limited to, oxidized hyaluronic acid and/or reduced hyaluronic acid. The term "hyaluronic acid" or "hyaluronic acid polymers" may also include hyaluronic acid, e.g., unmodified hyaluronic acid, oxidized hyaluronic acid or reduced hyaluronic acid, or methacrylated hyaluronic acid or acrylated hyaluronic acid. Hyaluronic acid may also refer to any number of derivatives of hyaluronic acid.

Porous and Pore Forming Scaffolds

The scaffolds of the present invention may be nonporous or porous. In certain embodiments, the scaffolds of the present invention are porous. Porosity of the scaffold composition influences migration of the cells through the device. Pores may be nanoporous, microporous, or macroporous. For example, the diameter of nanopores is less than about 10 nm. Micropores are in the range of about 100 nm to about 20 μm in diameter. Macropores are greater than about 20 μm (e.g., greater than about 100 μm or greater than about 400 μm) in diameter. Exemplary macropore sizes include about 50 μm, 100 μm, 150 μm, 200 μm, 250 μm, 300 μm, 350 μm, 400 μm, 450 μm, 500 μm, 550 μm, and 600 μm in diameter. It is intended that values and ranges intermediate to the recited values are part of this invention. Macropores are of a size that permits a eukaryotic cell to traverse into or out of the composition. In certain embodiments, a macroporous composition has pores of about 400 μm to 500 μm in diameter. The size of pores may be adjusted for different purpose. For example, for cell recruitment and cell release, the pore diameter may be greater than 50 μm. In certain embodiments, a macroporous composition has pores of about 50 μm-about 80 μm in diameter.

In some embodiments, the scaffolds contain pores before the administration into a subject. In some embodiments, the scaffolds comprise a pore-forming scaffold composition. Pore-forming scaffolds and the methods for making pore-forming scaffolds are known in the art. See, e.g., U.S. Patent Publication US2014/0079752A1, the content of which is incorporated herein by reference. In certain embodiments, the pore-forming scaffolds are not initially porous, but become macroporous over time resident in the body of a recipient animal such as a mammalian subject. In certain embodiments, the pore-forming scaffolds are hydrogel scaffolds. The pore may be formed at different time, e.g., after about 12 hours, or 1, 3, 5, 7, or 10 days or more after administration, i.e., resident in the body of the subject.

In certain embodiments, the pore-forming scaffolds comprise a first hydrogel and a second hydrogel, wherein the first hydrogel degrades at least about 10% faster (e.g., at least about 15%, at least about 20%, at least about 25%, at least about 30%, at least about 35%, at least about 40%, at least about 45%, at least about 50% faster, at least about 2 times faster, or at least about 5 times faster) than the second hydrogel. It is intended that values and ranges intermediate to the recited values are part of this invention. In certain embodiments, the first hydrogel comprises a porogen that degrades leaving a pore in its place. For example, the first hydrogel is a porogen and the resulting pore after degradation in situ is within 25% of the size of the initial porogen, e.g., within 20%, within 15%, or within 10% of the size of the initial porogen. Preferably, the resulting pore is within 5% of the size of the initial porogen. It is intended that values and ranges intermediate to the recited values are part of this invention. The first hydrogel may degrade faster than the second hydrogel due to the difference in their physical, chemical, and/or biological properties. In certain embodiments, the first hydrogel degrades more rapidly than the second hydrogel, because the first hydrogel is more soluble in water (comprises a lower solubility index). In certain embodiments, the first hydrogel degrades more rapidly because it is cross-linked to protease-mediated degradation motifs as described in U.S. Patent Publication US2005/0119762A1, the content of which is incorporated herein by reference.

In certain embodiments, the molecular mass of the polymers used to form the first hydrogel composition (a porogen) is approximately 50 kilodaltons (kDa), and the molecular mass of the polymers used to form the second hydrogel composition (bulk) is approximately 250 kDa. A shorter polymer (e.g., that of a porogen) degrades more quickly compared to that of a longer polymer (e.g., that of the bulk composition). In certain embodiments, a composition is modified to render it more hydrolytically degradable by virtue of the presence of sugar groups (e.g., approximately 3-10% sugar of an alginate composition). In certain embodiments, the porogen hydrogel is chemically modified, such as oxidized, to render it more susceptible to degradation. In some embodiments, the porogen hydrogel is more enzymatically degradable compared to the bulk hydrogel. The composite (first and second hydrogel) composition is permeable to bodily fluids, e.g., containing an enzyme which is exposed to the composition and degrades the porogen hydrogel. In some embodiments, the second hydrogel is cross-linked around the first hydrogel, i.e., the porogens (first hydrogel) are completely physically entrapped in the bulk (second) hydrogel.

The click reagents disclosed herein can be provided in the bulk hydrogel or the porogen hydrogel. In exemplary embodiments, the click reagents, e.g., polymers or nanoparticles, are provided in the bulk hydrogel.

In certain embodiments, hydrogel micro-beads ("porogens") are formed. Porogens are encapsulated into a "bulk" hydrogel that is either non-degradable or which degrades at a slower rate compared to the porogens Immediately after hydrogel formation, or injection into the desired site in vivo, the composite material lacks pores. Subsequently, porogen degradation causes pores to form in situ. The size and distribution of pores are controlled during porogen formation, and mixing with the polymers which form the bulk hydrogel.

In some embodiments, the polymer utilized in the pore-forming scaffolds is naturally-occurring or synthetically made. In one example, both the porogens and bulk hydrogels are formed from alginate.

In certain embodiments, the alginate polymers suitable for porogen formation have a molecular weight from 5,000 to 500,000 Daltons. The polymers are optionally further modified (e.g., by oxidation with sodium periodate, (Bouhadir et al., 2001, *Biotech. Prog.* 17:945-950, hereby incorporated by reference), to facilitate rapid degradation. In certain embodiments, the polymers are crosslinked by extrusion through a nebulizer with co-axial airflow into a bath of divalent cation (for example, $Ca^{2+}$ or $Ba^{2+}$) to form hydrogel micro-beads. Higher airflow rate leads to lower the porogen diameter.

In some embodiments, the porogen hydrogel microbeads contain oxidized alginate. For example, the porogen hydrogel can contain about 1-50% (w/v) oxidized alginate. In exemplary embodiments, the porogen hydrogel can contain about 1-10% oxidized alginate. In one embodiment, the porogen hydrogel contains about 7.5% oxidized alginate.

In certain embodiments, the concentration of divalent ions used to form porogens may vary from about 5 to about 500 mM, and the concentration of polymer from about 1% to about 5% by weight/volume. However, any method which produces porogens that are significantly smaller than the bulk phase is suitable. Porogen chemistry can further be manipulated to produce porogens that interact with host proteins and/or cells, or inhibit interactions with host proteins and/or cells.

The alginate polymers suitable for formation of the bulk hydrogel have a molecular weight from about 5,000 to about 500,000 Da. The polymers may be further modified (for example, by oxidation with sodium periodate), to facilitate degradation, as long as the bulk hydrogel degrades more slowly than the porogen. The polymers may also be modified to present biological cues to control cell responses (e.g., integrin binding adhesion peptides such as RGD). Either the porogens or the bulk hydrogel may also encapsulate bioactive factors such as oligonucleotides, growth factors or drugs to further control cell responses. The concentration of divalent ions used to form the bulk hydrogel may vary from about 5 to about 500 mM, and the concentration of polymer from about 1% to about 5% by weight/volume. The elastic modulus of the bulk polymer is tailored for its purpose, e.g., to recruit stem cells or progenitor cells.

Methods relevant to generating the hydrogels described herein include the following. Bouhadir et al., 1999, *Polymer,* 40: 3575-84 (incorporated herein by reference in its entirety) describes the oxidation of alginate with sodium periodate, and characterizes the reaction. Bouhadir et al., 2001, *Biotechnol. Prog.,* 17: 945-50 (incorporated herein by reference in its entirety) describes oxidation of high molecular weight alginate to form alginate dialdehyde (alginate dialdehyde is high molecular weight ($M_w$) alginate in which a certain percent, e.g., 5%, of sugars in alginate are oxidized to form aldehydes), and application to make hydrogels degrade rapidly. Kong et al., 2002, *Polymer,* 43: 6239-46 (incorporated herein by reference in its entirety) describes the use of gamma-irradiation to reduce the weight-averaged molecular weight ($M_w$) of guluronic acid (GA) rich alginates without substantially reducing GA content (e.g., the gamma irradiation selectively attacks mannuronic acid, MA blocks of alginate). Alginate is comprised of GA blocks and MA blocks, and it is the GA blocks that give alginate its rigidity (elastic modulus). Kong et al., 2002, *Polymer,* 43: 6239-46 (incorporated herein by reference in its entirety) shows that binary combinations of high $M_w$, GA rich alginate with irradiated, low $M_w$, high GA alginate crosslinks with calcium to form rigid hydrogels, but which degrade more rapidly and also have lower solution viscosity than hydrogels made from the same overall weight concentration of only high $M_w$, GA rich alginate. Alsberg et al., 2003, *J Dent Res,* 82(11): 903-8 (incorporated herein by reference in its entirety) describes degradation profiles of hydrogels made from irradiated, low $M_w$, GA-rich alginate, with application in bone tissue engineering. Kong et al., 2004, *Adv. Mater,* 16(21): 1917-21 (incorporated herein by reference) describes control of hydrogel degradation profile by combining gamma irradiation procedure with oxidation reaction, and application to cartilage engineering.

Techniques to control degradation of hydrogen biomaterials are well known in the art. For example, Lutolf M P et al., 2003, *Nat Biotechnol.,* 21: 513-8 (incorporated herein by reference in its entirety) describes poly(ethylene glycol) based materials engineered to degrade via mammalian enzymes (MMPs). Bryant S J et al., 2007, *Biomaterials,* 28(19): 2978-86 (U.S. Pat. No. 7,192,693 B2; incorporated herein by reference in its entirety) describes a method to produce hydrogels with macro-scale pores. A pore template (e.g., poly-methylmethacrylate beads) is encapsulated within a bulk hydrogel, and then acetone and methanol are used to extract the porogen while leaving the bulk hydrogel intact. Silva et al., 2008, *Proc. Natl. Acad. Sci USA,* 105(38): 14347-52 (incorporated herein by reference in its entirety; US 2008/0044900) describes deployment of endothelial progenitor cells from alginate sponges. The sponges are made by forming alginate hydrogels and then freeze-drying them (ice crystals form the pores). Ali et al., 2009, *Nat Mater* (incorporated herein by reference in its entirety) describes the use of porous scaffolds to recruit dendritic cells and program them to elicit anti-tumor responses. Huebsch et al., 2010, *Nat Mater,* 9: 518-26 (incorporated herein by reference in its entirety) describes the use of hydrogel elastic modulus to control the differentiation of encapsulated mesenchymal stem cells.

In some embodiments, the scaffold composition comprises open interconnected macropores. Alternatively or in addition, the scaffold composition comprises a pore-forming scaffold composition. In certain embodiments, the pore-forming scaffold composition may comprise a sacrificial porogen hydrogel and a bulk hydrogel, wherein the pore-forming scaffold composition lacks macropores. For example, the sacrificial porogen hydrogel may degrade at least 10% faster than the bulk hydrogel leaving macropores in its place following administration of said pore-forming scaffold into a subject. In some embodiments, the sacrificial porogen hydrogel is in the form of porogens that degrade to form said macropores. For example, the macropores may comprise pores having a diameter of, e.g., about 10-400 μm.

Growth Factors

The compositions of the present invention can comprise a growth factor. The term "growth factor," as used herein, refers to an agent that is capable of stimulating cellular growth, proliferation, healing, and/or cellular differentiation. In certain embodiments, growth factors are polypeptides. Growth factor polypeptides typically act as signaling molecules. In certain embodiments, the growth factor polypeptides are cytokines.

In certain embodiments, the growth factor can recruit a cell to the scaffold following the administration of the composition to a subject. The recruited cell may be autologous. For example, the recruited cell may be a stromal cell from the subject. In certain embodiments, the autologous cell may be a stem cell (e.g., umbilical cord stem cells) of the subject. The recruited cell may also be syngeneic, allogeneic or xenogeneic. As used herein, the term "syngeneic" refers to genetically identical, or sufficiently identical and immunologically compatible as to allow for transplantation. For example, syngeneic cells may include transplanted cells obtained from an identical twin. As used herein, the term "allogeneic" refers to cells that are genetically dissimilar, although from individuals of the same species. As used herein, the term "xenogeneic" refers to cells derived from a different species and therefore genetically different.

For example, the recruited cell may be a donor cell in a transplantation. In certain embodiments, the transplantation is a hematopoietic stem cell transplantation (HSCT). As used herein, HSCT refers to the transplantation of multipotent hematopoietic stem cells or hematopoietic progenitor cells, usually derived from bone marrow, peripheral blood, or umbilical cord blood. ⁻HSCT may be autologous (the patient's own stem cells or progenitor cells are used), allogeneic (the stem cells or progenitor cells come from a donor), syngeneic (from an identical twin) or xenogenic (from different species).

The growth factors of the present invention may induce the formation of a tissue or organ within or around the administered composition. In certain embodiments, the tissue or organ is a bony tissue or hematopoietic tissue. The tissue formation may be restricted to the scaffold of the composition.

Methods of incorporating polypeptides (e.g., growth factor polypeptides) are known in the art. See, U.S. Pat. Nos. 8,728,456; 8,067,237; and 10,045,947; US Patent Publication No.: US20140079752; International Patent Publication No.: WO2017/136837; incorporated herein by reference in their entirety. The release of the growth factor polypeptides may be controlled. The methods of controlled release of polypeptides (e.g., growth factor polypeptides) are known in the art. See, U.S. Pat. Nos. 8,728,456; 8,067,237; 10,045, 946, incorporated by reference in their entirety. In certain embodiments, the growth factors (e.g., BMP-2) may be released over an extended period of time, such as 7-30 days or longer. The controlled release of the growth factors may affect the timing of the formation of the tissue or organ within the scaffold. In certain examples, the release of the growth factors is controlled with the goal of creating a functional, active bone nodule or tissue within one to two weeks after subcutaneous injection of the compositions of the present invention.

In certain embodiments, the growth factors retain their bioactivity over an extended period of time. The term "bioactivity," as used herein, refers to the beneficial or adverse effects of an agent, such as a growth factor. The bioactivity of the growth factor may be measured by any appropriate means. For example, the bioactivity of BMP-2 may be measured by its capacity to induce the formation of bone nodule or tissue and/or recruit cells into the scaffold. In certain example, the growth factors retain their bioactivity for at least 10 days, 12 days, 14 days, 20 days, or 30 days after the incorporation of the growth factors into the scaffold.

Exemplary growth factors include, but are not limited to, bone morphogenetic proteins (BMP), epidermal growth factor (EGF), transforming growth factor beta (TGF-β), granulocyte-colony stimulating factor (G-CSF), granulocyte-macrophage colony stimulating factor (GM-CSF), nerve growth factor (NGF), neurotrophins, Platelet-derived growth factor (PDGF), erythropoietin (EPO), thrombopoietin (TPO), myostatin (GDF-8), growth differentiation factor-9 (GDF9), acidic fibroblast growth factor (aFGF or FGF-1), basic fibroblast growth factor (bFGF or FGF-2), epidermal growth factor (EGF), hepatocyte growth factor (HGF), insulin-like growth factor (IGF), and interleukins.

In some embodiments, the growth factor comprises a protein belonging to the transforming growth factor beta (TGF-β) superfamily. As used herein, TGF-β superfamily is a large group of structurally related cell regulatory proteins. TGF-β superfamily includes four major subfamilies: the TGF-β subfamily, the bone morphogenetic proteins and the growth differentiation factors, the activing and inhibin subfamilies, and a group encompassing various divergent members. Proteins from the TGF-β superfamily are active as homo- or heterodimer, the two chains being linked by a single disulfide bond. TGF-β superfamily proteins interact with a conserved family of cell surface serine/threonine-specific protein kinase receptors, and generate intracellular signals using a conserved family of proteins called SMADs. TGF-β superfamily proteins play important roles in the regulation of basic biological processes such as growth, development, tissue homeostasis and regulation of the immune system.

Exemplary TGF-β superfamily proteins include, but are not limited to, AMH, ARTN, BMP10, BMP15, BMP2, BMP3, BMP4, BMP5, BMP6, BMP7, BMP8A, BMP8B, GDF1, GDF10, GDF11, GDF15, GDF2, GDF3, GDF3A, GDF5, GDF6, GDF7, GDF8, GDF9, GDNF, INHA, INHBA, INHBB, INHBC, INHBE, LEFTY1, LEFTY2, MSTN, NODAL, NRTN, PSPN, TGF-β1, TGF-β2, TGF-β3, and TGF-β4. In a particular embodiment, the growth factor is BMP2.

In certain embodiments, the growth factor comprises a bone morphogenetic protein (BMP). As used herein, a BMP is a protein belonging to a group of growth factors also known as cytokines and as metabologens. BMPs can induce the formation of bone and cartilage and constitute a group of important morphogenetic signals, orchestrating tissue architecture throughout the body. Absence or deficiency of BMP signaling may be an important factor in diseases or disorders.

In certain embodiments, the BMP is selected from a group consisting of a BMP-2, a BMP-4, a BMP-6, a BMP-7, a BMP-12, a BMP-14, and any combination thereof. In certain embodiments, the BMP is BMP-2. BMP-2 plays an important role in the development of bone and cartilage. BMP-2 can potently induce osteoblast differentiation in a variety of cell types.

In certain embodiments, the growth factor comprises a TGF-β subfamily protein. As used herein, TGF-β subfamily protein or TGF-β is a multifunctional cytokine that includes four different isoforms (TGF-β1, TGF-β2, TGF-β3, and TGF-β4). Activated TGF-β complexes with other factors to form a serine/threonine kinase complex that binds to TGF-β receptors, which is composed of both type 1 and type 2 receptor subunits. After the binding of TGF-β, the type 2 receptor kinase phosphorylates and activates the type 1 receptor kinase that activates a signaling cascade. This leads to the activation of different downstream substrates and regulatory proteins, inducing transcription of different target genes that function in differentiation, chemotaxis, proliferation, and activation of many immune cells.

In certain embodiments, the growth factor comprises a TGF-β1. TGF-β1 plays a role in the induction from CD4+ T cells of both induced Tregs (iTregs), which have a regulatory function, and $T_h17$ cells, which secrete proinflammatory cytokines. TGF-β1 alone precipitates the expression of Foxp3 and Treg differentiation from activated T helper cells.

The growth factors, (e.g., BMP-2 or TGF-β1), may be isolated from endogenous sources or synthesized in vivo or in vitro. Endogenous growth factor polypeptides may be isolated from healthy human tissue. Synthetic growth factor polypeptides are synthesized in vivo following transfection or transformation of template DNA into a host organism or cell, e.g., a mammalian or human cell line. Alternatively, synthetic growth factor polypeptides are synthesized in vitro by cell free translation or other art-recognized methods Sambrook, J., Fritsch, E. F., and Maniatis, T., Molecular Cloning: A Laboratory Manual. Cold Spring Harbor Laboratory Press, NY, Vol. 1, 2, 3 (1989), herein incorporated by reference.

In certain embodiments, growth factor (e.g., BMP-2 or TGF-β1) polypeptides may be recombinant. In some embodiments, growth factor polypeptides are humanized derivatives of mammalian growth factor polypeptides. Exemplary mammalian species from which growth factor polypeptides are derived include, but are not limited to, mouse, rat, hamster, guinea pig, ferret, cat, dog, monkey, or primate. In some embodiments, the growth factor is a recombinant human protein. In some embodiments, the growth factor is a recombinant murine (mouse) protein. In some embodiments, the growth factor is a humanized derivative of a recombinant mouse protein.

In certain embodiments, the growth factor polypeptides may be modified to increase protein stability in vivo. In certain embodiments, the growth factor polypeptides may be engineered to be more or less immunogenic. The terms "immunogenic" and "immunogenicity" refer to the ability of a particular substance, such as a protein, an antigen, or an epitope, to provoke an immune response in the body of a human and other animal.

In certain embodiments, the growth factors may be present at between about 0.001 nmol and about 1000 nmol per scaffold, or about 0.001 and about 100 nmol per scaffold, or about 0.001 nmol and about 1 nmol per scaffold.

In some embodiments, the growth factors may be present at between about 1 ng to 1000 micrograms per scaffold. For example, the growth factors may be present at an amount between about 1 μg and about 1000 μg, between about 1 μg and 500 μg, between about 1 μg and about 200 μg, between about 1 μg and about 100 μg, between about 1 μg and about 50 μg, or between about 1 μg and 10 μg.

In certain embodiments, the composition of the present invention comprises nanogram quantities of growth factors (e.g., about 1 ng to about 1000 ng of BMP-2). For example, the growth factors may be present at an amount between about 5 ng and about 500 ng, between about 5 ng and about 250 ng, between about 5 ng and about 200 ng, between about 10 ng and about 200 ng, between about 25 ng and about 200 ng, between about 50 ng and 200 ng, between about 100 ng and 200 ng, and about 200 ng. Nanogram quantities of the growth factor are also released in a controlled manner. The nanogram quantities of the growth factors and/or the controlled release can contribute to reduced toxicity of the compositions and methods of the present invention as compared to other delivery system, which uses high dose of growth factors and has suboptimal release kinetics.

In various embodiments, the amount of growth factors present in a scaffold may vary according to the size of the scaffold. For example, the growth factor may be present at about 0.03 ng/mm$^3$ (the ratio of the amount of growth factors in weight to the volume of the scaffold) to about 350 ng/mm$^3$, such as between about 0.1 ng/mm$^3$ and about 300 ng/mm$^3$, between about 0.5 ng/mm$^3$ and about 250 ng/mm$^3$, between about 1 ng/mm$^3$ and about 200 ng/mm$^3$, between about 2 ng/mm$^3$ and about 150 ng/mm$^3$, between about 3 ng/mm$^3$ and about 100 ng/mm$^3$, between about 4 ng/mm$^3$ and about 50 ng/mm$^3$, between about 5 ng/mm$^3$ and 25 ng/mm$^3$, between about 6 ng/mm$^3$ and about 10 ng/mm$^3$, or between about 6.5 ng/mm$^3$ and about 7.0 ng/mm$^3$.

In some embodiments, the amount of growth factors may be present at between about 300 ng/mm$^3$ and about 350 μg/mm$^3$, such as between about 400 ng/mm$^3$ and between about 300 μg/mm$^3$, between about 500 ng/mm$^3$ and about 200 μg/mm$^3$, between about 1 μg/mm$^3$ and about 100 μg/mm$^3$, between about 5 μg/mm$^3$ and about 50 μg/mm$^3$, between about 10 μg/mm$^3$ and about 25 μg/mm$^3$ Differentiation Factors The composition of the present invention can comprise a differentiation factor. As used herein, a differentiation factor is an agent that can induce the differentiation of a cell, for example, a recruited cell. In certain embodiments, the differentiation factor is a polypeptide. As used herein, "differentiation," "cell differentiation," "cellular differentiation," or other similar terms refer to the process where a cell changes from one cell type to another. In certain embodiments, the cell changes to a more specialized type, e.g., from a stem cell or a progenitor cell to a T cell progenitor cell. Differentiation occurs numerous times during the development of a multicellular organism as it changes from a simple zygote to a complex system of tissues and cell types. Differentiation continues in adulthood as adult stem cells divide and create fully differentiated daughter cells during tissue repair and during normal cell turnover. Differentiation may change a cell's size, shape, membrane potential, metabolic activity, and responsiveness to signals. These changes may be due to highly controlled modifications in gene expression.

Among dividing cells, there are multiple levels of cell potency, the cell's ability to differentiate into other cell types. A greater potency indicates a larger number of cell types that can be derived. A cell that can differentiate into all cell types, including the placental tissue, is known as totipotent. A cell that can differentiate into all cell types of the adult organism is known as pluripotent. In mammals, e.g., human being, a pluripotent cell may include embryonic stem cells and adult pluripotent cells. Induced pluripotent stem (iPS) cells may be created from fibroblasts by induced expression of certain transcription factors, e.g., Oct4, Sox2, c-Myc, and KIF4. A multipotent cell is one that can differentiate into multiple different, but closely related cell types. Oligopotent cells are more restricted than multipotent, but can still differentiate into a few closely related cell types. Finally, unipotent cells can differentiate into only one cell type, but are capable of self-renewal.

In certain embodiments, the differentiation factors of the present invention induce the differentiation of stem cells or progenitor cells into T-cell progenitor cells. As used herein, the term "T cell progenitor cell" refers to a progenitor cell that ultimately can differentiate to a T lymphocyte (T cell). The term "lymphocyte," as used herein, refers to one of the subtypes of white blood cell in a vertebrate's (e.g., human being) immune system. Lymphocytes include natural killer cells, T cells, and B cells. Lymphocytes originate from a common lymphoid progenitor during hematopoiesis, a process during which stem cells differentiate into several kinds of blood cells within the bone marrow, before differentiating into their distinct lymphocyte types.

In some embodiments, the T cell progenitor cell comprises a common lymphoid progenitor cell. The term "common lymphoid progenitor cell," as used herein, refers to the earliest lymphoid progenitor cells, which give rise to lymphocytes including T-lineage cells, B-lineage cells, and natural killer (NK) cells. In various embodiment, the T cell progenitor cell comprises a T cell competent common lymphoid progenitor cell. The term "T cell competent common lymphoid progenitor cell," as used herein, refers to a common lymphoid progenitor cell that differentiates into T-lineage progenitor cell. A T cell competent common lymphoid progenitor is usually characterized by lacking of biomarker Ly6D. The composition of the present invention can create an ectopic niche that mimics important features of bone marrow and induces the differentiation of stem cells or progenitor cells into T cell progenitor cells.

In certain embodiments, the lymphocytes comprise T cells. In some embodiments, the T cells are naïve T cells. As used herein, a naïve T cell is a T cell that has differentiated in bone marrow. Naïve T cells may include CD4$^+$ T cells, CD8$^+$ T cells, and regulatory T cells (T$_{reg}$).

In certain embodiments, the differentiation factors induce the differentiation of the recruited cells into T cell progenitor cells. In certain embodiments, the differentiation factors induce the differentiation of the recruited cells into T cell progenitor cells through the Notch signaling pathway. The Notch signaling pathway is a highly conserved cell signaling system present in many multicellular organisms. Mammals possess four different Notch receptors, referred to as Notch1, Notch2, Notch3, and Notch4. Notch signaling plays an important role in T cell lineage differentiation from common lymphoid progenitor cells. In certain embodiments, the differentiation factors bind to one or more Notch receptors and activates the Notch signaling pathway. In certain embodiments, the differentiation factor is selected from a group consisting of a Delta-like 1 (DLL-1), a Delta-like 2 (DLL-2), a Delta-like 3 (DLL-3), a Delta-like 3 (DLL-3), a Delta-like 4 (DLL-4), a Jagged 1, a Jagged 2, and any combination thereof. In certain embodiments, the binding of the differentiation factor to one or more Notch receptors activates the Notch signaling pathway and induces T cell lineage differentiation.

In certain embodiments, the differentiation factor is a Delta-like 4 (DLL-4). DLL-4 is a protein that is a homolog of the Drosophila Delta protein. The Delta protein family includes Notch ligands that are characterized by a DSL domain, EGF repeats, and a transmembrane domain.

In certain embodiments, the differentiation factor polypeptides are isolated from endogenous sources or synthesized in vivo or in vitro. Endogenous differentiation factor polypeptides may be isolated from healthy human tissue. Synthetic differentiation factor polypeptides are synthesized in vivo following transfection or transformation of template DNA into a host organism or cell, e.g., a mammal or cultured human cell line. Alternatively, synthetic differentiation factor polypeptides are synthesized in vitro by cell free translation or other art-recognized methods Sambrook, J., Fritsch, E. F., and Maniatis, T., Molecular Cloning: A Laboratory Manual. Cold Spring Harbor Laboratory Press, NY, Vol. 1, 2, 3 (1989), herein incorporated by reference).

In certain embodiments, differentiation factor polypeptides may be recombinant. In some embodiments, the differentiation factor polypeptides are humanized derivatives of mammalian differentiation factor polypeptides. Exemplary mammalian species from which the differentiation factor polypeptides are derived include, but are not limited to, mouse, rat, hamster, guinea pig, ferret, cat, dog, monkey, or primate. In some embodiments, the differentiation factor is a recombinant human protein. In some embodiments, the differentiation factor is a recombinant murine (mouse) protein. In some embodiments, the differentiation factor is a humanized derivative of a recombinant mouse protein.

In certain embodiments, the differentiation factor polypeptides may be modified to achieve a desired activity, for example, to increase protein stability in vivo. In certain embodiments, the differentiation factor polypeptides may be engineered to be more or less immunogenic.

In certain embodiments, the differentiation factor (e.g., DLL-4) may be covalently linked to the scaffold of the present invention. For example, rather than being released from a scaffold material, a differentiation factor may be covalently bound to polymer backbone and retained within the composition that forms following implantation of the composition in the subject. By covalently binding or coupling a differentiation factor to the scaffold material, such differentiation factor will be retained within the scaffold that forms following administration of the composition to a subject, and thus will be available to promote the differentiation of stem cells or progenitor cells, as contemplated herein. In certain embodiments, the differentiation factors are conjugated to the scaffold material utilizing N-hydroxysuccinimide (NHS) and 1-ethyl-3-(3-dimethylaminopropyl)carbodiimide hydrochloride (EDC) chemistry. Any methods of covalently binding or coupling differentiation factors known in the art may be used and are not limited. See "Bioconjugate Techniques Bioconjugate Techniques (Third Addition)", Greg T. Hermanson, Academic, Greg T. Hermanson, Academic Press, 2013 Press, 2013. In some embodiments, the differentiation factor may be covalently linked to the scaffold utilizing click chemistry. The methods of covalently binding or coupling differentiation factors include, but are not limited to, avidin-biotin reaction, azide and dibenzocycloocytne chemistry, tetrazine and transcyclooctene chemistry, tetrazine and norbornene chemistry, or di-sulfide bond.

In certain embodiments, the differentiation factors (e.g., DLL-4) of the present invention further comprise a tether (e.g., PEG, PEG$_{2k}$) and a methacrylate group (MA). In certain embodiments, the differentiation factor is methacrylated DLL-4-PEG$_{2k}$.

In certain embodiments, the covalent linking retains the differentiation factors within the scaffold to provide the differentiation signal to the recruited cells in the scaffold. For example, less than 1% of the total differentiation factor is detected outside of the scaffold. The bioactivity of the differentiation factor may be retained for an extended period of time, such as at least three months after incorporation to the scaffold. The bioactivity of the differentiation factors may be measured by any appropriate methods, such as a colorimetric assay for DLL-4.

In certain embodiments, the differentiation factors may be present at between about 0.01 nmol and 1000 nmol, about 0.1 nmol and 100 nmol, or about 1 nmol and 10 nmol per scaffold.

In some embodiments, the differentiation factors may be present at between about 1 ng and 1000 micrograms per scaffold. For example, the differentiation factor may be present at between about 10 ng and about 500 μg, between about 50 ng and about 250 μg, between about 100 ng and about 200 μg, between about 1 μg and about 100 μg, between about 1 μg and about 50 μg, between about 1 μg and about 25 μg, between about 1 μg and about 10 μg, between about 2 μg and about 10 μg, or about 6 μg.

In various embodiments, the amount of differentiation factor present in a scaffold may vary according to the size of the scaffold. For example, the differentiation factor may be present at about 0.03 ng/mm$^3$ (the ratio of the amount of differentiation factor in weight to the volume of the scaffold) to about 350 µg/mm$^3$, such as between about 0.1 ng/mm$^3$ and about 300 µg/mm$^3$, between about 1 ng/mm$^3$ and about 250 µg/mm$^3$, between about 10 ng/mm$^3$ and about 200 µg/mm$^3$, between about 0.1 µg/mm$^3$ and about 100 µg/mm$^3$, between about 0.1 µg/mm$^3$ and 50 about µg/mm$^3$, or between about 0.1 µg/mm$^3$ and about 20 µg/mm$^3$, between about 0.1 µg/mm$^3$ and about 10 µg/mm$^3$, between about 0.1 µg/mm$^3$ and about 5 µg/mm$^3$, between about 0.1 µg/mm$^3$ and about 1 µg/mm$^3$, between about 0.1 µg/mm$^3$ and 0.5 µg/mm$^3$, or about 0.2 µg/mm$^3$.

In certain embodiments, the DLL-4 may be present at about 6 µg per scaffold.

Homing Factors

In certain embodiments, the composition of the present invention may further comprise a homing factor. As used herein, the term "homing factor" refers to an agent that is capable of inducing directed movement of a cell, e.g., a stem cell or a progenitor cell. In certain embodiments, the homing factors of the present invention are signaling proteins that can induce directed chemotaxis in nearby responsive cells. In various embodiments, the homing factors are cytokines and/or chemokines.

In certain embodiments, the inclusion of such homing factors in the compositions of the present invention promotes the homing of cells (e.g., transplanted stem cells and/or progenitor cells) to the scaffold composition administered to a subject. In certain aspects, such homing factors promote the infiltration of the cells (e.g., transplanted stem cells or progenitor cells) to the scaffold composition administered to the subject. In some embodiments, the homing factors comprise stromal cell derived factor (SDF-1). In certain embodiments, the homing factors are encapsulated in the material. In certain embodiments, the homing factors are released from the material over an extended period of time (e.g., about 7-30 days or longer, about 17-18 days).

In certain embodiments, the homing factors retain their bioactivity over an extended period of time. The bioactivity of the growth factor may be measured by any appropriate means. In certain example, the homing factors retain their bioactivity for at least 10 days, 12 days, 14 days, 20 days, or 30 days after the incorporation of the homing factors into the scaffold.

In some embodiments, the homing factors may be present at between about 0.01 nmol and 1000 nmol, about 0.1 nmol and 100 nmol, or about 1 nmol and 10 nmol per scaffold.

In some embodiments, the homing factors may be present at between about 1 ng and 1000 micrograms per scaffold. For example, the homing factor may be present at between about 10 ng and about 500 µg, between about 50 ng and about 250 µg, between about 100 ng and about 200 µg, between about 1 µg and about 100 µg, between about 1 µg and about 50 µg, between about 1 µg and about 25 µg, between about 1 µg and about 10 µg, between about 2 µg and about 10 µg, or about 6 µg.

In various embodiments, the amount of differentiation factor present in a scaffold may vary according to the size of the scaffold. For example, the differentiation factor may be present at about 0.03 ng/mm$^3$ (the ratio of the amount of differentiation factor in weight to the volume of the scaffold) to about 350 µg/mm$^3$, such as between about 0.1 ng/mm$^3$ and about 300 µg/mm$^3$, between about 1 ng/mm$^3$ and about 250 µg/mm$^3$, between about 10 ng/mm$^3$ and about 200

µg/mm$^3$, between about 0.1 µg/mm$^3$ and about 100 µg/mm$^3$, between about 0.1 µg/mm$^3$ and 50 about µg/mm$^3$, or between about 0.1 µg/mm$^3$ and about 20 µg/mm$^3$, between about 0.1 µg/mm$^3$ and about 10 µg/mm$^3$, between about 0.1 µg/mm$^3$ and about 5 µg/mm$^3$, between about 0.1 µg/mm$^3$ and about 1 µg/mm$^3$, between about 0.1 µg/mm$^3$ and 0.5 µg/mm$^3$, or about 0.2 µg/mm$^3$ Exemplary Scaffold Compositions The present invention provides scaffold composition for modulating the immune system in a subject. The compositions of the present invention include a porous scaffold, a growth factor present at an amount effective for inducing formation of a tissue or an organ with the scaffold and recruiting a cell into the scaffold, and a differentiation factor that induces the differentiation of the recruited cell into a T cell progenitor cell.

In one aspect, the present invention provides a composition for modulating the immune system in a subject, including a porous scaffold; a growth factor present at between about 1 ng to about 1000 µg per scaffold, and in an amount effective for inducing formation of a tissue or an organ within the scaffold and recruiting a cell into the scaffold; and a differentiation factor that induces the differentiation of the recruited cell into a lymphocyte T cell progenitor cell. For example, the growth factors may be present at an amount between about 1 ng and about 500 µg, between about 1 ng and about 200 µg, between about 1 ng and about 100 µg, between about 1 ng and about 50 µg, or between about 1 ng and 10 µg.

In another aspect, the present invention provides a composition for modulating the immune system in a subject, including a porous scaffold; a growth factor present at between about 1 ng to about 1000 ng per scaffold, and in an amount effective for inducing formation of a tissue or an organ within the scaffold and recruiting a cell into the scaffold; and a differentiation factor that induces the differentiation of the recruited cell into a lymphocyte T cell progenitor cell. In more particular embodiments, the growth factors are present at between about 5 ng to about 500 ng, between about 5 ng to about 250 ng, between about 5 ng to about 200 ng, or at about 200 ng.

In yet a further aspect, the present invention is directed to a composition for modulating the immune system in a subject, including a porous scaffold; a growth factor present at between about 0.03 ng/mm$^3$ to about 350 ng/mm$^3$ by volume of scaffold, and in an amount effective for inducing formation of a tissue or an organ within the scaffold and recruiting a cell into the scaffold; and a differentiation factor that induces the differentiation of the recruited cell into a T cell progenitor cell. In various embodiments, the growth factor may be present at about 0.1 ng/mm$^3$ and about 300 ng/mm$^3$, between about 0.5 ng/mm$^3$ and about 250 ng/mm$^3$, between about 1 ng/mm$^3$ and about 200 ng/mm$^3$, between about 2 ng/mm$^3$ and about 150 ng/mm$^3$, between about 3 ng/mm$^3$ and about 100 ng/mm$^3$, between about 4 ng/mm$^3$ and about 50 ng/mm$^3$, between about 5 ng/mm$^3$ and 25 ng/mm$^3$, between about 6 ng/mm$^3$ and about 10 ng/mm$^3$, or between about 6.5 ng/mm$^3$ and about 7.0 ng/mm$^3$.

The composition may be designed to release growth factors in a controlled manner. The reduced quantities of the growth factor and/or the controlled release offers advantages over the art, such as reduced toxicity associated with the use of high level of growth factors, e.g., BMP-2, and suboptimal release kinetics.

In various embodiments, the growth factors are a bone morphogenetic protein, such as BMP-2, BMP-4, BMP-7, BMP-12, BMP-14, or any combination thereof. In some embodiments, the growth factors are BMP-2. In certain embodiments, the growth factors are a TGF-β, such as TGF-β1, TGF-β2, TGF-β3, TGF-β4, or any combination thereof. In a particular embodiment, the growth factor includes TGF-β1.

The porous scaffolds of the compositions according to the present invention can be any biocompatible and biodegradable scaffolds. In certain embodiments, the porous scaffolds comprises a hydrogel or cryogel. In various embodiments, the hydrogel or cryogel comprises an alginate or an alginate derivative, a gelation or a gelatin derivative, or a hyaluronic acid or a hyaluronic acid derivative.

In certain embodiments, the differentiation factors of the present invention comprise a polypeptide that binds to a Notch receptor. In various embodiments, the differentiation factors are selected from the group consisting of a Delta-like 1 (DLL-1), a Delta-like 2 (DLL-2), a Delta-like 3 (DLL-3), a Delta-like 3 (DLL-3), a Delta-like 4 (DLL-4), a Jagged 1, a Jagged 2, and any combination thereof. In some embodiments, the differentiation factors comprise DLL-4. In certain embodiments, the differentiation factors are covalently linked to the porous scaffold.

In a particular embodiments, the compositions of the present invention comprise an injectable cryogel, which comprises an alginate or an alginate derivative, such as methacrylated alginate, or a hyaluronic acid or a hyaluronic acid derivative; a growth factor that is a bone morphogenetic protein, such as BMP-2; and a differentiation factor that is a Delta-like family protein, such as DLL-4. The growth factor may be present at about 200 ng per scaffold or between about 6.5 ng/mm$^3$ and 7.0 ng/mm$^3$.

III. Methods of Modulating Immune System

The present invention features methods of modulating the immune system of a subject. In certain embodiments of the present inventions, the methods of modulating the immune system of the subject comprise administering to the subject one or more compositions of the present invention. The composition may include a porous scaffold, a growth factor present in an amount effective for inducing formation of a tissue or an organ within the scaffold and recruiting a cell into the scaffold, and a differentiation factor that induces the differentiation of the recruited cell into a T cell progenitor cell. In a particular embodiment, the composition includes a porous scaffold; a growth factor present at between about 1 ng to about 1000 ng per scaffold and in an amount effective for inducing formation of a tissue or an organ within the scaffold and recruiting a cell into the scaffold; and a differentiation factor that induces the differentiation of the recruited cell into a lymphocyte.

In certain embodiments, the methods further comprise administering to the subject a hematopoietic stem cell or a hematopoietic progenitor cell.

In certain embodiments, the cells are stem cells or progenitor cells. As used herein, the term "stem cell" refers to a biological cell that can differentiate into other types of cells and can divide to produce more of the same type of stem cells. Stem cells include embryonic stem cells, which are isolated from the inner cell mass of blastocysts, and adult stem cells, which are found in various tissues. In adult organisms, stem cells and progenitor cells act as a repair system for the body, replenishing adult tissues. In certain embodiments, the stem cells are embryonic stem cells, fetal stem cells, amniotic stem cells, umbilical cord stem cells, adult stem cells, or induced pluripotent stem cells. In certain embodiments, the stem cells are hematopoietic stem cells.

Hematopoietic stem cells are the stem cells that give rise to other blood cells, including both myeloid and lymphoid lineage of blood cells.

As used herein, the term "progenitor cell" refers to a biological cell that can differentiate into a specific type of cell. Progenitor cells are generally more differentiated than stem cells. Typically, progenitor cells can only divide a limited number of times.

In certain embodiments, the progenitor cells are blast cells, such as thymocytes, lymphoblasts, myeloid, or bone marrow precursor cells. In certain embodiments, the progenitor cells are cells that are capable of differentiating into T cell progenitor cells. In certain embodiments, the lymphocytes include T cells, such as naïve T cells.

In certain embodiments, the recruited cells are hematopoietic bone marrow cells, or mobilized peripheral blood cells.

In certain embodiments, the cells may be recombinant cells. The term "recombinant cell," as used herein, refers to a cell into which a genetic modification has been introduced. The genetic modification may be at chromosomal level or extra-chromosomal. "Genetic modification at chromosomal level" refers to the genetic modification in the genome of the cell, e.g., insertion, deletion, and/or substitution on the chromosome of the cell. Extra-chromosomal genetic modification refers to the genetic modification not located in the genome of the cell. For example, a plasmid containing a protein encoding gene may be introduced to the cell. The plasmid may replicate and transmit from parental cells to offspring cells.

In various embodiments, the genetic modification introduces a gene into the cell. The introduced gene may compensate for the function of a defective gene of the cell. For example, the cell may contain a mutant defective gene. The genetic modification may introduce a wild type functional gene into the cell to restore the function of the gene. In some embodiment, the genetic modification may increase or decrease the expression of certain gene. For example, the genetic modification may introduce a small interfering RNA (siRNA) specific to a gene to inhibit the expression of the gene.

The methods to genetically modify a cell are commonly known in the art such as the methods described in Sambrook, J., Fritsch, E. F., and Maniatis, T., Molecular Cloning: A Laboratory Manual. Cold Spring Harbor Laboratory Press, NY, Vol. 1, 2, 3 (1989), herein incorporated by reference.

In certain embodiments, the genetic modification may be introduced through gene editing, also known as genome editing. Gene editing is a group of technologies that give skilled artisans the ability to change an organism's DNA. These technologies allow genetic material to be added, removed, or altered at particular locations in the genome. Gene editing technologies include, but are not limited to, meganucleases system, Zinc finger nucleases (ZFN) system, transcription activator-like effector nucleases (TALENs) system, and CRISPR-Cas system. CRISPR-Cas systems, which is short for clustered regularly interspaced short palindromic repeats and CRISPR-associated protein systems, in particular CRISP-Cas9, is faster, cheaper, more accurate, and more efficient than other existing genome editing methods.

In certain embodiments, the present invention features methods that modulate the immune system of a subject after the subject receives a transplantation. For example, the subject may receive a hematopoietic stem cell transplantation. In certain embodiments, the compositions of the present invention are administered to the subject concurrently with, or after, the hematopoietic stem cell transplantation.

In certain embodiments, at least two compositions are administered to the subject. The compositions can be of similar size.

In certain embodiments, the methods of the present invention modulate the immune response of a human over 30 years of age. For example, the human may be over 40, over 50, over 60, over 70, over 80 years of age.

In some embodiments, one or more compositions of the present invention (e.g., bone marrow cryogels) may be administered in conjunction with stem cell mobilization techniques. Stem cell mobilization is a process by which certain cell mobilization agents are used to cause the movement of stem cells from the bone marrow into the blood, such as described in Hopman and DiPersio, Advances in Stem Cell Mobilization, Blood Rev., 2014, 28(1): 31-40, the content of which is incorporated herein by reference. Such techniques may also be used for mobilization of progenitor cells.

Accordingly, in certain embodiments, a subject is administered a stem and/or progenitor cell mobilization agent in an amount effective to induce the movement of stem/progenitor cells from bone marrow into the blood. Released stem and/or progenitor cells are subsequently recruited to the composition of the present invention (e.g., a bone marrow cryogel) to differentiate into T cell progenitor cells. The stem and/or progenitor cell mobilization agent may be administered prior to, concurrently with, or following the administration of the composition (e.g., a bone marrow cryogel).

In various embodiments, the composition of the present invention (e.g., a bone marrow cryogel) may be administered to a subject in conjunction with a stem and/or progenitor cell mobilization agent. In particular embodiments, the subject is a human with advanced age, for example, the human may be over 30, 40, 50, 60, 70, or 80 years old. The stem and/or progenitor cell mobilization agent may mobilize the subject's own stem and/or progenitor cells out of the bone marrow so these cells can home to the composition of the present invention, thereby enhancing generation of T cells in the subject without involving other conditioning or stem cell transplant.

In certain embodiments, the composition of the present invention (e.g., a bone marrow cryogel) may be administered to a subject in conjunction with stem and/or progenitor cell mobilization techniques and stem cell transplantation. The transplantation may be autologous, allogeneic, or xenogeneic.

In some embodiments, a therapeutically-effective amount of one, or more cell mobilization agents that can stimulate mobilization into the peripheral bloodstream, production and/or improve function of one or more cell types is administered. The agent(s) could be given through any desired route of administration, including orally, rectally, intravenously, intramuscularly, subcutaneously, or an aerosol. Some non-limiting embodiments of an agent that can stimulate mobilization into the peripheral bloodstream, production of and/or improve function of a cell type include IL-1, IL-2, IL-3, IL-6, GM-CSF, G-CSF, plerixafor, PDGF, TGF-beta, NGF, IGFs, growth hormone, erythropoietin, thrombopoietin, and the like. In addition to naturally occurring growth factors, growth factor analogs and growth factor derivatives such as fusion proteins can be used as well. In some embodiments, the method involves administration of a therapeutically-effective amount of G-CSF and a therapeutically-effective amount of electromagnetic radiation. In some embodiments, the method comprises administering a combination of a therapeutically-effective amount of plerixafor and a therapeutically-effective amount of electromagnetic radiation. In some embodiments, a therapeutically-effective amount of electromagnetic radiation is combined with another agent that, in some embodiments, could be a hematopoietic stem cell mobilizer. In some embodiments, a therapeutically-effective amount of electromagnetic radiation is combined with combinations of two or more of G-CSF, GM-CSF, plerixafor, IL-1, IL-2, IL-3, IL-6, PDGF, TGF-beta, NGF, IGFs, growth hormone, erythropoietin, thrombopoietin or another agent.

Recruitment and Differentiation of Cells into T Cell Progenitor Cells

In one aspect, the present invention features methods for recruiting cells into a scaffold and inducing the differentiation of the recruited cells into T cell progenitor cells. Specifically, the methods include administering to the subject one or more compositions of the present invention including a porous scaffold, a growth factor present in an amount effective for inducing formation of a tissue or an organ within the scaffold and recruiting a cell into the scaffold, and a differentiation factor that induces the differentiation of the recruited cell into a lymphocyte. In a particular embodiment, the subject is administered a composition including a porous scaffold; a growth factor present at between about 1 ng and about 1000 ng per scaffold, e.g., between about 5 ng and about 500 ng, between about 5 ng and about 250 ng, between about 5 ng and about 200 ng or at about 200 ng, and in an amount effective for inducing formation of a tissue or an organ within the scaffold and recruiting a cell into the scaffold; and a differentiation factor that induces the differentiation of the recruited cell into a lymphocyte. In another particular embodiment, the subject is administered a composition including a porous scaffold; a growth factor present at between about 1 ng and about 1000 $\mu$g per scaffold, e.g., between about 1 ng and about 500 $\mu$g, between about 5 $\mu$g and about 250 $\mu$g, or between about 10 $\mu$g and about 100 $\mu$g, and in an amount effective for inducing formation of a tissue or an organ within the scaffold and recruiting a cell into the scaffold; and a differentiation factor that induces the differentiation of the recruited cell into a lymphocyte. In yet another embodiment, the subject is administered a composition including a porous scaffold; a growth factor present at about 0.03 ng/mm$^3$ (the ratio of the amount of growth factors in weight to the volume of the scaffold) to about 350 ng/mm$^3$, e.g., such as between about 0.1 ng/mm$^3$ and about 300 ng/mm$^3$, between about 0.5 ng/mm$^3$ and about 250 ng/mm$^3$, between about 1 ng/mm$^3$ and about 200 ng/mm$^3$, between about 2 ng/mm$^3$ and about 150 ng/mm$^3$, between about 3 ng/mm$^3$ and about 100 ng/mm$^3$, between about 4 ng/mm$^3$ and about 50 ng/mm$^3$ or between about 5 ng/mm$^3$ and 25 ng/mm$^3$, and in an amount effective for inducing formation of a tissue or an organ within the scaffold and recruiting a cell into the scaffold; and a differentiation factor that induces the differentiation of the recruited cell into a lymphocyte.

In certain embodiments, the growth factors and/or homing factors serve to recruit cells into the scaffold of the present invention. The differentiation factors and, optionally, the growth factors of the composition subsequently induce the differentiation of the cells into T cell progenitor cells.

In some embodiments, the methods further comprise administering to the subject a hematopoietic stem cell or a hematopoietic progenitor cell.

In certain embodiments, the growth factors (e.g., BMP-2) and/or the homing factors (e.g., SDF-1) recruit stem cells or progenitor cells that are capable of differentiating into T cell progenitor cells. The differentiation factors (e.g., DLL-4) induce the differentiation of the stem cells or the progenitor cells into T cell progenitor cells. In certain embodiments, the lymphocytes include naïve T cells. In certain embodiments, the lymphocytes include T cells such as CD4$^+$ T cells, CD8$^+$ T cells, and/or regulatory T cells (T$_{regs}$).

In certain embodiments, the recruited cells are transplanted cells. The transplanted cells (e.g., hematopoietic stem cells or progenitor cells) may be autologous. For example, the transplanted cells may be the subject's own umbilical cord stem cells or stem cells obtained from the subject before a treatment, such as radiation treatment. The transplanted cells may be syngeneic, such as hematopoietic stem cells or progenitor cells from an identical twin of the subject. The transplanted cells may also be allogeneic, such as hematopoietic stem cells or progenitor cells obtained from a donor of the same species. The transplanted cells may also be xenogeneic, such as hematopoietic stem cells or progenitor cells obtained from a different species.

In certain embodiments, the cells may be bone marrow stromal cells from the subject. Stromal cells refer to connective tissue cells of an organ, such as bone marrow. Stromal cells support the function of the parenchymal cells of that organ (e.g., bone marrow). Bone marrow stromal cells produces DLL-4, which provide a functional environment important for generating T-cell competent common lymphoid progenitor cells. The growth factors (e.g., BMP-2) may also facilitate the stromal cells' osteolineage differentiation.

In certain embodiments, the recruited cells may be cells that are not stem cells or progenitor cells.

Reduction of Immune Over-Reactivity

In one aspect, the present invention provides methods to reduce immune over-reactivity of the subject by administering to the subject one or more compositions of the present invention including a porous scaffold, a growth factor present in an amount effective for inducing formation of a tissue or an organ within the scaffold and recruiting a cell into the scaffold (for example, at between about 1 ng to about 1000 ng per scaffold, between about 5 ng to about 500 ng, between about 5 ng to about 250 ng, between about 5 ng to about 200 ng or at about 200 ng), and a differentiation factor that induces the differentiation of the recruited cell into a T cell progenitor cell.

In another aspect, the present invention provides methods to reduce immune over-reactivity of the subject by administering to the subject one or more compositions of the present invention including a porous scaffold; a growth factor present at between about 1 ng and about 1000 μg per scaffold, e.g., between about 1 ng and about 500 μg, between about 5 μg and about 250 μg, or between about 10 μg and about 100 μg, and in an amount effective for inducing formation of a tissue or an organ within the scaffold and recruiting a cell into the scaffold; and a differentiation factor that induces the differentiation of the recruited cell into a lymphocyte.

In another aspect, the present invention provides methods to reduce immune over-reactivity of the subject by administering to the subject one or more compositions of the present invention including a porous scaffold; a growth factor present at about 0.03 ng/mm$^3$ (the ratio of the amount of growth factors in weight to the volume of the scaffold) to about 350 ng/mm$^3$, e.g., such as between about 0.1 ng/mm$^3$ and about 300 ng/mm$^3$, between about 0.5 ng/mm$^3$ and about 250 ng/mm$^3$, between about 1 ng/mm$^3$ and about 200 ng/mm$^3$, between about 2 ng/mm$^3$ and about 150 ng/mm$^3$, between about 3 ng/mm$^3$ and about 100 ng/mm$^3$, between about 4 ng/mm$^3$ and about 50 ng/mm$^3$ or between about 5 ng/mm$^3$ and 25 ng/mm$^3$, and in an amount effective for inducing formation of a tissue or an organ within the scaffold and recruiting a cell into the scaffold; and a differentiation factor that induces the differentiation of the recruited cell into a lymphocyte.

In some embodiments, the methods further comprise administering to the subject a hematopoietic stem cell or a hematopoietic progenitor cell.

The immune system is a tightly regulated network that is able to maintain a balance of immune homeostasis under normal physiological conditions. Normally, when challenged with foreign antigen, specific appropriate responses are initiated that are aimed at restoring homeostasis. However, under particular circumstances, this balance is not maintained and immune responses either under or over react. When the immune response over-reacts, this can result in conditions such as autoimmune diseases, allergy, and/or GVHD.

In certain embodiments, the present invention features methods that increase the level of regulatory T cells (T$_{reg}$) in the subject. T$_{reg}$ cells, also known as suppressor T cells, are a subpopulation of T cells that modulate the immune system, maintain tolerance to self-antigens, and prevent and/or treat autoimmune disease. T$_{reg}$ cells are immunosuppressive and generally suppress or downregulate induction and proliferation of effector T cells. T$_{reg}$ cells express the biomarkers CD4, FOXP3, and CD25. Without wishing to be bound by any theory, the increased level of T$_{reg}$ cells by the methods of the present invention are believed to lead to the reduction of immune over-reactivity.

Autoimmune Diseases

In a particular aspect, the present invention provides methods to prevent and/or treat autoimmune disease by administering to the subject one or more compositions of the present invention including a porous scaffold, a growth factor present in an amount effective for inducing formation of a tissue or an organ within the scaffold and recruiting a cell into the scaffold (for example, at between about 1 ng to about 1000 ng per scaffold, between about 5 ng to about 500 ng, between about 5 ng to about 250 ng, between about 5 ng to about 200 ng or at about 200 ng), and a differentiation factor that induces the differentiation of the recruited cell into a T cell progenitor cell. As used herein, the term "autoimmune disease" refers to a disease, a disorder, or an illness in which the immune system of the subject attacks and/or damages its own tissues. Exemplary autoimmune diseases include, but are not limited to, type 1 diabetes, rheumatoid arthritis, psoriasis, arthritis, multiple sclerosis, systemic lupus erythermatosus, inflammatory bowel disease, Addison's disease, Graves' disease, Sjogren's syndrome, Hashimoto's thyroiditis, Myasthenia gravis, Vasculitis, Pernicious anemia, and Celiac disease.

In certain embodiments, the subject is deficient in T$_{reg}$ cells and develops autoimmune diseases. The subject may be administered a composition of the present invention and hematopoietic stem cells or progenitor cells. The hematopoietic stem cells or progenitor cells may be obtained from the subject. The compositions of the present invention may comprise a growth factor (e.g., TGF-β family protein) to induce the differentiation of the hematopoietic stem cells into T$_{reg}$ cells.

Allergy

In certain embodiments, the present invention features methods that prevent and/or treat allergy by administering to the subject one or more compositions of the present invention including a porous scaffold, a growth factor present in an amount effective for inducing formation of a tissue or an organ within the scaffold and recruiting a cell into the scaffold (for example, at between about 1 ng to about 1000 ng per scaffold, between about 5 ng to about 500 ng, between about 5 ng to about 250 ng, between about 5 ng to about 200 ng or at about 200 ng), and a differentiation factor that induces the differentiation of the recruited cell into a T cell progenitor cell.

Allergies, also known as allergic diseases, are a number of conditions caused by hypersensitivity of the immune system to typically harmless substances in the environment. Without wishing to be bound by any theory, the increased level of $T_{reg}$ cells by the methods of the present invention may prevent and/or treat allergies.

GVHD

In another aspect, the present method provides methods to mitigate graft-versus-host disease (GVHD) associated symptoms by administering to the subject one or more compositions of the present invention including a porous scaffold, a growth factor present in an amount effective for inducing formation of a tissue or an organ within the scaffold and recruiting a cell into the scaffold (for example, at between about 1 ng to about 1000 ng per scaffold, between about 5 ng to about 500 ng, between about 5 ng to about 250 ng, between about 5 ng to about 200 ng or at about 200 ng), and a differentiation factor that induces the differentiation of the recruited cell into a T cell progenitor cell. GVHD is a medical condition following the receipt of transplanted tissue from a genetically different donor. GVHD is commonly associated with stem cell transplantation such as hematopoietic stem cell transplantation. GVHD also occurs to other forms of transplanted tissues such as solid organ transplants.

In certain embodiments, the GVHD is associated with hematopoietic stem cell transplantation. In certain embodiments, the GVHD is associated with solid organ transplantation.

In certain embodiments, the present invention features methods that increase the level of $T_{reg}$ cells. In certain embodiments, the $T_{reg}$ cells are differentiated from the transplanted hematopoietic stem cells (e.g., donor hematopoietic stem cells). Without wishing to be bound by any theory, enhancement of the donor $T_{reg}$ cells in hematopoietic stem cell transplantation likely contributes to the mitigation of GVHD symptoms in the subject that receives hematopoietic stem cell transplantation given that the donor $T_{reg}$ cells play an important role in GVHD suppression. In certain embodiments, the present invention features methods that increase the level of autologous $T_{reg}$ cells of the subjects.

Enhancement of Donor Chimerism in Transplantation-Receiving Subject

In another aspect, the present invention provides methods to enhance donor chimerism in a subject that receives transplantation by administering to the subject one or more compositions of the present invention including a porous scaffold, a growth factor present in an amount effective for inducing formation of a tissue or an organ within the scaffold and recruiting a cell into the scaffold, and a differentiation factor that induces the differentiation of the recruited cell into a T cell progenitor cell. In a particular embodiment, the subject is administered a composition including a porous scaffold; a growth factor present at between about 1 ng to about 1000 ng per scaffold, e.g., between about 5 ng to about 500 ng, between about 5 ng to about 250 ng, between about 5 ng to about 200 ng or at about 200 ng, and in an amount effective for inducing formation of a tissue or an organ within the scaffold and recruiting a cell into the scaffold; and a differentiation factor that induces the differentiation of the recruited cell into a T cell progenitor cell. In another particular embodiment, the subject is administered a composition including a porous scaffold; a growth factor present at between about 1 ng and about 1000 μg per scaffold, e.g., between about 1 ng and about 500 μg, between about 5 μg and about 250 μg, or between about 10 μg and about 100 μg, and in an amount effective for inducing formation of a tissue or an organ within the scaffold and recruiting a cell into the scaffold; and a differentiation factor that induces the differentiation of the recruited cell into a lymphocyte. In yet another embodiment, the subject is administered a composition including a porous scaffold; a growth factor present at about 0.03 ng/mm³ (the ratio of the amount of growth factors in weight to the volume of the scaffold) to about 350 ng/mm³, e.g., such as between about 0.1 ng/mm³ and about 300 ng/mm³, between about 0.5 ng/mm³ and about 250 ng/mm³, between about 1 ng/mm³ and about 200 ng/mm³, between about 2 ng/mm³ and about 150 ng/mm³, between about 3 ng/mm³ and about 100 ng/mm³, between about 4 ng/mm³ and about 50 ng/mm³ or between about 5 ng/mm³ and 25 ng/mm³, and in an amount effective for inducing formation of a tissue or an organ within the scaffold and recruiting a cell into the scaffold; and a differentiation factor that induces the differentiation of the recruited cell into a lymphocyte.

In some embodiments, the methods further comprise administering to the subject a hematopoietic stem cell or a hematopoietic progenitor cell.

Donor chimerism usually occurs when the subject receives hematopoietic stem cell transplantation. The term "chimerism," as used herein, refers to the presence of lympho-hematopoietic cells of nonhost origin. Full or complete chimerism generally refers to complete replacement of host by donor lymphohematopoiesis. Mixed chimerism indicates the presence of both donor and recipient cells within a given cellular compartment, e.g., lymphocytes. Low level of donor chimerism is frequently associated with deficiency in T-cell generation in allogeneic hematopoietic stem cell or progenitor cell transplantation, which renders patients susceptible to infectious agents and may contribute to GVHD.

Balanced Reconstitution of T Cells

In another aspect, the present invention provides methods that lead to a balanced reconstitution of T cells in a subject by administering to the subject one or more compositions of the present invention including a porous scaffold, a growth factor present in an amount effective for inducing formation of a tissue or an organ within the scaffold and recruiting a cell into the scaffold, and a differentiation factor that induces the differentiation of the recruited cell into a T cell progenitor cell. In a particular embodiment, the subject is administered a composition including a porous scaffold; a growth factor present at between about 1 ng to about 1000 ng per scaffold, e.g., between about 5 ng to about 500 ng, between about 5 ng to about 250 ng, between about 5 ng to about 200 ng or at about 200 ng, and in an amount effective for inducing formation of a tissue or an organ within the scaffold and recruiting a cell into the scaffold; and a differentiation factor that induces the differentiation of the recruited cell into a T cell progenitor cell. In another particular embodiment, the subject is administered a composition including a porous scaffold; a growth factor present at between about 1 ng and about 1000 μg per scaffold, e.g., between about 1 ng and about 500 μg, between about 5 μg and about 250 μg, or between about 10 μg and about 100 μg, and in an amount effective for inducing formation of a tissue or an organ within the scaffold and recruiting a cell into the scaffold; and a differentiation factor that induces the differentiation of the recruited cell into a lymphocyte. In yet another embodiment, the subject is administered a composition including a porous scaffold; a growth factor present at about 0.03 ng/mm$^3$ (the ratio of the amount of growth factors in weight to the volume of the scaffold) to about 350 ng/mm$^3$, e.g., such as between about 0.1 ng/mm$^3$ and about 300 ng/mm$^3$, between about 0.5 ng/mm$^3$ and about 250 ng/mm$^3$, between about 1 ng/mm$^3$ and about 200 ng/mm$^3$, between about 2 ng/mm$^3$ and about 150 ng/mm$^3$, between about 3 ng/mm$^3$ and about 100 ng/mm$^3$, between about 4 ng/mm$^3$ and about 50 ng/mm$^3$ or between about 5 ng/mm$^3$ and 25 ng/mm$^3$, and in an amount effective for inducing formation of a tissue or an organ within the scaffold and recruiting a cell into the scaffold; and a differentiation factor that induces the differentiation of the recruited cell into a lymphocyte.

In some embodiments, the subject is further administered hematopoietic stem cells or progenitor cells. The composition of the present invention may be administered concurrently with or after the hematopoietic stem cells or progenitor cells administration.

The term "balanced reconstitution of T cells," as used herein, refers to the reconstitution of T cells that is characterized by CD4$^+$: CD8$^+$ ratio in a normal range within a certain period of time, such as 30 days. For example, the reconstitution of CD4$^+$ cells is usually delayed in a HSCT recipient. The methods of the present invention may accelerate the reconstitution of CD4$^+$ T cells and lead to a balanced reconstitution of T cells.

Hematopoietic stem cell transplantation (HSCT) is a curative treatment for multiple disorders, but allogeneic HSCT is limited by deficiency and dysregulation of T-cells. In a subject that receives allogeneic HSCT, CD4$^+$ T-cell recovery is usually delayed, leading to an inversion of the normal CD4/CD8 ratio, which is about 0.9 to about 2.5 in periphery blood. The ratio may be different in other tissue or organ.

In certain embodiments, the methods of the present invention stabilize the CD4$^+$: CD8$^+$ ratio to a normal range, while CD4$^+$ T-cell compartment in a subject receiving HSCT only has not fully reconstituted. In certain embodiments, a balanced T cell reconstitution is characterized by homeostatic CD4$^+$: CD8$^+$ ratio in a normal range in 30 days or less after the transplantation of the hematopoietic stem cells and the administration of the composition of the present invention.

In certain embodiments according to the present invention, a subject, such as a human, receives between about 1×10$^5$ and about 50×10$^6$ hematopoietic stem cells or progenitor cells per kilogram of the subject's weight in a hematopoietic stem cell transplantation. In certain embodiments, the subject receives about 1×10$^5$ hematopoietic stem cells per kilogram of the subject's weight.

The methods of the present invention result in similar or better curative and/or therapeutic effects when compared to a subject that receives hematopoietic stem cell or T-cell progenitor infusion alone (i.e., without receiving the treatment of the compositions of the present invention). For example, treatment with the compositions of the present invention may result in a higher number of T-cell progenitors and functional T-cells in the thymus and the periphery, for example, even when used with a lower dose relative to T-cell progenitor infusion alone. In some embodiments, similar or better curative and/or therapeutic effects can be achieved when less than ten percent (10%) of hematopoietic stem cells or progenitor cells used in a HSCT alone are administered to a subject in combination with the compositions of the present invention.

In various embodiments, the balanced reconstitution of T-cells is also characterized by enhanced T-cell neogenesis. The term "neogenesis," as used herein, refers to the generation of new cells. In various embodiments, the enhanced T-cell neogenesis is characterized by enhanced T-cell receptor excision circles (TRECs). In certain embodiments, T-cell neogenesis using the compositions and methods of the present invention achieves a baseline or normal number of TRECs. The term "baseline number of TRECs," as used herein, refers to the subject's TRECs number before the subject receives any treatment that impairs the subject's immune system. The term "normal number of TRECs," as used herein, refers to the number of TRECs of an individual with uncompromised immune system. The normal number of TRECs may be within certain range. In certain embodiments, TRECs may be assessed in a quantitative and non-invasive fashion in human by estimating TRECs in peripheral blood cells.

Antigen Specific T-Cell Responses

In another aspect, the present invention provides methods to induce antigen specific T-cell response in a subject by administering to the subject one or more compositions of the present invention including a porous scaffold, a growth factor present in an amount effective for inducing formation of a tissue or an organ within the scaffold and recruiting a cell into the scaffold, and a differentiation factor that induces the differentiation of the recruited cell into a T cell progenitor cell; and administering to the subject a vaccine comprising an antigen; thereby inducing antigen specific T cell responses in the subject. In a particular embodiment, the subject is administered a composition including a porous scaffold; a growth factor present at between about 1 ng to about 1000 ng per scaffold, e.g., between about 5 ng to about 500 ng, between about 5 ng to about 250 ng, between about 5 ng to about 200 ng or at about 200 ng, and in an amount effective for inducing formation of a tissue or an organ within the scaffold and recruiting a cell into the scaffold; and a differentiation factor that induces the differentiation of the recruited cell into a T cell progenitor cell. In another particular embodiment, the subject is administered a composition including a porous scaffold; a growth factor present at between about 1 ng and about 1000 μg per scaffold, e.g., between about 1 ng and about 500 μg, between about 5 μg and about 250 μg, or between about 10 μg and about 100 μg, and in an amount effective for inducing formation of a tissue or an organ within the scaffold and recruiting a cell into the scaffold; and a differentiation factor that induces the differentiation of the recruited cell into a lymphocyte. In yet another embodiment, the subject is administered a composition including a porous scaffold; a growth factor present at about 0.03 ng/mm$^3$ (the ratio of the amount of growth factors in weight to the volume of the scaffold) to about 350 ng/mm$^3$, e.g., such as between about 0.1 ng/mm$^3$ and about 300 ng/mm$^3$, between about 0.5 ng/mm$^3$ and about 250 ng/mm$^3$, between about 1 ng/mm$^3$ and about 200 ng/mm$^3$, between about 2 ng/mm$^3$ and about 150 ng/mm$^3$, between about 3 ng/mm$^3$ and about 100 ng/mm$^3$, between about 4 ng/mm$^3$ and about 50 ng/mm$^3$ or between about 5 ng/mm$^3$ and 25 ng/mm$^3$, and in an amount effective for inducing formation of a tissue or an organ within the scaffold and recruiting a cell into the scaffold; and a differentiation factor that induces the differentiation of the recruited cell into a lymphocyte.

In some embodiments, the methods further comprise administering to the subject a hematopoietic stem cell or a hematopoietic progenitor cell.

In certain embodiments, the subject has a compromised immune system. As used herein, the term "compromised immune system" refers to a state in which the immune system's ability to fight infectious disease and cancer is compromised or entirely absent. Many cases of compromised immune system are acquired ("secondary") due to extrinsic factors that affect the subject's immune system. Examples of these extrinsic factors include HIV infection, age, and environmental factors, such as nutrition. In certain embodiments, the immunosuppression by some drugs, such as steroids, can be either an adverse effect or the intended purpose of the treatment. Examples of such use include (i) in organ transplant surgery as an anti-rejection measure and (ii) in patients suffering from an overactive immune system, as in autoimmune diseases. In certain embodiments, some therapies for cancer, such as radiation therapy and/or chemotherapy, causes a compromised immune system. The condition that a subject has a compromised immune system may be referred as "immunodeficiency."

In certain embodiments, the subject has received a hematopoietic stem cell transplantation. In certain embodiments, the subject has cancer with blood or bone marrow, such as myeloma or leukemia. The subject may undergo a conditioning cytotoxic radiation and/or chemotherapy regimen to destroy the tumor cell, which results in severe lymphopenia due to the T- and B-cell destruction of the adaptive immune system.

In certain embodiments, the methods of inducing antigen-specific responses comprise administering to the subject a composition of the present invention and a vaccine comprising an antigen.

Modulation of Immune System in Immunocompromised Subject

In one aspect, the present invention provides methods to modulate the immune system in an immunocompromised subject by administering to the subject one or more compositions of the present invention including a porous scaffold, a growth factor present in an amount effective for inducing formation of a tissue or an organ within the scaffold and recruiting a cell into the scaffold (for example, at between about 1 ng to about 1000 ng per scaffold, between about 5 ng to about 500 ng, between about 5 ng to about 250 ng, between about 5 ng to about 200 ng or at about 200 ng), and a differentiation factor that induces the differentiation of the recruited cell into a T cell progenitor cell.

In another aspect, the present invention provides methods to modulate the immune system in an immunocompromised subject by administering to the subject one or more compositions including a porous scaffold; a growth factor present at between about 1 ng and about 1000 µg per scaffold, e.g., between about 1 ng and about 500 µg, between about 5 µg and about 250 µg, or between about 10 µg and about 100 µg, and in an amount effective for inducing formation of a tissue or an organ within the scaffold and recruiting a cell into the scaffold; and a differentiation factor that induces the differentiation of the recruited cell into a lymphocyte.

In yet another aspect, the present invention provides methods to modulate the immune system in an immunocompromised subject by administering to the subject one or more compositions including a porous scaffold; a growth factor present at about 0.03 ng/mm³ (the ratio of the amount of growth factors in weight to the volume of the scaffold) to about 350 ng/mm³, e.g., such as between about 0.1 ng/mm³ and about 300 ng/mm³, between about 0.5 ng/mm³ and about 250 ng/mm³, between about 1 ng/mm³ and about 200 ng/mm³, between about 2 ng/mm³ and about 150 ng/mm³, between about 3 ng/mm³ and about 100 ng/mm³, between about 4 ng/mm³ and about 50 ng/mm³ or between about 5 ng/mm³ and 25 ng/mm³, and in an amount effective for inducing formation of a tissue or an organ within the scaffold and recruiting a cell into the scaffold; and a differentiation factor that induces the differentiation of the recruited cell into a lymphocyte.

In some embodiments, the subject is further administered hematopoietic stem cells or progenitor cells.

In certain embodiments, the subject is further administered a stem and/or progenitor cell mobilization agent such that released stem and/or progenitor cells are recruited to the composition of the present invention (e.g., a bone marrow cryogel). The stem/progenitor cell mobilization agent may be administered prior to, concurrently with, or following the administration of the composition of the present invention (e.g., a bone marrow cryogel).

In some embodiments, the compromised immune system is caused by immunosenescence. The term "immunosenescence," as used herein, refers to the deterioration of the immune system brought on by natural age advancement. It involves both the host's capacity to respond to infections and the development of long-term immune memory, especially by vaccination Immunosenescence is a multifactorial condition leading to many pathologically significant health problems in the aged population Immunosenescence is associated with hematopoietic stem cells reduced self-renewal capacity. A subject with immunosenescence may show reduction in the CD4+/CD8+ ratio, shrinkage of antigen-recognition repertoire of T-cell receptor (TCR) diversity, and/or impaired proliferation in response to antigenic stimulation. Immunosenescence may commence even in early age, such as 30 years old in human.

In some embodiments, the subject has a compromised immune system due to a congenital immunodeficiency. As used herein, "congenital immunodeficiency," also known as "primary immunodeficiency," refers to a deficiency, absence, or defect in one or more of the main components of the immune system. These disorders are genetically determined and typically manifest during infancy and childhood as frequent, chronic, or opportunistic infections. Classification is based on the main component of the immune system that is deficient, absent, or defective. The diagnosis is confirmed with tests such as differential WBC count, absolute lymphocyte count, quantitative immunoglobulin (Ig) measurements, and antibody titers. Treatment usually consists of prophylactic antibiotics to manage and prevent infections. The prognosis in primary immunodeficiency disorders is variable and depends on the specific disorder.

Exemplary congenital immunodeficiency disorders include, but are not limited to, congenital B-cell immunodeficiencies, such as Bruton agammaglobulinemia, selective IgA deficiency, common variable immunodeficiency, congenital T-cell immunodeficiencies, such as DiGeorge syndrome, autosomal dominant hyperimmunoglobulin E syndrome, IL-12 receptor deficiency, chronic mucocutaneous candidiasis, IPEX syndrome (Immune dysregulation, polyendocrinopathy, enteropathy, X-linked), congenital mixed immunodeficiencies, such as severe combined immunodeficiency (SCID, Bubble boy disease, Glanzmann-Riniker syndrome, Alymphocytosis), Wiskott-Aldrich syndrome, Hyper-IgM syndrome, Ataxia telangiectasia, congenital neutrophil and phagocyte disorders, such as chronic granulomatous disease (CGD), leukocyte adhesion deficiency type 1, Chediak-Higashi syndrome, myeloperoxidase deficiency, severe congenital neutropenia, congenital complement deficiencies, such as terminal complement deficiency, C3 deficiency.

In certain embodiments, the subject has a compromised immune system due to an acquired immunodeficiency. As used herein, the term "acquired immunodeficiency" refers to immunodeficiency due to extrinsic factors that affect the subject's immune system. Acquired immunodeficiencies, also known as secondary immunodeficiencies, can result from various immunosuppressive agents, for example, malnutrition, aging, particular medications or treatment (e.g., chemotherapy (cytotoxic drug), disease-modifying anti-rheumatic drugs, immunosuppressive drugs after organ transplants, glucocorticoids, radiation therapy) and environmental toxins like mercury and other heavy metals, pesticides and petrochemicals like styrene, dichlorobenzene, xylene, and ethylphenol. For medications, the term "immunosuppression" generally refers to both beneficial and potential adverse effects of decreasing the function of the immune system, while the term "immunodeficiency" generally refers solely to the adverse effect of increased risk for infection.

Many specific diseases directly or indirectly cause immunosuppression. This includes many types of cancer, particularly those of the bone marrow and blood cells (leukemia, lymphoma, multiple myeloma), and certain chronic infections Immunodeficiency is also the hallmark of acquired immunodeficiency syndrome (AIDS), caused by the human immunodeficiency virus (HIV). HIV directly infects a small number of T helper cells, and also impairs other immune system responses indirectly. Various hormonal and metabolic disorders can also result in immune deficiency including, but not limited to, anemia, hypothyroidism, diabetes and hypoglycemia. Smoking, alcoholism and drug abuse also depress immune response.

Without wishing to be bound by any theory, the balanced reconstitution of T cells and antigen specific T-cell response provided by the compositions and methods of the present invention may modulate the immune system of a subject with compromised immune system.

IV. Kits

Any of the compositions described herein may be included in a kit. In a non-limiting example, the kit includes a composition comprising a porous scaffold, a growth factor present in an amount effective for inducing formation of a tissue or an organ within the scaffold and recruiting a cell into the scaffold; and differentiation factor that induces the differentiation of the recruited cell into a T cell progenitor cell. In a particular embodiment, the kit includes a composition including a porous scaffold; a growth factor present at between about 1 ng to about 1000 ng per scaffold, e.g., between about 5 ng to about 500 ng, between about 5 ng to about 250 ng, between about 5 ng to about 200 ng or at about 200 ng, and in an amount effective for inducing formation of a tissue or an organ within the scaffold and recruiting a cell into the scaffold; and a differentiation factor that induces the differentiation of the recruited cell into a T cell progenitor cell. In another particular embodiment, the kit includes a composition including a porous scaffold; a growth factor present at between about 1 ng and about 1000 µg per scaffold, e.g., between about 1 ng and about 500 µg, between about 5 µg and about 250 µg, or between about 10 µg and about 100 µg, and in an amount effective for inducing formation of a tissue or an organ within the scaffold and recruiting a cell into the scaffold; and a differentiation factor that induces the differentiation of the recruited cell into a lymphocyte. In yet another embodiment, the kit includes a composition including a porous scaffold; a growth factor present at about 0.03 $ng/mm^3$ (the ratio of the amount of growth factors in weight to the volume of the scaffold) to about 350 $ng/mm^3$, e.g., such as between about 0.1 $ng/mm^3$ and about 300 $ng/mm^3$, between about 0.5 $ng/mm^3$ and about 250 $ng/mm^3$, between about 1 $ng/mm^3$ and about 200 $ng/mm^3$, between about 2 $ng/mm^3$ and about 150 $ng/mm^3$, between about 3 $ng/mm^3$ and about 100 $ng/mm^3$, between about 4 $ng/mm^3$ and about 50 $ng/mm^3$ or between about 5 $ng/mm^3$ and 25 $ng/mm^3$, and in an amount effective for inducing formation of a tissue or an organ within the scaffold and recruiting a cell into the scaffold; and a differentiation factor that induces the differentiation of the recruited cell into a lymphocyte.

In some embodiments, the kit includes the composition described elsewhere herein.

In a particular embodiment, the kit comprises a syringe or alternative injection device for administering the composition. In a specific embodiment, the prefilled syringe or injection device is prefilled with the composition.

The kit may further include reagents or instructions for administering the composition of the present invention to a subject. It may also include one or more reagents.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. The kits may also comprise a second container means for containing a sterile, pharmaceutically acceptable buffer and/or other diluent. However, various combinations of components may be comprised in a vial. The kits of the present invention also will typically include a means for containing the compositions of the invention, e.g., the compositions for modulating immune system, and any other reagent containers in close confinement for commercial sale.

When the components of the kit are provided in one and/or more liquid solutions, the liquid solution is an aqueous solution, with a sterile aqueous solution being particularly preferred. However, the components of the kit may be provided as dried powder(s). When reagents and/or components are provided as a dry powder, the powder can be reconstituted by the addition of a suitable solvent. It is envisioned that the solvent may also be provided in another container means.

The present invention is further illustrated by the following examples, which should not be construed as limiting. All cited sources, for example, references, publications, databases, database entries, and art cited herein, are incorporated into this application by reference, even if not expressly stated in the citation. In case of conflicting statements of a cited source and the instant application, the statement in the instant application shall control.

Section and table headings are not intended to be limiting.

EXAMPLES

Abstract
Allogeneic hematopoietic stem cell transplantation (HSCT) is a curative treatment for multiple disorders, but deficiency and dysregulation of T cells limit its utility. Here it is reported a biomaterial based scaffold that mimics features of T-cell lymphopoiesis in the bone marrow. The bone marrow cryogel (BMC) releases bone morphogenetic protein-2 to recruit stromal cells, and presents the Notch ligand Delta-like ligand-4 to facilitate T-cell lineage specification of mouse and human hematopoietic progenitor cells. BMCs subcutaneously injected in mice at the time of HSCT enhanced T-cell progenitor seeding of the thymus, T-cell neogenesis and diversification of the T-cell receptor repertoire. Peripheral T-cell reconstitution increased ~6-fold in mouse HSCT and ~2-fold in human xenogeneic HSCT. Furthermore, BMCs promoted donor CD4+ regulatory T-cell generation and improved survival after allogeneic HSCT. Compared with adoptive transfer of T-cell progenitors, BMCs increased donor chimerism, T cell generation and antigen-specific T-cell responses to vaccination. BMCs may provide an off the-shelf approach for enhancing T-cell regeneration and mitigating graft-versus-host disease in HSCT.

Introduction

T-cells are important helper, effector and regulatory cells of antigen-specific immunity that are important for life. Reduced T-cell numbers and functional deficiencies are causally implicated in diseases ranging from congenital immunodeficiency to autoimmune and impaired immune surveillance disorders (Goronzy, J. J. & Weyand, C. M. Successful and maladaptive T cell aging. *Immunity* 46, 364-378 (2017); Liston, A., Enders, A. & Siggs, O. M. Unravelling the association of partial T-cell 883 immunodeficiency and immune dysregulation. *Nature Reviews Immunology* 8, 545-558 884 (2008)). In allogeneic HSCT, there is a marked deficiency in T-cell generation, which renders patients susceptible to infectious agents and may contribute to graft-versus-host disease (GVHD) (Blazar, B. R., Murphy, W. J. & Abedi, M. Advances in graft-versus-host disease biology and therapy. *Nature Reviews Immunology* 12, 443-458 (2012)). These complications can be fatal and limit the use of HSCT in settings where it can be curative. Balanced reconstitution of the naïve helper and effector T-cell subsets, along with the restoration of the T-cell receptor repertoire remains a significant unmet clinical need (Krenger, W., Blazar, B. R. & Hollander, G. A. Thymic T-cell development in allogeneic stem cell transplantation. *Blood* 117, 6768-6776 (2011)).

New T-cell regeneration from transplanted hematopoietic cells requires the availability of an adequate pool of T-cell progenitors (Zlotoff, D. A. et al. Delivery of progenitors to the thymus limits T-lineage reconstitution after bone marrow transplantation. *Blood* 118, 1962-1970 (2011)) arising from bone marrow and adequate thymic function (Chaudhry, M. S., Velardi, E., Dudakov, J. A. & Brink, M. R. Thymus: the next (re) generation. *Immunological reviews* 271, 56-71 (2016)). While there is currently no clinical standard for enhancing T-cell generation in vivo, most efforts have focused on using cytokines and cell-based therapies from the post-bone marrow phases of T-cell lymphopoiesis. However, in clinical trials, T-cell expansion cytokines IL-7 and IL-2 (Mohtashami, M., Shukla, S., Zandstra, P. & Zúñiga-Pflücker, J. C. in Synthetic Immunology 95-120 (Springer, 2016)) increased primarily mature T-cell subsets (Perales, M.-A. et al. Recombinant human interleukin-7 (CYT107) promotes T-cell recovery after allogeneic stem cell transplantation. *Blood* 120, 4882-4891 (2012)), and IL-2 was further limited by toxicity (Skrombolas, D. & Frelinger, J. G. Challenges and developing solutions for increasing the benefits of IL-2 treatment in tumor therapy. *Expert review of clinical immunology* 10, 207-217 (2014)). In contrast, the administration of IL-22 has been shown to enhance early thymocyte recovery in preclinical mouse studies (Dudakov, J. A. et al. Interleukin-22 drives endogenous thymic regeneration in mice. *Science* 336, 91-95 (2012). Alternatively, adoptive donor T-cell infusion has been used to provide antigen-specific T cell protection against commonly encountered pathogens (Cobbold, M. et al. Adoptive transfer of cytomegalovirus-specific CTL to stem cell transplant patients after selection by HLA-peptide tetramers. *Journal of Experimental Medicine* 202, 379-386 (2005); Rooney, C. M. et al. Infusion of cytotoxic T cells for the prevention and treatment of Epstein-Ban virus-induced lymphoma in allogeneic transplant recipients. *Blood* 92, 1549-1555 (1998)), but has been associated with a transient response, increased risk of GVHD, and T-cell exhaustion. The above strategies are all limited by the availability of an adequate pool of T-cell progenitors to promote thymus-dependent T-cell generation. T-cell precursors can be robustly generated ex-vivo by the activation of Notch signaling, and co-administration of these cells with HSCT improves thymopoiesis and thymic architecture without exogenously co-administered cytokines (Zakrzewski, J. L. et al. Tumor immunotherapy across MHC barriers using allogeneic T-cell precursors. *Nature biotechnology* 26, 453 (2008); Van Coppernolle, S. et al. Functionally mature CD4 and CD8 TCRαβ cells are generated in OP9-DL1 cultures from human CD34+ hematopoietic cells. *The Journal of Immunology* 183, 4859-4870 (2009); Awong, G. et al. Human proT-cells generated in vitro facilitate hematopoietic stem cell-derived T-lymphopoiesis in vivo and restore thymic architecture. *Blood* 122, 4210-4219 (2013)). However, ex-vivo cell culture to generate sufficient progenitors is laborious and only a transient enhancement in thymopoiesis of donor cells has been demonstrated. Thus, the widespread clinical translation of this approach would likely be complex.

Seeking to develop a broadly applicable technology, the focus was placed on the pre-thymic bone marrow resident common lymphoid progenitors (CLPs), which have the capacity to differentiate into naïve T-lymphocytes when Notch signaling is activated, and are a major source of thymopoiesis (Love, P. E. & Bhandoola, A. Signal integration and crosstalk during thymocyte migration and emigration. *Nature Reviews Immunology* 11, 469 (2011); Radtke, F., MacDonald, H. R. & Tacchini-Cottier, F. Regulation of innate and adaptive immunity by Notch. *Nature Reviews Immunology* 13, 427 (2013); Serwold, T., Ehrlich, L. I. R. & Weissman, I L Reductive isolation from bone marrow and blood implicates common lymphoid progenitors as the major source of thymopoiesis. *Blood* 113, 807-815 (2009)). The stromal component of the bone marrow niche that enhances T-cell lineage specification consists of osteocalcin-expressing bone marrow stromal cells producing delta-like ligand-4 (DLL-4), which provide a functional microenvironment critical for generating T-cell competent CLPs (Vionnie, W. et al. Specific bone cells produce DLL4 to generate thymus-seeding progenitors from bone marrow. *Journal of Experimental Medicine*, jem. 20141843 (2015)). These stromal cells are damaged by the process of preconditioning which likely impacts their T-cell lineage-instructive function. Additionally, the clinical experience with AIDS patients indicates that the adult thymus has the capacity to markedly improve in cellular composition and T-cell neogenesis despite prior dysfunction and atrophy (Smith, K. Y. et al. Thymic size and lymphocyte restoration in patients with human immunodeficiency virus infection after 48 weeks of zidovudine, lamivudine, and ritonavir therapy. *The Journal of infectious diseases* 181, 141-147 (2000). These prior findings supported the development of a niche based on specific biologic aspects of T-cell lymphopoiesis in the bone marrow.

It is hypothesized that a T-cell lymphopoietic bone marrow niche might be engineered to foster production of T-cell progenitors in vivo that emigrate into the native thymus and thereby undergo host driven selection to create a more balanced and broad immune repertoire. To test this hypothesis, an injectable, biomaterial-based cryogel (BMC) scaffold was created. The BMC scaffold promotes T-cell development in vivo by integrating molecular signals that are presented in the bone marrow niche. The BMC comprises a macroporous hydrogel-based scaffold permitting cellular infiltration. It releases bone morphogenetic protein-2 (BMP-2) to facilitate the recruitment of host stromal cells and their osteolineage differentiation and presents bioactive Notch ligand DLL-4 at predefined densities to infiltrating hematopoietic cells. These T-lineage cues enhanced thymic seeding of progenitors and enabled donor T-cell reconstitution after syngeneic (syn) and allogeneic (allo) HSCT in mice. The BMC-reconstituted T-cells were functional, with a diverse T-cell receptor (TCR) repertoire, and reduced induction of GVHD.

Example 1: Bioactive Macroporous Bone Marrow Cryogels (BMCs) Differentiate Hematopoietic Progenitors into Progenitor T-Cells In Vitro The scaffold-based Alginate-PEG BMC is a macroporous hydrogel with interconnected pores 50-80 μm in diameter (FIGS. 1A-1C). DLL-4 was incorporated into the polymer backbone to promote the T-cell lineage program in hematopoietic progenitor cells (Radtke, F., MacDonald, H. R. & Tacchini-Cottier, F. Regulation of innate and adaptive immunity by Notch. *Nature Reviews Immunology* 13, 427 (2013)). To enable de novo bone formation (Wozney, J. M. et al. Novel regulators of bone formation: molecular clones and activities. *Science* 242, 1528-1534 (1988)), BMP-2 was added to the reaction mixture prior to cryo-polymerization for subsequent release in soluble form in vivo. These cryogels present both immobilized (DLL-4) and soluble (BMP-2) cues, unlike previous cryogels which were solely designed for controlled release of proteins (Koshy, S. T., Zhang, D. K., Grolman, J. M., Stafford, A. G. & Mooney, D. J. Injectable nanocomposite cryogels for versatile protein drug delivery. *Acta biomaterialia* 65, 36-43 (2018)).

In this work, the BMCs additionally support the growth of bone and hematopoietic tissue. In vitro BMP-2 release (encapsulation efficiency 90%) displayed an initial burst of about 5% of the loaded amount, and then released in a sustained manner (FIG. 1D). Less than 1% of the total loaded DLL4 was detected in the supernatant, and modified DLL-4 had similar binding kinetics to that of the unmodified protein (FIG. 1E). In the pooled release samples, over 90% of the bioactivity of the released BMP-2, relative to freshly reconstituted BMP-2 was retained (FIG. 1F). The bioactivity of BMP-2 ranged from 95% at Day 3 of release to ~85% at Day 12, confirming the released BMP-2 is highly active (FIG. 1G). The highest in vitro bioactivity of DLL-4 was found at the early time points, at Days 0 and 10 (FIGS. 1H and 1I). The bioactivity decreased at subsequent time points but was still above baseline after 3 months. To measure the capacity of the BMC to induce the differentiation of hematopoietic progenitor mouse and human cells via Notch signaling, primary lineage depleted bone marrow cells from mice and cord-blood derived human CD34+ hematopoietic cells were cultured in the BMC (FIG. 1J).

The expansion of the common lymphoid progenitors saturated at 1% functionalization of the MA-COOH groups on the polymer backbone with MA-DLL4, corresponding to approximately 6 μg MA-DLL4 per gel and this condition was selected for further evaluation. There were no significant differences in the fold expansion and viability numbers of overall human or mouse cells in any of the experimental conditions analyzed (FIGS. 1K and 1L). However, the fraction of lymphoid progenitor cells was enhanced only when DLL-4 was incorporated in the BMC, alone or in combination with BMP-2 (FIG. 1M).

Example 2: BMC Form a Bone Nodule with Features of Hematopoietic Tissue In Vivo

The BMC was next analyzed for its ability to induce the trafficking of host and transplanted cells in a mouse model of HSCT. After lethal total body irradiation (L-TBI) mice were transplanted intravenously with lineage-depleted hematopoietic cells ($5\times10^4$; ~93% lineage depleted, FIG. 2A) isolated from donor mice bone marrow, and the BMCs (without cells) were simultaneously injected in the subcutaneous tissue of the dorsal flank (FIG. 2B). To grossly quantify cell infiltration in the BMCs, the size of each subcutaneous nodule was measured over a period of 6 weeks (FIG. 2C). In the BMC with BMP-2, the nodule size rapidly increased to approximately 3 times over the initial volume by 10 day following transplantation and was substantially infiltrated with donor hematopoietic cells (FIG. 2D), and formed a local bone nodule over a period of approximately 2 weeks, (FIGS. 2E and 2F). Notably, bone formation was accompanied by vascularization, the DLL-4 remained accessible, and bone was restricted to the BMC scaffold, demonstrating the control afforded by the BMC over this process at an ectopic site (FIGS. 2G-2L).

Hematopoietic tissue was visible in the bone nodule on the interior surface of the BMC around areas of lamellar bone (FIG. 2F). A capillary network infiltrating the BMC was noted as early as 2 days post-transplant (FIG. 2G) and quantified starting at Day 10. Histomorphometry was used to assess blood vessel density in the BMC at multiple time intervals, up to 3-months post transplant (FIG. 2F). Blood vessels were present at approximately 25 vessels/mm² by Day 10 (FIG. 2I). The density of vessels increased to 70 vessels/mm² and was constant after Day 30. In order to quantify the distribution and accessibility of the alginate/DLL-4 in the BMC, a histomorphometric analysis using Safranin-O staining was performed. Approximately 85% of the alginate was accessible at the earliest time point Day 10, and this gradually decreased to 25% by Day 90 (FIGS. 2I-2K). The alginate was not sequestered in any particular region within the BMC at any time point.

Example 3: BMCs Recruit and Expand Host Stromal and Transplanted Hematopoietic Cells The infiltration and cell composition of the transplanted hematopoietic cells in the BMC at various time points post-transplant were assessed. The donor GFP⁺ cells expanded when BMP-2 was included but not in the presence of DLL-4 alone (FIGS. 3A and 3B). The stromal cells populating the BMCs and the native bone marrow were found to be similar, there was no difference in the engraftment of hematopoietic cells in native bone marrow of BMC treated and non-treated mice, and SDF-1α and interleukin-7 concentrations were similar in the BMCs and native bone marrow (FIGS. 3C-3G).

Stromal cells populating the BMC were identified using immunophenotypic markers typically associated with mouse mesenchymal stromal cells (Sca-1, CD29, CD44, CD73, CD105, CD106), and compared to the bone marrow of transplanted 469 mice (FIG. 3C). The Sca-1+ stromal subset was modestly elevated in the BMC relative to the bone marrow, but the overall repopulation kinetics of these stromal subsets were similar in the two tissues. In the BMP-2 containing BMCs, bone alkaline phosphatase (BAP) was comparable to native bone (FIG. 3D). Oil Red O (ORO) was used to quantify adipose tissue and was found to be lower in the BMCs relative to native bone overall. Higher ORO was quantified in BMP-2 containing BMCs relative to BMCs without BMP-2 (FIG. 3D). To measure if the BMC impacted engraftment of transplanted, cells in the endogenous bone marrow, colony formation assays were conducted at 3 time points (FIG. 3E). No differences in the total number or type of CFUs arising from cells from the bone marrow of mice treated with or without the dual BMC were noted. The concentrations of homing factor stromal cell-derived factor-1 alpha (SDF-1a) and lymphoid progenitor supporting cytokine interleukin-7 (IL-7) ((Brainard, D. M. et al. Induction of robust cellular and humoral virus-specific adaptive immune responses in human immunodeficiency virus-infected humanized BLT mice. *Journal of virology* 83, 7305-7321 (2009)) in harvested BMCs were also either comparable to or higher than in irradiated bone marrow from the same mice (FIG. 2F). No ETP, DN2 and DN3-like cells were detected in the BMC.

At the later time points (>5 days post transplant), more primitive donor hematopoietic cells (HSCs) and lymphoid-primed multipotential progenitors (LMPPs) were quantified in the BMC. At Day 14, between 6 and 7 million total GFP+ cells were quantified in the BMCs containing single factor BMP-2 or dual factor BMP-2 and DLL-4. Over 80% of cells were CD11b+ myeloid cells in both groups. However, the CLP fraction in the transplanted donor cells expanded only within dual factor BMCs, resulting in a ~100-fold increase relative to BMCs with only BMP-2 at 2-weeks post-transplant (FIG. 3A). At 6-weeks post-transplant CLPs were ~10-fold higher in the dual factor BMCs, of which approximately 30% and 70% respectively were in the T-cell competent Ly6D− subset (FIG. 3G).

Progenitor T-cells from the bone marrow migrate to the thymus to differentiate into naïve T cells. To directly assess whether cells from the BMC migrate to the thymus, the dual factor BMC in concert with stem cell therapy was delivered into an initial set of lethally irradiated mice (FIGS. 3H and 3I). The dual BMC was then explanted from these mice at day 10, and surgically transplanted into sublethally irradiated recipients subcutaneously in the dorsal flank. On day 20 post-BMC transplantation, the donor GFP+ and host cells in the thymus of these mice were quantified. GFP+ DP, SP CD4+ and SP CD8+ cells were quantified in the thymus of BMC transplanted recipient mice confirming migration of T-cell progenitor cells from the BMC to the thymus. In a separate study, Dual BMC treatment resulted in a greater enhancement of the number of ETPs in the thymus when compared to a 10-fold increase in the administered transplant cell dose without BMC (FIG. 3J). The Dual BMC also significantly outperformed bolus delivery of the factors placed in the BMC, and the BMP-2 only BMC, in generating thymocyte subsets over time (FIGS. 3K-3P).

To analyze the impact of cell dose on the seeding of T-cell progenitors in the thymus, the early thymic progenitor (ETP) subset was quantified at escalating doses of lineage-depleted cells for transplant after L-TBI ($5\times10^4$-$5\times10^5$ cells). Dose-dependent enhancement of ETPs was found in this dose range (FIGS. 3A and 3H). When dual functionalized BMCs with the lowest cell dose ($5\times10^4$ cells) were administered, there was a 5-fold increase in ETPs in the thymus relative to the transplant only group with the highest cell dose. The dual BMC-treatment initially enhanced ETPs (3-fold at Day 12 and Day 42), and at subsequent time points there was an increase in DN2, DN3, DP and SP thymocyte subsets (FIGS. 3I-3N and FIG. 5Q). The thymus cellularity and weight of mice from the dual-BMC treatment was significantly higher than that of mice from the transplant-only group between days 12-42. At 22 days post-HSCT, there were no significant differences in number of thymic stromal subsets (mTEC, cTEC, fibroblasts and endothelial cells; FIGS. 3S and 3T).

Example 4. BMCs Enhance T-Cell Regeneration after HSCT and Mitigate GVHD

In the peripheral blood of mice treated with the dual functionalized BMC, acceleration in T-cell reconstitution was observed approximately 4 weeks post-transplant, but no significant difference was observed in B-cell or myeloid cell reconstitution (FIGS. 4A-4C). An analysis of T-cell subsets in the blood, spleen and bone marrow indicated that the homeostatic CD4+:CD8+ T-cell ratio was restored in mice with the dual functionalized BMCs after 30 days post-transplant in the spleen and bone marrow, and 40 days post-transplant in the peripheral blood (FIGS. 4D-4F). When the BMC treatment was used in the context of HSCT after sublethal total body irradiation (SL-TBI), there was enhanced T-cell reconstitution (FIGS. 4G-4N). At 28 days-post transplant the donor chimerism and absolute number of DP donor thymocytes were 1.5-fold and 2-fold higher respectively in BMC treated mice relative to mice that received just the transplant (FIG. 4G). There was also a higher donor chimerism and absolute number of donor-derived single-positive CD4+ (by 2-fold and 3-fold respectively) and single-positive CD8+ (by 1.7-fold and 15-fold respectively) thymocytes, in BMC treated mice than in mice that received just the transplant (FIGS. 4H and 4I). In the periphery, the donor chimerism was higher in the CD4+ (by 3.5-fold) and CD8+ (by 2.5-fold) T cells. No difference was observed in the chimerism or absolute number of B-cells.

The rate of human T-cell reconstitution was next measured using an established xenogeneic NSG-BLT mouse model (Brainard, D. M. et al. Induction of robust cellular and humoral virus-specific adaptive immune responses in human immunodeficiency virus-infected humanized BLT mice. *Journal of virology* 83, 7305-7321 (2009)). In BMC-treated NSG-BLT mice, there was an early enhancement in the initial rate of T-cell reconstitution, and a modest, transient reduction in the rate of B-cell reconstitution (FIGS. 5A and 5B), with transiently fewer pre-B cell CFUs in the bone marrow of BMC treated NSG-BLT mice (FIG. 5C). The peripheral CD4+:CD8+ T-cell ratio was stabilized in BMC-treated mice between 50 and 60 days post-transplant, whereas the CD4+ compartment in control NSG-BLT was not fully reconstituted (FIG. 5D). Strikingly, the enhanced rate of T-cell reconstitution did not accelerate the rate of GVHD-related death. Instead, NSG-BLT mice that received the dual functionalized BMC survived longer than the NSG-BLT mice (FIG. 5F). In BMC-treated NSG-BLT mice, CD4+FoxP3+ regulatory T-cells ($T_{reg}$) were 2-fold higher in the thymus and spleen of BMC-treated mice at 50 days post-transplant in this model (FIGS. 5G and 5H). A similar enhancement in survival was observed in an allogeneic MHC-mismatch HSCT mouse model that received the BMC (FIG. 5I), and donor derived CD4+FoxP3+ $T_{reg}$ were 5-fold and 4-fold higher in the thymus and spleen, respectively, of BMC-treated mice 15 days post-transplant in this model (FIG. 5J).

Figure 5L:
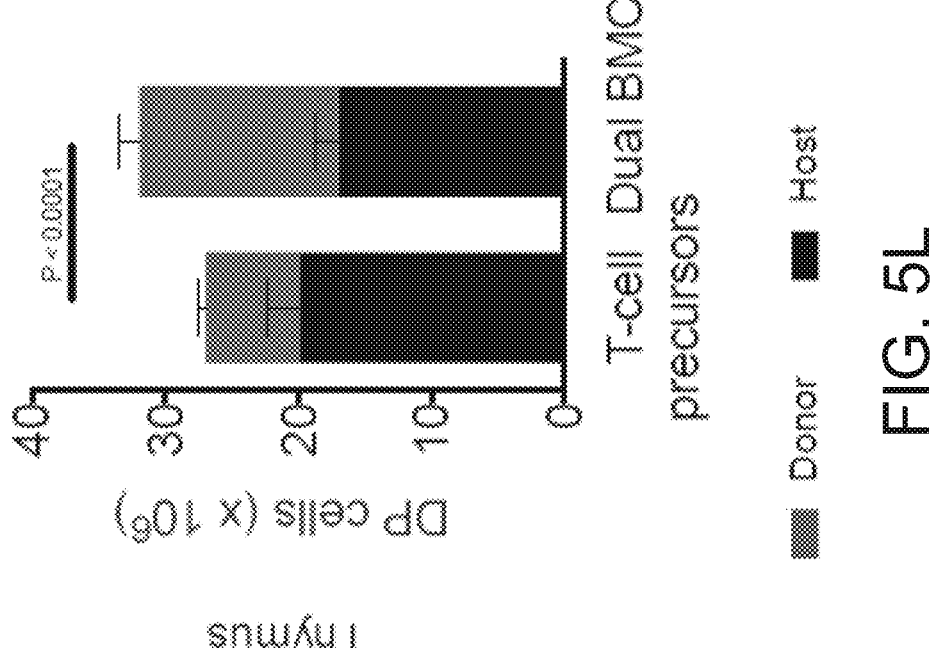
Figure 5M:
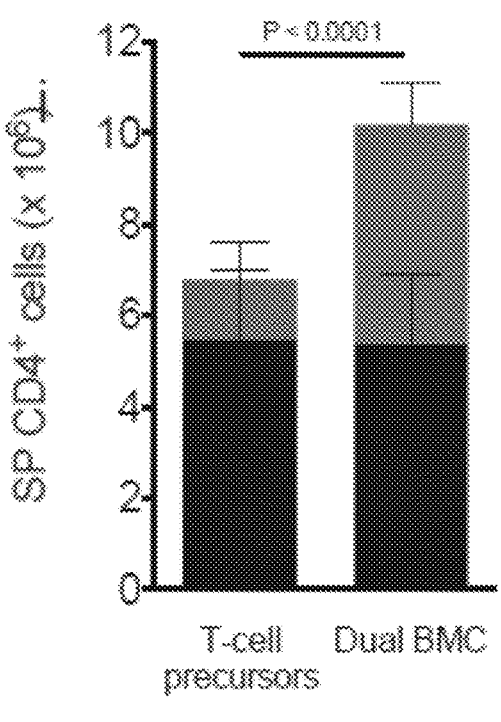
Figure 5M:
Figure 5N:
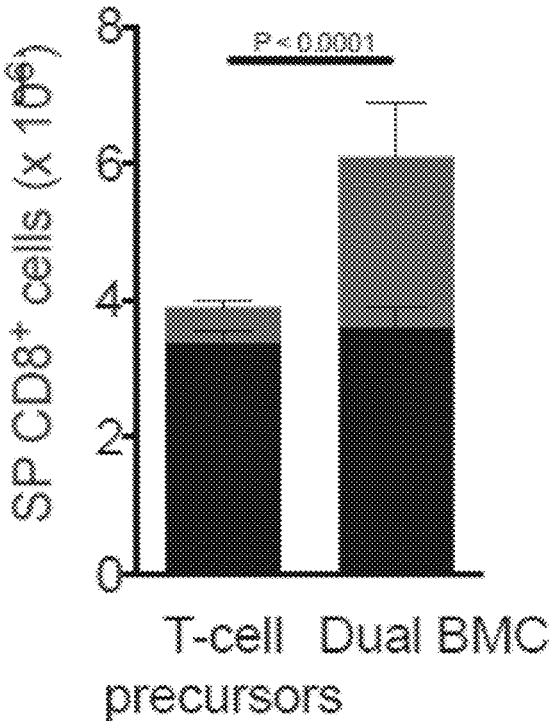
Figures 5O, 5P:
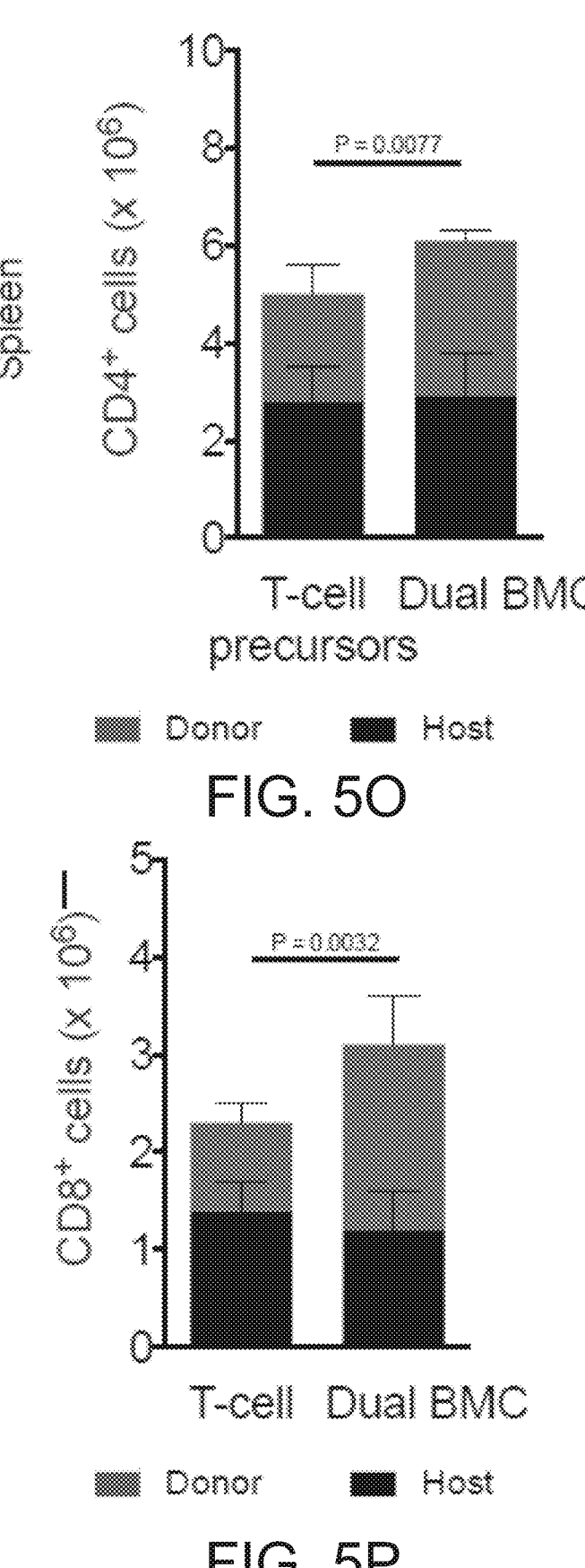
Figure 5Q:
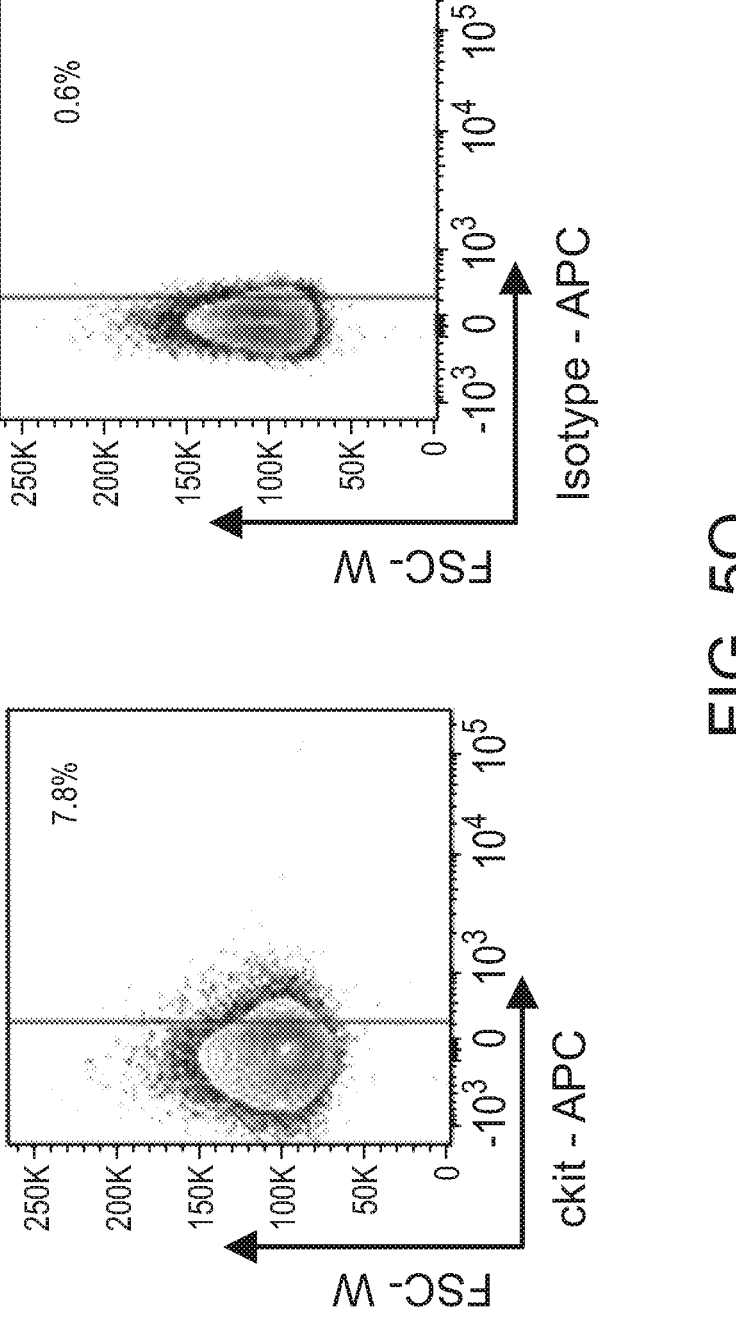

The BMC treatment of this invention was next compared to a widely studied T-cell progenitor infusion approach, consisting predominantly of double negative (DN) 2 and double negative (DN) 3 precursors (>90%) generated ex vivo using OP9-DL1 feeder cells (FIG. 5K). At 28 days post-HSCT, donor chimerism was significantly higher in the BMC-treated mice in the DP, SP4 and SP8 thymocyte populations (FIGS. 5L-5N). In the spleen, donor chimerism was higher for both CD4$^+$ and CD8$^+$ T-cells, and higher absolute numbers of donor CD4+ and CD8+ T-cells were found with BMC-treatment (FIGS. 5O and 5P).

Example 5: BMCs Enhance the Diversity and Function of Regenerated T-Cells

The diversity in T-cell receptors (TCR diversity) is produced by stochastic somatic recombination of gene segments in the thymus. In dual BMC treated mice, the thymus cellularity and the thymus weight were significantly higher than transplant-only controls upto ~6 weeks post-transplant (FIGS. 3Q and 3R). To characterize whether the increase in thymic cellularity also enhanced the functionality and diversity of the regenerated T-cells in syngeneic transplants, TCR excision circles (TRECs) were quantified. TRECs are a signature of TCR rearrangement. A TCR repertoire analysis was also conducted. TREC number in the thymus of dual BMC-treated mice 1 month after transplantation were similar to that in non-irradiated control mice, and both were greater than in transplant only mice and BMP-2 BMC treated mice (FIG. 6A). In the spleen, an overall lower number of TRECs were noted in the same groups relative to the non-irradiated control, but mice treated with dual BMCs still had a higher TREC count relative to the transplant only and single factor BMP-2 BMC groups (FIG. 6B). The diversity of the TCR V and J segments in the CDR3 beta chain was evaluated in the BMC treated and transplanted mice 30 days post-HSCT using the Simpson's index (SI), which takes into account the number of T-cell clones present, as well as the relative abundance of each clone. The SI of mice with the dual functional BMC was 40% that of non-irradiated control mice, whereas the SI in mice administered the transplant alone or with BMP-2 BMC were lower (16% and 8%, respectively) (FIG. 6C). In HSCT, the lack of naive T cells with a broad TCR repertoire has been associated with increased risk of immunological complications and opportunistic infections (Douek, D. C. et al. Assessment of thymic output in adults after haematopoietic stem cell transplantation and prediction of T-cell reconstitution. *The Lancet* 355, 1875-1881 1076 (2000)). The recovery of a greater number of TRECs in the thymus and periphery of dual BMC treated mice mirrors the enhancement in thymopoiesis. Relatively high frequencies of specific TCR clones were also observed in mice treated with dual BMCs, but a greater overall diversity suggested a more balanced thymus-derived reconstitution.

To measure the capacity of regenerated T-cells to respond in an antigen-specific manner, syngeneic transplants were vaccinated and subsequently challenged with a model protein ovalbumin (OVA) 30 days after transplantation (FIG. 6D). OVA epitope (SIINFEKL)-tetramer$^+$CD8+ T-cells were significantly higher in mice that received the dual functional BMC, as compared to transplanted mice that did not receive BMC or that received the BMC with BMP-2 only (FIG. 6E). Similarly, in dual BMC-treated mice that received the allogeneic transplant, the donor antigen-specific T-cell response was approximately 3-fold higher, as compared to that resulting from the pro-T-cell therapy approach (FIG. 6F). It was found that the production of interferon (IFN)-γ and tumor necrosis factor-α (TNF-α) upon ex vivo stimulation was comparable for donor CD4$^+$ and CD8$^+$ T-cells in the BMC treatment and T-cell progenitor treatment groups at Day 22, but a significantly greater fraction of T-cells from the BMC-treated group produced these factors at Day 42 (FIGS. 6G and 6H). The robust antigen-specific generation of CD8$^+$ T-cells after vaccination in BMC treated mice post-HSCT suggests that the BMC treatment has the potential to be used in combination with post-HSCT vaccination.

Example 6: Materials and Methods

The invention was made using the following materials and methods.

General Methods and Statistics

Sample sizes for animal studies were based on prior work without the use of additional statistical estimations (Brainard, D. M. et al. Induction of robust cellular and humoral virus-specific adaptive immune responses in human immunodeficiency virus-infected humanized BLT mice. *Journal of virology* 83, 7305-7321 (2009); Bencherif, S. A. et al. Injectable cryogel-based whole-cell cancer vaccines. *Nature communications* 6, 7556 (2015); Palchaudhuri, R. et al. Non-genotoxic conditioning for hematopoietic stem cell 1066 transplantation using a hematopoietic-cell-specific internalizing immunotoxin. *Nature biotechnology* 34, 738 (2016))). Results were analyzed by using one-way ANOVA with a Tukey post hoc test using GraphPad Prism software. Where ANOVA was used, variance between groups was found to be similar by Bartlett's test. Survival curves were analyzed by using the log-rank (Mantel-Cox) test. Alphanumeric coding was used to blind pathology samples and blood counting.

Materials

UP LVG sodium alginate with high guluronate content was purchased from ProNova Biomedical; 2-morpholinoethanesulfonic acid (MES), sodium chloride (NaCl), sodium hydroxide (NaOH), N-hydroxysuccinimide (NHS), 1-ethyl-3-(3-dimethylaminopropyl)-carbodiimide hydrochloride (EDC), 2-aminoethyl methacrylate hydrochloride (AEMA) and acetone were purchased from Sigma-Aldrich. ACRL-PEG-NH2 (3.5 kDa) and 4arm PEG Acrylate (10 kDa) were purchased from JenKem Technology.

Bone Marrow Cryogel (BMC) Fabrication

The bone marrow cryogel was made following a previously described technique with some modifications (Bencherif, S. A. et al. Injectable preformed scaffolds with shape-memory properties. *Proceedings of the National Academy of Sciences of the United States of America* 109, 19590-19595 (2012). Methacrylated alginate (MA-alginate) was prepared by reacting alginate with AEMA. Sodium alginate was dissolved in a buffer solution (0.6% (wt/vol), pH ~6.5) of 100 mM MES buffer. NHS and EDC were added to the mixture to activate the carboxylic acid groups on the alginate backbone followed by AEMA (molar ratio of NHS: EDC:AEMA=1:1.3:1.1), and the solution was stirred at room temperature (RT) for 24 hours. The mixture was precipitated in acetone, filtered and dried in a vacuum oven overnight at RT. Alginate-PEG BMCs were synthesized by preparing a 2.5 wt % solution of MA-alginate and 4arm PEG Acrylate macromonomers (molar ratio MA-alginate:4arm PEG Acrylate=4:1) in deionized water and subsequently adding tetramethylethylenediamine (TEMED) (0.5% (wt/ vol)) and ammonium persulfate (APS) (0.25% (wt/vol)). ACRYL-PEG-NH2 was conjugated with the Delta-like ligand 4 (DLL-4) (R&D Systems) using carbodiimide chemistry (molar ratio of NHS:EDC:DLL4=1:1.3:1.1). BMP-2 (R&D Systems) was added to the polymer solution before cryopolymerization. All precursor solution was precooled to 4° C. to decrease the rate of polymerization before freezing. After addition of the initiator to the prepolymer solution, the solution was quickly transferred onto a precooled (−20° C.) Teflon mold. After overnight incubation, the gels were thawed and collected in petri dishes on ice.

For scanning electron microscopy (SEM), BMCs were incubated in increasing concentration of freshly prepared ethanol solution (30, 50, 70, 90 and 100%) for 20 minutes each. BMCs were then incubated in hexamethyldisilazane (Electron Microscopy Sciences) for 10 min and dried in a desiccator/vacuum chamber for at least 1 hour prior to mounting them for SEM. Dried BMCs were adhered onto sample stubs using carbon tape and coated with a platinum/palladium in a sputter coater. Samples were imaged using secondary electron detection on a Carl Zeiss Supra 55 VP field emission scanning electron microscope (SEM).

Biomolecule Release Quantification

The stock concentration of the BMP-2 was known from the manufacturer and verified using ELISA. To determine the release kinetics encapsulation efficiency of BMP-2 and to confirm stable conjugation of DLL-4, the BMCs were incubated in 1 ml of sterile PBS at 37° C. with shaking Media was replaced periodically. Released agents in the supernatant were detected by ELISA (Peprotech). The samples were released until no more BMP-2 was detectable in the release medium. Subsequently, the cryogel was digested using at least 1000 U of the enzyme Alginate Lyase. The digested product was analyzed for BMP-2 using ELISA. The amounts of BMP-2 and DLL-4 in the cryogel and release medium were compared with the known amount of loaded BMP-2 and DLL-4 to calculate the encapsulation efficiency.

Biomolecule Activity Assays

Alkaline Phosphatase Activity Assay for BMP-2 Bioactivity

MC3T3-E1 Subclone 4 cells were used to conduct an alakaline phosphatase assay as previously described Macdonald, M. L. et al. Tissue integration of growth factor-eluting layer-by-layer polyelectrolyte multilayer coated implants. *Biomaterials* 32, 1446-1453 (2011). Cells were cultured under different experimental conditions: (1) growth medium, (2) differentiation medium supplemented with BMP-2 release from BMCs and (3) Native BMP-2.

Notch Activation Assay for DLL-4 Bioactivity

To quantify the in vitro bioactivity of DLL-4 after exposure to serum proteins, which could deactivate this morphogen in vivo, a previously characterized Notch reporter cell line, CHO-K1+2×HS4-UAS-H2B-Citrine-2×HS4 cH1+hNECD-Gal4esn c9, a kind gift from M. Elowitz (Caltech), was used (Sprinzak, D. et al. Cis-interactions between Notch and Delta generate mutually exclusive signaling states. *Nature* 465, 86 (2010); Nandagopal, N. et al. Dynamic ligand discrimination in the Notch signaling pathway. *Cell* 172, 869-880. e819 (2018)). These cells were grown in Alpha MEM Earle's Salts (Irvine Scientific) supplemented with 10% Tet System Approved FBS (Clontech), 100 U/ml penicillin-100 ug/ml streptomycin −0.292 mg/ml L_glutamine (Gibco), at 37° C. in the presence of 5% CO2 under a humidified atmosphere. BMCs both with and without the DLL-4 were incubated in 96-well plates with the complete cell culture medium, without cells. At pre-determined time intervals (up to 3 months), twenty-thousand Notch reporter cells were seeded in the wells on the BMCs. After 24 hours, confocal microscopy was performed using a Zeiss LSM 710 confocal system. The colorimetric output in response to binding with Notch ligand DLL-4 was quantified and used as an indicator of DLL-4 bioactivity in the scaffold (FIG. 1H). In particular, the total YFP fluorescence of each cell in a field of view (50-100; 4-5 field of views encompassing over 80% of the gel surface) was calculated and background fluorescence was subtracted. The median YFP fluorescence was calculated and divided by the median fluorescence of the cells seeded on the BMCs without DLL-4 and reported.

Affinity Determination by Surface Plasmon Resonance

Dissociation constants of wild-type DLL4 and MA-DLL4 for Notch1 were determined by surface plasmon resonance using a BIAcore T200 instrument (GE Healthcare) as described previously (Heliotis, M., Lavery, K., Ripamonti, U., Tsiridis, E. & Di Silvio, L. Transformation of a prefabricated hydroxyapatite/osteogenic protein-1 implant into a vascularised pedicled bone flap in the human chest. *International journal of oral and maxillofacial surgery* 35, 265-269 (2006). Briefly, biotinylated, recombinant Notch1 were immobilized on a streptavidin coated sensor chip (GE Healthcare). Increasing concentrations of wild-type of methacrylated DLL4 proteins in buffer were flowed over the chip at 20° C. Binding and dissociation phases were performed at 10 µl/min for 120 seconds and 60 seconds, respectively. Steady-state binding curves were fitted using the BIAcore evaluation software to a 1:1 Langmuir model to determine the $K_d$.

In Vitro Cell Culture in Bone Marrow Cryogel (BMC)

Mouse BM cells were harvested from the limbs. Crushed tissue and cells were filtered through a 70-micron mesh. A single cell suspension was prepared by passing the cells once through a 20-gauge needle. Total cellularity was determined by counting cells using a hemacytometer. BM cells were depleted of mature immune cells (expressing CD3-ε, CD45R/B220, Ter-119, CD11b or Gr-1) by magnetic selection (BD Biosciences). Cells were incubated with a mix of Pacific Blue-conjugated lineage antibodies (antibodies to CD3, NK1.1, Gr-1, CD11b, CD19, CD4 and CD8) and with Sca-1- and c-kit-specific antibodies. Hematopoietic cells (Lin−Sca-1$^{hi}$c-kit$^{hi}$) were isolated using a FacsAria cell sorter (BD). Sorted cells were ≥95% pure. Human cord-blood derived CD34+ cells were purchased (Allcells) and expanded for seven days using expansion supplements (Stemcell Technologies). CD34+ cells were isolated using a positive selection kit (StemCell Technologies). 96 well plates were pre-coated with Pluronic F127 (Sigma). Each BMC was individually placed in a well of the 96 well plate. Ten thousand mouse or human cells, isolated as described above were added to the same well in a 200 µl volume of RPMI (with L-Glutamine) 1640 with 10% fetal bovine serum (FBS) and 1% of antibiotic and anti mycotic solution (containing penicillin, streptomycin and amphotericin B). For mouse cells, the media was supplemented with 10 ng/ml of stem cell factor (SCF; R&D Systems), 10 ng/mL FMS-like tyrosine kinase 3 ligand (Flt3L; R&D Systems) and 1 ng/mL interleukin-7 (IL-7; R&D Systems) with a 50% medium exchange step at day 2, 4 and 6. For human cells, the media was supplemented with 100 ng/mL SCF, 100 ng/mL Flt3L, 100 ng/mL TPO (R&D Systems), and 100 ng/mL IL-7 (R&D Systems). After one week of culture, cells were isolated by digesting the BMC with 1 mg/ml Alginate Lyase (Sigma). The solution was passed through a 70-micron filter and cells were processed for FACS analysis as described below.

BM Transplantation and Blood Analysis

All animal work was approved by the Harvard Institutional Animal Care and Use Committee and followed the National Institutes of Health guidelines and relevant ethical regulations. C57BL/6 (B6, H-2$^b$), BALB/c (H-2$^d$), C57BL/6 (CD 45.1$^+$), CByJ.B6-Tg(UBC-GFP)30Scha/J (GFP) and NSG mice (Jackson Laboratories) were female and between 6 and 8 weeks old at the start of the experiment. All mice within each experiment were age-matched and no randomization was performed. Pre-established criterion for animal omission was failure to inject desired cell dose in transplanted mice and death due to post-surgical complications in humanized mice. Health concerns unrelated to the procedure (e.g., malocclusion, severe dermatitis) were criteria for omission and euthanasia.

Transplant Models

All TBI experiments were performed with a Cs-137 γ-radiation source. Sublethal-TBI (SL-TBI, B6 recipient), 1×500 cGy+5×10$^5$ lineage-depleted bone marrow cells; syngeneic HSCT (syn-HSCT, B6 recipient) 1×1000 cGy+5×10$^4$ to 5×10$^5$ (as indicated in the figures) lineage depleted GFP BM cells; allogeneic-HSCT with GVHD (BALB/c MHC-mismatched recipient) 1×850 cGy+5×10$^5$ lineage depleted GFP BM cells+1×10$^6$ GFP splenocytes; allogeneic-HSCT without GVHD (BALB/c MHC-mismatched recipient) 1×850 cGy+5×10$^5$ lineage depleted GFP BM cells or 5×10$^6$ in vitro generated GFP T-cell progenitors+10$^3$ syngeneic HSCs as described elsewhere without modification48. Humanized BLT (bone marrow-liver-thymus) mouse studies were conducted by the MGH and Ragon Institute Human Immune System Mouse Program, with Institutional IACUC approval as described previously (Brainard, D. M. et al. Induction of robust cellular and humoral virus-specific adaptive immune responses in human immunodeficiency virus-infected humanized BLT mice. *Journal of virology* 83, 7305-7321 (2009)). BM cells for transplantation or analysis were harvested by crushing all limbs or one femur, respectively and processed as described above. While the mice were anesthetized, they received subcutaneous injections of two BMCs, which were suspended in 0.2 ml of sterile PBS, into the dorsal flank by means of a 16-gauge needle. One BMC was injected on each side of the spine and positioned approximately midway between the hind and forelimbs. Subcutaneous nodule size was quantified over time by measuring the nodule length, width and height using a caliper. All cohorts of mice (typically 10 mice/group) were serially bled. White blood cell, hemoglobin, red blood cell, platelet, and hematocrit levels were quantified by CBC analysis (Abaxis VetScan HM5).

For directly assessing whether cells from the BMC migrate to the thymus, the dual factor BMC in concert with stem cell therapy was delivered into an initial set of lethally irradiated mice (B6 recipients receiving 1000 cGy L-TBI and 5×10$^5$ lineage depleted GFP BM cells with dual factor BMC. 10-days post-HSCT, the dual factor BMC was explanted and immediately surgically transplanted in the subcutaneous pocket of a second set of B6 mice which had received 500 cGy SL-TBI 48-hours prior without any additional cell transplantation. 20-days post surgery, mice were sacrificed and the thymocytes were analyzed in these mice.

Flow Cytometry (FACS) Analysis

Anti-mouse antibodies to CD8-α (53-6.7), CD3-ε (145-2C11), B220 (RA3-6B2), CD11b (M1/70), CD25 (PC61), CD117 (2B8), Sca-1 (D7), CD127 (A7R34), and anti-human antibodies to CD45 (H130), CD3 (HIT3a), CD4 (SK3), CD19 (HIB19), CD34 (581), CD38 (HB-7) and CD7 (CD7-6B7), IFN-γ (XMG1.1), TNF-α (MP6-XT22) and the corresponding isotype antibodies were purchased from BioLegend. Anti-human CD8 (RPA-T8) was purchased from BD Biosciences. CD44 (IM7) was purchased from eBioscience. SIINFEKL tetramer (Alexa Fluor 647 H-2K$^b$ OVA) were obtained from the NIH Tetramer Core Facility. All cells were gated based on forward and side-scatter characteristics to limit debris including dead cells. Antibodies were diluted according to the manufacturer's suggestions. Cells were gated based on fluorescence minus one controls, and the frequencies of cells staining positive for each marker was recorded. For quantifying T, B, and myeloid cells, blood samples were red blood cell-lysed and stained with anti-CD45, -B220, -CD3, -CD4, -CD8, and -CD11b antibodies, and absolute numbers of T, B, and myeloid cells were calculated using flow cytometry frequencies and white blood cell values obtained by CBC analysis. Analysis was based on donor events within the CD45+ for blood cells and the CD45− gate for stromal cells.

Bone, Fat Quantification and Histology

After euthanasia, BMCs and tissues were explanted. For quantification of bone using bone alkaline phosphatase (BALP), the BMCs and femurs were crushed and homogenized and strained through a 70 micron filter. Subsequently, a BALP ELISA kit (Creative Diagnostics) was used to quantify the BALP by following the manufacturer's protocol. Oil Red O staining kit (Biovision) was used for lipid quantification. Harvested BMCs and bones were washed, fixed, processed and stained following the manufacturer's protocol. BMCs and bone were subsequently crushed, strained and resuspended in equal volumes before measuring absorbance (OD$_{492}$). For histological staining, tissues were fixed in 4% paraformaldehyde (PFA). PFA-fixed samples were partially decalcified for about 4 hours using a rapid decalcifying formic acid/hydrochloric acid mixture (Decalcifying Solution, VWR) and embedded in paraffin wax. Sections (5 μm) of the samples were stained with routine trichrome, Safranin-O or Verhoeff-Van Gieson stain.

Quantification of Thymic T-Cell Receptor Excision Circles (TRECs)

TREC quantification was performed as previously described (Warnke, P. et al. Growth and transplantation of a custom vascularised bone graft in a man *The Lancet* 364, 766-770 (2004)). Briefly, thymi were harvested from non-irradiated C57BL/6 mice, transplanted mice, and transplanted mice with the injected BMC (30 d after conditioning). Total DNA was extracted using TRIZOL following tissue homogenization in a Bullet Blender Storm BBX24 instrument (Next Advance, Inc.). DNA was quantified by UV-Vis and 1 μg of DNA per sample was used as input for real-time PCR. A standard curve of mouse sjTREC plasmid was used to calculate the absolute number of single joint TRECS (sjTRECs) per sample.

TCR Analysis

Extracted lymphocyte RNA was quantified using UV-Vis. Equimolar amounts of RNA from each sample was submitted to iRepertoire for sequencing and bioinformatics analysis, where samples were reverse transcribed and amplified using a primer set which specifically amplifies beta TCR RNA. The results of the sequencing gave a range of total reads and numbers of unique CDR3s for each sample.

Vaccination and Non-Specific T-Cell-Stimulation Study

Thirty (30) days after transplantation, animals were immunized with a bolus vaccine containing 100 μg ovalbumin (OVA), 100 μg CpG-ODN and 1 μg GM-CSF. After 10 days, animals were challenged with an intravenous injection of ovalbumin. On Day 12, spleens were collected from euthanized mice in the vaccination studies. Splenocytes were isolated by mechanical disruption of the spleen against 70-μm cell strainers. Red blood cells in the harvested tissues were lysed and leukocytes were prepared for analysis. For unspecific stimulation, cells were incubated for 5 hours with PMA (10 ng/mL)+ionomycin (2 μM). Brefeldin A (10 μg/mL) was added after 2 hours of incubation. The cells were then harvested, washed, and stained with fluoro-chrome-conjugated antibodies to T-cell surface antigens. Subsequently, cell were fixed and permeabilized with fixation/permeabilization solution kit reagents (BD) and stained with IFN-γ, TNF-α-specific antibodies.

Discussion

Here, it was demonstrated that a cell-free biomaterial-based BMC mimicked key features of the T-cell lymphopoietic bone marrow niche and promoted the regeneration of immune competent T cells after hematopoietic stem cell transplantation. Subcutaneously administered BMCs interfaced with the host vasculature to form a host-device interface and presented lineage instructive cues to donor recruited progenitor cells in vivo. It is well established that BMP-2 induces osteolineage differentiation of recruited mesenchymal cells and indirectly promotes rapid neoangiogenesis (Smadja, D. M. et al. Bone morphogenetic proteins 2 and 4 are selectively expressed by late outgrowth endothelial progenitor cells and promote neoangiogenesis. *Arteriosclerosis, thrombosis, and vascular biology* 28, 2137-2143 (2008). In this work, it was observed early neoangiogenesis, followed by maturation of the vasculature to densities consistent with those observed in endogenous bone marrow (Lafage-Proust, M.-H. et al. Assessment of bone vascularization and its role in bone remodeling. *BoneKEy reports* 4 (2015)). The finding of various hematopoietic and stromal progenitor populations quantified within the BMC are consistent with previous observations of hematopoiesis occurring within an ectopic bone nodule (Kuznetsov, S. A. et al. The interplay of osteogenesis and hematopoiesis: expression of a constitutively active PTH/PTHrP receptor in osteogenic cells perturbs the establishment of hematopoiesis in bone and of skeletal stem cells in the bone marrow. *J Cell Biol* 167, 1113-1122 (2004)); Song, J. et al. An in vivo model to study and manipulate the hematopoietic stem cell niche. *Blood* 115, 2592-2600 (2010)). The incorporation of bioactive Notch ligand DLL-4 on the polymer scaffold promoted an early enhancement in the generation of T-cell progenitors in the BMC and led to a significant increase in the number of thymic progenitors relative to controls receiving lineage-depleted bone marrow grafts, and the controls were consistent with established models of syngeneic- and allogeneic-HSCT (Wils, E.-J. et al. Flt3 ligand expands lymphoid progenitors prior to recovery of thymopoiesis and accelerates T cell reconstitution after bone marrow transplantation. *The Journal of Immunology* 178, 3551-3557 (2007); Maillard, I. et al. Notch-dependent T-lineage commitment occurs at extrathymic sites following bone marrow transplantation. *Blood* 107, 3511-3519 (2006). This finding is supported by the observation of enhanced generation of TRECs, the increased complexity of the TCR repertoire and the increased vaccination efficacy.

The BMC approach is distinct conceptually and in practice from other strategies to promote post-HSCT T-cell regeneration and its relevance in HSCT is supported by the preclinical studies in this work. It resulted in a higher number of T-cell progenitors and functional T-cells in the thymus and the periphery when used with a 10-fold lower dose relative to T-cell progenitor infusion. The BMC treatment varies from other methods in that it can be administered at the time of HSCT. In contrast, T-cell progenitors are produced in vitro from donor hematopoietic cells over 2-4 weeks, have complex cell culture requirements in pre-clinical models and are patient specific. By providing the T-cell promoting cues to the transplanted HSCs in vivo without the need for ex-vivo culture, the BMC approach may be an off-the-shelf product, avoid the considerable infrastructure needed for cell manufacturing (Garber, K. (Nature Publishing Group, 2018) and may complement the activities of cytokine therapies. When a lower radiation dose was used prior to HSCT, the BMC modestly enhanced T-cell reconstitution in the periphery, but significantly increased donor derived T-cell generation in the thymus and donor T-cell chimerism. The finding suggests the application of the BMCs will be relevant in settings of lower intensity HSCT.

The enhancement in the reconstitution of human T-cells in xenogeneic NSG-BLT mice was accompanied by a modest and transient reduction in B-cell reconstitution, consistent with a corresponding decrease in pre-B CFUs. While this humanized mouse model is widely accepted for human immune cells, it is also known that key mouse cytokines are inefficient at inducing hematopoiesis including the development of human B-cells from human CD34$^+$ cells in this model ((Jangalwe, S., Shultz, L. D., Mathew, A. & Brehm, M A Improved B cell development in humanized NOD-scid IL2Rγ null mice transgenically expressing human stem cell factor, granulocyte-macrophage colony-stimulating factor and interleukin-3. *Immunity, inflammation and disease* 4, 427-440 (2016)). It is likely that the Notch activation of the fraction of the transplanted cells, which seed the BMC enhances T cell specification at the expense of B cell specification. However, the transient reduction in B-cell production is modest and unlikely to be of clinical significance.

The formation of a bone nodule is restricted to the geometry of the scaffold, consistent with previous reports of scaffold-induced bone formation, which has been well tolerated in many species, including non-human primates (Ripamonti, U. Bone induction by recombinant human osteogenic protein-1 (hOP-1, BMP-7) in the primate *Papio ursinus* with expression of mRNA of gene products of the TGF-β superfamily. *Journal of cellular and molecular medicine* 9, 911-928 (2005) and in humans (Heliotis, M., Lavery, K., Ripamonti, U., Tsiridis, E. & Di Silvio, L. Transformation of a prefabricated hydroxyapatite/osteogenic protein-1 implant into a vascularised pedicled bone flap in the human chest. *International journal of oral and maxillofacial surgery* 35, 265-269 (2006); Warnke, P. et al. Growth and transplantation of a custom vascularised bone graft in a man *The Lancet* 364, 766-770 (2004)). The past clinical experience with other scaffold-based systems indicates that the size of the device may remain constant between species (Hodi, S. (2012)). Even with the larger growth factor dose that may be necessary for use in humans, it is anticipate that the controlled release provided by this polymer-based hydrogel system would permit the use of BMP-2 at a dose several orders of magnitude lower than the large dose currently used in the clinic, which are delivered as a bolus release and have been associated with undesirable side effects (Carragee, E. J., Hurwitz, E. L. & Weiner, B. K. A critical review of recombinant human bone morphogenetic protein-2 trials in spinal surgery: emerging safety concerns and lessons learned. *The Spine Journal* 11, 471-491 (2011)). After T cell regeneration, the BMC may be readily removed similar to other devices that are often used in HSCT or made with biodegradable materials to resorb (Biffi, R. et al. Use of totally implantable central venous access ports for high-dose chemotherapy and peripheral blood stem cell transplantation: results of a monocentre series of patients. *Annals of oncology* 15, 296-300 (2004)).

CD4$^+$ T-cell recovery after allogeneic HSCT is usually delayed, leading to an inversion of the normal CD4/CD8 ratio (Li, M. O. & Rudensky, A. Y. T cell receptor signalling in the control of regulatory T cell differentiation and function. *Nature Reviews Immunology* 16, 220 (2016)). In BMC treated mice, there was a more balanced reconstitution of T cells and an enhancement in donor CD4$^+$ regulatory T-cells (T$_{reg}$) in the thymus and the spleen of humanized and allogeneically transplanted mice. Given the key role of donor T$_{reg}$ in GVHD suppression (Hoffmann, P., Ermann, J., Edinger, M., Fathman, C. G. & Strober, S. Donor-type CD4$^+$CD25$^+$ regulatory T cells suppress lethal acute graft-versus-host disease after allogeneic bone marrow transplantation. *Journal of Experimental Medicine* 196, 389-399 (2002)), BMC-mediated enhancement of donor T$_{reg}$ generation likely contributed to the mitigation of GVHD-like pathology and the enhanced survival of mice, potentially through BMP-2 regulation of TGF-beta family proteins, which are key regulators of T$_{reg}$ expansion ((Wan, Y. Y. & Flavell, R. A. 'Yin-Yang' functions of transforming growth factor-β and T regulatory cells in immune regulation. *Immunological reviews* 220, 199-213 (2007)). Moreover, the time course in the allogeneic GVHD model is consistent with at least some of the BMC role being due to an effect on pre-existing T-committed or mature T cells.

In sum, these findings suggest that the BMC represents a simple to administer, off-the-shelf system that can enhance T cell regeneration after HSCT. If the BMC system performs similarly in a human context, it may be a means of abrogating the immunological complications and opportunistic infections that limit clinical application of potentially curative HSCT.

INCORPORATION BY REFERENCE

All publications, patents, and patent applications mentioned herein are hereby incorporated by reference in their entirety as if each individual publication, patent or patent application was specifically and individually indicated to be incorporated by reference. In case of conflict, the present application, including any definitions herein, will control.

EQUIVALENTS

Those skilled in the art will recognize, or be able to ascertain using no more than routine experimentation, many equivalents to the specific embodiments of the present invention described herein. Such equivalents are intended to be encompassed by the following claims.

What is claimed is:

1. A composition for modulating the immune system in a subject, comprising:
a porous scaffold comprising a click-hydrogel or a click-cryogel, wherein the porous scaffold comprises macropores having a diameter greater than about 20 μm;
a growth factor comprising a bone morphogenetic protein-2 (BMP-2) present at between about 1 ng to about 1000 ng per scaffold or at about 0.03 ng/mm$^3$ to about 350 ng/mm$^3$ by volume of scaffold, and in an amount effective for inducing formation of a tissue or an organ within the scaffold and recruiting a cell into the scaffold; and
a differentiation factor comprising a Delta-like 4 (DLL-4) that induces the differentiation of the recruited cell into a T cell progenitor cell, wherein the T cell progenitor cell is capable of differentiating to a T cell.

2. The composition of claim 1, wherein the scaffold comprises a click hydrogel.

3. The composition of claim 1, wherein the scaffold comprises a polymer or co-polymer selected from the group consisting of polylactic acid, polyglycolic acid, PLGA, alginate or an alginate derivative, gelatin, collagen, agarose, hyaluronic acid, poly(lysine), polyhydroxybutyrate, poly-epsilon-caprolactone, polyphosphazines, poly(vinyl alcohol), poly(alkylene oxide), poly(ethylene oxide), poly(allylamine), poly(acrylate), poly(4-aminomethylstyrene), pluronic polyol, polyoxamer, poly(uronic acid), poly(anhydride), poly(vinylpyrrolidone), and any combination thereof.

4. The composition of claim 1, wherein:
(i) the scaffold comprises a polymer or co-polymer selected from the group consisting of alginate, alginate derivative, and the combination thereof; and/or
(ii) the scaffold comprises a polymer or co-polymer selected from the group consisting of hyaluronic acid, hyaluronic acid derivative, and the combination thereof.

5. The composition of claim 1, wherein:
(i) the scaffold comprises pores having a diameter between about 20 μm and 100 μm;
(ii) the scaffold comprises a macropore, optionally wherein the macropore has a diameter between about 50 μm and 80 μm, and/or
(iii) the scaffold comprises macropores of different sizes.

6. The composition of claim 1, wherein the scaffold is injectable.

7. The composition of claim 1, wherein:
(i) the scaffold comprises methacrylated alginate (MA-alginate);
(ii) the scaffold comprises a hyaluronic acid or a hyaluronic acid-derivative;
(iii) the click-hydrogel or click cryogel comprises a click-alginate, a click-gelatin, or a click-hyaluronic acid; and/or
(iv) the scaffold comprises hydroxyapatite.

8. The composition of claim 1, wherein the scaffold comprises porogen hydrogel microbeads and a bulk hydrogel, wherein the porogen hydrogel microbeads degrade at least 10% faster than the bulk hydrogel polymer scaffold following administration of the scaffold into a subject and/or wherein the porogen hydrogel microbeads comprise oxidized alginate.

9. The composition of claim 1, wherein:
(i) the cell is a stem cell;
(ii) the cell is a progenitor cell;
(iii) the cell is a stromal cell; or
(iv) the cell is a hematopoietic stem cell.

10. The composition of claim 1, wherein:
(i) the tissue or the organ comprises a bone tissue or a hematopoietic tissue;
(ii) the tissue or the organ is formed about 7-21 days after the composition is administered to the subject; and/or
(iii) the tissue or the organ is formed about 14 days after the composition is administered to the subject.

11. The composition of claim 1, wherein:
the growth factor retains its bioactivity for at least twelve days after the growth factor is incorporated into the scaffold.

12. The composition of claim 1, wherein the T cell comprises a cell selected from the group consisting of a CD4+ T cell, a CD8+ T cell, a regulatory T cell (Treg), and any combination thereof, or wherein the T cell comprises a Treg.

13. The composition of claim 1, wherein:

(i) the differentiation factor is covalently linked to the scaffold;

(ii) the differentiation factor is covalently linked to the scaffold utilizing click chemistry;

(iii) the differentiation factor is covalently linked to the scaffold utilizing N-hydroxysuccinimide (NHS) and 1-ethyl-3-(3-dimethylaminopropyl) carbodiimide hydrochloride (EDC) chemistry, NHS and dicyclohexylcarbodiimide (DCC) chemistry, avidin-biotin reaction, azide and dibenzocycloocytne chemistry, tetrazine and transcyclooctene chemistry, tetrazine and nor-bornene chemistry, or di-sulfide chemistry; and/or (iv) the differentiation factor retains its bioactivity for at least about three months after the differentiation factor is incorporated to the scaffold.

14. The composition of claim 1, wherein:

(i) the recruited cell is a transplanted cell;

(ii) the recruited cell is not a transplanted cell;

(iii) the recruited cell is autologous;

(iv) the recruited cell is allogeneic; or (v) the recruited cell is xenogeneic.

15. The composition of claim 1, wherein the differentiated cell is capable of migrating out of the scaffold, and/or wherein the differentiated cell is capable of homing to a tissue in a subject after the composition is administered to the subject.

16. The composition of claim 1, further comprising a homing factor that is capable of promoting the recruitment of the cell to the scaffold.

17. The composition of claim 16, wherein the homing factor comprises a stromal cell derived factor.

18. A method of modulating the immune system, reducing immune over-reactivity, increasing donor chimerism, and/or promoting balanced reconstitution of T cells of a human having a compromised immune system, comprising administering to the human a composition comprising:

a porous scaffold comprising a click-hydrogel or a click-cryogel;

a growth factor comprising a bone morphogenetic protein-2 (BMP-2) present in an amount effective for inducing formation of a tissue or an organ within the scaffold and recruiting a cell into the scaffold; and a differentiation factor comprising a Delta-like 4 (DLL-4) that induces the differentiation of the recruited cell into a T cell progenitor cell, thereby modulating the immune system of the human, wherein the human has a compromised immune system due to immunosenescence, congenital immunodeficiency, or acquired immunodeficiency.

19. A syringe comprising:

a needle;

a reservoir that comprises the composition of claim 1; and a plunger.

20. A kit comprising:

the composition of claim 1; and instructions to administer the composition.

*    *    *    *    *